(12) United States Patent
Chen et al.

(10) Patent No.: US 12,247,036 B2
(45) Date of Patent: Mar. 11, 2025

(54) TRICYCLIC COMPOUNDS FOR THE TREATMENT OF CANCER

(71) Applicant: Hoffmann-La Roche Inc., Little Falls, NJ (US)

(72) Inventors: Jianguo Chen, Shanghai (CN); Lei Guo, Shanghai (CN); Haixia Liu, Shanghai (CN); Hong Shen, Shanghai (CN); Junwei Xi, Shanghai (CN); Weixing Zhang, Shanghai (CN); Dan Zhao, Shanghai (CN); Wei Zhu, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 18/812,060

(22) Filed: Aug. 22, 2024

(65) Prior Publication Data

US 2024/0417410 A1    Dec. 19, 2024

Related U.S. Application Data

(63) Continuation of application No. PCT/CN2024/076886, filed on Feb. 8, 2024.

(30) Foreign Application Priority Data

Feb. 14, 2023 (WO) ................ PCT/CN2023/075911
Aug. 29, 2023 (WO) ................ PCT/CN2023/115515
Jan. 29, 2024 (WO) ................ PCT/CN2024/074420

(51) Int. Cl.
| | |
|---|---|
| *C07D 513/22* | (2006.01) |
| *A61K 31/5025* | (2006.01) |
| *A61K 31/506* | (2006.01) |
| *A61K 31/5377* | (2006.01) |
| *A61K 31/5383* | (2006.01) |
| *A61K 31/553* | (2006.01) |
| *A61P 35/00* | (2006.01) |
| *C07D 519/00* | (2006.01) |

(52) U.S. Cl.
CPC ........ *C07D 513/22* (2013.01); *A61K 31/5025* (2013.01); *A61K 31/506* (2013.01); *A61K 31/5377* (2013.01); *A61K 31/5383* (2013.01); *A61K 31/553* (2013.01); *A61P 35/00* (2018.01); *C07D 519/00* (2013.01)

(58) Field of Classification Search
CPC .................................................. C07D 513/22
USPC .................................................. 514/211.09
See application file for complete search history.

(56) References Cited

U.S. PATENT DOCUMENTS

| | | | |
|---|---|---|---|
| 11,566,007 B2 * | 1/2023 | Koltun ..................... | A61P 35/00 |
| 2021/0130303 A1 | 5/2021 | Koltun et al. | |

FOREIGN PATENT DOCUMENTS

| | | |
|---|---|---|
| CN | 117534684 A | 2/2024 |
| CN | 117534685 A | 2/2024 |
| CN | 117534687 A | 2/2024 |
| CN | 117597354 A | 2/2024 |
| CN | 117720554 A | 3/2024 |
| CN | 117720556 A | 3/2024 |
| LU | 505464 B1 | 5/2024 |
| LU | 505465 B1 | 5/2024 |
| LU | 505620 B1 | 5/2024 |
| WO | 2018/091634 A1 | 5/2018 |
| WO | 2020/132597 A1 | 6/2020 |
| WO | 2021/091956 A1 | 5/2021 |
| WO | 2021/091967 A1 | 5/2021 |
| WO | 2021/091982 A1 | 5/2021 |
| WO | 2022/060583 A1 | 3/2022 |
| WO | 2022/060836 A1 | 3/2022 |
| WO | 2022/212894 A1 | 10/2022 |
| WO | 2022/217053 A1 | 10/2022 |
| WO | 2022/235864 A1 | 11/2022 |
| WO | 2022/235870 A1 | 11/2022 |
| WO | 2022/251292 A1 | 12/2022 |
| WO | 2023/015559 A1 | 2/2023 |

(Continued)

OTHER PUBLICATIONS

"International Search Report—PCT/CN2024/076886" (w/Written Opinion),:pp. 1-11 (May 21, 2024).

(Continued)

*Primary Examiner* — Niloofar Rahmani

(74) *Attorney, Agent, or Firm* — Katherine J. Mackenzie

(57) ABSTRACT

The present invention relates to compounds of formula (Ib),

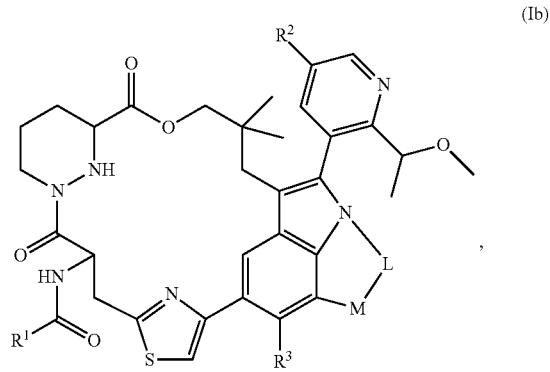

(Ib)

wherein $R^1$ to $R^3$, M and L are as described herein, and their pharmaceutically acceptable salt, enantiomers and diastereomers thereof, and compositions including the compounds and methods of using the compounds.

27 Claims, 4 Drawing Sheets

(56) References Cited

FOREIGN PATENT DOCUMENTS

| | | |
|---|---|---|
| WO | 2023/025832 A1 | 3/2023 |
| WO | 2023/060253 A1 | 4/2023 |
| WO | 2023/086341 A1 | 5/2023 |
| WO | 2023/133543 A1 | 7/2023 |
| WO | 2023/172940 A1 | 9/2023 |
| WO | 2023/208005 A1 | 11/2023 |
| WO | 2023/232776 A1 | 12/2023 |
| WO | 2023/240263 A1 | 12/2023 |
| WO | 2024/008610 A1 | 1/2024 |
| WO | 2024/008834 A1 | 1/2024 |
| WO | 2024/017859 A1 | 1/2024 |
| WO | 2024/040131 A1 | 2/2024 |
| WO | 2024/060966 A1 | 3/2024 |
| WO | 2024/067857 A1 | 4/2024 |
| WO | 2024/081363 A1 | 4/2024 |
| WO | 2024/104364 A1 | 5/2024 |
| WO | 2024/107686 A1 | 5/2024 |
| WO | 2024/149819 A1 | 7/2024 |
| WO | 2024/153208 A1 | 7/2024 |
| WO | 2024/206858 | 10/2024 |
| WO | 2024/211663 | 10/2024 |
| WO | 2024/211712 | 10/2024 |

OTHER PUBLICATIONS

USPTO et al., "U.S. Appl. No. 18/687,262 entitled 'Macrocyclic Compounds for the Treatment of Cancer' filed Feb. 27, 2024".

* cited by examiner

TRICYCLIC COMPOUNDS FOR THE TREATMENT OF CANCER

CROSS-REFERENCE TO RELATED APPLICATIONS

This application is a continuation of International Application No. PCT/CN2024/076886, filed Feb. 8, 2024; which claims the benefit of foreign priority to Chinese Application No. PCT/CN2023/075911 filed Feb. 14, 2023, and Chinese Application No. PCT/CN2023/115515 filed Aug. 29, 2023, and Chinese Application No. PCT/CN2024/074420 filed Jan. 29, 2024, the disclosures of each of which are incorporated herein by reference in their entireties.

The present invention relates to organic compounds useful for therapy and/or prophylaxis in a mammal, and in particular to inhibition of KRAS mutant useful for treating cancers.

FIELD OF THE INVENTION

RAS is one of the most well-known proto-oncogenes. Approximately 30% of human cancers contain mutations in three most notable members, KRAS, HRAS, and NRAS, making them the most prevalent oncogenic drivers. KRAS mutations are generally associated with poor prognosis especially in colorectal cancer, pancreatic cancer, lung cancers. As the most frequently mutated RAS isoform, KRAS has been intensively studied in the past years. Among the most commonly occurring KRAS alleles (including G12D, G12V, G12C, G13D, G12R, G12A, G12S, Q61H, etc), G12C, G12D, G12V represent more than half of all KRAS-driven cancers across colorectal cancer (CRC), pancreatic ductal adenocarcinoma (PDAC), lung adenocarcinoma (LUAD). Of note, KRAS wild-type amplifications are also found in around 7% of all KRAS-altered cancers (ovarian, esophagogastric, uterine), ranking among the top alterations.

All RAS proteins belong to a protein family of small GTPases that hydrolyze GTP to GDP. KRAS is structurally divided into an effector binding lobe followed by the allosteric lobe and a carboxy-terminal region that is responsible for membrane anchoring. The effector lobe comprises the P-loop, switch I, and switch II regions. The switch I/II loops play a critical role in KRAS downstream signaling through mediating protein-protein interactions with effector proteins that include RAF in the mitogen-activated protein kinase (MAPK) pathway or PI3K in the phosphatidylinositol 3-kinase (PI3K)/protein kinase B (AKT) pathway.

KRAS protein switches between an inactive to an active form via binding to GTP and GDP, respectively. Under physiological conditions, the transition between these two states is regulated by guanine nucleotide exchange factors (GEFs), such as Son Of Sevenless Homolog 1 (SOS1), or GTPase-activating proteins (GAPs) that involve catalyzing the exchange of GDP for GTP, potentiating intrinsic GTPase activity or accelerating RAS-mediated GTP hydrolysis. In response to extracellular stimuli, the inactive RAS-GDP is converted to active RAS-GTP which directly binds to RAF RAS binding domains (RAF$^{RBD}$), recruiting RAF kinase family from cytoplasm to membranes, where they dimerize and become active. The activated RAF subsequently carries out a chain of phosphorylation reactions to its downstream Mitogen-activated protein kinase (MEK) and extracellular signal-regulated kinase (ERK), and propagates the growth signal. Of the RAF family of protein kinases (three known isoforms ARAF, BRAF, CRAF/RAF1), BRAF is most frequently mutated and remains the most potent activator of MEK. Despite that individual RAS and RAF family members revealed distinct binding preferences, all RAFs possess the conserved RBD for forward transmission of MAPK signaling, frequently used for characterize KRAS inhibition (e.g. KRAS-BRAF$^{RBD}$ herein). For KRAS, mutations at positions 12, 13, 61, and 146 lead to a shift toward the active KRAS form through impairing nucleotide hydrolysis or activating nucleotide exchange, leading to hyper-activation of the MAPK pathway that results in tumorigenesis.

Despite its well-recognized importance in cancer malignancy, continuous efforts in the past failed to develop approved therapies for KRAS mutant cancer until recently, the first selective drug AMG510 has fast approval as second line treatment in KRAS G12C driven non-small cell lung cancer (NSCLC). Nevertheless, the clinical acquired resistance to KRAS G12C inhibitors emerge rigorously with disease progresses after around 6 month of treatment. All of the mutations converge to reactivate RAS-MAPK signaling, with secondary RAS mutants at oncogenic hotspots (e.g. G12/G13/Q61) and within the switch II pocket (e.g. H95, R68, and Y96) have been observed; moreover, over 85% of all KRAS-mutated or wild-type amplified driven cancers still lack novel agents. Altogether, both the myriad of escape mechanism and various oncogenic alleles, highlight the urgent medical need for additional RAS therapies. As such, we invented oral compounds that target and inhibit RAS alleles for the treatment of RAS mutant driven cancers.

SUMMARY OF THE INVENTION

The present invention relates to novel compounds of formula (Ib),

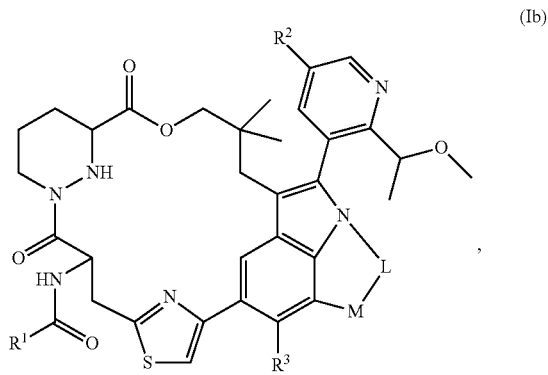

wherein
R$^1$ is 2-oxabicyclo[2.1.1]hexanyl,
  3-oxabicyclo[3.1.0]hexanyl,
  6-bicyclo[3.1.0]hexanyl substituted twice by halogen,
  6-tricyclo[3.1.1.0$^{3,6}$]heptanyl,
  C$_{3-7}$cycloalkyl substituted once, twice or three times by the substituents independently selected from C$_{1-6}$alkyl, C$_{1-6}$alkylpyridinyl, C$_{1-6}$alkylpyrimidinyl, C$_{1-6}$alkyltetrazolyl, C$_{3-7}$cycloalkyl, haloC$_{1-6}$alkyl, halogen, halophenyl, hydroxy, phenyl, pyrazinyl, pyridazinyl, pyridinyl, pyrimidinyl and thiazolyl, or
  tetrahydropyranyl;
R$^2$ is 1,3,4,6,7,8,9,9a-octahydropyrido[1,2-a]pyrazinyl,
  3,4,6,7,9,9a-hexahydro-1H-pyrazino[2,1-c][1,4]oxazinyl,
  morpholinyl, or
  piperazinyl unsubstituted or substituted by substituents independently selected from C$_{1-6}$alkoxyC$_{1-6}$alkyl, C$_{1-6}$alkyl, C$_{3-7}$cycloalkyl, haloC$_{1-6}$alkyl, hydroxyC$_{1-6}$ alkyl, morpholinylC$_{1-6}$alkyl, oxetanyl, oxopyrrolidinylC$_{1-6}$alkyl and tetrahydrofuranyloxyC$_{1-6}$alkyl;

R$^3$ is H or halogen;

M is C$_{1-6}$alkylene or O;

L is C$_{1-6}$alkylene, hydroxyC$_{1-6}$alkylene or haloC$_{1-6}$alkylene;

or a pharmaceutically acceptable salt, enantiomers and diastereomers thereof.

The invention also relates to their manufacture medicaments based on a compound in accordance with the invention and their production as well as the use of compounds of formula (I), (Ia), (Ib) or (Ic) thereof as inhibitor of KRAS.

The compounds of formula (I), (Ia), (Ib) or (Ic) showed good KRAS inhibition for G12C, G12D and G12V.

In another embodiment, the compounds of current invention have significantly improved single dose pharmacokinetics (PK) properties comparing with the reference compounds suggesting that compounds of this invention are more suitable for treating cancers with RAS mutation as an orally therapeutic active ingredient in clinic (Example 128).

In another embodiment, the compounds of this invention showed superior human hepatocyte stability which is advantageous to improve in vivo performance of the compound, such as dose reduction, exposure enhancement, and half-life prolongation (Example 129).

In another embodiment, the compounds of this invention exhibited less inhibitory effect on hERG potassium channel compared to reference compound, suggesting that compounds of this invention could have less concern regarding cardiovascular toxicity associated with hERG channel blockade (Example 138).

In another embodiment, the compounds of this invention showed better selectivity compared to reference compounds on WT KRAS/HRAS/NRAS potentially indicating an improved tolerability and safety profile (Example 132).

In another embodiment, the compounds of this invention consistently exhibited more potent anti-proliferative activity across 119 cell panels, significantly differentiated from reference compound treated group, that potentially could result in more robust anti-tumor responses in clinic (Example 131).

In another embodiment, the compounds of this invention exhibited longer and sustained pathway inhibition over treatment period, and demonstrated significantly enhanced anti-tumor activities compared with reference compound that potentially could result in more durable anti-tumor responses in clinic (Example 130).

In another embodiment, the compounds of this invention showed much higher binding affinity to CYPA and an obviously much lower dissociation rate that revealed a stronger stability of formed CYPA-compound binary complex. This result is consistent with the less potency shift of Example 24 observed in washout assay in Example 140, which further suggesting more persistent cell growth inhibition that would be advantageous for achieving durable efficacy in clinic (Example 139 and 140).

In addition, the compounds of current invention showed excellent tumor growth inhibition (TGI) in brain metastasis intracranial model, improved toxicity and solubility profiles. Furthermore, the compounds of current invention avoided generating unfavorable or even toxic metabolite in vivo compared to reference compounds.

DETAILED DESCRIPTION OF THE INVENTION

Definitions

Figure 1:
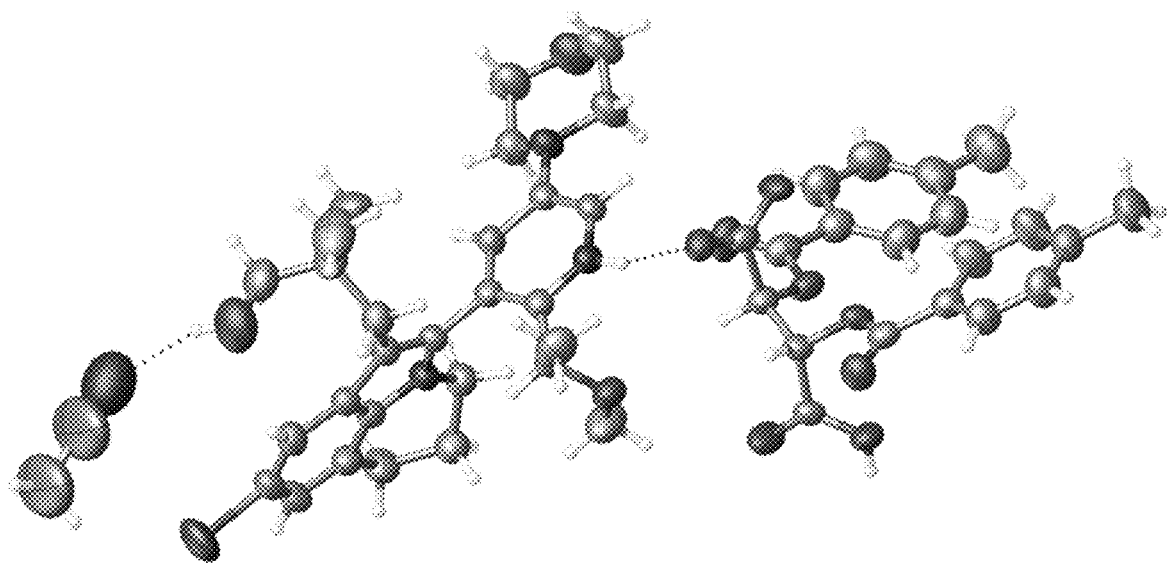
FIG. 1. Absolute configuration structure of compound F6 in the form of its (2S,3S)-2,3-bis[(4-methylbenzoyl)oxy] butanedioic acid salt acetonitrile solvate.

The term "C$_{1-6}$alkyl" denotes a saturated, linear or branched chain alkyl group containing 1 to 6, particularly 1 to 4 carbon atoms, for example methyl, ethyl, n-propyl, isopropyl, n-butyl, isobutyl, tert-butyl and the like. Particular "C$_{1-6}$alkyl" groups are methyl, ethyl and n-propyl.

The term "C$_{1-6}$alkylene" denotes a linear saturated divalent hydrocarbon group of 1 to 6 carbon atoms or a divalent branched saturated hydrocarbon group of 3 to 6 carbon atoms. Examples of C$_{1-6}$alkylene groups include methylene, ethylene, propylene, 2-methylpropylene, butylene, 2-ethylbutylene, pentylene, hexylene.

The term "halogen" and "halo" are used interchangeably herein and denote fluoro, chloro, bromo, or iodo.

The term "haloC$_{1-6}$alkyl" denotes a C$_{1-6}$alkyl group wherein at least one of the hydrogen atoms of the C$_{1-6}$alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl.

The term "haloC$_{1-6}$alkylene" denotes a C$_{1-6}$alkylene group wherein at least one of the hydrogen atoms of the C$_{1-6}$alkylene group has been replaced by same or different halogen atoms.

The term "halophenyl" denotes a phenyl group wherein at least one of the hydrogen atoms of the phenyl group has been replaced by same or different halogen atoms.

The term "C$_{3-7}$cycloalkyl" denotes a monovalent saturated monocyclic or bicyclic hydrocarbon group of 3 to 7 ring carbon atoms. Bicyclic means consisting of two saturated carbocycles having one or more carbon atoms in common. Examples for monocyclic cycloalkyl are cyclopropyl, cyclobutyl, cyclopentyl, cyclohexyl or cycloheptyl. Examples for bicyclic cycloalkyl are bicyclo[1.1.0]butyl, bicyclo[2.2.1]heptanyl, bicyclo[1.1.1]pentanyl, or bicyclo[2.2.2]octanyl.

The term "cis" and "trans" denote the relative stereochemistry of the molecule or moiety. For example: intermediate R$^1$ as the trans-isomer, refers to a mixture of

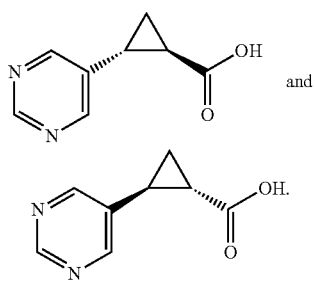

The way of showing relative stereochemistry also applies to the final compounds.

The skilled of the art would understand that the following structures of compounds of formula (Ia) and (Ia') are equal especially for the chiral centers:

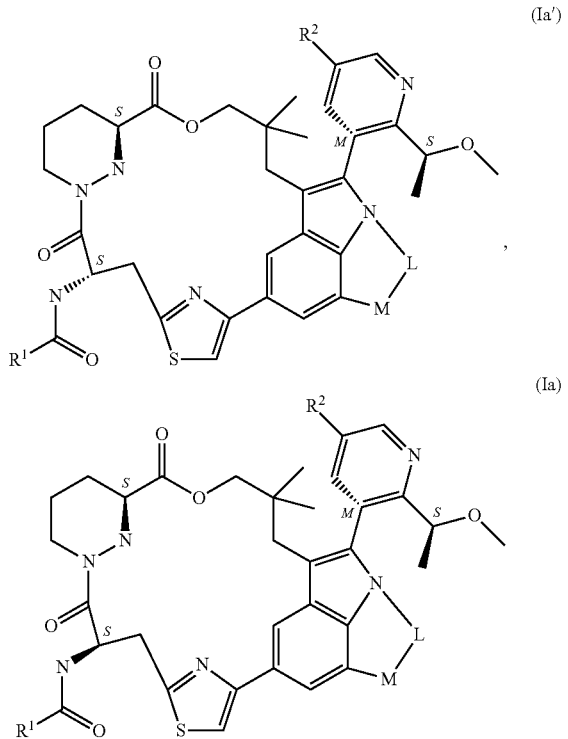

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The term "A pharmaceutically active metabolite" denotes a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being nontoxic to the subject administered, such as disintegrators, binders, fillers, solvents, buffers, tonicity agents, stabilizers, antioxidants, surfactants, carriers, diluents or lubricants used in formulating pharmaceutical products.

Inhibitor of Kras

The present invention relates to (i') a compound of formula (Ib),

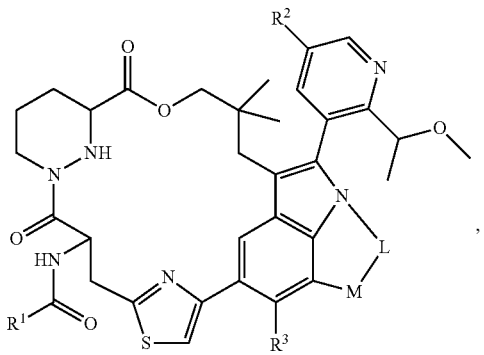

(Ib)

wherein
R¹ is 2-oxabicyclo[2.1.1]hexanyl,
3-oxabicyclo[3.1.0]hexanyl,
6-bicyclo[3.1.0]hexanyl substituted twice by halogen,
6-tricyclo[3.1.1.0$^{3,6}$]heptanyl,
$C_{3-7}$cycloalkyl substituted once, twice or three times by the substituents independently selected from $C_{1-6}$alkyl, $C_{1-6}$alkylpyridinyl, $C_{1-6}$alkylpyrimidinyl, $C_{1-6}$alkyltetrazolyl, $C_{3-7}$cycloalkyl, halo$C_{1-6}$alkyl, halogen, halophenyl, hydroxy, phenyl, pyrazinyl, pyridazinyl, pyridinyl, pyrimidinyl and thiazolyl, or tetrahydropyranyl;
R² is 1,3,4,6,7,8,9,9a-octahydropyrido[1,2-a]pyrazinyl, 3,4,6,7,9,9a-hexahydro-1H-pyrazino[2,1-c][1,4]oxazinyl,
morpholinyl, or
piperazinyl unsubstituted or substituted by substituents independently selected from $C_{1-6}$alkoxy$C_{1-6}$alkyl, $C_{1-6}$alkyl, $C_{3-7}$cycloalkyl, halo$C_{1-6}$alkyl, hydroxy$C_{1-6}$ alkyl, morpholinyl$C_{1-6}$alkyl, oxetanyl, oxopyrrolidinyl$C_{1-6}$alkyl and tetrahydrofuranyloxy$C_{1-6}$alkyl;
R³ is H or halogen;
M is $C_{1-6}$alkylene or O;
L is $C_{1-6}$alkylene, hydroxy$C_{1-6}$alkylene or halo$C_{1-6}$alkylene;
or a pharmaceutically acceptable salt, enantiomers and diastereomers thereof.

Another embodiment of present invention is (ii') a compound of formula (Ic),

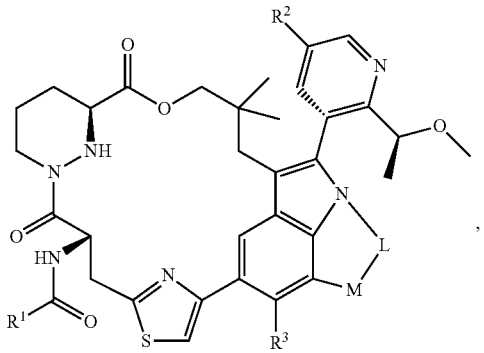

(Ic)

wherein
R¹ is 2-oxabicyclo[2.1.1]hexanyl,
3-oxabicyclo[3.1.0]hexanyl,
6-bicyclo[3.1.0]hexanyl substituted twice by halogen,
6-tricyclo[3.1.1.0$^{3,6}$]heptanyl,
$C_{3-7}$cycloalkyl substituted once, twice or three times by the substituents independently selected from $C_{1-6}$alkyl, $C_{1-6}$alkylpyridinyl, $C_{1-6}$alkylpyrimidinyl, $C_{1-6}$alkyltetrazolyl, $C_{3-7}$cycloalkyl, halo$C_{1-6}$alkyl, halogen, halophenyl, hydroxy, phenyl, pyrazinyl, pyridazinyl, pyridinyl, pyrimidinyl and thiazolyl, or tetrahydropyranyl;
R² is 1,3,4,6,7,8,9,9a-octahydropyrido[1,2-a]pyrazinyl, 3,4,6,7,9,9a-hexahydro-1H-pyrazino[2,1-c][1,4]oxazinyl,
morpholinyl, or
piperazinyl unsubstituted or substituted by substituents independently selected from $C_{1-6}$alkoxy$C_{1-6}$alkyl, $C_{1-6}$alkyl, $C_{3-7}$cycloalkyl, halo$C_{1-6}$alkyl, hydroxy$C_{1-6}$ alkyl, morpholinyl$C_{1-6}$alkyl, oxetanyl, oxopyrrolidinyl$C_{1-6}$alkyl and tetrahydrofuranyloxy$C_{1-6}$alkyl;
R³ is H or halogen;
M is $C_{1-6}$alkylene or O;
L is $C_{1-6}$alkylene, hydroxy$C_{1-6}$alkylene or halo$C_{1-6}$alkylene;
or a pharmaceutically acceptable salt, enantiomers and diastereomers thereof.

A further embodiment of present invention is (iii') a compound of formula (Ib) or (Ic) according to (i') or (ii'), or a pharmaceutically acceptable salt, enantiomers and diastereomers thereof, wherein R¹ is $C_{3-7}$cycloalkyl substituted once or twice by the substituents independently selected from $C_{1-6}$alkyl and pyridinyl.

A further embodiment of present invention is (iv') a compound of formula (Ib) or (Ic), according to any one of (i') to (iii'), or a pharmaceutically acceptable salt, enantiomers and diastereomers thereof, wherein R¹ is cyclopropyl once substituted by pyridinyl or twice substituted by methyl.

A further embodiment of present invention is (v') a compound of formula (Ib) or (Ic), or a pharmaceutically acceptable salt, enantiomers and diastereomers thereof, according to any one of (i') to (iv'), wherein R¹ is 2,3-dimethyl-cyclopropyl or 2-(3-pyridinyl)cyclopropyl.

A further embodiment of present invention is (vi') a compound of formula (Ib) or (Ic), or a pharmaceutically acceptable salt, enantiomers and diastereomers thereof, according to any one of (i') to (v'), wherein R² is morpholinyl or $C_{1-6}$alkylpiperazinyl.

A further embodiment of present invention is (vii') a compound of formula (Ib) or (Ic), or a pharmaceutically acceptable salt, enantiomers and diastereomers thereof, according to any one of (i') to (vi'), wherein R² is morpholinyl or 4-methylpiperazin-1-yl.

A further embodiment of present invention is (viii') a compound of formula (Ib) or (Ic), or a pharmaceutically acceptable salt, enantiomers and diastereomers thereof, according to any one of (i') to (vii'), wherein M is $C_{1-6}$alkylene.

A further embodiment of present invention is (ix') a compound of formula (Ib) or (Ic), or a pharmaceutically acceptable salt, enantiomers and diastereomers thereof, according to any one of (i') to (viii'), wherein M is $CH_2$.

A further embodiment of present invention is (x') a compound of formula (Ib) or (Ic), or a pharmaceutically acceptable salt, enantiomers and diastereomers thereof, according to any one of (i') to (ix'), wherein L is ethylene or difluoroethylene.

9

A further embodiment of present invention is (xi') a compound of formula (Ib) or (Ic), or a pharmaceutically acceptable salt, enantiomers and diastereomers thereof, according to any one of (i') to (x'), wherein L is $$-\underset{H_2}{C}-\underset{H_2}{C}- \quad \text{or} \quad -\underset{H_2}{C}-\underset{F}{\overset{F}{C}}-a,$$

wherein bond "a" connects to M.

A further embodiment of present invention is (xii') a compound of formula (Ib) or (Ic), according to any one of (i') to (xi'), wherein
  $R^1$ is $C_{3-7}$cycloalkyl substituted once or twice by the substituents independently selected from $C_{1-6}$alkyl and pyridinyl;
  $R^2$ is morpholinyl or $C_{1-6}$alkylpiperazinyl;
  $R^3$ is H;
  M is $C_{1-6}$alkylene;
  L is $C_{1-6}$alkylene or halo$C_{1-6}$alkylene;
  or a pharmaceutically acceptable salt, enantiomers and diastereomers thereof.

A further embodiment of present invention is (xiii') a compound of formula (Ib) or (Ic), according to any one of (i') to (xii'), wherein
  $R^1$ is 2,3-dimethyl-cyclopropyl or 2-(3-pyridinyl)cyclopropyl;
  $R^2$ is morpholinyl or 4-methylpiperazin-1-yl;
  $R^3$ is H;
  M is $CH_2$;
  L is $$-\underset{H_2}{C}-\underset{H_2}{C}- \quad \text{or} \quad -\underset{H_2}{C}-\underset{F}{\overset{F}{C}}-a,$$

wherein bond "a" connects to M;
  or a pharmaceutically acceptable salt, enantiomers and diastereomers thereof.

The present invention relates to (i) a compound of formula (I), (I)

wherein
  $R^1$ is 2-oxabicyclo[2.1.1]hexanyl,
    3-oxabicyclo[3.1.0]hexanyl,
    6-bicyclo[3.1.0]hexanyl substituted twice by halogen,
    6-tricyclo[3.1.1.0$^{3,6}$]heptanyl,
    $C_{3-7}$cycloalkyl substituted once, twice or three times by the substituents independently selected from $C_{1-6}$alkyl, $C_{1-6}$alkyltetrazolyl, $C_{3-7}$cycloalkyl, halo$C_{1-6}$alkyl, halogen, halophenyl, hydroxy, phenyl, pyridazinyl, pyridinyl and pyrimidinyl, or
    tetrahydropyranyl;
  $R^2$ is 1,3,4,6,7,8,9,9a-octahydropyrido[1,2-a]pyrazinyl, 3,4,6,7,9,9a-hexahydro-1H-pyrazino[2,1-c][1,4]oxazinyl, morpholinyl, (halo$C_{1-6}$alkyl) piperazinyl or $C_{1-6}$alkylpiperazinyl;
  M is $C_{1-6}$alkylene or O;
  L is $C_{1-6}$alkylene or halo$C_{1-6}$alkylene;
  or a pharmaceutically acceptable salt, enantiomers and diastereomers thereof.

Another embodiment of present invention is (ii) a compound of formula (Ia), (Ia)

wherein
  $R^1$ is 2-oxabicyclo[2.1.1]hexanyl,
    3-oxabicyclo[3.1.0]hexanyl,
    6-bicyclo[3.1.0]hexanyl substituted twice by halogen,
    6-tricyclo[3.1.1.0$^{3,6}$]heptanyl,
    $C_{3-7}$cycloalkyl substituted once, twice or three times by the substituents independently selected from $C_{1-6}$alkyl, $C_{1-6}$alkyltetrazolyl, $C_{3-7}$cycloalkyl, halo$C_{1-6}$alkyl, halogen, halophenyl, hydroxy, phenyl, pyridazinyl, pyridinyl and pyrimidinyl, or
    tetrahydropyranyl;
  $R^2$ is 1,3,4,6,7,8,9,9a-octahydropyrido[1,2-a]pyrazinyl, 3,4,6,7,9,9a-hexahydro-1H-pyrazino[2,1-c][1,4]oxazinyl, morpholinyl, (halo$C_{1-6}$alkyl) piperazinyl or $C_{1-6}$alkylpiperazinyl;
  M is $C_{1-6}$alkylene or O;
  L is $C_{1-6}$alkylene or halo$C_{1-6}$alkylene;
  or a pharmaceutically acceptable salt, enantiomers and diastereomers thereof.

A further embodiment of present invention is (iii) a compound of formula (I) or (Ia) according to (i) or (ii), or a pharmaceutically acceptable salt, enantiomers and diastereomers thereof, wherein $R^1$ is $C_{3-7}$cycloalkyl substituted once or twice by the substituents independently selected from $C_{1-6}$alkyl and pyridinyl.

A further embodiment of present invention is (iv) a compound of formula (I) or (Ia), according to any one of (i) to (iii), or a pharmaceutically acceptable salt, enantiomers and diastereomers thereof, wherein $R^1$ is cyclopropyl once substituted by pyridinyl or twice substituted by methyl.

A further embodiment of present invention is (v) a compound of formula (I) or (Ia) according to any one of (i) to (iv), wherein $R^1$ is 2,3-dimethyl-cyclopropyl or 2-(3-pyridinyl)cyclopropyl.

A further embodiment of present invention is (vi) a compound of formula (I) or (Ia), or a pharmaceutically acceptable salt, enantiomers and diastereomers thereof, according to any one of (i) to (v), wherein $R^2$ is morpholinyl or $C_{1-6}$alkylpiperazinyl.

A further embodiment of present invention is (vii) a compound of formula (I) or (Ia), or a pharmaceutically acceptable salt, enantiomers and diastereomers thereof, according to any one of (i) to (vi), wherein $R^2$ is morpholinyl or 4-methylpiperazin-1-yl.

A further embodiment of present invention is (viii) a compound of formula (I) or (Ia), or a pharmaceutically acceptable salt, enantiomers and diastereomers thereof, according to any one of (i) to (vii), wherein M is $C_{1-6}$alkylene.

A further embodiment of present invention is (ix) a compound of formula (I) or (Ia), or a pharmaceutically acceptable salt, enantiomers and diastereomers thereof, according to any one of (i) to (viii), wherein M is $CH_2$.

A further embodiment of present invention is (x) a compound of formula (I) or (Ia), or a pharmaceutically acceptable salt, enantiomers and diastereomers thereof, according to any one of (i) to (ix), wherein L is ethylene or difluoroethylene.

A further embodiment of present invention is (xi) a compound of formula (I) or (Ia), or a pharmaceutically acceptable salt, enantiomers and diastereomers thereof, according to any one of (i) to (x), wherein L is

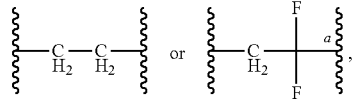

wherein bond "a" connects to M.

A further embodiment of present invention is (xii) a compound of formula (I) or (Ia), according to any one of (i) to (xi), wherein
$R^1$ is $C_{3-7}$cycloalkyl substituted once or twice by the substituents independently selected from $C_{1-6}$alkyl and pyridinyl;
$R^2$ is morpholinyl or $C_{1-6}$alkylpiperazinyl;
M is $C_{1-6}$alkylene;
L is $C_{1-6}$alkylene or halo$C_{1-6}$alkylene;
or a pharmaceutically acceptable salt, enantiomers and diastereomers thereof.

A further embodiment of present invention is (xiii) a compound of formula (I) or (Ia), according to any one of (i) to (xii), wherein
$R^1$ is 2,3-dimethyl-cyclopropyl or 2-(3-pyridinyl)cyclopropyl;
$R^2$ is morpholinyl or 4-methylpiperazin-1-yl;
M is $CH_2$;
L is

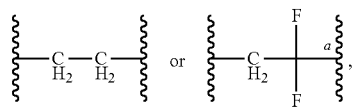

wherein bond "a" connects to M;
or a pharmaceutically acceptable salt, enantiomers and diastereomers thereof.

In a more particular embodiment, the present invention is a compound of formula (I'),

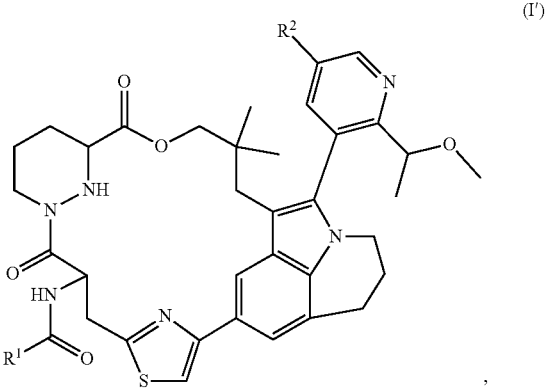

wherein
$R^1$, $R^2$ are as defined previously,
or a pharmaceutically acceptable salt, enantiomers and diastereomers thereof.

In a more particular embodiment, the present invention is a compound of formula (I'),

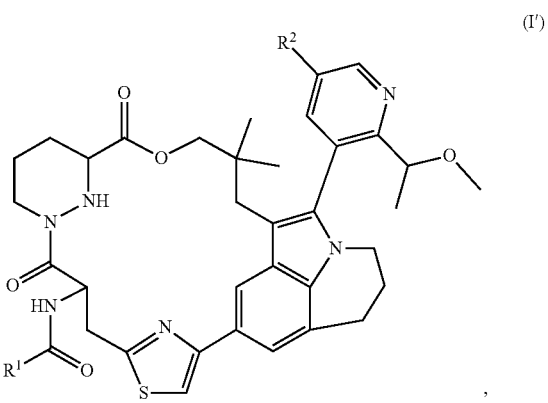

wherein
$R^1$ is 2,3-dimethyl-cyclopropyl or 2-(3-pyridinyl)cyclopropyl; and
$R^2$ is morpholinyl or 4-methylpiperazin-1-yl;
or a pharmaceutically acceptable salt, enantiomers and diastereomers thereof.

In a more particular embodiment, the present invention is a compound of formula (I'a),

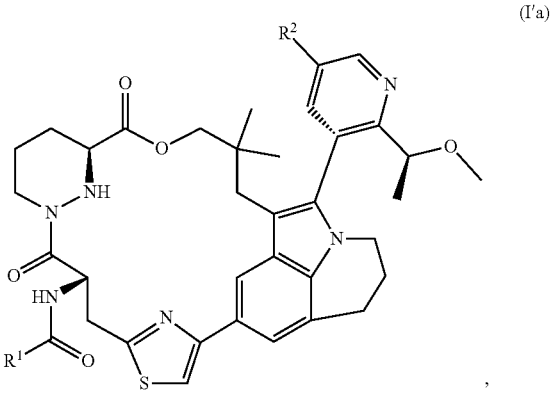

wherein
R¹, R² are as defined previously,
or a pharmaceutically acceptable salt, enantiomers and diastereomers thereof.

In a more particular embodiment, the present invention is a compound of formula (I'a),

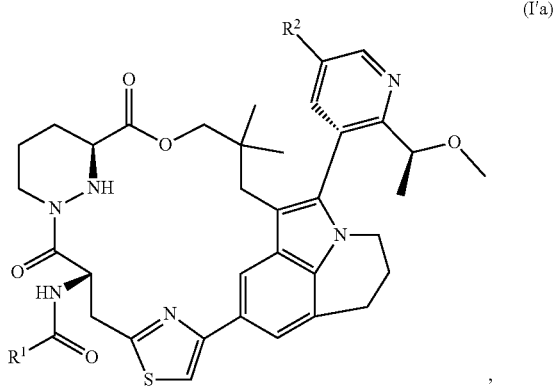

(I'a)

wherein
R¹ is 2,3-dimethyl-cyclopropyl or 2-(3-pyridinyl)cyclopropyl; and
R² is morpholinyl or 4-methylpiperazin-1-yl;
or a pharmaceutically acceptable salt, enantiomers and diastereomers thereof.

Another embodiment of present invention is (xiv') a compound of formula (I), (Ia), (Ib) or (Ic) selected from the following:

(1S,2S)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28), 2,5(31),19,25(29),26-hexaen-7-yl]-2-methyl-cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]-2-methyl-cyclopropanecarboxamide;

(1S,2S)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-methyl-cyclopropanecarboxamide;

(1S,2S)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-methyl-cyclopropanecarboxamide;

(1S,2S)-2-(difluoromethyl)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]cyclopropanecarboxamide;

(1S,5R,6r)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-3-oxabicyclo[3.1.0]hexane-6-carboxamide;

(1S,2S)-N-[(7S,13S)-(20M)-20-[2-[(1S)-1-methoxyethyl]-5-morpholino-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-methyl-cyclopropanecarboxamide;

(1S,2S)-2-(difluoromethyl)-N-[(7S,13S)-(20M)-20-[2-[(1S)-1-methoxyethyl]-5-morpholino-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]cyclopropanecarboxamide;

(1S,5R,6r)-N-[(7S,13S)-(20M)-20-[2-[(1S)-1-methoxyethyl]-5-morpholino-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-3-oxabicyclo[3.1.0]hexane-6-carboxamide;

(1S,2S)-2-(difluoromethyl)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]cyclopropanecarboxamide;

(1S,5R,6r)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-3-oxabicyclo[3.1.0]hexane-6-carboxamide;

(1S,2S)-2-(difluoromethyl)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]cyclopropanecarboxamide;

(1S,5R,6r)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-3-oxabicyclo[3.1.0]hexane-6-carboxamide;

(1R,2S)-2-cyclopropyl-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-methyl-cyclopropanecarboxamide;

(1S,2S)-N-[(7S,13S)-23,23-difluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]-2-methyl-cyclopropanecarboxamide;

2,2-difluoro-N-[(7S,13S)-(20M)-20-[2-[(1S)-1-methoxy-ethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{19,13}$.0$^{19,27}$.0$^{21,26}$]hentriaconta-1(28),2,5(31),19,25(29),26-hexaen-7-yl]-1-methyl-cyclopropanecarboxamide;

(1S,2S)-2-(difluoromethyl)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-phenyl-cyclopropanecarboxamide;

(1r,2R,3S)-N-[(7S,13S)-(20M)-20-[2-[(1S)-1-methoxy-ethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide;

(1S,2S)-N-[(7S,13S)-(20M)-20-[5-[(9αS)-3,4,6,7,9,9α-hexahydro-1H-pyrazino[2,1-c][1,4]oxazin-8-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$0.1$^{9,13}$ 0.0$^{19,27}$0.0$^{21,26}$]hentriaconta-1(28),2,5(31),19,25(29),26-hexaen-7-yl]-2-methyl-cyclopropanecarboxamide;

(1R,2R)-2-(2-fluorophenyl)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{19,13}$.0$^{19,27}$.0$^{21,26}$]hentriaconta-1(28),2,5(31),19,25(29),26-hexaen-7-yl]cyclopropanecarboxamide;

(1S,2S)-2-(2-fluorophenyl)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]-2-(2-pyridyl)cyclopropanecarboxamide;

(1S,2S)-N-[(7S,13S)-23,23-difluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(29),2,5(31),19,25,27-hexaen-7-yl]-2-(difluoromethyl)cyclopropanecarboxamide;

(1S,2R)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]-2-methyl-cyclopropanecarboxamide;

(1S,2S)-2-(difluoromethyl)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]cyclopropanecarboxamide;

(1S,5R,6r)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-3-oxabicyclo[3.1.0]hexane-6-carboxamide;

(1R,2S)-2-cyclopropyl-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(29),2,5(31),19,25,27-hexaen-7-yl]cyclopropanecarboxamide;

(1S,2S)-N-[(7S,13S)-(20M)-20-[2-[(1S)-1-methoxyethyl]-5-morpholino-3-pyridyl]-17,17,23,23-tetramethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-methyl-cyclopropanecarboxamide; (1S,5R,6r)-N-[(7S,13S)-(20M)-20-[5-[(9αS)-3,4,6,7,9,9α-hexahydro-1H-pyrazino[2,1-c][1,4]oxazin-8-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-3-oxabicyclo[3.1.0]hexane-6-carboxamide;

(1S,2S)-N-[(7S,13S)-(20M)-20-[5-[(9αS)-3,4,6,7,9,9α-hexahydro-1H-pyrazino[2,1c][1,4]oxazin-8-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$0.1$^{9,13}$0.0$^{19,27}$0.0$^{21,26}$]hentriaconta-1(28),2,5(31),19,25(29),26-hexaen-7-yl]-2-(difluoromethyl)cyclopropanecarboxamide;

(1R,5S,6s)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$0.1$^{9,13}$0.0$^{19,27}$0.0$^{21,26}$]hentriaconta-1(28),2,5(31),19,25(29),26-hexaen-7-yl]-3-oxabicyclo[3.1.0]hexane-6-carboxamide;

(1S,2S)-N-[(7S,13S)-(20M)-20-[2-[(1S)-1-methoxyethyl]-5-morpholino-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(29),2,5(31),19,25,27-hexaen-7-yl]-2-phenyl-cyclopropanecarboxamide;

(1S,2S)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15,24-dioxa-4-thia-9,21,30,31-tetrazahexacyclo[23.3.1.1$^{2,5}$.1$^{9,13}$0.0$^{19,27}$0.0$^{21,26}$]hentriaconta-1(29),2,5(31),19,25,27-hexaen-7-yl]-2-phenyl-cyclopropanecarboxamide;

(1r,2S,3R)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide;

(1S,2S)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(29),2,5(31),19,25,27-hexaen-7-yl]-2-phenyl-cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-pyrimidin-5-yl-cyclopropanecarboxamide;

(1S,5R)-3,3-difluoro-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]bicyclo[3.1.0]hexane-6-carboxamide;

(1S,2S)-N-[(7S,13S)-(20M)-20-[5-[(9αR)-1,3,4,6,7,8,9,9α-octahydropyrido[1,2-a]pyrazin-2-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]-2-methyl-cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]-2-pyrimidin-4-yl-cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(29),2,5(31),19,25,27-hexaen-7-yl]-2-phenyl-cyclopropanecarboxamide;

(1R,5S,6s)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-3-oxabicyclo[3.1.0]hexane-6-carboxamide;

(1S,2S)-N-[(7S,13S,22S)-(20M)-20-[2-[(1S)-1-methoxyethyl]-5-morpholino-3-pyridyl]-17,17,22-trimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-methyl-cyclopropanecarboxamide;

2,2-difluoro-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(29),2,5(31),19,25,27-hexaen-7-yl]-1-methyl-cyclopropanecarboxamide;

N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,11}$.0$^{19,27}$.0$^{21,26}$]hentriaconta-1(29),2,5(31),19,25,27-hexaen-7-yl]-1,2-dimethyl-cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-(3-pyridyl)cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-(4-pyridyl)cyclopropanecarboxamide;

(1R,2R)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-(4-pyridyl)cyclopropanecarboxamide;

2-(4-fluorophenyl)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(29),2,5(31),19,25,27-hexaen-7-yl]cyclopropanecarboxamide;

(1S,5R,6r)-N-[(7S,13S)-23,23-difluoro-(20M)-20-[2-[(1S)-1-methoxyethyl]-5-(4-1 methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-3-oxabicyclo[3.1.0]hexane-6-carboxamide;

(1r,2R,3S)-N-[(7S,13S)-(20M)-20-[2-[(1S)-1-methoxyethyl]-5-morpholino-3-pyridyl]-17,17,23,23-tetramethyl-8,14-dioxo-15,24-dioxa-4-thia-9,21,30,31-tetrazahexacyclo[23.3.1.1$^{2,5}$.1$^{19,13}$.0$^{19,27}$.0$^{21,26}$]hentriaconta-1(28),2,5(31),19,25(29),26-hexaen-7-yl]-2,3-dimethyl-cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-pyridazin-3-yl-cyclopropanecarboxamide;

(1R,2S)-2-cyclopropyl-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,11}$.0$^{19,27}$.0$^{21,26}$]hentriaconta-1(29),2,5(31),19,25,27-hexaen-7-yl]cyclopropanecarboxamide;

3,3-difluoro-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]cyclopentanecarboxamide;

N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]-2-oxabicyclo[2.1.1]hexane-1-carboxamide;

(1S,2S)-N-[(7S,13S)-23,23-difluoro-(20M)-20-[2-[(1S)-1-methoxyethyl]-5-[4-(2,2,2-trifluoroethyl)piperazin-1-yl]-3-pyridyl]-17,17-dimethyl-8,14-dioxo-15-oxa-4-thia-9,21,30,31 tetrazahexacyclo[23.3.1.1$^{2,5}$.1$^{19,13}$.0$^{19,27}$.0$^{21,26}$]hentriaconta-1(28),2,5(31),19,25(29),26-hexaen-7-yl]-2-methyl-cyclopropanecarboxamide;

(1r,2R,3S)-N-[(7S,13S)-(20M)-20-[2-[(1S)-1-methoxyethyl]-5-morpholino-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(29),2,5(31),19,25,27-hexaen-7-yl]-2,3-dimethyl-cyclopropanecarboxamide;

(1r,2S,3R)-N-[(7S,13S)-(20M)-20-[2-[(1S)-1-methoxyethyl]-5-(4-methylpiperazin-1-yl)-3-pyridyl]-17,17,23,23-tetramethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide;

trans-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(29),2,5(31),19,25,27-hexaen-7-yl]-4-(1-methyltetrazol-5-yl)cyclohexanecarboxamide;

trans-4-hydroxy-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]-4-methyl-cyclohexanecarboxamide;

N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]tricyclo[3.1.1.0$^{3,6}$]heptane-6-carboxamide;

(1r,2S,3R)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide;

(1S,2S)-N-[(7S,13S)-23,23-difluoro-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-methyl-cyclopropanecarboxamide;

(1r,2S,3R)-N-[(7S,13S)-23,23-difluoro-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide;

N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]tetrahydropyran-4-carboxamide;

(1S,2S)-N-[(7S,13S)-23,23-difluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{19,13}$.0$^{19,27}$.0$^{21,26}$]hentriaconta-1(28),2,5(31),19,25(29),26-hexaen-7-yl]-2-phenyl-cyclopropanecarboxamide;

(1S,2S)-N-[(7S,13S)-23,23-difluoro-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-phenyl-cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]-2-pyrimidin-2-yl-cyclopropanecarboxamide;

(1R,2R)-N-[(7S,13S)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]-2-pyrimidin-2-yl-cyclopropanecarboxamide;

(1r,2S,3R)-N-[(7S,13S)-23,23-difluoro-(20M)-20-[2-[(1S)-1-methoxyethyl]-5-(4-1 methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(29),2,5(31),19,25,27-hexaen-7-yl]-2,3-dimethyl-cyclopropanecarboxamide;

(1r,2S,3R)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15,24-dioxa-4-thia-9,21,30,31-tetrazahexacyclo[23.3.1.1$^{2,5}$.0.1$^{9,11}$.0.0$^{19,27}$ 0.0$^{21,26}$]hentriaconta-1(28),2,5(31),19,25(29),26-hexaen-7-yl]-2,3-dimethyl-cyclopropanecarboxamide;

(1r,2R,3S)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]-2,3-dimethyl-cyclopropanecarboxamide;

(1r,2S,3R)-N-[(7S,13S)-23,23-difluoro-(20M)-20-[2-[(1S)-1-methoxyethyl]-5-[4-(2,2,2-trifluoroethyl)piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]-2,3-dimethyl-cyclopropanecarboxamide;

(1S,2S)-N-[(7S,13S)-(20M)-20-[2-[(1S)-1-methoxyethyl]-5-morpholino-3-pyridyl]-17,17-dimethyl-8,14-dioxo-15,24-dioxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]-2-pyrimidin-5-yl-cyclopropanecarboxamide;

(1S,2S)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]-2-(3-pyridyl)cyclopropanecarboxamide;

(1S,2S)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-(3-pyridyl)cyclopropanecarboxamide;

(1S,2S)-N-[(7S,13S)-23,23-difluoro-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-(3-pyridyl)cyclopropanecarboxamide;

(1S,2S)-N-[(7S,13S)-23,23-difluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-(3-pyridyl)cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-pyrimidin-5-yl-cyclopropanecarboxamide;

(1S,2S)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-pyrimidin-5-yl-cyclopropanecarboxamide;

(1S,2S)-N-[(7S,13S)-23,23-difluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-pyrimidin-5-yl-cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8, 14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-(3-pyridyl)cyclopropanecarboxamide;

(1S,2S)-N-[(7S,13S)-(20M)-20-[2-[(1S)-1-methoxyethyl]-5-morpholino-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-(3-pyridyl)cyclopropanecarboxamide;

(1S,2S)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-(3-pyridyl)cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-pyrazin-2-yl-cyclopropanecarboxamide;

(1r,2R,3S)-N-[(7S,13S)-(20M)-20-[2-[(1S)-1-methoxyethyl]-5-(4-methylpiperazin-1-yl)-3-pyridyl]-17,17-dimethyl-8,14-dioxo-15,25-dioxa-4-thia-9,21,31,32-tetrazahexacyclo[24.3.1.1$^{2,5}$.1$^{9,13}$.0$^{19,28}$.0$^{21,27}$]dotriaconta-1(29),2,5(32),19,26(30),27-hexaen-7-yl]-2,3-dimethyl-cyclopropanecarboxamide;

(1r,2S,3R)-N-[(7S,13S)-(20M)-20-[5-[(9αR)-1,3,4,6,7,8,9,9a-octahydropyrido[1,2-a]pyrazin-2-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide;

(1S,2S)-N-[(7S,13S)-(20M)-20-[5-[(9αR)-1,3,4,6,7,8,9,9α-octahydropyrido[1,2-a]pyrazin-2-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-(3-pyridyl)cyclopropanecarboxamide;

(1S,2S)-N-[(7S,13S)-(20M)-20-[5-[(9αR)-1,3,4,6,7,8,9,9α-octahydropyrido[1,2-a]pyrazin-2-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-pyrimidin-5-yl-cyclopropanecarboxamide;

(1S,2S)-N-[(7S,13S)-(20M)-20-[5-[(9αS)-3,4,6,7,9,9α-hexahydro-1H-pyrazino[2,1-c][1,4]oxazin-8-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-(3-pyridyl)cyclopropanecarboxamide;

(1S,2S)-N-[(7S,13S)-(20M)-20-[5-[(9αS)-3,4,6,7,9,9α-hexahydro-1H-pyrazino[2,1-c][1,4]oxazin-8-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$0.1$^{9,13}$0.0$^{19,27}$0.0$^{21,26}$]hentriaconta-1(28),2,5(31),19,25(29),26-hexaen-7-yl]-2-pyrimidin-5-yl-cyclopropanecarboxamide;

(1r,2R,3S)-N-[(7S,13S)-(20M)-20-[5-(4-cyclopropylpiperazin-1-yl)-2-[(1S)-1-methoxyethyl]-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide;

(1r,2R,3S)-N-[(7S,13S,23S)-23-hydroxy-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide;

(1r,2R,3S)-N-[(7S,13S)-(20M)-20-[2-[(1S)-1-methoxyethyl]-5-piperazin-1-yl-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide;

(1r,2R,3S)-N-[(7S,13S)-(20M)-20-[5-[4-(2,2-difluoroethyl)piperazin-1-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide;

(1r,2R,3S)-N-[(7S,13S)-(20M)-20-[5-[4-(2-fluoroethyl)piperazin-1-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide;

(1r,2R,3S)-N-[(7S,13S)-(20M)-20-[5-[4-(3-hydroxypropyl)piperazin-1-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide;

(1R,2R)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]-2-(4-methylpyrimidin-5-yl)cyclopropanecarboxamide;

(1r,2R,3S)-N-[(7S,13S)-(20M)-20-[5-(4-ethylpiperazin-1-yl)-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]-2,3-dimethyl-cyclopropanecarboxamide;

(1R,2R)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]-2-thiazol-4-yl-cyclopropanecarboxamide;

(1r,2S,3R)-N-[(7S,13S)-(20M)-20-[2-[(1S)-1-methoxyethyl]-5-[4-(2-methoxyethyl)piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide;

(1R,2R)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-(2-methyl-3-pyridyl)cyclopropanecarboxamide;

(1r,2R,3S)-N-[(7S,13S)-(20M)-20-[2-[(1S)-1-methoxyethyl]-5-(4-tetrahydropyran-4-ylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide;

(1r,2R,3S)-N-[(7S,13S)-(20M)-20-[2-[(1S)-1-methoxy-ethyl]-5-[4-(oxetan-3-yl)piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide;

(1r,2S,3R)-N-[(7S,13S)-(20M)-20-[2-[(1S)-1-methoxy-ethyl]-5-[4-[[(2S)-morpholin-2-yl]methyl]piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]-2,3-dimethyl-cyclopropanecarboxamide;

(1R,2R)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,11}$.0$^{19,27}$.0$^{21,26}$]hentriaconta-1(28),2,5(31),19,25(29),26-hexaen-7-yl]-2-(5-methyl-3-pyridyl)cyclopropanecarboxamide;

(1r,2R,3S)-N-[(7S,13S)-(20M)-20-[2-[(1S)-1-methoxy-ethyl]-5-[4-[2-(2-oxopyrrolidin-1-yl)ethyl]piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide;

(1r,2R,3S)-N-[(7S,13S)-(20M)-20-[2-[(1S)-1-methoxy-ethyl]-5-[4-(2-tetrahydrofuran-3-yloxyethyl)piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide;

(1r,2R,3S)-N-[(7S,13S)-(20M)-20-[2-[(1S)-1-methoxy-ethyl]-5-[4-(3-methoxy-3-methyl-butyl)piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide;

(1r,2S,3R)-N-[(7S,13S)-29-fluoro-(20M)-20-[2-[(1S)-1-methoxyethyl]-5-(4-1 methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide;

(1S,2S)-N-[(7S,13S)-(20M)-20-[2-[(1S)-1-methoxyethyl]-5-morpholino-3-pyridyl]-17,17,22,22-tetramethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(29),2,5(31),19,25,27-hexaen-7-yl]-2-1 methyl-cyclopropanecarboxamide;

(1r,2R,3S)-N-[(7S,13S)-(20M)-20-[2-[(1S)-1-methoxy-ethyl]-5-morpholino-3-pyridyl]-17,17-dimethyl-8,14-dioxo-15-oxa-4-thia-9,21,31,32-tetrazahexacyclo[24.3.1.1$^{2,5}$.0$^{9,13}$.0$^{19,28}$.0$^{21,27}$]dotriaconta-1(29),2,5(32),19,26(30),27-hexaen-7-yl]-2,3-dimethyl-cyclopropanecarboxamide; and (1r,2R,3S)-N-[(7S,13S)-(20M)-20-[2-[(1S)-1-methoxy-ethyl]-5-(4-methylpiperazin-1-yl)-3-pyridyl]-17,17-dimethyl-8,14-dioxo-15-oxa-4-thia-9,21,32,33-tetrazahexacyclo[25.3.1.1$^{2,5}$.0$^{9,13}$.0$^{19,29}$.0$^{21,28}$]tritriaconta-1(30),2,5(33),19,27(31),28-hexaen-7-yl]-2,3-dimethyl-cyclopropanecarboxamide;

or a pharmaceutically acceptable salt, enantiomers and diastereomers thereof.

A further embodiment of present invention is (xv') a compound selected from:

(Example 24)

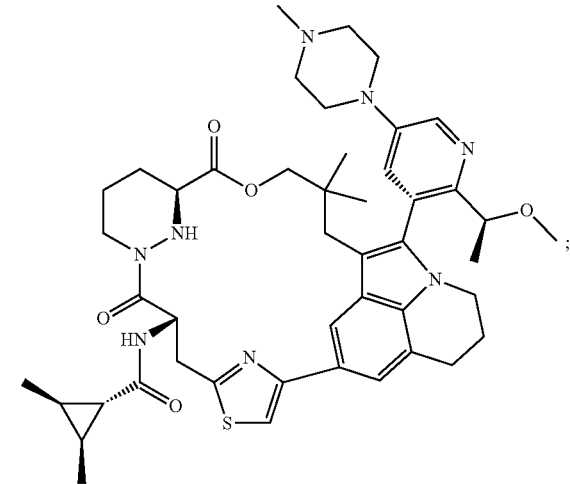

(Example 56)

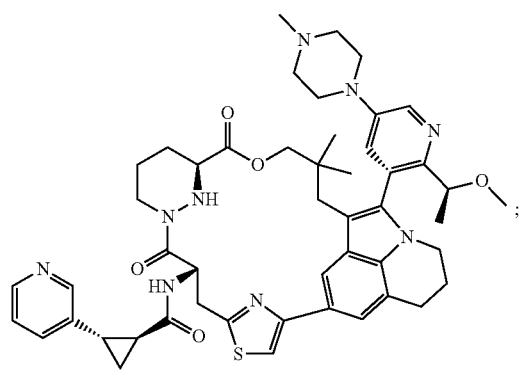

(Example 73)

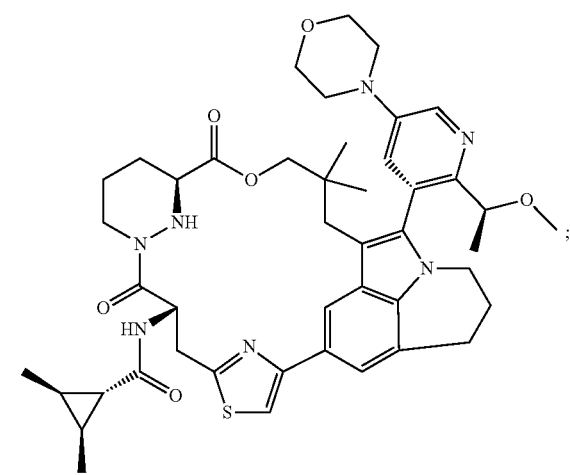

(Example 83)

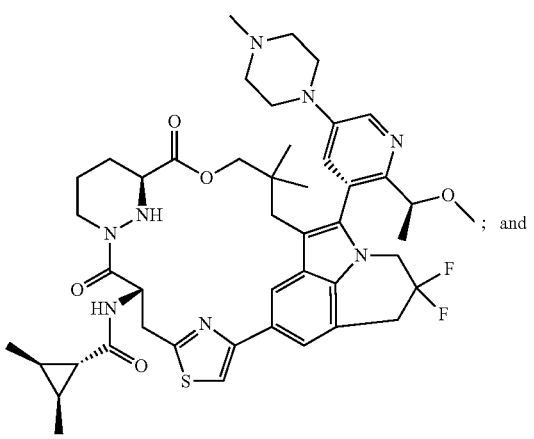

; and (Example 89)

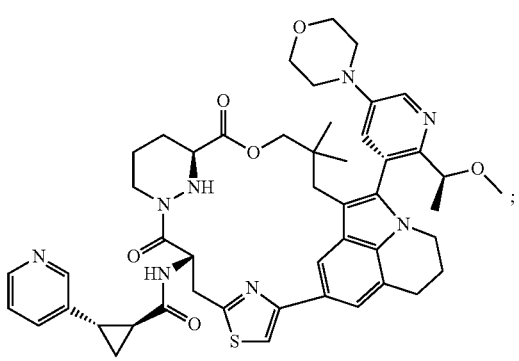

;

or a pharmaceutically acceptable salt, enantiomers and diastereomers thereof.

Another embodiment of present invention is related to (xvi) a process for the preparation of a compound according to any one of (i) to (xiii) and (xv') comprising the following step:

a) coupling reaction between compound of formula (II),

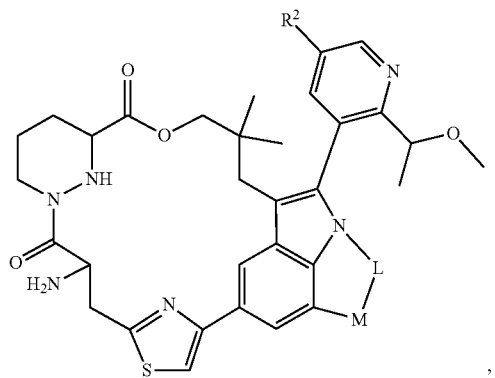

, and acid (III),

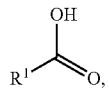
(III)

in the presence of a coupling reagent and a base to form the compound of formula (Ib);
wherein $R^1$, $R^2$, M and L are defined as in any one of (i) to (xiii); the coupling reagent is $T_3P$, HATU, PyBOP or EDCI/HOBt; the base is TEA, DIEPA or DMAP.

Another embodiment of present invention is related to (xvi') a process for the preparation of a compound according to any one of (i') to (xv') comprising the following step:

a) coupling reaction between compound of formula (IIb),

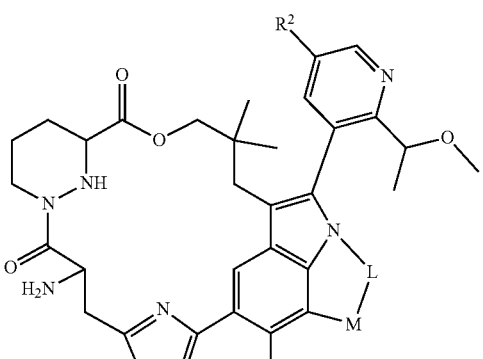

, and acid (III),

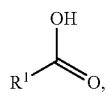
(III)

in the presence of a coupling reagent and a base to form the compound of formula (Ib);
wherein $R^1$, $R^2$, M and L are defined as in any one of (i') to (xiii'); the coupling reagent is $T_3P$, HATU, PyBOP or EDCI/HOBt; the base is TEA, DIEPA or DMAP.

Another embodiment of present invention is (xvii') a compound or pharmaceutically acceptable salt according to any one of (i') to (xv') or (i) to (xiii) for use as therapeutically active substance.

Another embodiment of present invention is (xviii') a pharmaceutical composition comprising a compound in accordance with any one of (i') to (xv') or (i) to (xiii) and a pharmaceutically acceptable excipient.

Another embodiment of present invention is (xix') the use of a compound according to any one of (i') to (xv') or (i) to (xiii) for treating a KRAS G12C protein-related disease.

Another embodiment of present invention is (xx') the use of a compound according to any one of (i') to (xv') or (i) to (xiii) for treating a KRAS G12C, G12D and G12V protein-related disease.

Another embodiment of present invention is (xxi') the use of a compound according to any one of (i') to (xv') or (i) to (xiii) for inhibiting RAS interaction with downstream effectors, wherein the downstream effectors are RAF and PI3K.

Another embodiment of present invention is (xxii') the use of a compound according to any one of (i') to (xv') or (i) to (xiii) for inhibiting the propagating oncogenic MAPK and PI3K signaling.

Another embodiment of present invention is (xxiii') the use of a compound according to any one of (i') to (xv') or (i) to (xiii) for the treatment or prophylaxis of cancers in a subject in need thereof, wherein the cancer comprises a first RAS mutation that is G12C and a second RAS mutation at a position selected from the group consisting of V8A, V9Y, S17E, A59T, T58I, D69P, M72I, S65W, R68S, D92R, H95N, Y96D, Q99W and F156L.

Another embodiment of present invention is (xxiv') the use of a compound according to any one of (i') to (xv') or (i) to (xiii) for the preparation of a medicament for the treatment or prophylaxis of cancers in a subject in need thereof, wherein the cancer comprises a first RAS mutation that is G12C and a second RAS mutation at a position selected from the group consisting of V8A, V9Y, S17E, A59T, T58I, D69P, M72I, S65W, R68S, D92R, H95N, Y96D, Q99W and F156L.

Another embodiment of present invention is (xxv') the use of a compound according to any one of (i') to (xv') or (i) to (xiii) for the treatment or prophylaxis of KRAS mutation driven cancers, wherein the cancer is selected from pancreatic cancer, colorectal cancer, lung cancer, esophageal cancer, gallbladder cancer, melanoma ovarian cancer and endometrial cancer.

Another embodiment of present invention is (xxvi') the use of a compound according to any one of (i') to (xv') or (i) to (xiii) for the treatment or prophylaxis of KRAS mutation driven cancers, wherein the cancer is selected from pancreatic adenocarcinoma, colorectal cancer and non-small cell lung cancer.

Another embodiment of present invention is (xxvii') the use of a compound according to any one of (i') to (xv') or (i) to (xiii) for the treatment or prophylaxis of primary central nervous system (CNS) tumors harboring RAS mutations or RAS driven cancers with brain metastases; wherein the CNS tumor is primary melanocytic tumors of the CNS harboring NRAS mutation; wherein the cancer is selected from pancreatic adenocarcinoma, colorectal cancer, non-small cell lung cancer.

Another embodiment of present invention is (xxviii') the use of a compound according to any one of (i') to (xv') or (i) to (xiii) for the treatment or prophylaxis of primary central nervous system (CNS) tumors harboring RAS mutations or RAS driven cancers with brain metastases; wherein the CNS tumor is primary melanocytic tumors of the CNS harboring NRAS mutation; wherein the cancer is non-small cell lung cancer.

Another embodiment of present invention is (xxix') a compound or pharmaceutically acceptable salt according to any one of (i') to (xv') or (i) to (xiii) for the treatment or prophylaxis of KRAS mutation driven cancers, wherein the cancer is selected from pancreatic adenocarcinoma, colorectal cancer and non-small cell lung cancer.

Another embodiment of present invention is (xxx') the use of a compound according to any one of (i') to (xv') or (i) to (xiii) for the preparation of a medicament for the treatment or prophylaxis of KRAS mutation driven cancers, wherein the cancer is selected from pancreatic adenocarcinoma, colorectal cancer and non-small cell lung cancer.

Another embodiment of present invention is (xxxi') a method for the treatment or prophylaxis of KRAS mutation driven cancers, wherein the cancer is selected from pancreatic adenocarcinoma, colorectal cancer and non-small cell lung cancer, which method comprises administering a therapeutically effective amount of a compound as defined in any one of (i') to (xv') or (i) to (xiii).

Another embodiment of present invention is (xxxii') a compound or pharmaceutically acceptable salt according to any one of (i') to (xv') or (i) to (xiii), when manufactured according to a process of (xvi) or (xvi').

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit mutant RAS (e.g. KRAS G12C) interaction with RAF, blocking the oncogenic MAPK signaling. For example, such amount may be below the amount that is toxic to normal cells, or the mammal as a whole.

In one example, the pharmaceutically effective amount of the compound of the invention administered parenterally per dose will be in the range of about 0.1 to 1000 mg/kg, alternatively about 0.1 to 1000 mg/kg of patient body weight per day, with the typical initial range of compound used being 0.3 to 15 mg/kg/day. In another embodiment, oral unit dosage forms, such as tablets and capsules, preferably contain from about 1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 1 to 1000 mg of the compound of the invention compounded with about 1 to 1000 mg anhydrous lactose, about 1 to 1000 mg sodium croscarmellose, about 1 to 1000 mg polyvinylpyrrolidone (PVP) K30, and about 1 to 1000 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 to 400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of formula (I), or a stereoisomer or pharmaceutically acceptable salt thereof. In a further embodiment includes a pharmaceutical composition comprising a compound of formula (I), or a stereoisomer or pharmaceutically acceptable salt thereof, together with a pharmaceutically acceptable carrier or excipient.

Another embodiment includes a pharmaceutical composition comprising a compound of formula (I) for use in the treatment of mutant KRAS-driven cancers. Another embodiment includes a pharmaceutical composition comprising a compound of Formula (I) for use in the treatment of mutant KRAS-driven cancers.

The following composition A and B illustrate typical compositions of the present invention, but serve merely as representative thereof.

Composition A

A compound of the present invention can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Composition B

A compound of the present invention can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Indications and Methods of Treatment

The compounds of the invention induce a new binding pocket in KRAS by driving formation of a high affinity tri-complex between KRAS protein and the widely expressed cyclophilin A (CYPA), which inhibit KRAS interaction with downstream effectors, such as RAF and PI3K. Accordingly, the compounds of the invention are useful for inhibiting the propagating oncogenic MAPK and PI3K signaling, reducing cell proliferation, in particular cancer cells. Compounds of the invention are useful for termination of RAS signaling in cells that express RAS mutant, e.g. KRAS mutation driven pancreatic cancer, colorectal cancer, lung cancer, esophageal cancer, gallbladder cancer, melanoma ovarian cancer, endometrial cancer, etc. Alternatively, compounds of the invention are useful for termination of RAS signaling in malignant solid tumor where the oncogenic role of KRAS mutation is reinforced by dysregulation or mutation of effector pathways as MAPK, PI3K-AKT-mTOR (Mammalian target of rapamycin) driven signaling, for targeted therapy in pancreatic adenocarcinoma, colorectal cancer, non-small cell lung cancer, etc.

Another embodiment includes a method of treating or preventing cancer in a mammal in need of such treatment, wherein the method comprises administering to said mammal a therapeutically effective amount of a compound of formula (I), a stereoisomer, tautomer or pharmaceutically acceptable salt thereof.

Synthesis

The compounds of the present invention can be prepared by any conventional means. Suitable processes for synthesizing these compounds as well as their starting materials are provided in the schemes below and in the examples. All substituents, in particular, $R^1$, $R^2$, M and L are as defined above unless otherwise indicated. Furthermore, and unless explicitly otherwise stated, all reactions, reaction conditions, abbreviations and symbols have the meanings well known to a person of ordinary skill in organic chemistry.

General synthetic routes for preparing the compound of formula (I) or (Ia) are shown below.

Scheme 1

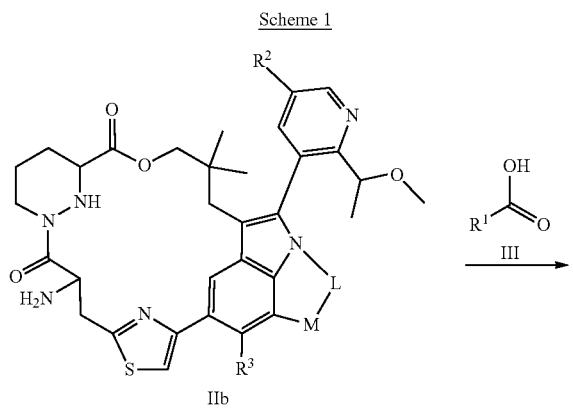

Compound of formula Ib was synthesized according to the procedure described in Intermediate B to V. Compound of formula (Ib) can be obtained by a coupling reaction between acid (III) and compound of formula (IIb) with coupling reagent(s), such as T₃P, HATU, PyBOP and EDCI/HOBt, in the presence of a base, such as TEA, DIEPA and DMAP.

Compounds of this invention can be obtained as mixtures of diastereomers or enantiomers, which can be separated by methods well known in the art, e.g. (chiral) HPLC or SFC. In another embodiment, compound of formula (Ia) and (Ic) can be obtained according to above scheme by using corresponding chiral starting materials.

This invention also relates to a process for the preparation of a compound of formula (I), (Ia), (Ib) and (Ic) comprising following step:

a) coupling reaction between compound of formula (IIb),

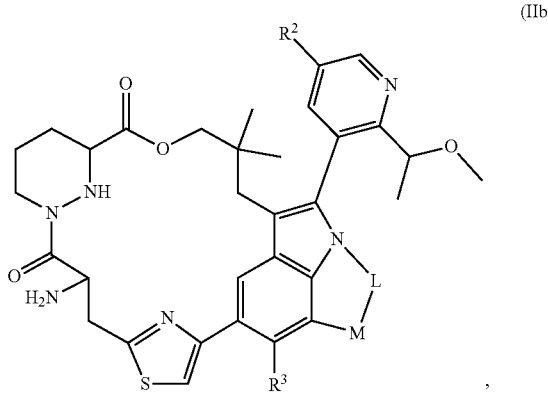

and acid (III), $$\underset{R^1}{\overset{OH}{\underset{O}{\bigvee}}} \quad (III)$$

in the presence of a coupling reagent and a base to form the compound of formula (Ib);

wherein in step a) the coupling reagent can be, for example, T₃P, HATU, PyBOP or EDCI/HOBt; the base can be, for example, TEA, DIEPA or DMAP.

A compound of formula (I), (Ia), (Ib) and (Ic) when manufactured according to the above process is also an object of the invention.

EXAMPLES

The invention will be more fully understood by reference to the following examples. They should not, however, be construed as limiting the scope of the invention.

Abbreviations

The invention will be more fully understood by reference to the following examples. They should not, however, be construed as limiting the scope of the invention.

Abbreviations used herein are as follows:

ACN acetonitrile
aq. Aqueous
Ad₂nBuP-Pd-G₃ [(Di(1-adamantyl)-butylphosphine)-2-(2'-amino-1,1'-biphenyl)]palladium(II) methanesulfonate
(Boc)₂O Di-tert-butyldicarbonate
(R)-binap (R)-(+)-2,2'-Bis(diphenylphosphino)-1,1'-binaphthyl
CDCl₃: deuterated chloroform
CuI copper(I) iodide
DIEPA: N, N-diethylpropylamine
DMAP: 4-Dimethylaminopyridine
EDCI: N-Ethyl-N'-(3-dimethylaminopropyl)carbodiimide hydrochloride
EtOAc or EA: ethyl acetate
FRET fluorescence resonance energy transfer
HATU: (1-[Bis(dimethylamino)methylene]-1H-1,2,3-triazolo[4,5-b]pyridinium 3-oxid hexafluorophosphate)
hr(s): hour(s)
HPLC: high performance liquid chromatography
HOBt: N-hydroxybenzotriazole
LDA: Lithium diisopropylamide
MS: (ESI): mass spectroscopy (electron spray ionization)
min(s) minute(s)
MTBE Methyl tert-butyl ether
NMI 1-Methylimidazole
NMM N-Methylmorpholine
NBS N-Bromosuccinimide
NIS N-iodosuccinimide
NMR: nuclear magnetic resonance
obsd. Observed
Pd(dppf)Cl₂ [1,1'-Bis(diphenylphosphino)ferrocene]dichloropalladium(II)
Pd(dtbpf)Cl₂ [1,1'-Bis(di-tert-butylphosphino)ferrocene] dichloropalladium(II)
prep-HPLC preparative high performance liquid chromatography PyBOP: benzotriazol-1-yloxytripyrrolidinophosphonium hexafluorophosphate RT or rt: room temperature sat. saturated Selectfluor 1-Chloromethyl-4-fluoro-1,4-diazoniabicyclo[2.2.2]octane bis(tetrafluoroborate)

SFC: supercritical fluid chromatography

TCFH: [chloro(dimethylamino)methylene]-dimethyl-ammonium; hexafluorophosphate

TEA: triethylamine

TFA: trifluoroacetic acid $T_3P$: propylphosphonic anhydride

General Experimental Conditions

Intermediates and final compounds were purified by flash chromatography using one of the following instruments: i) Biotage SP1 system and the Quad 12/25 Cartridge module. ii) ISCO combi-flash chromatography instrument. Silica gel brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using XBridge™ Prep-C18 (5 μm, OBDTM30×100 mm) column, SunFire™ Prep-C18 (5 μm, OBD™ 30×100 mm) column, Phenomenex Synergi-C18 (10 μm, 25×150 mm) or Phenomenex Gemini-C18 (10 μm, 25×150 mm). Waters AutoP purification System (Sample Manager 2767, Pump 2525, Detector: Micromass ZQ and UV 2487, solvent system: acetonitrile and 0.1% ammonium hydroxide in water; acetonitrile and 0.1% FA in water or acetonitrile and 0.1% TFA in water). Or Gilson-281 purification System (Pump 322, Detector: UV 156, solvent system: acetonitrile and 0.05% ammonium hydroxide in water; acetonitrile and 0.225% FA in water; acetonitrile and 0.05% HCl in water; acetonitrile and 0.075% TFA in water; or acetonitrile and water).

For SFC chiral separation, intermediates were separated by chiral column (Daicel chiralpak IC, 5 μm, 30×250 mm), AS (10 μm, 30×250 mm) or AD (10 μm, 30×250 mm) using Mettler Toledo Multigram III system SFC, Waters 80Q preparative SFC or Thar 80 preparative SFC, solvent system: $CO_2$ and IPA (0.5% TEA in IPA) or $CO_2$ and MeOH (0.1% $NH_3 \cdot H_2O$ in MeOH), back pressure 100 bar, detection UV@ 254 or 220 nm.

LC/MS spectra of compounds were obtained using a LC/MS (Waters™ Alliance 2795-Micromass ZQ, Shimadzu Alliance 2020-Micromass ZQ or Agilent Alliance 6110-Micromass ZQ), LC/MS conditions were as follows (running time 3 or 1.5 mins):

Acidic condition I: A: 0.1% TFA in $H_2O$; B: 0.1% TFA in acetonitrile;

Acidic condition II: A: 0.0375% TFA in $H_2O$; B: 0.01875% TFA in acetonitrile;

Basic condition I: A: 0.1% $NH_3 \cdot H_2O$ in $H_2O$; B: acetonitrile;

Basic condition II: A: 0.025% $NH_3 \cdot H_2O$ in $H_2O$; B: acetonitrile;

Neutral condition: A: $H_2O$; B: acetonitrile.

Mass spectra (MS): generally only ions which indicate the parent mass are reported, and unless otherwise stated the mass ion quoted is the positive mass ion $(MH)^+$.

NMR Spectra were obtained using Bruker Avance 400 MHz or 500 MHz.

The microwave assisted reactions were carried out in a Biotage Initiator Sixty microwave synthesizer. All reactions involving air-sensitive reagents were performed under an argon or nitrogen atmosphere. Reagents were used as received from commercial suppliers without further purification unless otherwise noted.

Preparative Examples

The following examples are intended to illustrate the meaning of the present invention but should by no means represent a limitation within the meaning of the present invention:

Preparation of Intermediate

Intermediate B

Methyl (3S)-1-[(2S)-3-(4-bromothiazol-2-yl)-2-(tert-butoxycarbonylamino)propanoyl]hexahydro-pyridazine-3-carboxylate

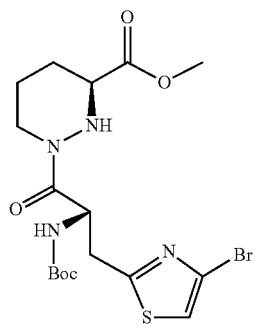 [SMILES: COC(=O)[C@@H]1CCCN(C(=O)[C@H](Cc2nc(Br)cs2)NC(=O)OC(C)(C)C)N1]

The intermediate B was prepared according to the following scheme:

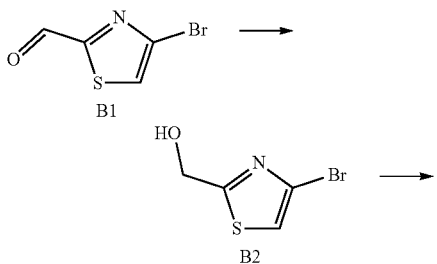

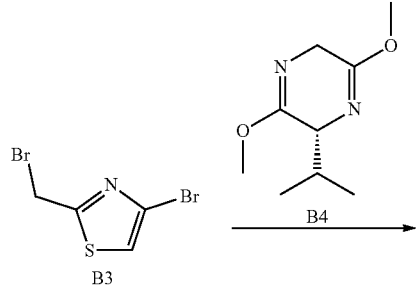

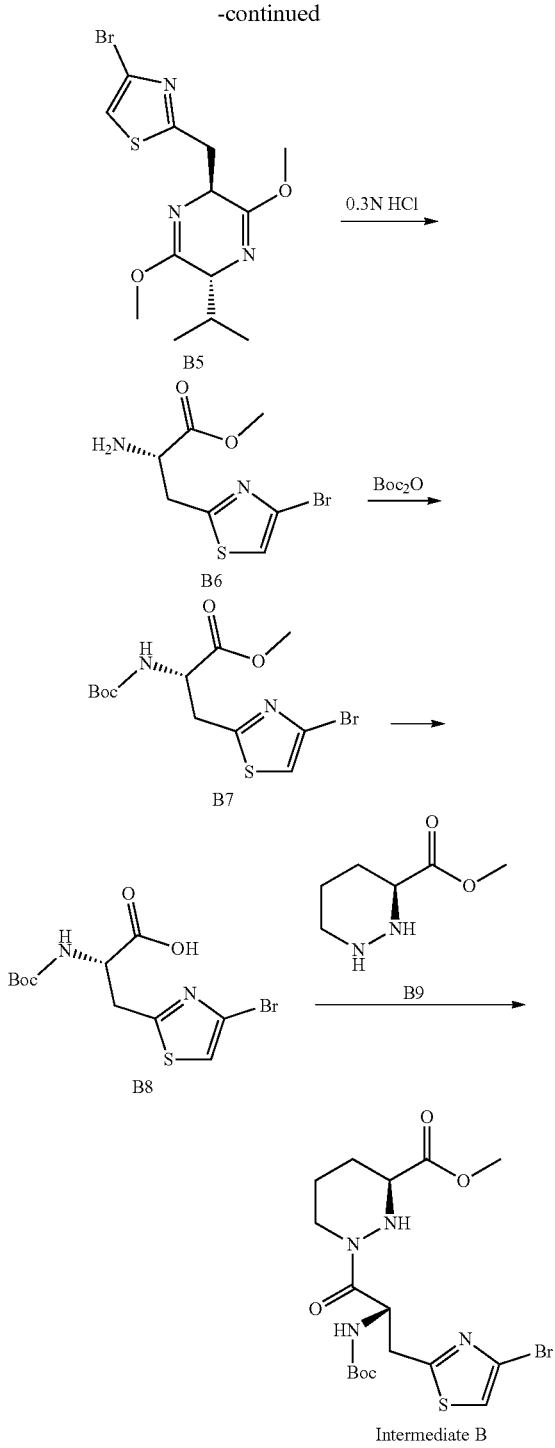

Step 1: Preparation of (4-Bromothiazol-2-Yl) Methanol (Compound B2)

To a solution of 4-bromothiazole-2-carboxaldehyde (compound B1, 6.0 g, 31.25 mmol) in methanol (70 mL) was added sodium borohydride (1.7 g, 46.87 mmol) at 0° C. The mixture was stirred at 25° C. for 1 hour. The reaction was quenched with water (300 mL) at 0° C. and the reaction mixture was extracted by ethyl acetate (200 mL, three times). The combined organic phase was washed with brine (150 mL, twice), dried over anhydrous sodium sulfate, filtered and the filtrate was concentrated under vacuum to afford (4-bromothiazol-2-yl) methanol (compound B2, 6 g) as colorless oil.

Step 2: Preparation of 4-Bromo-2-(Bromomethyl) Thiazole (Compound B3)

To a solution of (4-bromothiazol-2-yl) methanol (compound B2, 6.0 g, 30.92 mmol) in DCM (80 mL) was added $CBr_4$ (15.4 g, 46.38 mmol) and triphenylphosphine (12.1 g, 46.38 mmol) at 0° C. After being stirred at 25° C. for 1 hour, the mixture was filtered and the filtrate was concentrated under vacuum. The residue was purified by silica gel column, eluted with ethyl acetate in petroleum ether (0~10%) to afford 4-bromo-2-(bromomethyl) thiazole (compound B3, 6.0 g) as yellow oil. MS calc'd 255.9 ($MH^+$), measured 255.9 ($MH^+$).

Step 3: Preparation of 4-bromo-2-[[(2S,5R)-5-isopropyl-3,6-dimethoxy-2,5-dihydropyrazin-2-yl]methyl]thiazole (compound B5)

To a mixture of (2R)-2-isopropyl-3,6-dimethoxy-2,5-dihydropyrazine (compound B4, 4.3 g, 23.45 mmol) in THF (60 mL) was added n-butyllithium (10 mL, 25.22 mmol, 2.5 M) at −78° C. slowly. After addition, the mixture was stirred for 0.5 hour at −78° C. 4-bromo-2-(bromomethyl) thiazole (compound B3, 5.4 g, 21.02 mmol) was added into above mixture at −78° C. which was stirred for another 1 hour. The reaction was quenched with saturated solution of $NH_4Cl$ (100 mL) and the reaction mixture was extracted with EtOAc (100 mL, twice). The combined organic layer was washed with brine (150 mL), dried over anhydrous sodium sulfate, filtered and the filtrate was concentrated under vacuum. The residue was purified by reversed-phase chromatography to afford 4-bromo-2-[[(2S,5R)-5-isopropyl-3,6-dimethoxy-2,5-dihydropyrazin-2-yl]methyl]thiazole (compound B5, 3.6 g) as yellow oil. MS calc'd 360 ($MH^+$), measured 359.9 ($MH^+$).

Step 4: Preparation of methyl (2S)-2-amino-3-(4-bromothiazol-2-yl) propanoate (compound B6)

To a solution of 4-bromo-2-[[(2S,5R)-5-isopropyl-3,6-dimethoxy-2,5-dihydropyrazin-2-yl]methyl]thiazole (compound B5, 3.6 g, 10 mmol) in ACN (20 mL) was added hydrochloric acid (66.6 mL, 0.3 M). The mixture was stirred at 25° C. for 2 hours. The mixture was basified by saturated solution of $NaHCO_3$ until pH=8. The mixture was extracted with EtOAc (80 mL, six times). The combined organic layer was dried over anhydrous sodium sulfate, filtered and the filtrate was concentrated under vacuum to afford methyl (2S)-2-amino-3-(4-bromothiazol-2-yl) propanoate (compound B6, 3.1 g) as yellow oil. MS calc'd 264.9 ($MH^+$), measured 264.9 ($MH^+$).

Step 5: Preparation of methyl (2S)-3-(4-bromothiazol-2-yl)-2-(tert-butoxycarbonylamino) propanoate (compound B7)

To a solution of methyl (2S)-2-amino-3-(4-bromothiazol-2-yl) propanoate (compound B6, 3.1 g, 11.69 mmol) in DCM (40 mL) were added TEA (2.9 g, 29.23 mmol) and (Boc) 20 (3.8 g, 17.54 mmol). After being stirred at 30° C. for 12 hours, the mixture was concentrated under vacuum. The residue was purified by silica gel column, eluted with ethyl acetate in petroleum ether (0~30%) to afford methyl (2S)-3-(4-bromothiazol-2-yl)-2-(tert-butoxycarbonylamino) propanoate (compound B7, 3.2 g) as yellow oil. MS calc'd 387 ($MNa^+$), measured 386.9 ($MNa^+$).

Step 6: Preparation of (2S)-3-(4-bromothiazol-2-yl)-2-(tert-butoxycarbonylamino)-propanoic acid (compound B8)

To a solution of methyl (2S)-3-(4-bromothiazol-2-yl)-2-(tert-butoxycarbonylamino) propanoate (compound B7, 3.2 g, 8.76 mmol) in THF (30 mL), methanol (2 mL) and water (10 mL) was added lithium hydroxide (0.4 mL, 43.81 mmol). After being stirred at 25° C. for 1 hour, the reaction mixture was acidified by 1 M solution of HCl until pH=5. The mixture was extracted with EtOAc (40 mL, twice). The combined organic layer was washed with brine (100 mL), dried over anhydrous sodium sulfate, filtered and the filtrate was concentrated under vacuum to afford (2S)-3-(4-bromothiazol-2-yl)-2-(tert-butoxycarbonylamino) propanoic acid (compound B8, 3.1 g) as yellow oil. MS calc'd 373 (MNa$^+$), measured 372.9 (MNa$^+$).

Step 7: Preparation of methyl (3S)-1-[(2S)-3-(4-bromothiazol-2-yl)-2-(tert-butoxycarbonylamino) propanoyl] hexahydropyridazine-3-carboxylate (Intermediate B)

To a solution of (2S)-3-(4-bromothiazol-2-yl)-2-(tert-butoxycarbonylamino) propanoic acid (compound B8, 3.1 g, 8.83 mmol) in DCM (50 mL) was added methyl (3S)-hexahydropyridazine-3-carboxylate; hydrochloride (compound B9, 2.4 g, 13.24 mmol), EDCI (3.4 g, 17.65 mmol), 1-Hydroxybenzotriazole (238.5 mg, 1.77 mmol) and NMM (9.92 mL, 88.26 mmol) at 0° C. After being stirred at 25° C. for 1 hour, the reaction mixture was diluted with water (60 mL) and extracted with EtOAc (60 mL, three times). The combined organic layer was washed with brine (100 mL), dried over anhydrous sodium sulfate, filtered and the filtrate was concentrated under vacuum. The residue was purified by silica gel column and eluted with ethyl acetate in petroleum ether (10~30%) to afford methyl (3S)-1-[(2S)-3-(4-bromothiazol-2-yl)-2-(tert-butoxycarbonylamino) propanoyl]hexahydropyridazine-3-carboxylate (intermediate B, 2.4 g). MS calc'd 477 (MH$^+$), measured 476.9 (MH$^+$).

Intermediate C1

Benzyl 4-[5-ethynyl-6-[(1S)-1-methoxyethyl]-3-pyridyl]piperazine-1-carboxylate

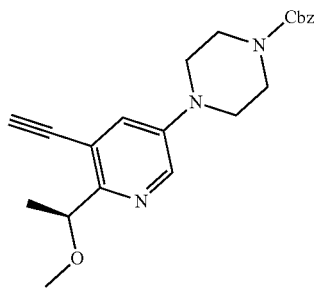 [SMILES: C#Cc1cc(N2CCN(C(=O)OCc3ccccc3)CC2)cnc1[C@H](C)OC]

The compound C1 was prepared according to the following scheme:

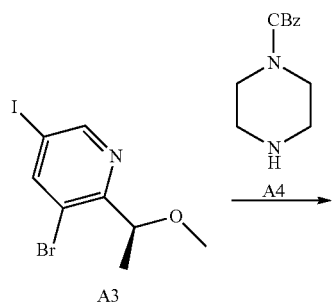

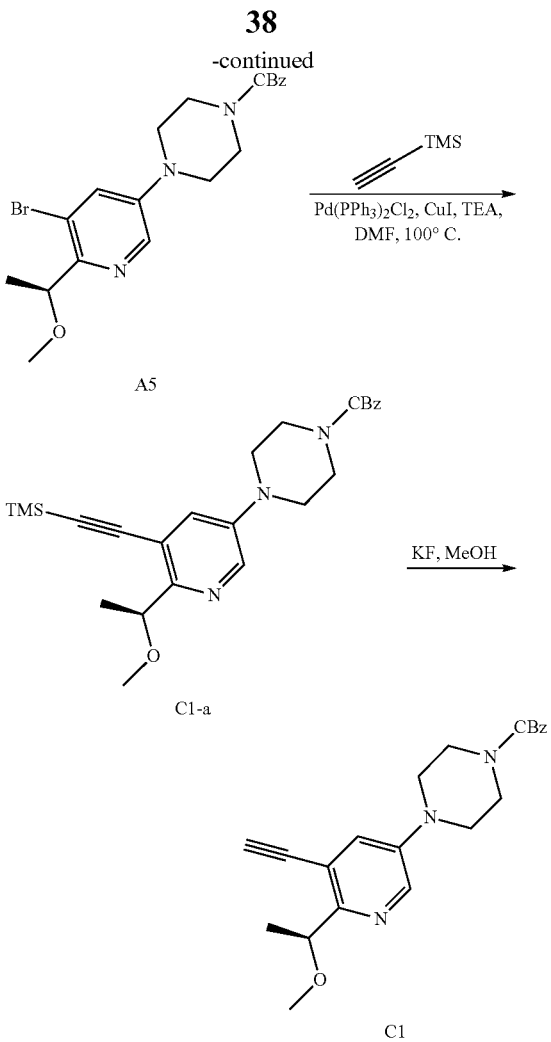

Step 1: Preparation of benzyl 4-[5-bromo-6-[(1S)-1-methoxyethyl]-3-pyridyl]piperazine-1-carboxylate (compound A5)

To a solution of 3-bromo-5-iodo-2-[(1S)-1-methoxyethyl] pyridine (compound A3, 660 mg, 1.9 mmol, CAS 2641451-76-3, PBWZ170, PharmaBlock (Nanjing) R&D Co. Ltd) and 1-Cbz-piperazine (compound A4, 425.1 mg, 1.9 mmol) in toluene (10 mL) were added cesium carbonate (1.6 g, 4.83 mmol), (R)-BINAP (60.1 mg, 0.1 mmol) and palladium (II) acetate (43.3 mg, 0.19 mmol). After being stirred at 100° C. for 12 hrs under N$_2$ protection, the mixture was filtered and then the filtrate was concentrated under vacuum. The residue was purified by silica gel chromatography (EA/PE: 0-50%) to afford benzyl 4-[5-bromo-6-[(1S)-1-methoxyethyl]-3-pyridyl]piperazine-1-carboxylate (compound A5, 740 mg) as a yellow solid. MS calc'd 434.1 (MH$^+$), measured 434.1 (MH$^+$).

Step 2: Preparation of benzyl 4-[6-[(1S)-1-methoxyethyl]-5-(2-trimethylsilylethynyl)-3-pyridyl]piperazine-1-carboxylate (compound C1-a)

To a solution of benzyl 4-[5-bromo-6-[(1S)-1-methoxyethyl]-3-pyridyl]piperazine-1-carboxylate (compound A5, 33.0 g, 75.98 mmol) in DMF (1 L) was added trimethylsilylacetylene (85.9 mL, 607.83 mmol), Pd(PPh$_3$)$_2$Cl$_2$ (5.3 g, 7.6 mmol), CuI (1.5 g, 7.6 mmol) and TEA (52.9 mL, 379.9 mmol) under a nitrogen atmosphere. The reaction mixture was degassed with nitrogen for three times and then it was stirred at 100° C. for 12 hrs. After the reaction was completed, the reaction mixture was cooled to room temperature, filtered and the filtrate was added with H₂O (3 L). The reaction mixture was extracted with EtOAc (1 L, three times). The combined organic layer was washed with brine (3 L), dried over Na₂SO₄, filtered and concentrated under vacuum to give a residue, which was purified by column chromatography to afford benzyl 4-[6-[(1S)-1-methoxyethyl]-5-(2-trimethylsilylethynyl)-3-pyridyl]piperazine-1-carboxylate (compound C₁-a, 21.0 g) as a yellow solid. MS calc'd 452.2 (MH⁺), measured 452.2 (MH⁺).

Step 3: Preparation of benzyl 4-[5-ethynyl-6-[(1S)-1-methoxyethyl]-3-pyridyl]piperazine-1-carboxylate (intermediate C1)

To a solution of benzyl 4-[6-[(1S)-1-methoxyethyl]-5-(2-trimethylsilylethynyl)-3-pyridyl]piperazine-1-carboxylate (compound C1-a, 31 g, 68.6 mmol) in Methanol (500 mL) was added potassium fluoride (8.1 g, 139.8 mmol) at 0° C. The mixture was stirred at 20° C. for 1 h. After the reaction was completed, the reaction mixture was concentrated under vacuum to give a residue, which was purified by column chromatography to afford benzyl 4-[5-ethynyl-6-[(1S)-1-methoxyethyl]-3-pyridyl]piperazine-1-carboxylate (intermediate C1, 25 g) as a brown solid. MS calc'd 380.2 (MH⁺), measured 380.2 (MH⁺).

Intermediate C2

4-[5-ethynyl-6-[(1S)-1-methoxyethyl]-3-pyridyl] morpholine

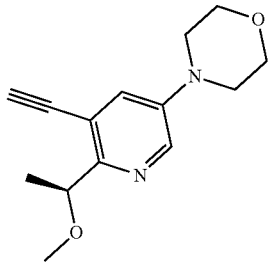 [SMILES: C#Cc1cc(N2CCOCC2)cnc1[C@H](C)OC]

The title compound was prepared in analogy to the preparation of Intermediate C1 by using morpholine instead of 1-Cbz-piperazine (compound A4).

Intermediate C3

1-[5-ethynyl-6-[(1S)-1-methoxyethyl]-3-pyridyl]-4-(2,2,2-trifluoroethyl) piperazine

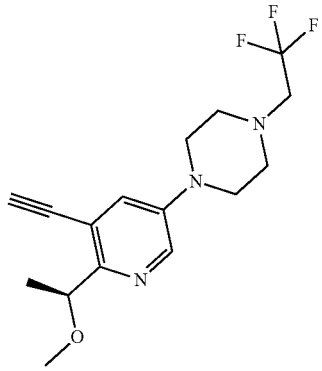 [SMILES: C#Cc1cc(N2CCN(CC(F)(F)F)CC2)cnc1[C@H](C)OC]

The title compound was prepared in analogy to the preparation of Intermediate C1 by using 1-(2,2,2-trifluoroethyl) piperazine instead of 1-Cbz-piperazine (compound A4).

Intermediate C4

(9αS)-8-[5-ethynyl-6-[(1S)-1-methoxyethyl]-3-pyridyl]-3,4,6,7,9,9a-hexahydro-1H-pyrazino[2,1-c][1,4]oxazine

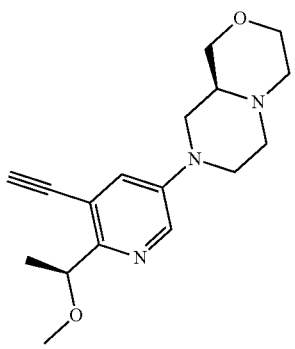 [SMILES: C#Cc1cc(N2CCN3CCOC[C@@H]3C2)cnc1[C@H](C)OC]

The title compound was prepared in analogy to the preparation of Intermediate C1 by using (9αS)-1,3,4,6,7,8,9,9a-octahydropyrazino[2,1-c][1,4]oxazine instead of 1-Cbz-piperazine (compound A4).

Intermediate C5

(9αR)-2-[5-ethynyl-6-[(1S)-1-methoxyethyl]-3-pyridyl]-1,3,4,6,7,8,9,9a-octahydropyrido[1,2-a]pyrazine

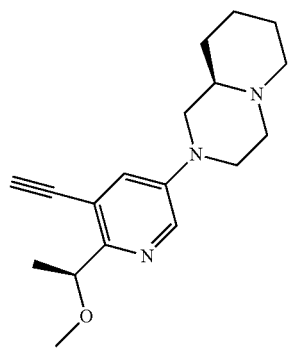 [SMILES: C#Cc1cc(N2CCN3CCCC[C@@H]3C2)cnc1[C@H](C)OC]

The title compound was prepared in analogy to the preparation of Intermediate C1 by using (9αR)-2,3,4,6,7,8,9,9a-octahydro-1H-pyrido[1,2-a]pyrazine instead of 1-Cbz-piperazine (compound A4).

Intermediate D1

6-bromo-8-iodo-1,2,3,4-tetrahydroquinoline

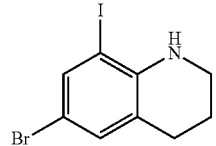

The compound was prepared according to the following scheme:

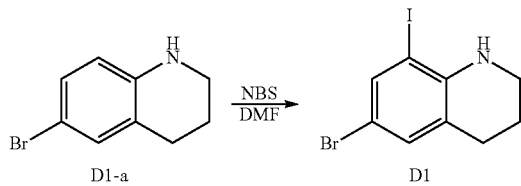

To a solution of 6-bromo-1,2,3,4-tetrahydroquinoline (compound D1-a, 40.0 g, 188.6 mmol) in DMF (1.3 L) was added NIS (42.4 g, 188.6 mmol) portion-wise at 0° C. After being stirred for 2 h at 25° C., the reaction mixture was poured into water (4 L) and extracted with EtOAc (2 L, three times). The combined organic layer was washed with brine (2 L, three times), dried with anhydrous $Na_2SO_4$, filtered and concentrated under vacuum to give a residue. The residue was purified by reversed phase chromatography to give 6-bromo-8-iodo-1,2,3,4-tetrahydroquinoline (Intermediate D1, 37 g) as a brown gum. MS calc'd 337.9 ($MH^+$), measured 338.0 ($MH^+$).

Intermediate D2

7-bromo-5-iodo-3,4-dihydro-2H-1,4-benzoxazine

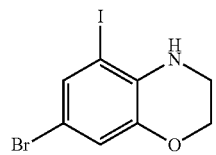

The compound was prepared according to the following scheme:

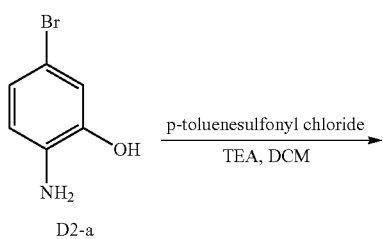

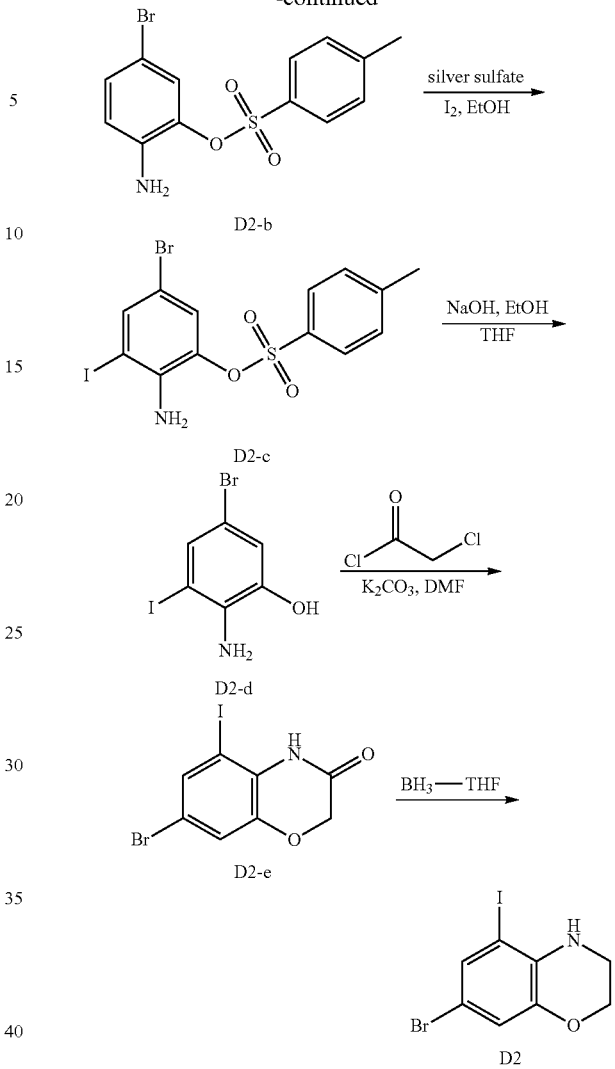

Step 1: Preparation of (2-amino-5-bromo-phenyl) 4-methylbenzenesulfonate (compound D2-b)

To a solution of 2-amino-5-bromophenol (compound D2-a, 75.0 g, 398.89 mmol) and TEA (66.7 mL, 478.67 mmol) in DCM (1.5 L) was added p-toluenesulfonyl chloride (83.6 g, 438.78 mmol). After being stirred at 25° C. for 1 h, the reaction was quenched with sat. $NaHCO_3$ aq. (400 mL) and EtOAc (500 mL, three times). The organic layer was washed with brine (200 mL), dried over $Na_2SO_4$, filtered and concentrated under vacuum to afford crude (2-amino-5-bromo-phenyl) 4-methylbenzenesulfonate (compound D2-b, 146.5 g) as a dark brown solid, which was used in the next step without purification. MS calc'd 342 ($MH^+$), measured 342 ($MH^+$).

Step 2: Preparation of (2-amino-5-bromo-3-iodo-phenyl) 4-methylbenzenesulfonate (compound D2-c)

To a solution of (2-amino-5-bromo-phenyl) 4-methylbenzenesulfonate (compound D2-b, 146.5 g, 428.1 mmol) in ethanol (1.5 L) was added silver sulfate (133.5 g, 428.1 mmol) and iodine (108.7 g, 428.1 mmol). After being stirred at 25° C. for 12 hrs, the reaction was quenched by sat. $NaHCO_3$ aq. (400 mL) and EtOAc (500 mL, three times). The organic layer was washed with brine (200 mL), dried over $Na_2SO_4$, filtered and concentrated under vacuum to afford (2-amino-5-bromo-3-iodo-phenyl) 4-methylbenzenesulfonate (compound D2-c, 210.0 g) as a dark brown solid, which was used directly in the next step without purification. MS calc'd 467.8 (MH$^+$), measured 467.8 (MH$^+$).

Step 3: Preparation of 2-amino-5-bromo-3-iodo-phenol (compound D2-d)

To a solution of (2-amino-5-bromo-3-iodo-phenyl) 4-methylbenzenesulfonate (compound D2-c, 210.0 g, 448.62 mmol) in ethanol (1.5 L) and THF (500 mL) was added sodium hydroxide (62.8 g, 1570.18 mmol). The mixture was heated to reflux for 1 h. After being cooled to room temperature, the reaction mixture was concentrated under vacuum to give a residue. The residue was neutralized until pH=7 by using 6 N HCl and extracted with EtOAc (1 L, twice). The organic layer was dried with Na$_2$SO$_4$, filtered and concentrated under vacuum to give a residue. The crude product was purified by column chromatography to afford 2-amino-5-bromo-3-iodo-phenol (compound D2-d, 120.0 g) as a dark brown solid. MS calc'd 313.9 (MH$^+$), measured 313.9 (MH$^+$).

Step 4: Preparation of 7-bromo-5-iodo-4H-1,4-benzoxazin-3-one (compound D2-e)

To a solution of 2-amino-5-bromo-3-iodo-phenol (compound D2-d, 50.0 g, 159.28 mmol) and potassium carbonate (33.0 g, 238.91 mmol) in DMF (2 L) was added chloroacetyl chloride (19.0 mL, 238.91 mmol). After being stirred at 25° C. for 12 hrs, the reaction mixture was concentrated under vacuum to give a residue. The residue was poured into H$_2$O (1 L), and extracted with EtOAc (1 L, three times). The organic layer was washed with brine (1.5 L, twice), dried over Na$_2$SO$_4$, filtered and concentrated under vacuum to give a residue. The crude product was triturated with MTBE (100 mL) at 25° C. for 30 min. The suspension was filtered, the collected solid was collected to afford 7-bromo-5-iodo-4H-1,4-benzoxazin-3-one (compound D2-e, 175.0 g) as a dark brown solid. MS calc'd 353.9 (MH$^+$), measured 353.9 (MH$^+$).

Step 5: Preparation of 7-bromo-5-iodo-3,4-dihydro-2H-1,4-benzoxazine (Intermediate D2)

To a stirred solution of 7-bromo-5-iodo-4H-1,4-benzoxazin-3-one (compound D2-e, 20.0 g, 56.51 mmol) in THF (500 mL) under N$_2$ atmosphere was added borane tetrahydrofuran complex solution (113.0 mL, 113.01 mmol) at 0° C. After being stirred at 80° C. for 1 h, the mixture was cooled to room temperature, and then follow by addition of MeOH (100 mL). The mixture was poured into H$_2$O (100 mL), extracted with EtOAc (200 mL, three times). The organic layer was washed with brine (100 mL, twice), dried over Na$_2$SO$_4$, filtered and concentrated under vacuum to give a residue. The crude product was purified by column chromatography to afford 7-bromo-5-iodo-3,4-dihydro-2H-1,4-benzoxazine (intermediate D2, 17.6 g) as a pink solid. MS calc'd 340.0 (MH$^+$), measured 340.0 (MH$^+$). $^1$H NMR (400 MHZ, DMSO-d$_6$) δ=7.31 (d, J=2.4 Hz, 1H), 6.88 (d, J=2.4 Hz, 1H), 5.42 (br s, 1H), 4.07 (t, J=4.4 Hz, 2H), 3.38-3.33 (m, 2H).

Intermediate D3

6-bromo-3,3-difluoro-8-iodo-2,4-dihydro-1H-quinoline

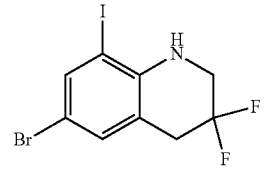

The compound was prepared according to the following scheme:

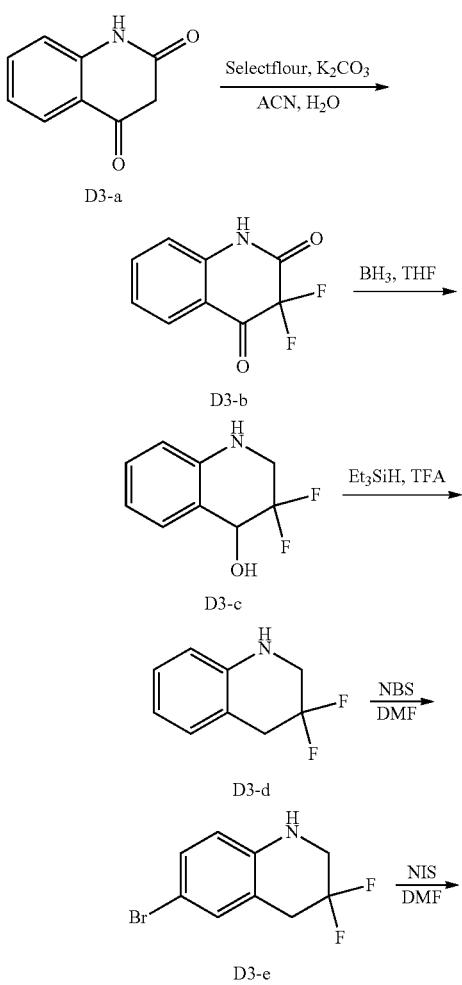

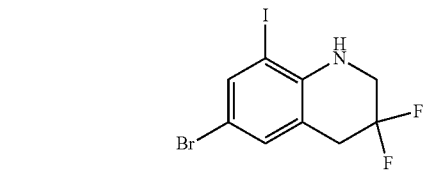

Intermediate D3

Step 1: Preparation of 3,3-difluoro-1H-quinoline-2,4-dione (compound D3-b)

To a solution of 1H-quinoline-2,4-dione (compound D3-a, 8.0 g, 49.64 mmol) and potassium carbonate (13.7 g, 99.28 mmol) in ACN (160 mL) and water (80 mL) was added Selectfluor (40.0 g, 112.91 mmol) at 0° C. After being stirred at 25° C. for 1 h, the reaction mixture was concentrated in vacuo and the residue was filtered. The filtrate was added to water (1 L). The resultant mixture was extracted with EtOAc (400 mL, three times). The combined organic layer was washed with brine (400 mL, twice), dried over $Na_2SO_4$, filtered and concentrated in vacuo to afford 3,3-difluoro-1H-quinoline-2,4-dione (compound D3-b, 46.0 g) as a yellow solid. $^1$H NMR (400 MHZ, CHLOROFORM-d) δ=9.77 (s, 1H), 8.22-7.94 (m, 1H), 07.81-7.64 (m, 1H), 7.33-7.28 (m, 1H), 7.17 (d, J=8.0 Hz, 1H).

Step 2: Preparation of 3,3-difluoro-2,4-dihydro-1H-quinolin-4-ol (compound D3-c)

To a solution of 3,3-difluoro-1H-quinoline-2,4-dione (compound D3-b, 69.0 g, 350.01 mmol) in THF (700 mL) was added borane-tetrahydrofuran complex (700.0 mL, 700.0 mmol) at 0° C. After being stirred at 25° C. for 16 hrs, the reaction was quenched with MeOH (500 mL) at 0° C. dropwise, and then concentrated in vacuo to afford 3,3-difluoro-2,4-dihydro-1H-quinolin-4-ol (compound D3-c, 64.8 g) as yellow oil. MS calc'd 185.1 ($MH^+$), measured 168.0, ($M-OH+H^+$).

Step 3: Preparation of 3,3-difluoro-2,4-dihydro-1H-quinoline (compound D3-d)

To a solution of 3,3-difluoro-2,4-dihydro-1H-quinolin-4-ol (compound D3-c, 64.8 g, 349.95 mmol) in $Et_3SiH$ (206.8 mL, 1.29 mol) was added TFA (405.4 mL, 5.26 mol) at 0° C. After being stirred at 25° C. for 16 hrs, the reaction mixture was concentrated in vacuo and adjusted to pH=8 by adding sat. $NaHCO_3$ aq., extracted with EtOAc (1 L, twice). The combined organic layer was washed by brine (1.6 L), dried over anhydrous sodium sulfate, filtered and concentrated under vacuum to give a residue, which was purified by silica gel column chromatography to afford 3,3-difluoro-2,4-dihydro-1H-quinoline (compound D3-d, 45.0 g) as a yellow solid. MS calc'd 170.1 ($MH^+$), measured 170.0 ($MH^+$).

Step 4: Preparation of 6-bromo-3,3-difluoro-2,4-dihydro-1H-quinoline (compound D3-e)

To a solution of 3,3-difluoro-2,4-dihydro-1H-quinoline (compound D3-d, 50.0 g, 295.56 mmol) in DMF (800 mL) was added NBS (50.0 g, 280.65 mmol) at 0° C. After being stirred at 0° C. for 1 h, the mixture was poured into water (1200 mL) and the resulting mixture was extracted with EtOAc (800 mL, three times). The combined organic layer was washed with brine (1 L, three times), dried over $Na_2SO_4$, filtered and concentrated in vacuo, which was purified by column chromatography to afford 6-bromo-3,3-difluoro-2,4-dihydro-1H-quinoline (compound D3-e, 57.0 g) as a yellow solid. MS calc'd 248.0 ($MH^+$), measured 247.9 ($MH^+$).

Step 5: Preparation of 6-bromo-3,3-difluoro-8-iodo-2,4-dihydro-1H-quinoline (Intermediate D3)

To a solution of 6-bromo-3,3-difluoro-2,4-dihydro-1H-quinoline (compound D3-e, 49.0 g, 197.52 mmol) in DMF (700 mL) was added NIS (48.9 g, 217.28 mmol) at 0° C. After being stirred at 0° C. for 5 hrs, the reaction mixture was poured into water (1.2 L) and the resultant mixture was extracted with EtOAc (650 mL, three times). The combined organic layer was washed with brine (1000 mL, three times), dried over $Na_2SO_4$, filtered and concentrated in vacuo. The residue was purified by column chromatography to afford 6-bromo-3,3-difluoro-8-iodo-2,4-dihydro-1H-quinoline (Intermediate D3, 68.0 g) as a white solid. MS calc'd 373.9 ($MH^+$), measured 373.9 ($MH^+$).

Intermediate D4

7-bromo-5-iodo-2,2-dimethyl-3,4-dihydro-1,4-benzoxazine

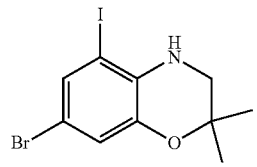

The title compound was prepared in analogy to the preparation of Intermediate D2 by using ethyl 2-bromo-2-methyl-propanoate instead of chloroacetyl chloride.

Intermediate D5

7-bromo-5-iodo-3-methyl-3,4-dihydro-2H-1,4-benzoxazine

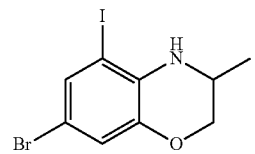

The compound was prepared according to the following scheme:

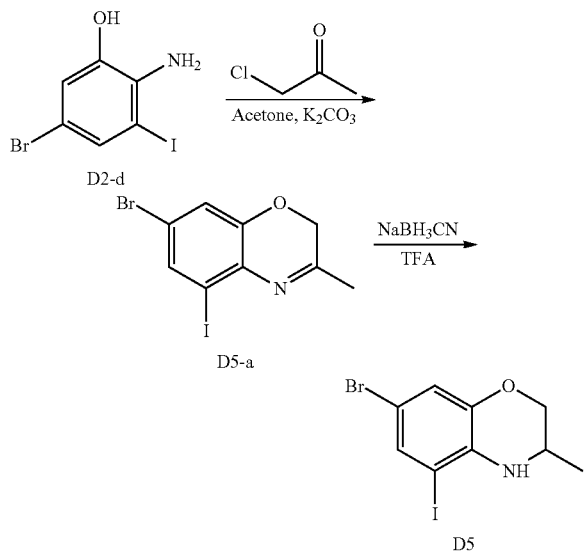

Step 1: Preparation of 7-bromo-5-iodo-3-methyl-2H-1,4-benzoxazine (compound D5-a)

To a solution of 2-amino-5-bromo-3-iodo-phenol (compound D2-d, 18 g, 57.34 mmol) in acetone (300 mL) was added potassium carbonate (15.8 g, 114.68 mmol) and chloroacetone (10.6 g, 114.68 mmol). After being stirred at 25° C. for 18 hrs, the reaction mixture was poured into EtOAc (200 mL)/water (400 mL), and layers were separated. The aqueous phase was extracted with EtOAc (200 mL, twice). The combined organic layer was washed with brine (300 mL), dried over Na$_2$SO$_4$, filtered, and concentrated under vacuum to give a residue. The residue was purified by flash chromatography to give 7-bromo-5-iodo-3-methyl-2H-1,4-benzoxazine (compound D5-a, 20 g) as light brown solid. MS calc'd 351.9 (MH$^+$), measured 351.9 (MH$^+$).

Step 2: Preparation of 7-bromo-5-iodo-3-methyl-3,4-dihydro-2H-1,4-benzoxazine (Intermediate D5)

To a solution of 7-bromo-5-iodo-3-methyl-2H-1,4-benzoxazine (compound D5-a, 20.0 g, 60 mmol) in TFA (1 L, 12.98 mmol) was added sodium cyanoborohydride (17 g, 270 mmol) and then stirred at 25° C. for 2 hrs. The mixture was slowly added to NaOH aq. (150 mL, 2M) and then extracted with EtOAc (100 mL, twice). The organic layer was washed with water, brine, dried over sodium sulfate, filtered, concentrated under vacuum to give a residue. The residue was purified by silica gel chromatography to afford 7-bromo-5-iodo-3-methyl-3,4-dihydro-2H-1,4-benzoxazine (Intermediate D5, 14.6 g) as brown thick oil. MS calc'd 353.9 (MH$^+$), measured 353.9 (MH$^+$).

Intermediate D6

6-bromo-8-iodo-3,3-dimethyl-2,4-dihydro-1H-quinoline

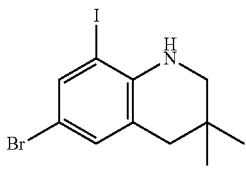

The title compound was prepared in analogy to the preparation of Intermediate D1 by using 6-bromo-3,3-dimethyl-2,4-dihydro-1H-quinoline instead of 6-bromo-1,2,3,4-tetrahydroquinoline (compound D1-a).

Intermediate D7

8-bromo-6-iodo-2,3,4,5-tetrahydro-1,5-benzoxazepine

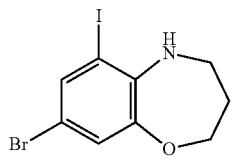 [SMILES: Brc1cc(I)c2c(c1)OCCCN2]

The compound was prepared according to the following scheme:

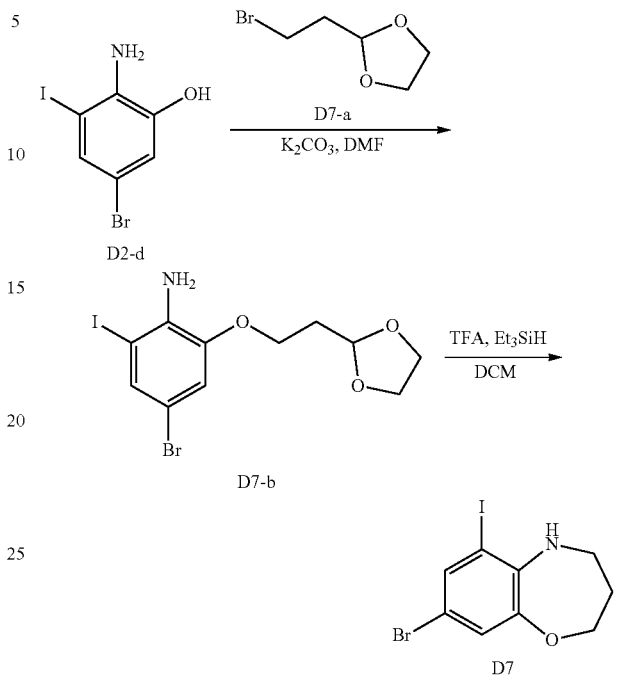

Step 1: Preparation of 4-bromo-2-[2-(1,3-dioxolan-2-yl) ethoxy]-6-iodo-aniline (compound D7-b).

To a solution of 2-amino-5-bromo-3-iodo-phenol (compound D2-d, 3.5 g, 11.05 mmol) in anhydrous DMF (80 mL) at 25° C. was added 2-(2-bromoethyl)-1,3-dioxolane (compound D7-a, 4.0 g, 22.11 mmol) and K$_2$CO$_3$ (4.6 g, 33.16 mmol). After being stirred at 25° C. for 15 hrs, the reaction mixture was poured into EtOAc (100 mL)/water (100 mL), and layers were separated. The aqueous phase was extracted with EtOAc (100 mL, twice). The combined organic layer was washed with brine (100 mL), dried over Na$_2$SO$_4$, filtered, and concentrated under vacuum to give a residue. The residue was purified by flash chromatography to afford 4-bromo-2-[2-(1,3-dioxolan-2-yl) ethoxy]-6-iodo-aniline (compound D7-b, 3.3 g) as a yellow solid. MS calc'd 414.0 (MH$^+$), measured 414.0 (MH$^+$).

Step 2: Preparation of 8-bromo-6-iodo-2,3,4,5-tetrahydro-1,5-benzoxazepine (intermediate D7).

To a solution of 4-bromo-2-[2-(1,3-dioxolan-2-yl) ethoxy]-6-iodo-aniline (compound D7-b, 3.3 g, 7.97 mmol) in DCM (24 mL) at 0° C. was added TFA (6.0 mL) via a syringe dropwise over 1 min under nitrogen atmosphere. After being stirred at 25° C. for 60 min, the reaction mixture was added with triethylsilane (4.63 g, 39.78 mmol) and stirred at 25° C. for another 14 hrs. After the reaction completed, the mixture was concentrated under vacuum to get a residue. The residue was diluted with sat. NaHCO$_3$ aq. (50 mL) and extracted with EtOAc (20 mL, three times). The combined organic layer was washed by brine (20 mL), dried over anhydrous sodium sulfate, filtered and concentrated under vacuum to give a residue, which was purified by column chromatography to afford 8-bromo-6-iodo-2,3,4,5-tetrahydro-1,5-benzoxazepine (intermediate D7, 1.98 g) as brown oil. MS calc'd 353.9 (MH$^+$), measured 354.0 (MH$^+$).

Intermediate D9

6-bromo-8-iodo-1,2,3,4-tetrahydroquinolin-3-ol

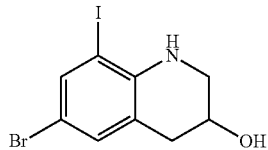 [SMILES: OC1CNc2c(I)cc(Br)cc2C1]

The title compound was prepared in analogy to the preparation of Intermediate D3 by using 1,2,3,4-tetrahydroquinolin-3-ol instead of 3,3-difluoro-2,4-dihydro-1H-quinoline (compound D3-d).

Intermediate D10

6-bromo-5-fluoro-8-iodo-1,2,3,4-tetrahydroquinoline

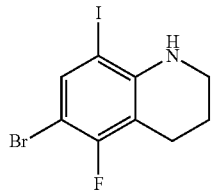 [SMILES: Fc1c(Br)cc(I)c2c1CCCN2]

The compound was prepared according to the following scheme:

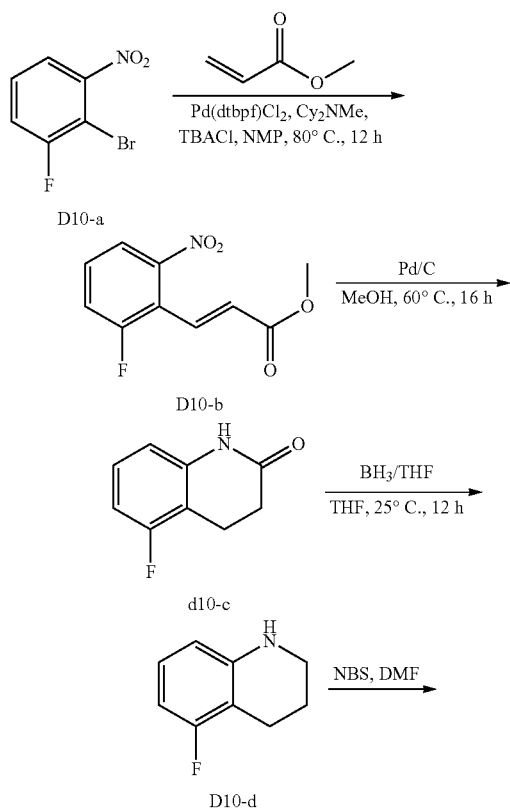

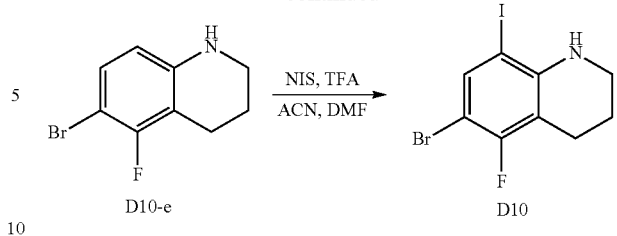

Step 1: Preparation of methyl (E)-3-(2-fluoro-6-nitro-phenyl) prop-2-enoate (compound D10-b).

To a mixture of 2-bromo-1-fluoro-3-nitro-benzene (compound D10-a, 14.2 g, 64.55 mmol) and methyl acrylate (9 g, 104.31 mmol) in NMP (150 mL) was added N,N-dicyclohexylmethylamine (37.8 g, 193.64 mmol), tetrabutylammonium chloride (1.8 g, 6.45 mmol) and Pd (dtbpf) $Cl_2$ (4.21 g, 6.45 mmol) in one portion. The mixture was purged under vacuum and degassed with nitrogen for 3 times before stirred at 80° C. for 12 hrs. After the reaction completed, the reaction mixture was cooled to rt and poured into water (300 mL). The mixture was extracted with EtOAc (100 mL, three times). The combined organic layer was washed with brine (100 mL), dried over anhydrous $Na_2SO_4$, filtered and concentrated under vacuum to get a residue. The residue was purified by column chromatography (PE:EtOAc=1:0 to 3:1) to afford methyl (E)-3-(2-fluoro-6-nitro-phenyl) prop-2-enoate (compound D10-b, 6.21 g) as a yellow solid. $^1$H NMR (400 MHZ, CHLOROFORM-d) δ=7.80 (d, J=8.0 Hz, 1H), 7.72 (d, J=16.4 Hz, 1H), 7.50 (dt, J=5.2, 8.4 Hz, 1H), 7.46-7.39 (m, 1H), 6.54 (dd, J=2.0, 16.4 Hz, 1H), 3.85 (s, 3H).

Step 2: Preparation of 5-fluoro-3,4-dihydro-1H-quinolin-2-one (compound D10-c).

To a mixture of methyl (E)-3-(2-fluoro-6-nitro-phenyl) prop-2-enoate (compound D10-b, 6.0 g, 26.65 mmol) in methanol (60 mL) was added Pd on activated carbon (2.8 g, 2.66 mmol) under Ar atmosphere. The reaction mixture was degassed and purged with Ar for 3 times before degassed and purged with hydrogen for 3 times. The mixture was stirred at 60° C. under hydrogen atmosphere (15 Psi) for 16 hrs. After the reaction completed, the mixture was filtered and the filtrate was concentrated under vacuum to afford 5-fluoro-3,4-dihydro-1H-quinolin-2-one (compound D10-c, 4.37 g) as an off-white solid. MS calc'd 166.1 (MH$^+$), measured 166.2 (MH$^+$).

Step 3: Preparation of 5-fluoro-1,2,3,4-tetrahydroquinoline (compound D10-d).

To a solution of 5-fluoro-3,4-dihydro-1H-quinolin-2-one (compound D10-c, 4.0 g, 24.22 mmol) in THF (80 mL) was added borane-tetrahydrofuran complex (48 mL, 48.44 mmol, 1 M) slowly at 0° C. under nitrogen atmosphere. After being stirred at 25° C. for 12 hrs, the reaction was quenched by addition of MeOH (100 mL) dropwise at 0° C. and stirred for 30 min. Then the mixture was concentrated under vacuum to remove most solvent, and then water (100 mL) was added and extracted with EtOAc (30 mL, three times). The combined organic layer was washed with brine (30 mL), dried over anhydrous sodium sulfate, filtered and concentrated under vacuum to give a residue, which was purified by column chromatography to afford 5-fluoro-1,2,3,4-tetrahydroquinoline (compound D10-d, 3.74 g) as yellow oil. MS calc'd 152.1 (MH$^+$), measured 152.0 (MH$^+$).

Step 4: Preparation of 6-bromo-5-fluoro-1,2,3,4-tetrahydroquinoline (compound D10-e).

To a solution of 5-fluoro-1,2,3,4-tetrahydroquinoline (compound D10-d, 3.5 g, 23.42 mmol) in DMF (60 mL) was added NBS (4.2 g, 23.42 mmol) slowly at 0° C. The mixture was stirred at 0° C. for 0.25 hour. After the reaction completed, the mixture was poured into water (30 mL) and extracted with EtOAc (100 mL, three times). The combined organic layer was washed by brine (100 mL, three times), dried over anhydrous sodium sulfate, filtered and concentrated under vacuum to give a residue, which was purified by column chromatography to afford 6-bromo-5-fluoro-1,2,3,4-tetrahydroquinoline (compound D10-e, 4.0 g) as yellow oil. MS calc'd 230.0 (MH+), measured 230.2 (MH+).

Step 5: Preparation of 6-bromo-5-fluoro-8-iodo-1,2,3,4-tetrahydroquinoline (intermediate D10).

To a solution of 6-bromo-5-fluoro-1,2,3,4-tetrahydroquinoline (compound D10-e, 3.5 g, 15.21 mmol) in DMF (50 mL) cooled to −10° C. was added TFA (3.5 mL, 45.64 mmol) followed by addition of a solution of NIS (3.6 g, 15.97 mmol) in ACN (20 mL)/DMF (20 mL). The reaction solution was stirred for another 30 minutes under nitrogen atmosphere. The reaction was quenched with slow addition of sat. Na$_2$SO$_3$ solution (100 mL) upon stirring. Then the reaction mixture was poured into water (300 mL) and the mixture was extracted with EtOAc (100 mL, three times). The combined organic layer was washed with brine (100 mL, five times), dried over Na$_2$SO$_4$, filtered and concentrated under vacuum to give a residue which was purified by column chromatography to afford 6-bromo-5-fluoro-8-iodo-1,2,3,4-tetrahydroquinoline (intermediate D10, 5.77 g) as a white solid. MS calc'd 355.9 (MH+), measured 356.0 (MH+).

Intermediate E (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaene-8,14-dione The compound was prepared according to the following scheme:

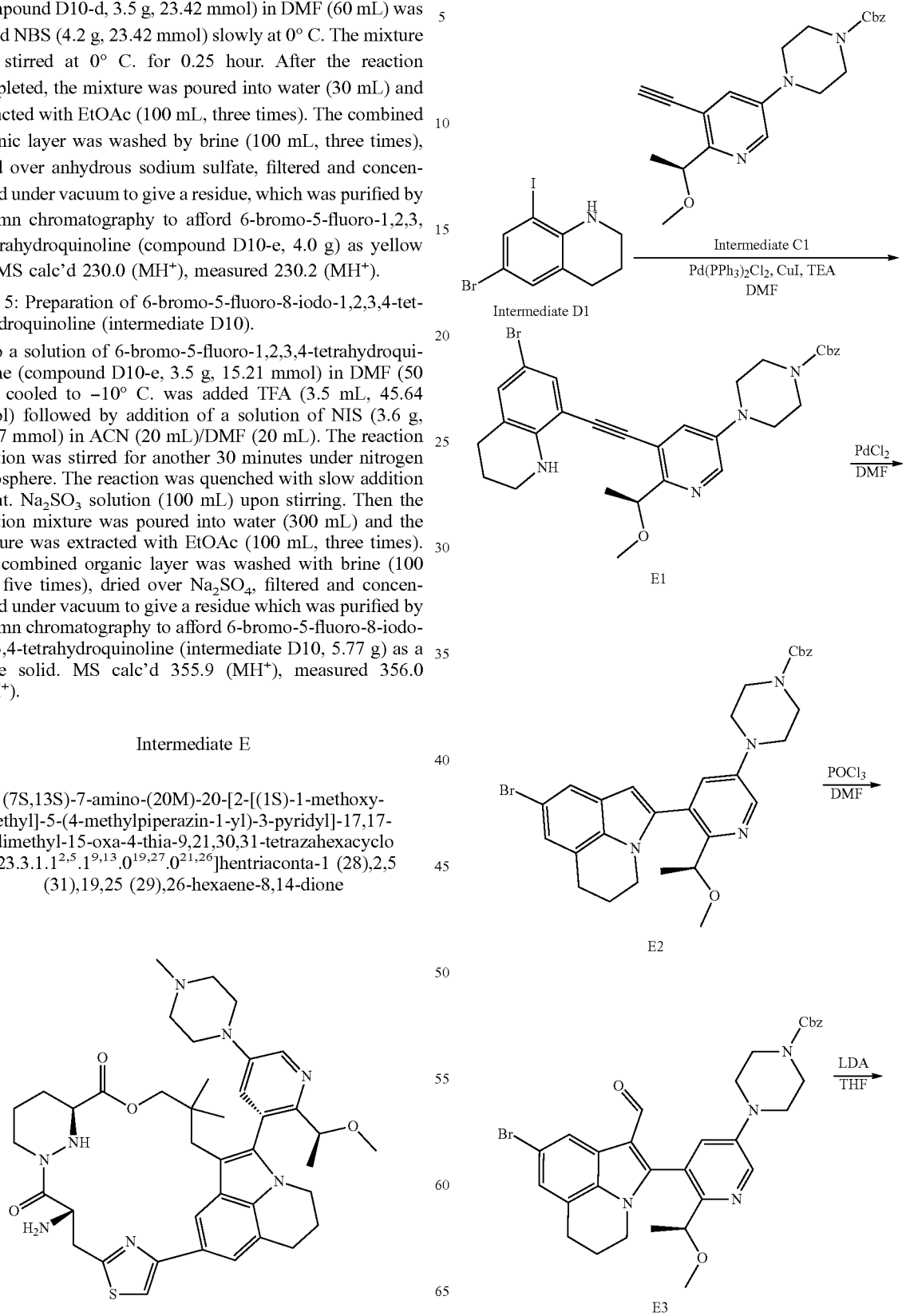

53
-continued
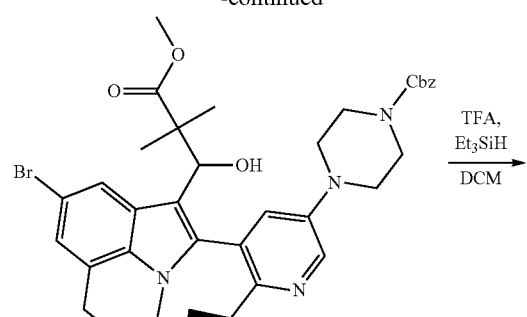
E4
TFA, Et₃SiH / DCM
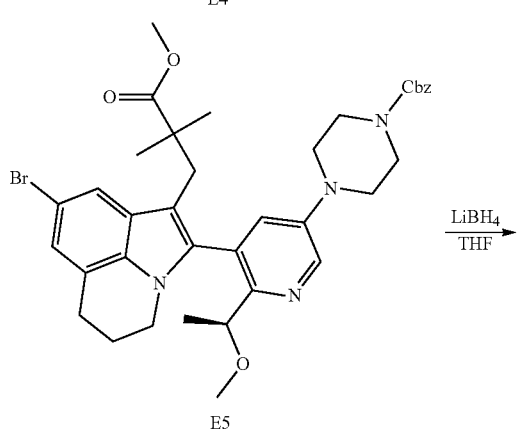
E5
LiBH₄ / THF
E6
Pd(dppf)Cl₂, KOAc / toluene
E7
Intermediate B
Pd(dtbpf)Cl₂, K₃PO₄
toluene, dioxane, water
54
-continued
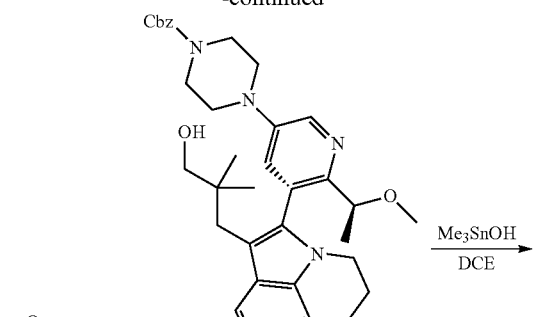
E8
Me₃SnOH / DCE
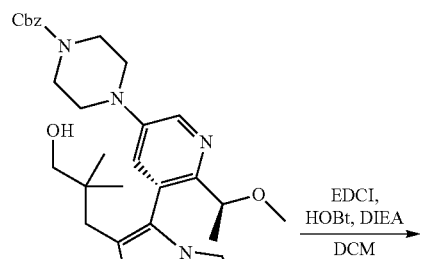
E9
EDCI, HOBt, DIEA / DCM
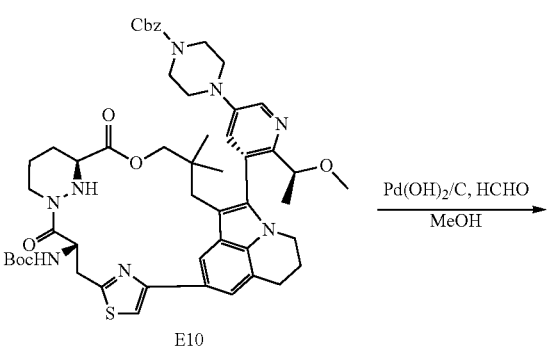
E10
Pd(OH)₂/C, HCHO / MeOH

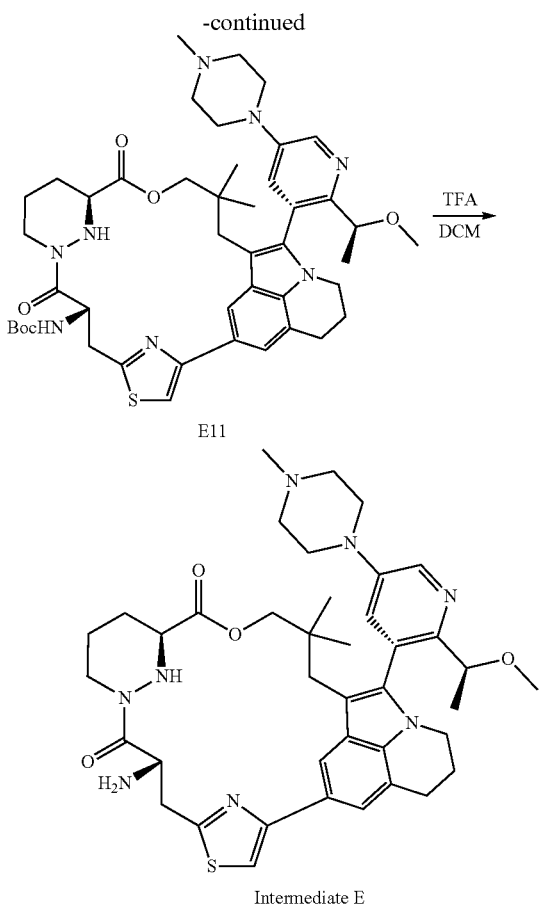

Intermediate E

Step 1: Preparation of benzyl 4-[5-[2-(6-bromo-1,2,3,4-tetrahydroquinolin-8-yl) ethynyl]-6-[(1S)-1-methoxyethyl]-3-pyridyl]piperazine-1-carboxylate (compound E1).

To a solution of benzyl 4-[5-ethynyl-6-[(1S)-1-methoxyethyl]-3-pyridyl]piperazine-1-carboxylate (Intermediate C1, 26.1 g, 68.8 mmol) in DMF (400 mL) were added 6-bromo-8-iodo-1,2,3,4-tetrahydroquinoline (Intermediate D1, 23.3 g, 68.8 mmol), TEA (47.9 mL, 343.92 mmol), CuI (1.3 g, 6.88 mmol) and Pd(PPh$_3$)$_2$Cl$_2$ (4.8 g, 6.88 mmol). The reaction mixture was degassed and purged with nitrogen for three times and then it was stirred at 25° C. for 12 hrs. After the reaction was completed, the reaction mixture was poured into water (1.4 L), and extracted with EtOAc (800 mL, three times). The combined organic layer was washed with brine (800 mL, four times), dried over Na$_2$SO$_4$, filtered and concentrated under vacuum to give a residue, which was purified by column chromatography to afford benzyl 4-[5-[2-(6-bromo-1,2,3,4-tetrahydroquinolin-8-yl) ethynyl]-6-[(1S)-1-methoxyethyl]-3-pyridyl]piperazine-1-carboxylate (compound E1, 30.0 g) as a yellow solid. MS calc'd 589.2 (MH$^+$), measured 589.2 (MH$^+$).

Step 2: Preparation of benzyl 4-[5-(6-bromo-1-azatricyclo[6.3.1.0$^{4,12}$]dodeca-2,4,6,8 (12)-tetraen-2-yl)-6-[(1S)-1-methoxyethyl]-3-pyridyl]piperazine-1-carboxylate (compound E2).

To a solution of benzyl 4-[5-[2-(6-bromo-1,2,3,4-tetrahydroquinolin-8-yl) ethynyl]-6-[(1S)-1-methoxyethyl]-3-pyridyl]piperazine-1-carboxylate (compound E1, 27.0 g, 45.8 mmol) in DMF (270 mL) was added PdCl$_2$ (1.6 g, 9.16 mmol) in one portion. The reaction mixture was degassed under vacuum, flashed with nitrogen for three times and then heated to 70° C. for 16 hrs. After being cooled to the room temperature, the mixture was poured into water (800 mL), and extracted with EtOAc (300 mL, three times). The combined organic layer was washed with brine (300 mL, three times), dried over Na$_2$SO$_4$, filtered and concentrated under vacuum to give a residue, which was purified by column chromatography to afford benzyl 4-[5-(6-bromo-1-azatricyclo[6.3.1.0$^{4,12}$]dodeca-2,4,6,8 (12)-tetraen-2-yl)-6-[(1S)-1-methoxyethyl]-3-pyridyl]piperazine-1-carboxylate (compound E2, 19.2 g) as a yellow solid. MS calc'd 589.2 (MH$^+$), measured 589.2 (MH$^+$).

Step 3: Preparation of benzyl 4-[5-(6-bromo-3-formyl-1-azatricyclo[6.3.1.04.12]dodeca-2,4,6,8 (12)-tetraen-2-yl)-6-[(1S)-1-methoxyethyl]-3-pyridyl]piperazine-1-carboxylate (compound E3).

Phosphorus oxychloride (30.4 mL, 325.69 mmol) was added into DMF (350 mL) dropwise slowly at 0° C. After being stirred at 0° C. for 0.5 h, the reaction mixture was added with a solution of benzyl 4-[5-(6-bromo-1-azatricyclo [6.3.1.0$^{4,12}$]dodeca-2,4,6,8 (12)-tetraen-2-yl)-6-[(1S)-1-methoxyethyl]-3-pyridyl]piperazine-1-carboxylate (compound E2, 19.2 g, 32.57 mmol) in DMF (150 mL) dropwise at 0° C. The reaction mixture was heated to 45° C., and then stirred for another 1 h. The reaction was quenched with sat. NaHCO$_3$ aq. solution (1.5 L), extracted with EtOAc (500 mL, three times). The organic phase was washed with brine (500 mL, three times), dried over anhydrous Na$_2$SO$_4$, filtered and concentrated under vacuum to give a residue. The residue was purified by column chromatography to afford benzyl 4-[5-(6-bromo-3-formyl-1-azatricyclo[6.3.1.0$^{4,12}$] dodeca-2,4,6,8 (12)-tetraen-2-yl)-6-[(1S)-1-methoxyethyl]-3-pyridyl]piperazine-1-carboxylate (compound E3, 14.6 g) as a yellow solid. MS calc'd 616.9 (MH$^+$), measured 617.2 (MH$^+$).

Step 4: Preparation of benzyl 4-[5-[6-bromo-3-(1-hydroxy-3-methoxy-2,2-dimethyl-3-oxo-propyl)-1-azatricyclo [6.3.1.0$^{4,12}$]dodeca-2,4,6,8 (12)-tetraen-2-yl]-6-[(1S)-1-methoxyethyl]-3-pyridyl]piperazine-1-carboxylate (compound E4)

To a solution of methyl isobutyrate (13.4 g, 131.17 mmol) in THF (150 mL) was added LDA (65.58 mL, 131.17 mmol) dropwise at −70° C. under nitrogen atmosphere. After being stirred for 0.5 h, the reaction mixture was added with a solution of benzyl 4-[5-(6-bromo-3-formyl-1-azatricyclo [6.3.1.0$^{4,12}$]dodeca-2,4,6,8 (12)-tetraen-2-yl)-6-[(1S)-1-methoxyethyl]-3-pyridyl]piperazine-1-carboxylate (compound E3, 13.5 g, 21.86 mmol) in THF (50 mL) dropwise at −70° C. The reaction mixture was then allowed warm up to room temperature and stirred for 1 h. After the reaction was completed, the mixture was quenched with sat. NH$_4$Cl (600 mL) aqueous solution and extracted with EtOAc (200 mL, three times). The organic phase was washed with brine (500 mL), dried with anhydrous Na$_2$SO$_4$, filtered and concentrated under vacuum to give a residue. The residue was purified by column chromatography to afford benzyl 4-[5-[6-bromo-3-(1-hydroxy-3-methoxy-2,2-dimethyl-3-oxo-propyl)-1-azatricyclo[6.3.1.0$^{4,12}$]dodeca-2,4,6,8 (12)-tetraen-2-yl]-6-[(1S)-1-methoxyethyl]-3-pyridyl]piperazine-1-carboxylate (compound E4, 14.01 g) as a yellow gum. MS calc'd 719.3 (MH$^+$), measured 719.2 (MH$^+$).

Step 5: Preparation of benzyl 4-[5-[6-bromo-3-(3-methoxy-2,2-dimethyl-3-oxo-propyl)-1-azatricyclo[6.3.1.0$^{4,12}$]dodeca-2,4,6,8 (12)-tetraen-2-yl]-6-[(1S)-1-methoxyethyl]-3-pyridyl]piperazine-1-carboxylate (compound E5)

To a solution of benzyl 4-[5-[6-bromo-3-(1-hydroxy-3-methoxy-2,2-dimethyl-3-oxo-propyl)-1-azatricyclo [6.3.1.0$^{4,12}$]dodeca-2,4,6,8 (12)-tetraen-2-yl]-6-[(1S)-1- methoxyethyl]-3-pyridyl]piperazine-1-carboxylate (compound E4, 14.0 g, 19.45 mmol) and Et$_3$SiH (18.1 g, 155.63 mmol) in DCM (280 mL) was added TFA (57.8 mL, 778.15 mmol) at 0° C. After being stirred at 25° C. for 12 hrs, the reaction mixture was concentrated under vacuum to give a residue, which was diluted with sat. NaHCO$_3$ aq. until pH=9 and extracted with EtOAc (300 mL, three times). The combined organic layer was dried with anhydrous Na$_2$SO$_4$, filtered and concentrated under vacuum to give a residue. The residue was purified by column to afford benzyl 4-[5-[6-bromo-3-(3-methoxy-2,2-dimethyl-3-oxo-propyl)-1-azatricyclo[6.3.1.0$^{4,12}$]dodeca-2,4,6,8 (12)-tetraen-2-yl]-6-[(1S)-1-methoxyethyl]-3-pyridyl]piperazine-1-carboxylate (compound E5, 14 g) as a yellow gum. MS calc'd 703.2 (MH$^+$), measured 703.2 (MH$^+$).

Step 6: Preparation of benzyl 4-[(5M)-5-[6-bromo-3-(3-hydroxy-2,2-dimethyl-propyl)-1-azatricyclo[6.3.1.0$^{4,12}$]dodeca-2,4,6,8 (12)-tetraen-2-yl]-6-[(1S)-1-methoxyethyl]-3-pyridyl]piperazine-1-carboxylate (compound E6)

To a solution of benzyl 4-[5-[6-bromo-3-(3-methoxy-2,2-dimethyl-3-oxo-propyl)-1-azatricyclo[6.3.1.0$^{4,12}$]dodeca-2,4,6,8 (12)-tetraen-2-yl]-6-[(1S)-1-methoxyethyl]-3-pyridyl]piperazine-1-carboxylate (compound E5, 14.0 g, 19.9 mmol) in THF (150 mL) was added lithium borohydride (99.48 mL, 198.96 mmol) dropwise under N$_2$ at 0° C. After being stirred at 20° C. for 15 hrs, the reaction was quenched by sat. NH$_4$Cl aq. (600 mL) at 0° C. and the resultant mixture was extracted with EtOAc (100 mL, three times). The combined organic layer was washed with brine (200 mL), dried over Na$_2$SO$_4$, filtered and concentrated in vacuo to give a residue. The residue was purified by column chromatography to afford benzyl 4-[(5M)-5-[6-bromo-3-(3-hydroxy-2,2-dimethyl-propyl)-1-azatricyclo[6.3.1.0$^{4,12}$]dodeca-2,4,6,8 (12)-tetraen-2-yl]-6-[(1S)-1-methoxyethyl]-3-pyridyl]piperazine-1-carboxylate (compound E6, 7 g, faster eluted) as a yellow solid. MS calc'd 675.3 (MH$^+$), measured 675.2 (MH$^+$).

Step 7: Preparation of benzyl 4-[(5M)-5-[3-(3-hydroxy-2,2-dimethyl-propyl)-6-(4,4,5,5-tetramethyl-1,3,2-dioxaborolan-2-yl)-1-azatricyclo[6.3.1.0$^{4,12}$]dodeca-2,4 (12),5,7-tetraen-2-yl]-6-[(1S)-1-methoxyethyl]-3-pyridyl]piperazine-1-carboxylate (compound E7)

To a solution of benzyl 4-[(5M)-5-[6-bromo-3-(3-hydroxy-2,2-dimethyl-propyl)-1-azatricyclo[6.3.1.0$^{4,12}$]dodeca-2,4,6,8 (12)-tetraen-2-yl]-6-[(1S)-1-methoxyethyl]-3-pyridyl]piperazine-1-carboxylate (compound E6, 7.0 g, 10.36 mmol) and bis(pinacolato)diboron (3.95 g, 15.54 mmol) in toluene (140 mL) was added KOAc (2.56 g, 26.05 mmol) and Pd (dppf) C$_{12}$ (760.87 mg, 1.04 mmol). The mixture was degassed, purged with nitrogen for three times and stirred at 75° C. for 16 hrs. After being cooled to the room temperature, the reaction mixture was filtered and concentrated under vacuum to give a residue. The residue was purified by column chromatography to afford benzyl 4-[(5M)-5-[3-(3-hydroxy-2,2-dimethyl-propyl)-6-(4,4,5,5-tetramethyl-1,3,2-dioxaborolan-2-yl)-1-azatricyclo[6.3.1.0$^{4,12}$]dodeca-2,4 (12),5,7-tetraen-2-yl]-6-[(1S)-1-methoxyethyl]-3-pyridyl]piperazine-1-carboxylate (compound E7, 7.3 g) as a yellow solid. MS calc'd 723.4 (MH$^+$), measured 723.4 (MH$^+$).

Step 8: Preparation of methyl (3S)-1-[(2S)-3-[4-[(2M)-2-[5-(4-benzyloxycarbonylpiperazin-1-yl)-2-[(1S)-1-methoxyethyl]-3-pyridyl]-3-(3-hydroxy-2,2-dimethyl-propyl)-1-azatricyclo[6.3.1.04.12]dodeca-2,4 (12), 5,7-tetraen-6-yl] thiazol-2-yl]-2-(tert-butoxycarbonylamino) propanoyl]hexahydropyridazine-3-carboxylate (compound E8)

To a solution of benzyl 4-[(5M)-5-[3-(3-hydroxy-2,2-dimethyl-propyl)-6-(4,4,5,5-tetramethyl-1,3,2-dioxaborolan-2-yl)-1-azatricyclo[6.3.1.0$^{4,12}$]dodeca-2,4 (12), 5,7-tetraen-2-yl]-6-[(1S)-1-methoxyethyl]-3-pyridyl]piperazine-1-carboxylate (compound E7, 6.8 g, 9.41 mmol) and methyl (3S)-1-[(2S)-3-(4-bromothiazol-2-yl)-2-(tert-butoxycarbonylamino) propanoyl]hexahydropyridazine-3-carboxylate (Intermediate B, 4.9 g, 10.35 mmol) in toluene (90 mL)/1,4-dioxane (30 mL)/water (30 mL) was added K$_3$PO$_4$ (5.0 g, 23.52 mmol) and Pd (dtbpf) Cl$_2$ (613.2 mg, 0.94 mmol) in one portion. The mixture was degassed, purged with nitrogen for three times and then stirred at 70° C. for 15 hrs. After being cooled to room temperature, the reaction mixture was filtered and the filtrate was concentrated under vacuum to give a residue. The residue was purified by column chromatography to afford methyl (3S)-1-[(2S)-3-[4-[(2M)-2-[5-(4-benzyloxycarbonylpiperazin-1-yl)-2-[(1S)-1-methoxyethyl]-3-pyridyl]-3-(3-hydroxy-2,2-dimethyl-propyl)-1-azatricyclo[6.3.1.0$^{4,12}$]dodeca-2,4 (12),5,7-tetraen-6-yl] thiazol-2-yl]-2-(tert-butoxycarbonylamino) propanoyl] hexahydropyridazine-3-carboxylate (compound E8, 8.1 g) as a yellow solid. MS calc'd 993.7 (MH$^+$), measured 993.7 (MH$^+$).

Step 9: Preparation of (3S)-1-[(2S)-3-[4-[(2M)-2-[5-(4-benzyloxycarbonylpiperazin-1-yl)-2-[(1S)-1-methoxyethyl]-3-pyridyl]-3-(3-hydroxy-2,2-dimethyl-propyl)-1-azatricyclo[6.3.1.0$^{4,12}$]dodeca-2,4 (12),5,7-tetraen-6-yl]thiazol-2-yl]-2-(tert-butoxycarbonylamino) propanoyl]hexahydropyridazine-3-carboxylic acid (compound E9)

To the mixture of methyl (3S)-1-[(2S)-3-[4-[(2M)-2-[5-(4-benzyloxycarbonylpiperazin-1-yl)-2-[(1S)-1-methoxyethyl]-3-pyridyl]-3-(3-hydroxy-2,2-dimethyl-propyl)-1-azatricyclo[6.3.1.0$^{4,12}$]dodeca-2,4 (12),5,7-tetraen-6-yl]thiazol-2-yl]-2-(tert-butoxycarbonylamino) propanoyl] hexahydropyridazine-3-carboxylate (compound E8, 8.1 g, 8.16 mmol) in DCE (160 mL) was added trimethyltin hydroxide (5.9 g, 32.62 mmol) in one portion. After being stirred at 60° C. for 16 hrs, the reaction mixture was poured into water (200 mL) and extracted with EtOAc (100 mL, three times). The combined organic layer was washed with brine (200 mL), dried over anhydrous Na$_2$SO$_4$, filtered. The filtrate was concentrated under vacuum to afford (3S)-1-[(2S)-3-[4-[(2M)-2-[5-(4-benzyloxycarbonylpiperazin-1-yl)-2-[(1S)-1-methoxyethyl]-3-pyridyl]-3-(3-hydroxy-2,2-dimethyl-propyl)-1-azatricyclo[6.3.1.0$^{4,12}$]dodeca-2,4 (12), 5,7-tetraen-6-yl]thiazol-2-yl]-2-(tert-butoxycarbonylamino) propanoyl]hexahydropyridazine-3-carboxylic acid (compound E9, 7.9 g) as a brown solid. MS calc'd 979.5 (MH$^+$), measured 979.5 (MH$^+$).

Step 10: Preparation of benzyl 4-[(5M)-5-[(7S,13S)-7-(tert-butoxycarbonylamino)-17,17-dimethyl-8,14-dioxo-15-oxa-4-thia-9,21,30,31-tetrazahexacyclo[23.3.1.1$^{2,5}$.1$^{9,13}$.0$^{19,27}$. 0$^{21,26}$]hentriaconta-1 (28),2,5 (31), 19,25 (29),26-hexaen-20-yl]-6-[(1S)-1-methoxyethyl]-3-pyridyl]piperazine-1-carboxylate (compound E10)

To a solution of (3S)-1-[(2S)-3-[4-[(2M)-2-[5-(4-benzyloxycarbonylpiperazin-1-yl)-2-[(1S)-1-methoxyethyl]-3-pyridyl]-3-(3-hydroxy-2,2-dimethyl-propyl)-1-azatricyclo[6.3.1.0$^{4,12}$]dodeca-2,4 (12), 5,7-tetraen-6-yl]thiazol-2-yl]-2-(tert-butoxycarbonylamino) propanoyl]hexahydropyridazine-3-carboxylic acid (compound E9, 6.8 g, 6.94 mmol) in DCM (700 mL) was added DIEA (24.2 mL, 138.89 mmol), EDCI (19.9 g, 104.17 mmol) and HOBt (2.4 g, 17.36 mmol) at 0° C. After being stirred at 30° C. for 15 hrs, the reaction mixture was poured into water (500 mL), and extracted with EtOAc (300 mL, three times). The combined organic layer was washed with brine (300 mL), dried over Na$_2$SO$_4$, filtered. The filtrate was concentrated under vacuum to give a residue, which was purified by silica column to afford benzyl 4-[(5M)-5-[(7S,13S)-7-(tert-butoxycarbonylamino)-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-20-yl]-6-[(1S)-1-methoxyethyl]-3-pyridyl]piperazine-1-carboxylate (compound E10, 5.6 g) as a yellow solid. MS calc'd 961.5 (MH$^+$), measured 961.5 (MH$^+$).

Step 11: Preparation of tert-butyl N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]carbamate (compound E11)

To a solution of benzyl 4-[(5M)-5-[(7S,13S)-7-(tert-butoxycarbonylamino)-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-20-yl]-6-[(1S)-1-methoxyethyl]-3-pyridyl]piperazine-1-carboxylate (compound E10, 5.6 g, 5.83 mmol) and formaldehyde (1.9 g, 23.3 mmol) in methanol (150 mL) was added Pd(OH)$_2$ on activated carbon (3.0 g, 2.91 mmol) under nitrogen atmosphere. The reaction mixture was degassed and purged with H$_2$ for three times and then it was stirred at 35° C. for 15 hrs under H$_2$ (15 psi). After being cooled to room temperature, the reaction mixture was filtered and the filtrate was concentrated under vacuum to give a residue. EtOAc (50 mL) and water (50 mL) were added into the residue and the layers were separated. The aqueous phase was extracted with EtOAc (50 mL, twice). The combined organic layer was washed with brine (60 mL), dried over Na$_2$SO$_4$, filtered. The filtrate was concentrated under vacuum to give tert-butyl N-[(7S,13S)-(20M)-20-[2-[(1S)-1-methoxyethyl]-5-(4-methylpiperazin-1-yl)-3-pyridnyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaen-7-yl]carbamate (compound E11, 3.9 g) as a yellow solid which was used in the next step without further purification. MS calc'd 841.5 (MH$^+$), measured 841.4 (MH$^+$).

Step 12: Preparation of (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate E)

To a solution of tert-butyl N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaen-7-yl]carbamate (compound E11, 3.9 g, 4.6 mmol) in DCM (30 mL) was added TFA (15.0 mL) in one portion. After being stirred at 25° C. for 1 h, the mixture was poured into water (100 mL) and extracted with EtOAc (200 mL). The organic phase was washed with water (50 mL, twice). The combined aqueous phase was basified with sat. NaHCO$_3$ aq. until pH=9 and extracted with EtOAc (100 mL, three times). The combined organic layer was washed with brine (200 mL), dried over anhydrous Na$_2$SO$_4$, filtered and concentrated under vacuum to afford (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate E, 2.95 g) as a yellow solid. MS calc'd 741.5 (MH$^+$), measured 741.4 (MH$^+$).

Intermediate F (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione

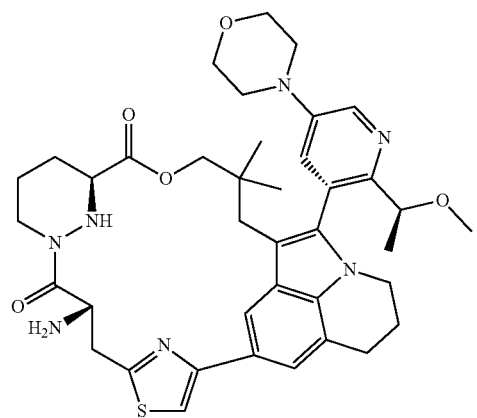

The compound was prepared according to the following scheme:

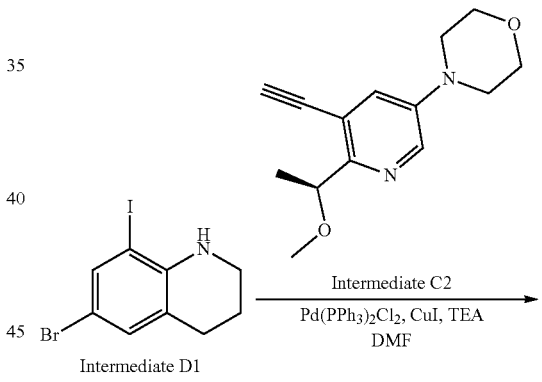

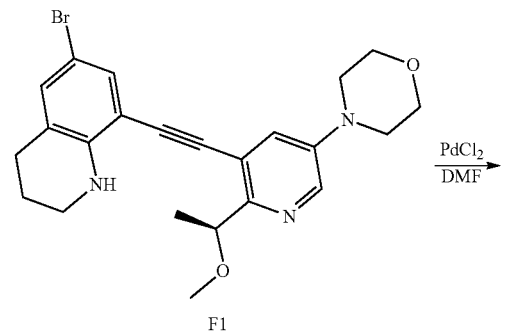

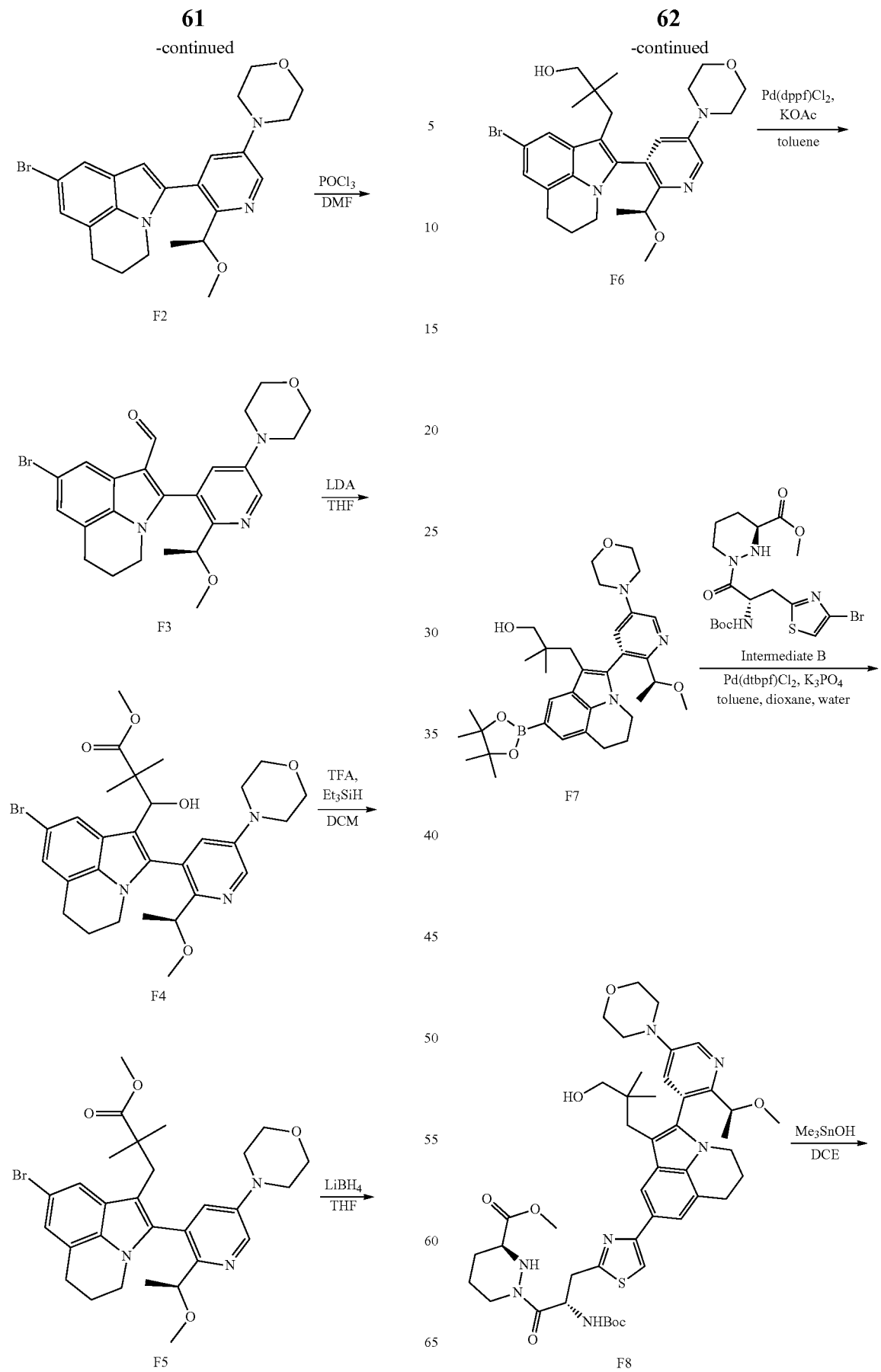

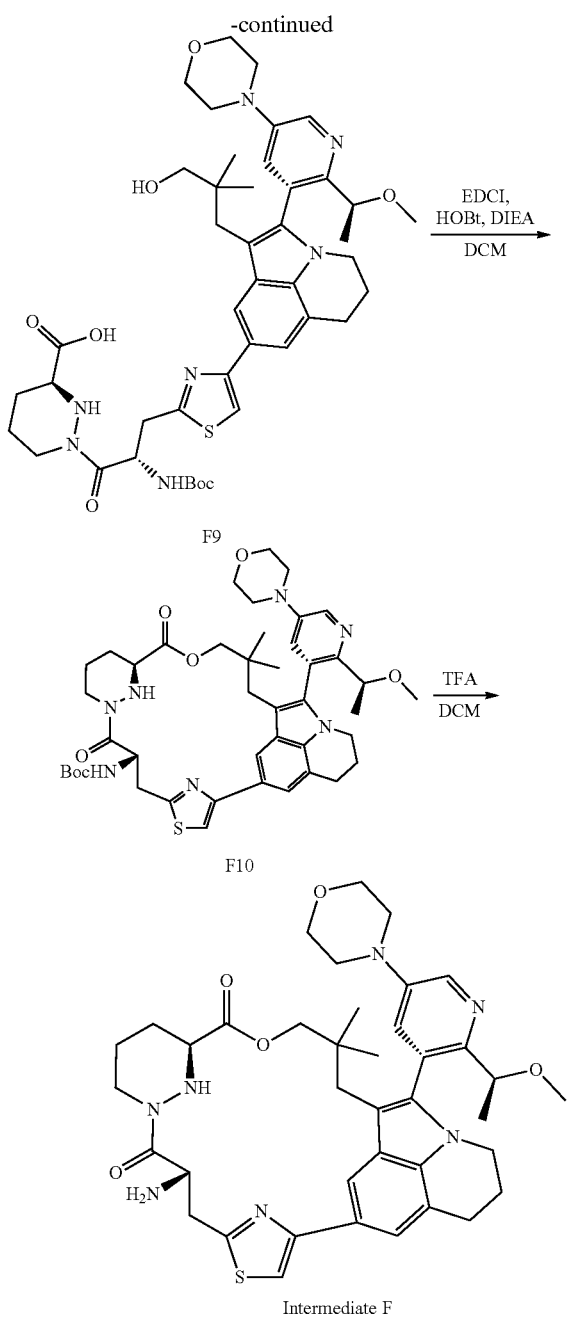

Step 1: Preparation of 4-[5-[2-(6-bromo-1,2,3,4-tetrahydroquinolin-8-yl) ethynyl]-6-[(1S)-1-methoxyethyl]-3-pyridyl] morpholine (compound F1).

To a solution of 4-[5-ethynyl-6-[(1S)-1-methoxyethyl]-3-pyridyl]morpholine (intermediate C2, 27.6 g, 112.06 mmol) in DMF (650 mL) were added 6-bromo-8-iodo-1,2,3,4-tetrahydroquinoline (intermediate D1, 37.9 g, 112.14 mmol), TEA (78 mL, 560.73 mmol), CuI (2.14 g, 11.24 mmol) and Pd(PPh$_3$)$_2$Cl$_2$ (7.9 g, 11.24 mmol). The reaction mixture was degassed and purged with nitrogen for three times and then it was stirred at 25° C. for 12 hrs. After the reaction completed, the reaction mixture was poured into water (1.4 L), and extracted with 10 EtOAc (800 mL, three times). The combined organic layer was washed with brine (800 mL, four times), dried over Na$_2$SO$_4$, filtered and concentrated under vacuum to give a residue, which was purified by column chromatography to afford 4-[5-[2-(6-bromo-1,2,3,4-tetrahydroquinolin-8-yl) ethynyl]-6-[(1S)-1-methoxyethyl]-3-pyridyl]morpholine (compound F1, 33.0 g) as a yellow solid. MS calc'd 456.1 (MH$^+$), measured 456.1 (MH$^+$).

Step 2: Preparation of 4-[5-(6-bromo-1-azatricyclo[6.3.1.0$^{4,12}$]dodeca-2,4,6,8 (12)-tetraen-2-yl)-6-[(1S)-1-methoxyethyl]-3-pyridyl]morpholine (compound F2).

To a solution of 4-[5-[2-(6-bromo-1,2,3,4-tetrahydroquinolin-8-yl) ethynyl]-6-[(1S)-1-methoxyethyl]-3-pyridyl] morpholine (compound F1, 33.0 g, 72.31 mmol) in DMF (400 mL) was added PdCl$_2$ (2.6 g, 14.46 mmol) in one portion. The reaction mixture was degassed under vacuum, flashed with nitrogen for three times and then heated to 60° C. for 15 hrs. After being cooled to the room temperature, the mixture was poured into water (800 mL), and extracted with EtOAc (500 mL, three times). The combined organic layer was washed with brine (400 mL, three times), dried over Na$_2$SO$_4$, filtered and concentrated under vacuum to give a residue, which was purified by column chromatography to afford 4-[5-(6-bromo-1-azatricyclo[6.3.1.0$^{4,12}$]dodeca-2,4,6,8 (12)-tetraen-2-yl)-6-[(1S)-1-methoxyethyl]-3-pyridyl]morpholine (compound F2, 25.0 g) as a yellow solid. MS calc'd 456.1 (MH$^+$), measured 456.1 (MH$^+$).

Step 3: Preparation of 6-bromo-2-[2-[(1S)-1-methoxyethyl]-5-morpholino-3-pyridyl]-1-azatricyclo[6.3.1.0$^{4,12}$]dodeca-2,4,6,8 (12)-tetraene-3-carbaldehyde (compound F3).

Phosphorus oxychloride (51.1 mL, 547.83 mmol) was added into DMF (500 mL) dropwise slowly at 0° C. After being stirred at 0° C. for 0.5 h, the reaction mixture was added with a solution of 4-[5-(6-bromo-1-azatricyclo [6.3.1.0$^{4,12}$]dodeca-2,4,6,8 (12)-tetraen-2-yl)-6-[(1S)-1-methoxyethyl]-3-pyridyl]morpholine (compound F2, 25.0 g, 54.78 mmol) in DMF (375 mL) dropwise at 0° C. The reaction mixture was heated to 45° C., and then stirred for another 1.5 h. The reaction was quenched with sat. NaHCO$_3$ aq. solution (1.5 L), extracted with EtOAc (1 L, three times). The organic phase was washed with brine (600 mL, three times), dried over anhydrous Na$_2$SO$_4$, filtered and concentrated under vacuum to give a residue. The residue was purified by column chromatography to afford 6-bromo-2-[2-[(1S)-1-methoxyethyl]-5-morpholino-3-pyridyl]-1-azatricyclo[6.3.1.0$^{4,12}$]dodeca-2,4,6,8 (12)-tetraene-3-carbaldehyde (compound F3, 20.0 g) as a yellow solid. MS calc'd 484.1 (MH$^+$), measured 484.1 (MH$^+$).

Step 4: Preparation of methyl 3-[6-bromo-2-[2-[(1S)-1-methoxyethyl]-5-morpholino-3-pyridyl]-1-azatricyclo [6.3.1.0$^{4,12}$]dodeca-2,4,6,8 (12)-tetraen-3-yl]-3-hydroxy-2,2-dimethyl-propanoate (compound F4)

To a solution of methyl isobutyrate (25.3 g, 247.72 mmol) in THF (700 mL) was added LDA (123.8 mL, 247.73 mmol) dropwise at −70° C. under nitrogen atmosphere. After being stirred for 0.5 h, the reaction mixture was added with a solution of 6-bromo-2-[2-[(1S)-1-methoxyethyl]-5-morpholino-3-pyridyl]-1-azatricyclo[6.3.1.0$^{4,12}$]dodeca-2,4,6,8 (12)-tetraene-3-carbaldehyde (compound F3, 20.0 g, 41.29 mmol) in THF (200 mL) dropwise at −70° C. The reaction mixture was then allowed to warm up to room temperature and stirred for 1 h. After the reaction completed, the mixture was quenched with sat. NH$_4$Cl (1 L) aqueous solution and extracted with EtOAc (800 mL, three times). The organic phase was washed with brine (500 mL), dried with anhydrous Na$_2$SO$_4$, filtered and concentrated under vacuum to give a residue. The residue was purified by column chromatography to afford methyl 3-[6-bromo-2-[2-[(1S)-1-methoxyethyl]-5-morpholino-3-pyridyl]-1-azatricyclo [6.3.1.0$^{4,12}$]dodeca-2,4,6,8 (12)-tetraen-3-yl]-3-hydroxy-2, 2-dimethyl-propanoate (compound F4, 20 g) as a yellow solid. MS calc'd 586.2 (MH+), measured 586.2 (MH+).

Step 5: Preparation of methyl 3-[6-bromo-2-[2-[(1S)-1-methoxyethyl]-5-morpholino-3-pyridyl]-1-azatricyclo[6.3.1.0^{4,12}]dodeca-2,4,6,8 (12)-tetraen-3-yl]-2,2-dimethyl-propanoate (compound F5)

To a solution of methyl 3-[6-bromo-2-[2-[(1S)-1-methoxyethyl]-5-morpholino-3-pyridyl]-1-azatricyclo[6.3.1.0^{4,12}]dodeca-2,4,6,8 (12)-tetraen-3-yl]-3-hydroxy-2,2-dimethyl-propanoate (compound F4, 20 g, 34.1 mmol) and Et$_3$SiH (31.7 g, 272.87 mmol) in DCM (550 mL) was added TFA (110.0 mL, 1480.88 mmol) at 0° C. After being stirred at 25° C. for 12 hrs, the reaction mixture was concentrated under vacuum to give a residue, which was diluted with sat. NaHCO$_3$ aq. until pH=9 and extracted with EtOAc (500 mL, three times). The combined organic layer was dried over anhydrous Na$_2$SO$_4$, filtered and concentrated under vacuum to give a residue. The residue was purified by column to afford methyl 3-[6-bromo-2-[2-[(1S)-1-methoxyethyl]-5-morpholino-3-pyridyl]-1-azatricyclo[6.3.1.0^{4,12}]dodeca-2,4,6,8 (12)-tetraen-3-yl]-2,2-dimethyl-propanoate (compound F5, 17 g) as a yellow solid. MS calc'd 570.2 (MH+), measured 570.2 (MH+).

Step 6: Preparation of 3-[6-bromo-(2M)-2-[2-[(1S)-1-methoxyethyl]-5-morpholino-3-pyridyl]-1-azatricyclo[6.3.1.0^{4,12}]dodeca-2,4,6,8 (12)-tetraen-3-yl]-2,2-dimethyl-propan-1-ol (compound F6)

To a solution of methyl 3-[6-bromo-2-[2-[(1S)-1-methoxyethyl]-5-morpholino-3-pyridyl]-1-azatricyclo[6.3.1.0^{4,12}]dodeca-2,4,6,8 (12)-tetraen-3-yl]-2,2-dimethyl-propanoate (compound F5, 17 g, 29.8 mmol) in THF (370 mL) was added lithium borohydride (7.8 g, 358.03 mmol) under N$_2$ at 0° C. After being stirred at 25° C. for 15 hrs, the reaction was quenched by sat. NH$_4$Cl aq. (500 mL) at 0° C. and the resultant mixture was extracted with EtOAc (600 mL, three times). The combined organic layer was washed with brine (200 mL), dried over Na$_2$SO$_4$, filtered and concentrated in vacuo to give a residue. The residue was purified by column chromatography to afford 3-[6-bromo-(2M)-2-[2-[(1S)-1-methoxyethyl]-5-morpholino-3-pyridyl]-1-azatricyclo[6.3.1.0^{4,12}]dodeca-2,4,6,8 (12)-tetraen-3-yl]-2,2-dimethyl-propan-1-ol (compound F6, 7.9 g, faster eluted) as a yellow solid. MS calc'd 542.2 (MH+), measured 542.2 (MH+).

X-Ray Crystallographic Analysis of Compound F6

Absolute configuration structure of compound F6 was confirmed by X-ray crystallographic analysis of its (2S,3S)-2,3-bis[(4-methylbenzoyl)oxy]butanedioic acid salt acetonitrile solvate. (FIG. 1).

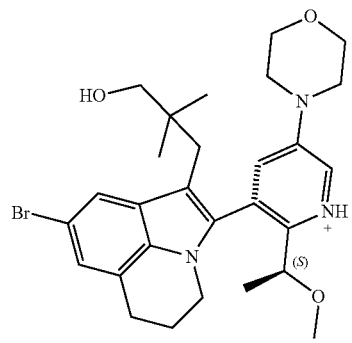

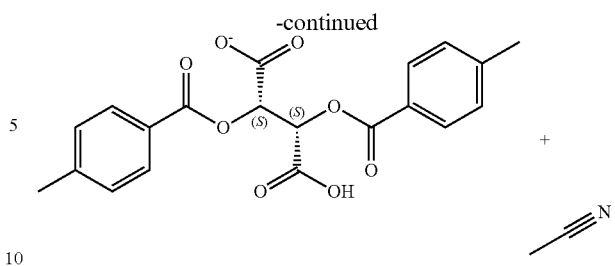

Step 7: Preparation of 3-[(2M)-2-[2-[(1S)-1-methoxyethyl]-5-morpholino-3-pyridyl]-6-(4,4,5,5-tetramethyl-1,3,2-dioxaborolan-2-yl)-1-azatricyclo[6.3.1.0^{4,12}]dodeca-2,4 (12), 5,7-tetraen-3-yl]-2,2-dimethyl-propan-1-ol (compound F7)

To a solution of 3-[6-bromo-(2M)-2-[2-[(1S)-1-methoxyethyl]-5-morpholino-3-pyridyl]-1-azatricyclo[6.3.1.0^{4,12}]dodeca-2,4,6,8 (12)-tetraen-3-yl]-2,2-dimethyl-propan-1-ol (compound F6, 7.3 g, 13.46 mmol) and bis(pinacolato)diboron (5.1 g, 20.2 mmol) in toluene (130 mL) was added KOAc (3.3 g, 33.63 mmol) and Pd (dppf) Cl$_2$ (993.0 mg, 1.36 mmol). The mixture was degassed, purged with nitrogen for three times and stirred at 90° C. for 12 hrs. After being cooled to the room temperature, the reaction mixture was filtered and concentrated under vacuum to give a residue. The residue was purified by column chromatography to afford 3-[(2M)-2-[2-[(1S)-1-methoxyethyl]-5-morpholino-3-pyridyl]-6-(4,4,5,5-tetramethyl-1,3,2-dioxaborolan-2-yl)-1-azatricyclo[6.3.1.0^{4,12}]dodeca-2,4 (12), 5,7-tetraen-3-yl]-2,2-dimethyl-propan-1-ol (compound F7, 7.14 g) as a yellow solid.MS calc'd 590.4 (MH+), measured 590.4 (MH+).

Step 8: Preparation of methyl (3S)-1-[(2S)-2-(tert-butoxycarbonylamino)-3-[4-[3-(3-hydroxy-2,2-dimethyl-propyl)-(2M)-2-[2-[(1S)-1-methoxyethyl]-5-morpholino-3-pyridyl]-1-azatricyclo[6.3.1.0^{4,12}]dodeca-2,4 (12),5,7-tetraen-6-yl]thiazol-2-yl]propanoyl]hexahydropyridazine-3-carboxylate (compound F8)

To a solution of 3-[(2M)-2-[2-[(1S)-1-methoxyethyl]-5-morpholino-3-pyridyl]-6-(4,4,5,5-tetramethyl-1,3,2-dioxaborolan-2-yl)-1-azatricyclo[6.3.1.0^{4,12}]dodeca-2,4 (12), 5,7-tetraen-3-yl]-2,2-dimethyl-propan-1-ol (compound F7, 7.14 g, 12.11 mmol) and methyl (3S)-1-[(2S)-3-(4-bromothiazol-2-yl)-2-(tert-butoxycarbonylamino) propanoyl]hexahydropyridazine-3-carboxylate (Intermediate B, 4.8 g, 10.1 mmol) in toluene (90 mL)/1,4-dioxane (30 mL)/water (30 mL) was added K$_3$PO$_4$ (5.4 g, 25.3 mmol) and Pd (dtbpf) Cl$_2$ (1.3 g, 2.03 mmol) in one portion. The mixture was degassed, purged with nitrogen for three times and then stirred at 70° C. for 12 hrs. After being cooled to room temperature, the reaction mixture was filtered and the filtrate was concentrated under vacuum to give a residue. The residue was purified by column chromatography to afford methyl (3S)-1-[(2S)-2-(tert-butoxycarbonylamino)-3-[4-[3-(3-hydroxy-2,2-dimethyl-propyl)-(2M)-2-[2-[(1S)-1-methoxyethyl]-5-morpholino-3-pyridyl]-1-azatricyclo[6.3.1.0^{4,12}]dodeca-2,4 (12), 5,7-tetraen-6-yl]thiazol-2-yl]propanoyl]hexahydropyridazine-3-carboxylate (compound F8, 7.9 g) as a yellow solid. MS calc'd 860.4 (MH+), measured 860.4 (MH+).

Step 9: Preparation of (3.5)-1-[(2S)-2-(tert-butoxycarbonylamino)-3-[4-[3-(3-hydroxy-2,2-dimethyl-propyl)-(2M)-2-[2-[(1S)-1-methoxyethyl]-5-morpholino-3-pyridyl]-1-azatricyclo[6.3.1.0^{4,12}]dodeca-2,4 (12),5,7-tetraen-6-yl]thiazol-2-yl]propanoyl]hexahydropyridazine-3-carboxylic acid (compound F9)

To the mixture of methyl (3S)-1-[(2S)-2-(tert-butoxycarbonylamino)-3-[4-[3-(3-hydroxy-2,2-dimethyl-propyl)-(2M)-2-[2-[(1S)-1-methoxyethyl]-5-morpholino-3-pyridyl]-1-azatricyclo[6.3.1.0$^{4,12}$]dodeca-2,4 (12),5,7-tetraen-6-yl] thiazol-2-yl]propanoyl]hexahydropyridazine-3-carboxylate (compound F8, 7.9 g, 9.19 mmol) in DCE (180 mL) was added trimethyltin hydroxide (8.3 g, 45.99 mmol) in one portion. After being stirred at 60° C. for 15 hrs, the reaction mixture was poured into water (80 mL) and extracted with EtOAc (200 mL, three times). The combined organic layer was washed with brine (200 mL), dried over anhydrous Na$_2$SO$_4$, filtered. The filtrate was concentrated under vacuum to afford (3S)-1-[(2S)-2-(tert-butoxycarbonylamino)-3-[4-[3-(3-hydroxy-2,2-dimethyl-propyl)-(2M)-2-[2-[(1S)-1-methoxyethyl]-5-morpholino-3-pyridyl]-1-azatricyclo[6.3.1.0$^{4,12}$]dodeca-2,4 (12), 5,7-tetraen-6-yl] thiazol-2-yl]propanoyl]hexahydropyridazine-3-carboxylic acid (compound F9, 7.5 g) as a yellow solid. MS calc'd 846.4 (MH$^+$), measured 846.4 (MH$^+$).

Step 10: Preparation of tert-butyl N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]carbamate (compound F10)

To a solution of (3S)-1-[(2S)-2-(tert-butoxycarbonylamino)-3-[4-[3-(3-hydroxy-2,2-dimethyl-propyl)-(2M)-2-[2-[(1S)-1-methoxyethyl]-5-morpholino-3-pyridyl]-1-azatricyclo[6.3.1.0$^{4,12}$]dodeca-2,4 (12), 5,7-tetraen-6-yl] thiazol-2-yl]propanoyl]hexahydropyridazine-3-carboxylic acid (compound F9, 7.5 g, 8.86 mmol) in DCM (1.5 L) was added DIEA (22.9 g, 177.38 mmol), EDCI (25.6 g, 133.61 mmol) and HOBt (3.0 g, 22.2 mmol) at 0° C. After being stirred at 25° C. for 12 hrs, the reaction mixture was poured into water (200 mL), and extracted with EtOAc (300 mL, three times). The combined organic layer was washed with brine (300 mL), dried over Na$_2$SO$_4$, and then filtered. The filtrate was concentrated under vacuum to give a residue, which was purified by column chromatography to afford tert-butyl N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaen-7-yl]carbamate (compound F10, 5.9 g) as a yellow solid. MS calc'd 828.4 (MH$^+$), measured 828.4 (MH$^+$).

Step 11: Preparation of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate F)

To a solution of tert-butyl N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaen-7-yl]carbamate (compound F10, 1.0 g, 1.21 mmol) in DCM (7 mL) was added TFA (3.5 mL) in one portion. After being stirred at 25° C. for 1 h, the mixture was poured into water (50 mL) and extracted with EtOAc (20 mL). The organic phase was washed with water (50 mL, twice). The combined aqueous phase was basified with sat. NaHCO$_3$ aq. until pH=9 and extracted with EtOAc (100 mL, three times). The combined organic layer was washed with brine (200 mL), dried over anhydrous Na$_2$SO$_4$, filtered and concentrated under vacuum to afford (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$] hentriaconta-1 (28),2,5 (31), 19,25 (29),26-hexaene-8,14-dione (Intermediate F, 760 mg) as a yellow solid. MS calc'd 741.4 (MH$^+$), measured 741.4 (MH$^+$).

Intermediate G (7S,13S)-7-amino-(20M)-20-[2-[(1S)-1-methoxyethyl]-5-[4-(2,2,2-trifluoroethyl) piperazin-1-yl]-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$] hentriaconta-1 (28),2,5 (31),19,25 (29),26-hexaene-8,14-dione

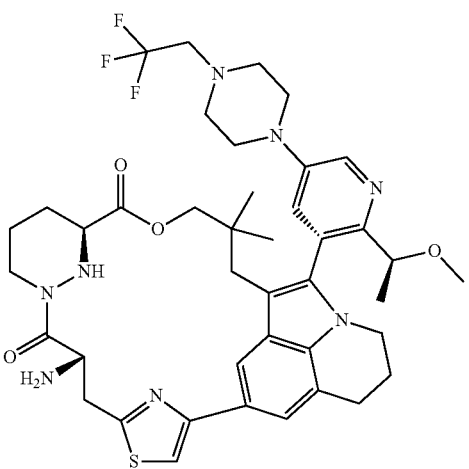

The compound was prepared according to the following scheme:

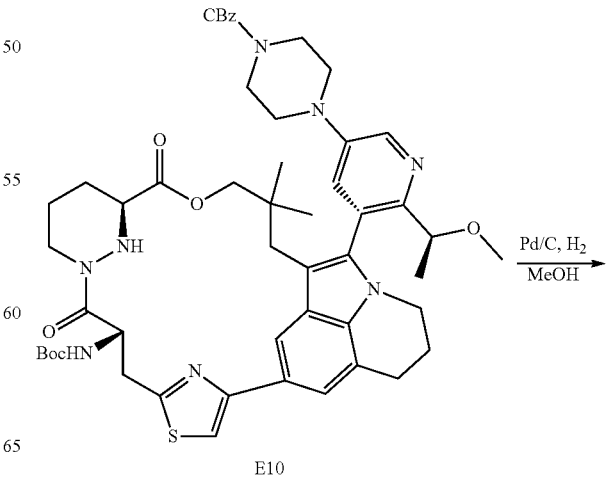

E10

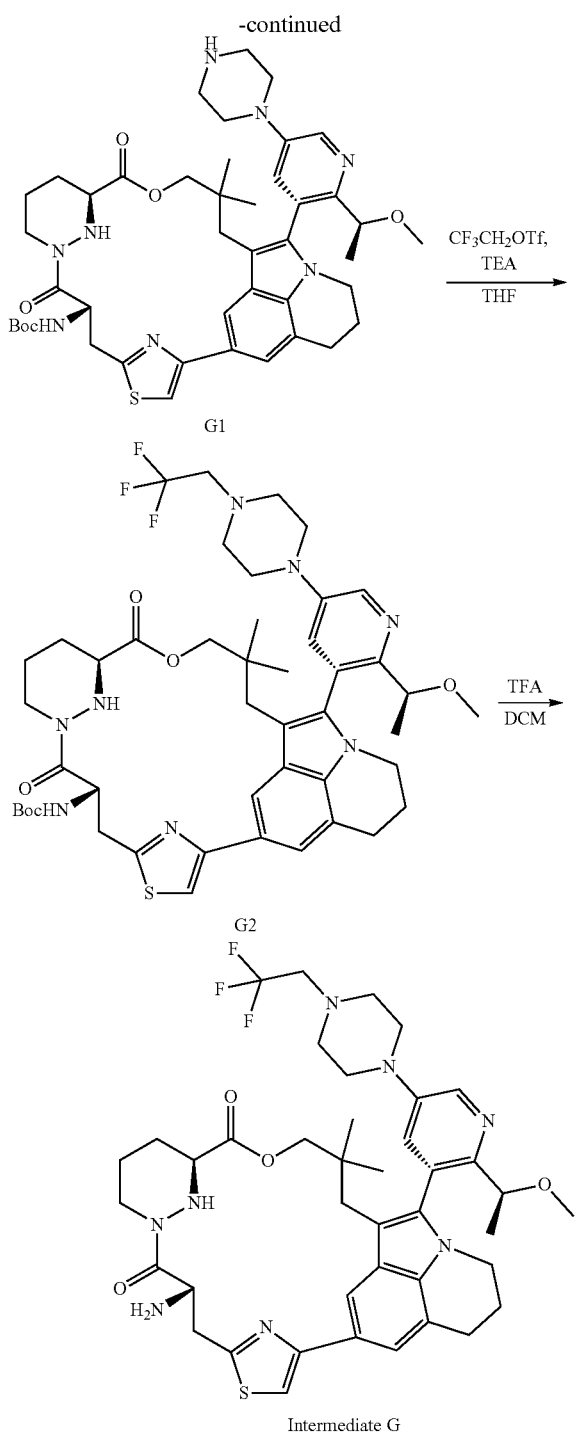

Step 1: Preparation of tert-butyl N-[(7S,13S)-(20M)-20-[2-[(1S)-1-methoxyethyl]-5-piperazin-1-yl-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]carbamate (compound G1)

To a solution of benzyl 4-[(5M)-5-[(7S,13S)-7-(tert-butoxycarbonylamino)-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-20-yl]-6-[(1S)-1-methoxyethyl]-3-pyridyl]piperazine-1-carboxylate (compound E10, 400.0 mg, 0.42 mmol) in EtOAc (8 mL) was added Pd/C on activated carbon (200.0 mg) under nitrogen atmosphere. The mixture was degassed and purged with H2 for three times and then stirred at 25° C. for 48 hrs under H$_2$ (15 psi). The reaction mixture was filtered and the filtrate was concentrated under vacuum to give tert-butyl N-[(7S,13S)-(20M)-20-[2-[(1S)-1-methoxyethyl]-5-piperazin-1-yl-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]carbamate (compound G1, 320.0 mg) as an off-white solid, which was used in the next step without further purification. MS calc'd 827.6 (MH$^+$), measured 827.4 (MH$^+$).

Step 2: Preparation of tert-butyl N-[(7S,13S)-(20M)-20-[2-[(1S)-1-methoxyethyl]-5-[4-(2,2,2-trifluoroethyl) piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]carbamate (compound G2).

To a solution of tert-butyl N-[(7S,13S)-(20M)-20-[2-[(1S)-1-methoxyethyl]-5-piperazin-1-yl-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaen-7-yl]carbamate (compound G1, 290.0 mg, 0.35 mmol) in THF (6 mL) was added TEA (0.15 mL, 1.05 mmol) and CF$_3$CH$_2$OTf (162.8 mg, 0.7 mmol). After being stirred at 60° C. for 15 hrs, the reaction mixture was concentrated under vacuum to give a residue. The residue was purified by silica gel column to afford tert-butyl N-[(7S,13S)-(20M)-20-[2-[(1S)-1-methoxyethyl]-5-[4-(2,2,2-trifluoroethyl) piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]carbamate (compound G2, 230.0 mg) as a white solid. MS calc'd 909.4 (MH$^+$), measured 909.4 (MH$^+$).

Step 3: Preparation of (7S,13S)-7-amino-(20M)-20-[2-[(1S)-1-methoxyethyl]-5-[4-(2,2,2-trifluoroethyl) piperazin-1-yl]-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (intermediate G).

To a solution of tert-butyl N-[(7S,13S)-(20M)-20-[2-[(1S)-1-methoxyethyl]-5-[4-(2,2,2-trifluoroethyl) piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaen-7-yl]carbamate (compound G2, 230.0 mg, 0.25 mmol) in DCM (2 mL) was added TFA (2 mL). After being stirred at 20° C. for 1 h, sat. NaHCO$_3$ solution (40 mL) was added into the reaction mixture and it was extracted with EtOAc (50 mL, three times). The combined organic layer was washed with brine (50 mL), dried over anhydrous sodium sulfate, filtered. The filtrate was concentrated under vacuum to afford (7S, 13S)-7-amino-(20M)-20-[2-[(1S)-1-methoxyethyl]-5-[4-(2, 2,2-trifluoroethyl) piperazin-1-yl]-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (intermediate G, 200.0 mg) as a yellow solid which was used in the next step without further purification. MS calc'd 809.4 (MH$^+$), measured 809.4 (MH$^+$).

Intermediate H (7S,13S)-7-amino-(20M)-20-[2-[(1S)-1-methoxy-ethyl]-5-(4-methylpiperazin-1-yl)-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1(28),2,5(31), 19,25(29),26-hexaene-8,14-dione

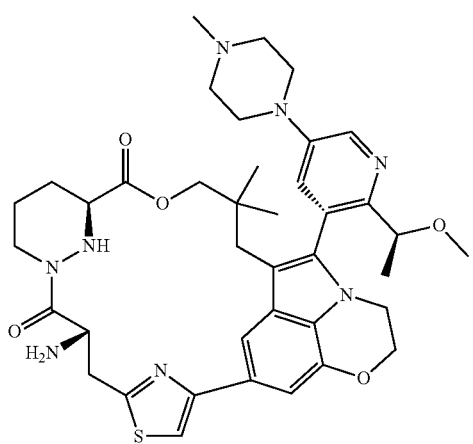

The title compound was prepared in analogy to the preparation of Intermediate E by using 7-bromo-5-iodo-3,4-dihydro-2H-1,4-benzoxazine (Intermediate D2) instead of 6-bromo-8-iodo-1,2,3,4-tetrahydroquinoline (Intermediate D1).

Intermediate I (7S,13S)-7-amino-(20M)-20-[2-[(1S)-1-methoxy-ethyl]-5-[4-(2,2,2-trifluoroethyl) piperazin-1-yl]-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1(28),2,5(31), 19,25(29),26-hexaene-8,14-dione

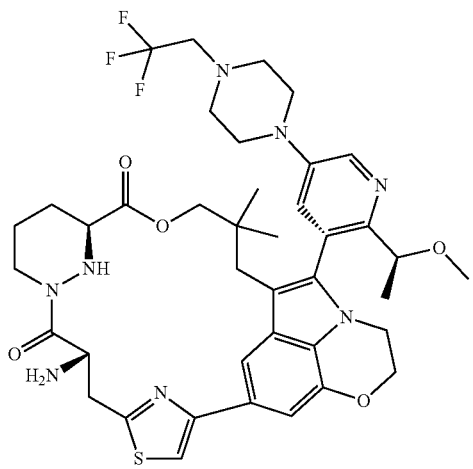

The title compound was prepared in analogy to the preparation of Intermediate E by using 1-[5-ethynyl-6-[(1S)-1-methoxyethyl]-3-pyridyl]-4-(2,2,2-trifluoroethyl) piperazine (Intermediate C3) and 7-bromo-5-iodo-3,4-dihydro-2H-1,4-benzoxazine (Intermediate D2) instead of Benzyl 4-[5-ethynyl-6-[(1S)-1-methoxyethyl]-3-pyridyl]piperazine-1-carboxylate (Intermediate C1) and 6-bromo-8-iodo-1,2,3,4-tetrahydroquinoline (Intermediate D1).

Intermediate J (7S,13S)-7-amino-(20M)-20-[2-[(1S)-1-methoxy-ethyl]-5-morpholino-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaene-8,14-dione

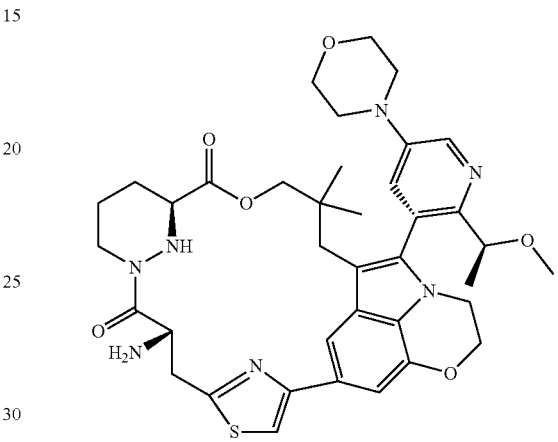

The title compound was prepared in analogy to the preparation of Intermediate E by using 4-[5-ethynyl-6-[(1S)-1-methoxyethyl]-3-pyridyl]morpholine (Intermediate C2) and 7-bromo-5-iodo-3,4-dihydro-2H-1,4-benzoxazine (Intermediate D2) instead of benzyl 4-[5-ethynyl-6-[(1S)-1-methoxyethyl]-3-pyridyl]piperazine-1-carboxylate (Intermediate C1) and 6-bromo-8-iodo-1,2,3,4-tetrahydroquinoline (Intermediate D1).

Intermediate K (7S,13S)-7-amino-23,23-difluoro-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaene-8,14-dione

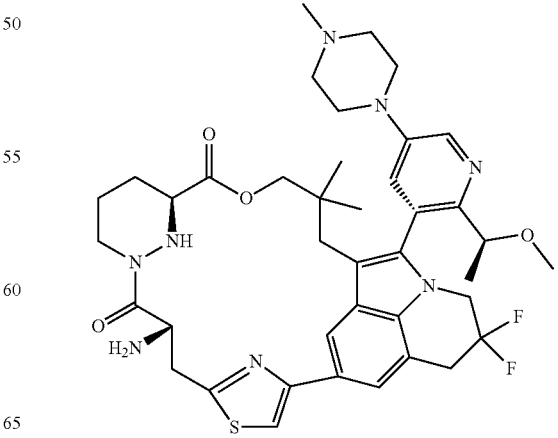

The title compound was prepared in analogy to the preparation of Intermediate E by using 6-bromo-3,3-difluoro-8-iodo-2,4-dihydro-1H-quinoline (Intermediate D3) instead of 6-bromo-8-iodo-1,2,3,4-tetrahydroquinoline (Intermediate D1).

Intermediate L (7S,13S)-(20M)-20-[5-[(9αS)-3,4,6,7,9,9a-hexahydro-1H-pyrazino[2,1-c][1,4]oxazin-8-yl]-2-[(1S)-1-methoxyethyl]-3-pyridyl]-7-amino-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione

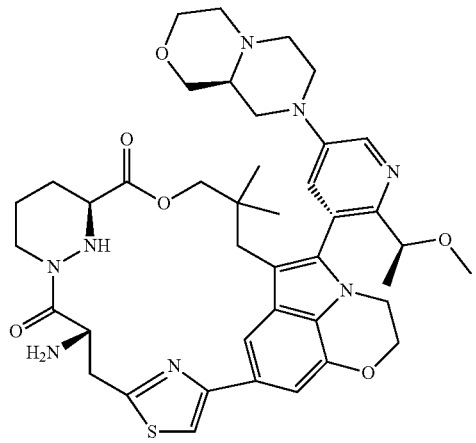

The title compound was prepared in analogy to the preparation of Intermediate E by using (9αS)-8-[5-ethynyl-6-[(1S)-1-methoxyethyl]-3-pyridyl]-3,4,6,7,9,9a-hexahydro-1H-pyrazino[2,1-c][1,4]oxazine (Intermediate C4) instead of benzyl 4-[5-ethynyl-6-[(1S)-1-methoxyethyl]-3-pyridyl]piperazine-1-carboxylate (Intermediate C1).

Intermediate L2

(7S,13S)-(20M)-20-[5-[(9αR)-1,3,4,6,7,8,9,9a-octahydropyrido[1,2-a]pyrazin-2-yl]-2-[(1S)-1-methoxyethyl]-3-pyridyl]-7-amino-17,17-dimethyl-15-oxa-4-thia-9,21,30,31-tetrazahexacyclo[23.3.1.1$^{2,5}$.0.1$^{19,13}$0.0$^{19,27}$0.0$^{21,26}$]hentriaconta-1 (28),2,5 (31), 19,25 (29),26-hexaene-8,14-dione

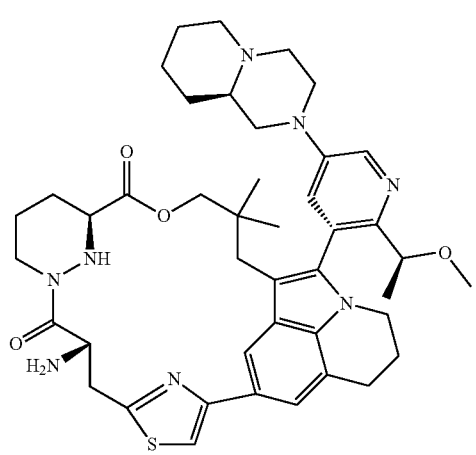

The title compound was prepared in analogy to the preparation of Intermediate L by using (9αR)-2-[5-ethynyl-6-[(1S)-1-methoxyethyl]-3-pyridyl]-1,3,4,6,7,8,9,9a-octahydropyrido[1,2-a]pyrazine (Intermediate C5) instead of (9αS)-8-[5-ethynyl-6-[(1S)-1-methoxyethyl]-3-pyridyl]-3,4,6,7,9,9a-hexahydro-1H-pyrazino[2,1-c][1,4]oxazine (Intermediate C4)

Intermediate M (7S,13S)-7-amino-(20M)-20-[2-[(1S)-1-methoxyethyl]-5-morpholino-3-pyridyl]-17,17,23,23-tetramethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione

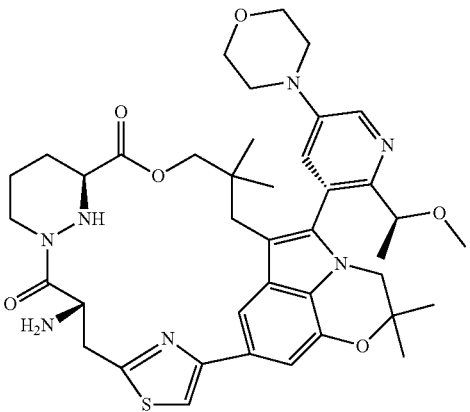

The title compound was prepared in analogy to the preparation of Intermediate E by using 7-bromo-5-iodo-2,2-dimethyl-3,4-dihydro-1,4-benzoxazine (Intermediate D4) and 4-[5-ethynyl-6-[(1S)-1-methoxyethyl]-3-pyridyl]morpholine (Intermediate C2) instead of 6-bromo-8-iodo-1,2,3,4-tetrahydroquinoline (compound D1) and benzyl 4-[5-ethynyl-6-[(1S)-1-methoxyethyl]-3-pyridyl]piperazine-1-carboxylate (Intermediate C1).

Intermediate N (7S,13S,22S)-7-amino-(20M)-20-[2-[(1S)-1-methoxyethyl]-5-morpholino-3-pyridyl]-17,17,22-trimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione

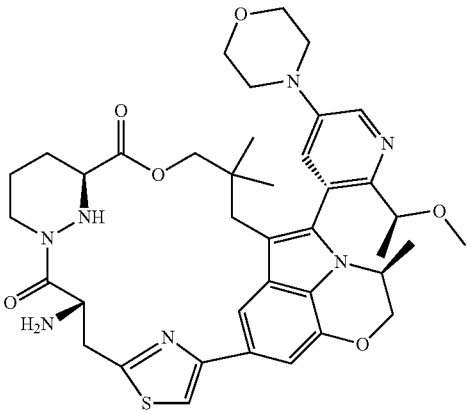

The title compound was prepared in analogy to the preparation of Intermediate E by using 7-bromo-5-iodo-3- methyl-3,4-dihydro-2H-1,4-benzoxazine (Intermediate D5) and 4-[5-ethynyl-6-[(1S)-1-methoxyethyl]-3-pyridyl]morpholine (Intermediate C2) instead of 6-bromo-8-iodo-1,2,3,4-tetrahydroquinoline (compound D1) and benzyl 4-[5-ethynyl-6-[(1S)-1-methoxyethyl]-3-pyridyl]piperazine-1-carboxylate (Intermediate C1).

Intermediate O (7S,13S)-7-amino-23,23-difluoro-(20M)-20-[2-[(1S)-1-methoxyethyl]-5-[4-(2,2,2-trifluoroethyl)piperazin-1-yl]-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaene-8,14-dione

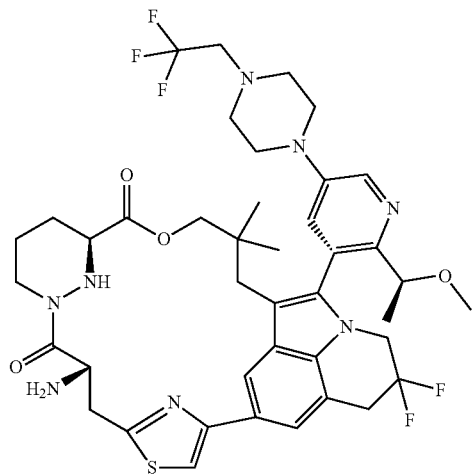

The title compound was prepared in analogy to the preparation of Intermediate E by using 6-bromo-3,3-difluoro-8-iodo-2,4-dihydro-1H-quinoline (Intermediate D3) and 1-[5-ethynyl-6-[(1S)-1-methoxyethyl]-3-pyridyl]-4-(2,2,2-trifluoroethyl) piperazine (Intermediate C3) instead of 6-bromo-8-iodo-1,2,3,4-tetrahydroquinoline (Intermediate D1) and benzyl 4-[5-ethynyl-6-[(1S)-1-methoxyethyl]-3-pyridyl]piperazine-1-carboxylate (Intermediate C1).

Intermediate P (7S,13S)-7-amino-(20M)-20-[2-[(1S)-1-methoxyethyl]-5-(4-methylpiperazin-1-yl)-3-pyridyl]-17,17,23,23-tetramethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaene-8,14-dione

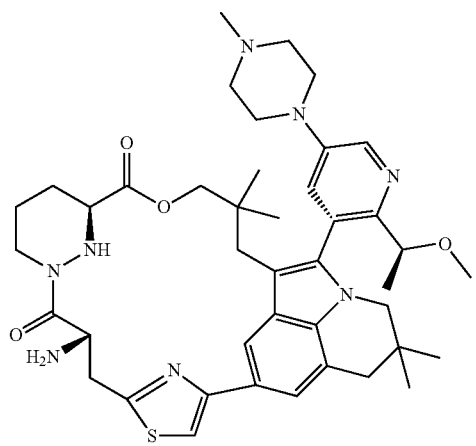

The title compound was prepared in analogy to the preparation of Intermediate E by using 6-bromo-8-iodo-3,3-dimethyl-2,4-dihydro-1H-quinoline (Intermediate D6) instead of 6-bromo-8-iodo-1,2,3,4-tetrahydroquinoline (Intermediate D1).

Intermediate Q (7S,13S)-7-amino-23,23-difluoro-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaene-8,14-dione

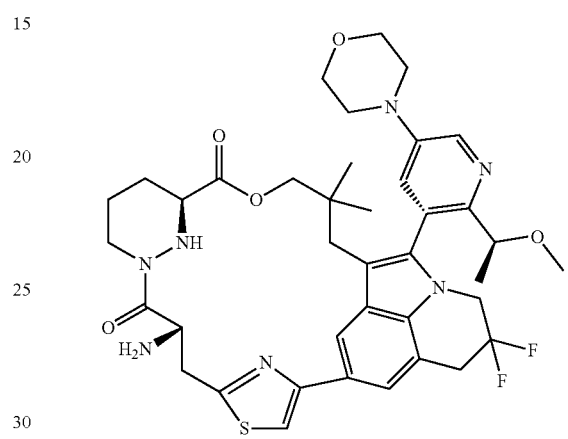

The title compound was prepared in analogy to the preparation of Intermediate E by using 6-bromo-3,3-difluoro-8-iodo-2,4-dihydro-1H-quinoline (Intermediate D3) and 4-[5-ethynyl-6-[(1S)-1-methoxyethyl]-3-pyridyl]morpholine (Intermediate C2) instead of 6-bromo-8-iodo-1,2,3,4-tetrahydroquinoline (compound D1) and benzyl 4-[5-ethynyl-6-[(1S)-1-methoxyethyl]-3-pyridyl]piperazine-1-carboxylate (Intermediate C1).

Intermediate R1

Trans-2-pyrimidin-5-ylcyclopropanecarboxylic acid

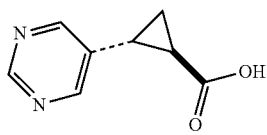

The compound was prepared according to the following scheme:

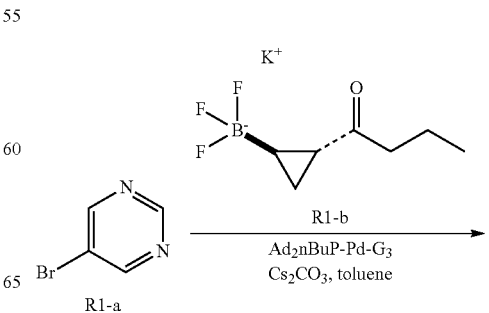

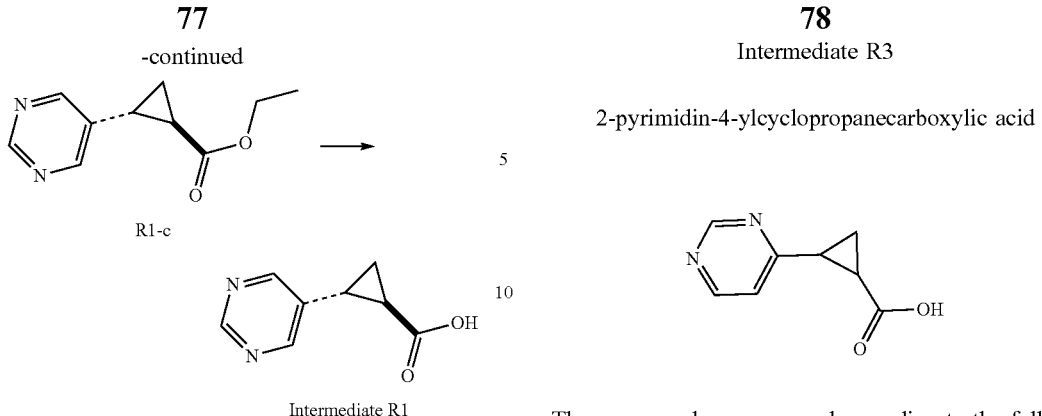

Step 1: trans-ethyl 2-pyrimidin-5-ylcyclopropanecarboxylate (compound R1-c)

To a solution of 5-bromopyrimidine (compound R1-a, 200.0 mg, 1.26 mmol), potassium (trans-2-(ethoxycarbonyl) cyclopropyl)trifluoroborate (compound R1-b, 276.8 mg, 1.26 mmol) in toluene/water (3 mL/0.3 mL) were added $Cs_2CO_3$ (819.7 mg, 2.52 mmol), $Ad_2nBuP$-Pd-$G_3$ (45.8 mg, 0.06 mmol). After being stirred at 90° C. for 16 hrs, the reaction mixture was cooled to room temperature. EtOAc (10 mL) and water (10 mL) were added to the reaction mixture and the layers were separated. The aqueous phase was extracted with EtOAc (10 mL, twice). The combined organic layer was washed with brine (10 mL), dried over $Na_2SO_4$, filtered and concentrated under vacuum to give a residue. The residue was purified by reversed-phase chromatography to afford trans-ethyl 2-pyrimidin-5-ylcyclopropanecarboxylate (compound R1-c, 100.0 mg) as yellow oil. MS calc'd 193.1 ($MH^+$), measured 193.1 ($MH^+$).

Step2: trans-2-pyrimidin-5-ylcyclopropanecarboxylic acid (Intermediate $R^1$)

To a solution of trans-ethyl 2-pyrimidin-5-ylcyclopropanecarboxylate (compound R1-c, 85.0 mg, 0.44 mmol) in ethanol (1 mL) was added NaOH aq. (1M, 0.5 mL, 0.53 mmol). After being stirred at 30° C. for 16 hrs, the reaction mixture was acidified by 1 M solution of HCl until pH=5. The mixture was concentrated directly and purified by reversed phase chromatography to give trans-2-pyrimidin-5-ylcyclopropanecarboxylic acid (Intermediate R1, 50.0 mg) as a white solid. MS calc'd 165.1 ($MH^+$), measured 165.1 ($MH^+$).

Intermediate R2

Trans-2-pyridazin-3-ylcyclopropanecarboxylic acid

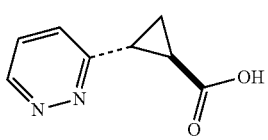

The title compound was prepared in analogy to the preparation of Intermediate $R^1$ by using 3-bromopyridazine instead of 5-bromopyrimidine (compound R1-a).

Intermediate R3

2-pyrimidin-4-ylcyclopropanecarboxylic acid

The compound was prepared according to the following scheme:

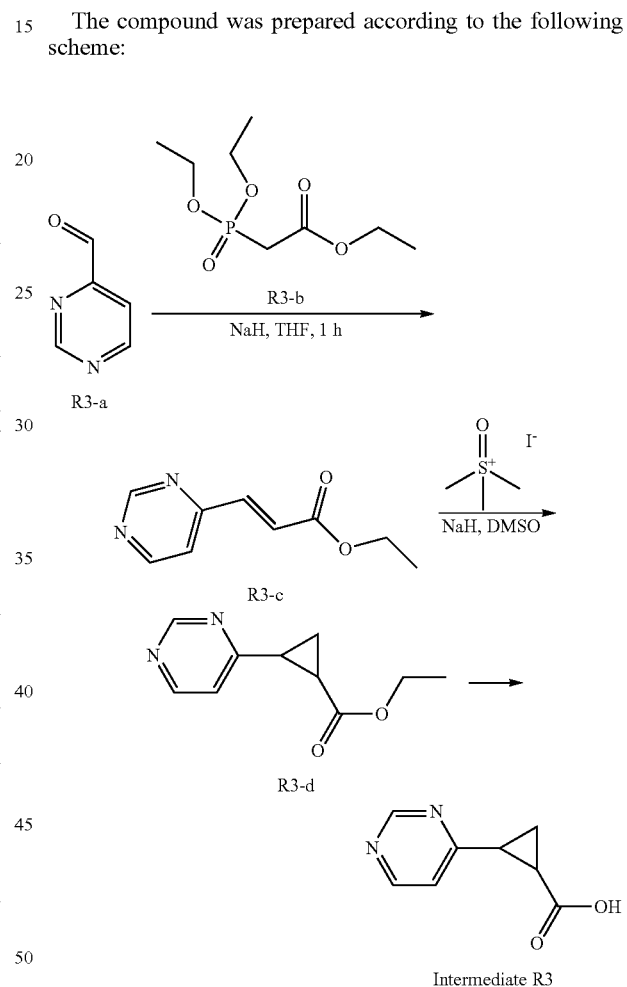

Step 1: ethyl (E)-3-pyrimidin-4-ylprop-2-enoate (compound R3-c)

To a stirred solution of pyrimidine-4-carboxaldehyde (compound R3-a, 400.0 mg, 3.7 mmol) and triethyl phosphonoacetate (compound R3-b, 829.6 mg, 3.7 mmol) in THF (10 mL) was added sodium hydride (177.6 mg, 7.4 mmol, 60% dispersion in mineral oil) at 0° C. After the reaction mixture was stirred for 2 hrs at 0° C., the reaction was quenched with $H_2O$ (5 mL) at the same temperature. The mixture was diluted by $H_2O$ (10 mL) and extracted by EA (20 mL, three times). The combined organic layer was washed with brine (30 mL), dried over $Na_2SO_4$, filtered, and concentrated under vacuum to give a residue. The residue was purified by flash chromatography to give ethyl (E)-3- pyrimidin-4-ylprop-2-enoate (compound R3-c, 530.0 mg) as a white solid. MS calc'd 179.1 (MH+), measured 179.1 (MH+).

Step 2: ethyl 2-pyrimidin-4-ylcyclopropanecarboxylate (compound R3-d)

To a solution of trimethylsulfoxonium iodide (2.2 g, 9.76 mmol) in DMSO (3 mL) was added sodium hydride (156.3 mg, 6.51 mmol, 60% dispersion in mineral oil) at 0° C. After being stirred at room temperature for 20 min under $N_2$, the reaction mixture was added with a solution of ethyl (E)-3-pyrimidin-4-ylprop-2-enoate (compound R3-c, 580.0 mg, 3.25 mmol) in THF (3 mL). After being stirred at room temperature for 1 h, EtOAc (10 mL) and water (10 mL) were added to the reaction mixture and the layers were separated. The aqueous phase was extracted with EtOAc (10 mL, twice). The combined organic layer was washed with brine (10 mL), dried over $Na_2SO_4$, filtered and concentrated under vacuum to give a residue. The residue was purified by flash chromatography to give ethyl 2-pyrimidin-4-ylcyclopropanecarboxylate (compound R3-d, 220.0 mg) as a white solid. MS calc'd 193.1 (MH+), measured 193.1 (MH+).

Step 3: 2-pyrimidin-4-ylcyclopropanecarboxylic acid (Intermediate $R^3$)

To a solution of ethyl 2-pyrimidin-4-ylcyclopropanecarboxylate (compound R3-d, 150.0 mg, 0.78 mmol) in ethanol (3 mL) was added NaOH aq. (1M, 0.9 mL, 0.9 mmol). After being stirred at 30° C. for 16 h, the reaction mixture was acidified by 1 M solution of HCl until pH=5. The mixture was concentrated directly and purified by reversed phase chromatography to give 2-pyrimidin-4-ylcyclopropanecarboxylic acid (Intermediate R3, 55.0 mg) as a white solid. MS calc'd 165.1 (MH+), measured 165.1 (MH+).

Intermediate R4

Trans-2-(4-pyridyl)cyclopropanecarboxylic acid

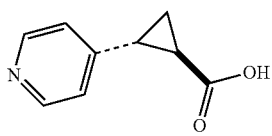

The title compound was prepared in analogy to the preparation of Intermediate R1 by using 4-bromopyridine instead of 5-bromopyrimidine (compound R1-a).

Intermediate R5

2-pyrimidin-2-ylcyclopropanecarboxylic acid

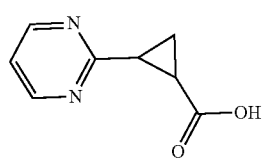 [SMILES: O=C(O)C1CC1c1ncccn1]

The title compound was prepared in analogy to the preparation of Intermediate R3 by using pyrimidine-2-carbaldehyde instead of pyrimidine-4-carboxaldehyde (compound R3-a)

Intermediate R6 trans-(1S,2S)-2-pyrazin-2-ylcyclopropanecarboxylic acid

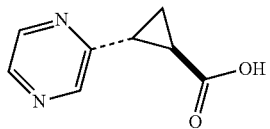

The title compound was prepared in analogy to the preparation of Intermediate R1 by using 2-bromopyrazine instead of 5-bromopyrimidine (compound R1-a).

Intermediate R7 trans-(1S,2S)-2-(4-methylpyrimidin-5-yl)cyclopropanecarboxylic acid

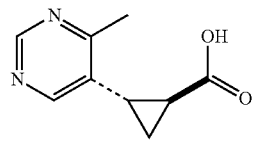

The title compound was prepared in analogy to the preparation of Intermediate R1 by using 5-bromo-4-methylpyrimidine instead of 5-bromopyrimidine (compound R1-a).

Intermediate R8 trans-(1S,2S)-2-thiazol-4-ylcyclopropanecarboxylic acid

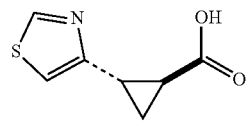

The title compound was prepared in analogy to the preparation of Intermediate R1 by using 4-bromothiazole instead of 5-bromopyrimidine (compound R1-a).

Intermediate R9 trans-(1S,2S)-2-(2-methyl-3-pyridyl)cyclopropanecarboxylic acid

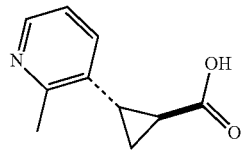

The title compound was prepared in analogy to the preparation of Intermediate R1 by using 3-bromo-2-methyl-pyridine instead of 5-bromopyrimidine (compound R1-a).

Intermediate R10 trans-(1S,2S)-2-(5-methyl-3-pyridyl)cyclopropan-ecarboxylic acid

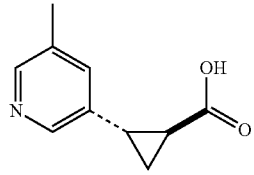

The title compound was prepared in analogy to the preparation of Intermediate R1 by using 3-bromo-5-methyl-pyridine instead of 5-bromopyrimidine (compound R1-a).

Intermediate S (7S,13S)-7-amino-(20M)-20-[2-[(1S)-1-methoxy-ethyl]-5-(4-methylpiperazin-1-yl)-3-pyridyl]-17,17-dimethyl-15,25-dioxa-4-thia-9,21,31,32-tetrazahexa-cyclo[24.3.1.1$^{2,5}$.0.1$^{9,13}$.0.0$^{19,28}$.0.0$^{21,27}$]dotriaconta-1(29),2,5(32),19,26(30),27-hexaene-8,14-dione

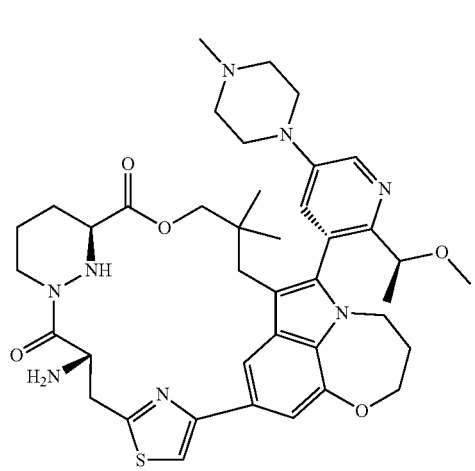

The title compound was prepared in analogy to the preparation of Intermediate E by using 8-bromo-6-iodo-2,3,4,5-tetrahydro-1,5-benzoxazepine (intermediate D7) instead of 6-bromo-8-iodo-1,2,3,4-tetrahydroquinoline (Intermediate D1).

Intermediate T (7S,13S)-7-amino-23-benzyloxy-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaene-8,14-dione

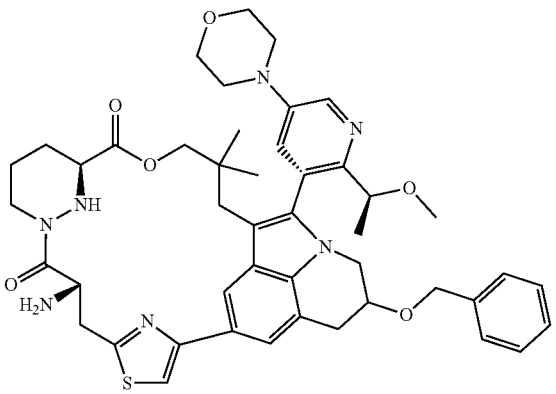

The compound was prepared according to the following scheme:

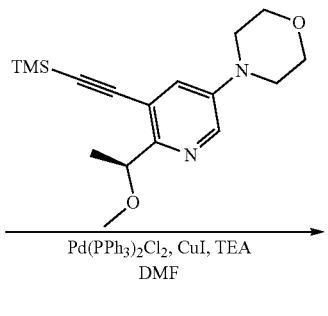

T1

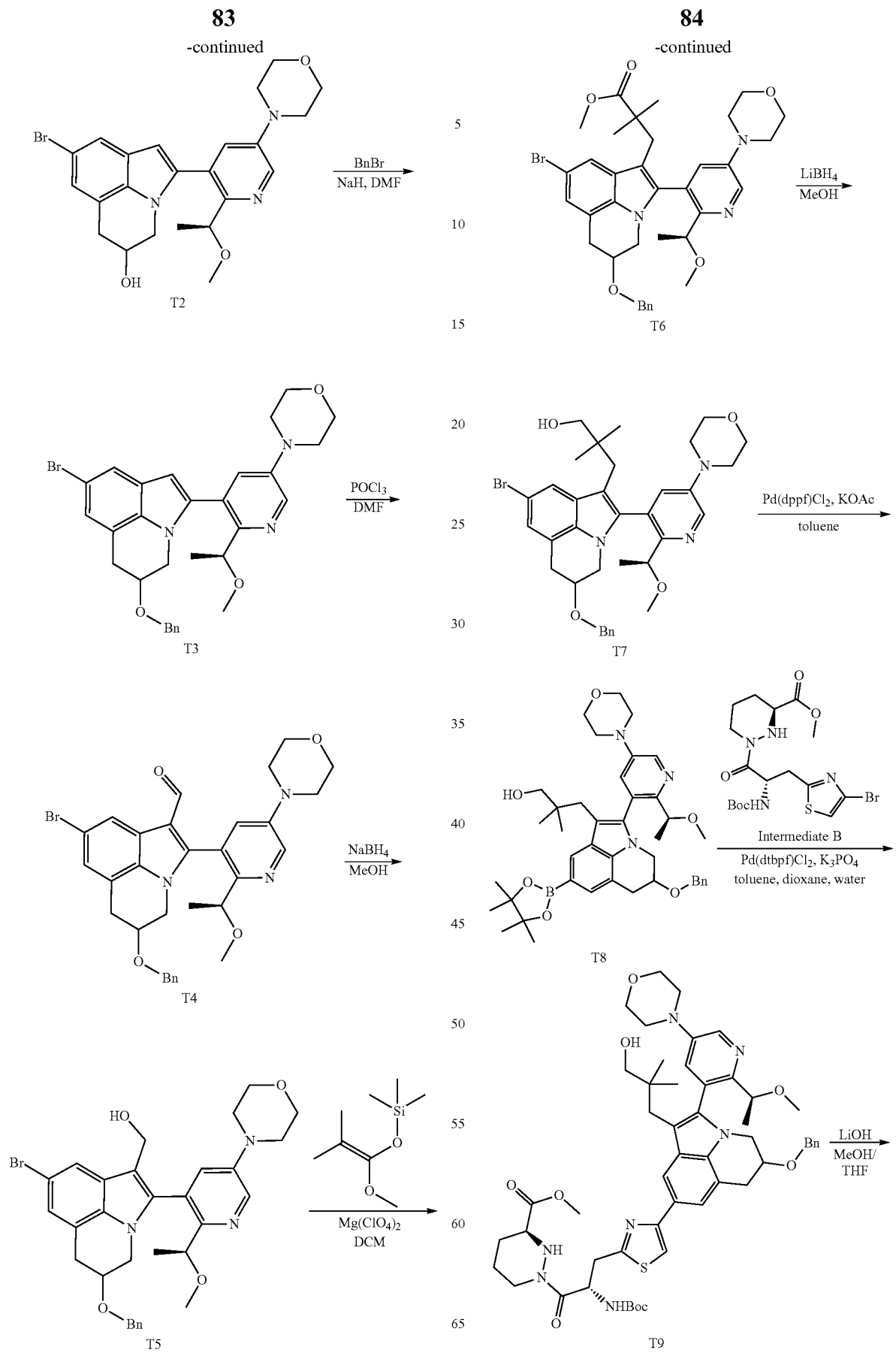

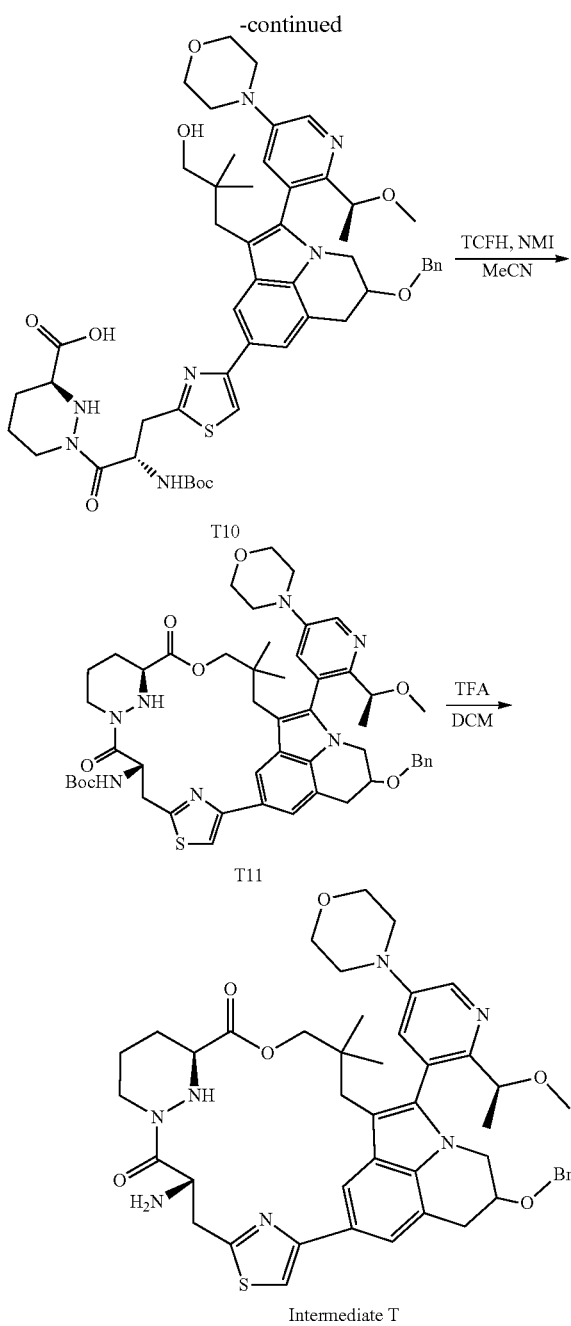

Step 1: Preparation of 6-bromo-8-[2-[2-[(1S)-1-methoxyethyl]-5-morpholino-3-pyridyl]ethynyl]-1,2,3,4-tetrahydroquinolin-3-ol (compound T1).

A suspension of 2-[2-[(1S)-1-methoxyethyl]-5-morpholino-3-pyridyl]ethynyl-trimethyl-silane (1.8 g, 5.65 mmol), 6-bromo-8-iodo-1,2,3,4-tetrahydroquinolin-3-ol (intermediate D9, 2 g, 5.65 mmol), Et$_3$N (1.71 g, 2.35 mL, 16.89 mmol), copper (I) iodide (107.3 mg, 0.56 mmol) and CsF (858.2 mg, 5.65 mmol) in THF (21 mL) was stirred at rt for 12 hrs under nitrogen atmosphere. After the reaction completed, the reaction mixture was filtered. The collected solid was washed with EtOAc (40 mL). The combined filtrate was washed with brine (10 mL), dried over Na$_2$SO$_4$ and concentrated under vacuum. The resulting residue was purified by silica gel chromatography to afford 6-bromo-8-[2-[2-[(1S)-1-methoxyethyl]-5-morpholino-3-pyridyl]ethynyl]-1,2,3,4-tetrahydroquinolin-3-ol (compound T1, 1.7 g) as a light yellow solid. MS calc'd 472.1 (MH$^+$), measured 472.1 (MH$^+$).

Step 2: Preparation of 6-bromo-2-[2-[(1S)-1-methoxyethyl]-5-morpholino-3-pyridyl]-1-azatricyclo[6.3.1.0$^{4,12}$]dodeca-2,4,6,8 (12)-tetraen-10-ol (compound T2).

To a solution of palladium (II) chloride (60 mg, 340.83 µmol) in DMF (25 mL) was stirred at 70° C. for 15 min under nitrogen atmosphere. A solution of 6-bromo-8-[2-[2-[(1S)-1-methoxyethyl]-5-morpholino-3-pyridyl]ethynyl]-1,2,3,4-tetrahydroquinolin-3-ol (compound T1, 1610 mg, 3.41 mmol) in DMF (25 mL) was added to the reaction mixture. After being stirred for another 18 hrs, the reaction mixture was added with water and then extracted with EA (100 mL, three times). The combined organic layer was concentrated and then purified by reversed-phase chromatography to afford 6-bromo-2-[2-[(1S)-1-methoxyethyl]-5-morpholino-3-pyridyl]-1-azatricyclo[6.3.1.0$^{4,12}$]dodeca-2,4,6,8 (12)-tetraen-10-ol (compound T2, 970 mg) as orange foam. MS calc'd 472.1 (MH$^+$), measured 472.1 (MH$^+$).

Step 3: Preparation of 4-[5-(10-benzyloxy-6-bromo-1-azatricyclo[6.3.1.0$^{4,12}$]dodeca-2,4,6,8 (12)-tetraen-2-yl)-6-[(1S)-1-methoxyethyl]-3-pyridyl]morpholine (compound T3).

A suspension of 6-bromo-2-[2-[(1S)-1-methoxyethyl]-5-morpholino-3-pyridyl]-1-azatricyclo[6.3.1.0$^{4,12}$]dodeca-2,4,6,8 (12)-tetraen-10-ol (compound T2, 970 mg, 1.95 mmol) in DMF (24 mL) was added NaH (60%, 156 mg, 3.9 mmol) at rt under nitrogen atmosphere. After being stirred at rt for 1 h, the reaction mixture was cooled to 0° C. and added with benzyl bromide (667 mg, 464 µL, 3.9 mmol). The reaction mixture was stirred at rt for 12 hrs. The reaction mixture was cooled to 0° C. and then the reaction was quenched with sat. NH$_4$Cl aq. (20 mL). EA (40 mL) was added to the reaction mixture and the water phase was extracted with EA (40 mL, three times). The combined organic layer was washed with brine and dried over Na$_2$SO$_4$, filtered and concentrated. The residue was purified by silica gel chromatography to afford 4-[5-(10-benzyloxy-6-bromo-1-azatricyclo[6.3.1.0$^{4,12}$]dodeca-2,4,6,8 (12)-tetraen-2-yl)-6-[(1S)-1-methoxyethyl]-3-pyridyl]morpholine (compound T3, 1 g) as orange oil. MS calc'd 562.1 (MH$^+$), measured 562.1 (MH$^+$).

Step 4: Preparation of 10-benzyloxy-6-bromo-2-[2-[(1S)-1-methoxyethyl]-5-morpholino-3-pyridyl]-1-azatricyclo[6.3.1.0$^{4,12}$]dodeca-2,4,6,8 (12)-tetraene-3-carbaldehyde (compound T4)

Phosphorus oxychloride (1 mL, 10.73 mmol) was added into DMF (10 mL) at 0° C. under nitrogen atmosphere. After being stirred at 0° C. for 0.5 h, the reaction mixture was added with a solution of 4-[5-(10-benzyloxy-6-bromo-1-azatricyclo[6.3.1.0$^{4,12}$]dodeca-2,4,6,8 (12)-tetraen-2-yl)-6-[(1S)-1-methoxyethyl]-3-pyridyl]morpholine (compound T3, 1 g, 1.78 mmol) in DMF (extra dry, 0.2 mL) dropwise under nitrogen atmosphere. After being stirred at room temperature for 2 hours, the reaction mixture was poured into cooled Sat. NaHCO$_3$ aq. (30 mL) at 0° C. and then extracted with EA (30 mL, three times). The combined organic layer was washed with brine (10 mL), dried over Na$_2$SO$_4$ and concentrated under vacuum to get a residue. The resulting residue was purified by silica gel chromatography to afford 10-benzyloxy-6-bromo-2-[2-[(1S)-1-methoxyethyl]-5-morpholino-3-pyridyl]-1-azatricyclo[6.3.1.0$^{4,12}$]dodeca-2,4,6,8 (12)-tetraene-3-carbaldehyde (compound T4, 900 mg, 77.16%) as an orange solid. MS calc'd 590.2 (MH$^+$), measured 590.2 (MH$^+$).

Step 5: Preparation of [10-benzyloxy-6-bromo-2-[2-[(1S)-1-methoxyethyl]-5-morpholino-3-pyridyl]-1-azatricyclo[6.3.1.0$^{4,12}$]dodeca-2,4,6,8 (12)-tetraen-3-yl]methanol (compound T5)

A solution of 10-benzyloxy-6-bromo-2-[2-[(1S)-1-methoxyethyl]-5-morpholino-3-pyridyl]-1-azatricyclo[6.3.1.0$^{4,12}$]dodeca-2,4,6,8 (12)-tetraene-3-carbaldehyde (compound T4, 900 mg, 1.37 mmol) in MeOH (20 mL) was added NaBH$_4$ (103.8 mg, 2.74 mmol) at rt. The reaction mixture was stirred at rt for 1 h. The solution was removed under vacuum to get a residue. The residue was purified by silica gel chromatography to afford [10-benzyloxy-6-bromo-2-[2-[(1S)-1-methoxyethyl]-5-morpholino-3-pyridyl]-1-azatricyclo[6.3.1.0$^{4,12}$]dodeca-2,4,6,8 (12)-tetraen-3-yl]methanol (compound T5, 740 mg) as light yellow oil. MS calc'd 592.2 (MH$^+$), measured 592.2 (MH$^+$).

Step 6: Preparation of methyl 3-[10-benzyloxy-6-bromo-2-[2-[(1S)-1-methoxyethyl]-5-morpholino-3-pyridyl]-1-azatricyclo[6.3.1.0$^{4,12}$]dodeca-2,4,6,8 (12)-tetraen-3-yl]-2,2-dimethyl-propanoate (compound T6)

A solution of 1-methoxy-1-(trimethylsiloxy)-2-methyl-1-propene (653.1 mg, 759.41 μL, 3.75 mmol) and [10-benzyloxy-6-bromo-2-[2-[(1S)-1-methoxyethyl]-5-morpholino-3-pyridyl]-1-azatricyclo[6.3.1.0$^{4,12}$]dodeca-2,4,6,8 (12)-tetraen-3-yl]methanol (compound T5, 740 mg, 1.25 mmol) in DCM (10 mL) was stirred at rt for 15 min. The reaction mixture was added with magnesium perchlorate (557.5 mg, 2.5 mmol) and then stirred for another 12 hrs. The reaction was quenched with Sat. NaHCO$_3$ aq. (10 mL) and DCM (30 mL). The organic layer was washed with water (3 mL, three times), brine (3 mL), dried over Na$_2$SO$_4$ and concentrated under vacuum to get a residue. The resulting residue was purified by silica gel chromatography to afford methyl 3-[10-benzyloxy-6-bromo-2-[2-[(1S)-1-methoxyethyl]-5-morpholino-3-pyridyl]-1-azatricyclo[6.3.1.0$^{4,12}$]dodeca-2,4,6,8 (12)-tetraen-3-yl]-2,2-dimethyl-propanoate (compound T6, 560 mg) as light yellow oil. MS calc'd 676.2 (MH$^+$), measured 676.2 (MH$^+$).

Step 7: Preparation of 3-[10-benzyloxy-6-bromo-2-[2-[(1S)-1-methoxyethyl]-5-morpholino-3-pyridyl]-1-azatricyclo[6.3.1.0$^{4,12}$]dodeca-2,4,6,8 (12)-tetraen-3-yl]-2,2-dimethyl-propan-1-ol (compound T7)

To a solution of methyl 3-[10-benzyloxy-6-bromo-2-[2-[(1S)-1-methoxyethyl]-5-morpholino-3-pyridyl]-1-azatricyclo[6.3.1.0$^{4,12}$]dodeca-2,4,6,8 (12)-tetraen-3-yl]-2,2-dimethyl-propanoate (compound T6, 560 mg, 0.828 mmol) in THF (5 mL) was added 2 M LiBH$_4$ (827 μL, 1.66 mmol) dropwise under N$_2$ at 0° C. After being stirred at rt for 15 hrs, the reaction was quenched by sat. NH$_4$Cl aq. (10 mL) at 0° C. and the resultant mixture was extracted with EtOAc (10 mL, three times). The combined organic layer was washed with brine (20 mL), dried over Na$_2$SO$_4$, filtered and concentrated in vacuo to give a residue. The residue was purified by column chromatography to afford 3-[10-benzyloxy-6-bromo-2-[2-[(1S)-1-methoxyethyl]-5-morpholino-3-pyridyl]-1-azatricyclo[6.3.1.0$^{4,12}$]dodeca-2,4,6,8 (12)-tetraen-3-yl]-2,2-dimethyl-propan-1-ol (compound T7, 525 mg) as light yellow oil. MS calc'd 648.2 (MH$^+$), measured 648.2 (MH$^+$).

Step 8: Preparation of 3-[10-benzyloxy-2-[2-[(1S)-1-methoxyethyl]-5-morpholino-3-pyridyl]-6-(4,4,5,5-tetramethyl-1,3,2-dioxaborolan-2-yl)-1-azatricyclo[6.3.1.0$^{4,12}$]dodeca-2,4 (12),5,7-tetraen-3-yl]-2,2-dimethyl-propan-1-ol (compound T8)

To a solution of 3-[10-benzyloxy-6-bromo-2-[2-[(1S)-1-methoxyethyl]-5-morpholino-3-pyridyl]-1-azatricyclo[6.3.1.0$^{4,12}$]dodeca-2,4,6,8 (12)-tetraen-3-yl]-2,2-dimethyl-propan-1-ol (compound T7, 525 mg, 809.4 μmol), bis(pinacolato)diboron (246.6 mg, 971.28 μmol) and KOAc (198 mg, 2.02 mmol) in 1,4-dioxane (6 mL) was added Pd (dppf) C12 (66 mg, 80.94 μmol). The mixture was degassed and purged with nitrogen atmosphere for three times and the mixture was stirred at 90° C. for 2 hrs. After the reaction completed, the mixture was cooled to room temperature, then filtered, and the filtrate was concentrated in vacuo to give a residue. The residue was purified by silica column chromatography to afford 3-[10-benzyloxy-2-[2-[(1S)-1-methoxyethyl]-5-morpholino-3-pyridyl]-6-(4,4,5,5-tetramethyl-1,3,2-dioxaborolan-2-yl)-1-azatricyclo[6.3.1.0$^{4,12}$]dodeca-2,4 (12), 5,7-tetraen-3-yl]-2,2-dimethyl-propan-1-ol (compound T8, 525 mg, 93.24%) as light yellow oil. MS calc'd 696.4 (MH$^+$), measured 696.4 (MH$^+$).

Step 9: Preparation of methyl (3S)-1-[(2S)-3-[4-[10-benzyloxy-3-(3-hydroxy-2,2-dimethyl-propyl)-2-[2-[(1S)-1-methoxyethyl]-5-morpholino-3-pyridyl]-1-azatricyclo[6.3.1.0$^{4,12}$]dodeca-2,4 (12),5,7-tetraen-6-yl]thiazol-2-yl]-2-(tert-butoxycarbonylamino) propanoyl]hexahydropyridazine-3-carboxylate (compound T9)

To a solution of 3-[10-benzyloxy-2-[2-[(1S)-1-methoxyethyl]-5-morpholino-3-pyridyl]-6-(4,4,5,5-tetramethyl-1,3,2-dioxaborolan-2-yl)-1-azatricyclo[6.3.1.0$^{4,12}$]dodeca-2,4 (12),5,7-tetraen-3-yl]-2,2-dimethyl-propan-1-ol (compound T8, 525 mg, 754.65 μmol) and methyl (3S)-1-[(2S)-3-(4-bromothiazol-2-yl)-2-(tert-butoxycarbonylamino) propanoyl]hexahydropyridazine-3-carboxylate (Intermediate B, 342 mg, 716.91 μmol) in 1,4-dioxane (7 mL)/water (2 mL) was added K$_3$PO$_4$ (400 mg, 1.89 mmol) and Pd (dtbpf) Cl$_2$ (49 mg, 75.46 μmol) in one portion. The mixture was degassed, purged with nitrogen for three times and then stirred at 70° C. for 15 hrs. After being cooled to room temperature, the reaction mixture was filtered and the filtrate was concentrated under vacuum to give crude product methyl (3S)-1-[(2S)-3-[4-[10-benzyloxy-3-(3-hydroxy-2,2-dimethyl-propyl)-2-[2-[(1S)-1-methoxyethyl]-5-morpholino-3-pyridyl]-1-azatricyclo[6.3.1.0$^{4,12}$]dodeca-2,4 (12), 5,7-tetraen-6-yl]thiazol-2-yl]-2-(tert-butoxycarbonylamino) propanoyl]hexahydropyridazine-3-carboxylate (compound T9, 700 mg) as black oil, which was used in the next step without purification. MS calc'd 966.5 (MH$^+$), measured 966.5 (MH$^+$).

Step 10: Preparation of (3.5)-1-[(2S)-3-[4-[10-benzyloxy-3-(3-hydroxy-2,2-dimethyl-propyl)-2-[2-[(1S)-1-methoxyethyl]-5-morpholino-3-pyridyl]-1-azatricyclo[6.3.1.0$^{4,12}$]dodeca-2,4 (12),5,7-tetraen-6-yl]thiazol-2-yl]-2-(tert-butoxycarbonylamino) propanoyl]hexahydropyridazine-3-carboxylic acid (compound T10)

A solution of methyl (3S)-1-[(2S)-3-[4-[10-benzyloxy-3-(3-hydroxy-2,2-dimethyl-propyl)-2-[2-[(1S)-1-methoxyethyl]-5-morpholino-3-pyridyl]-1-azatricyclo[6.3.1.0$^{4,12}$]dodeca-2,4 (12), 5,7-tetraen-6-yl]thiazol-2-yl]-2-(tert-butoxycarbonylamino) propanoyl]hexahydropyridazine-3-carboxylate (compound T9, 700 mg, 700 mg, 0.725 mmol) in MeOH (10 mL)/THF (10 mL) was added 2 M LiOH (2 mL, 4 mmol) and then stirred at rt for 2 hrs. The reaction mixture was acidified by 1 M solution of HCl until pH=5, and then extracted with EtOAc (40 mL, three times). The combined organic layer was concentrated and then purified by reversed-phase chromatography to afford (3S)-1-[(2S)-3-[4-[10-benzyloxy-3-(3-hydroxy-2,2-dimethyl-propyl)-2-[2-[(1S)-1-methoxyethyl]-5-morpholino-3-pyridyl]-1-azatricyclo[6.3.1.0$^{4,12}$]dodeca-2,4 (12), 5,7-tetraen-6-yl]thiazol-2-yl]-2-(tert-butoxycarbonylamino) propanoyl]

hexahydropyridazine-3-carboxylic acid (compound T10, 433 mg) as a light yellow powder. MS calc'd 952.5 (MH+), measured 952.5 (MH+).

Step 11: Preparation of tert-butyl N-[(7S,13S)-23-benzyloxy-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]carbamate (compound T11)

A solution of TCFH (229.8 mg, 819.18 μmol) and NMI (269 mg, 261 μL, 3.28 mmol) in MeCN (103 mL) was stirred at rt for 15 min. Another solution of (3S)-1-[(2S)-3-[4-[10-benzyloxy-3-(3-hydroxy-2,2-dimethyl-propyl)-2-[2-[(1S)-1-methoxyethyl]-5-morpholino-3-pyridyl]-1-azatricyclo[6.3.1.0$^{4,12}$]dodeca-2,4 (12), 5,7-tetraen-6-yl]thiazol-2-yl]-2-(tert-butoxycarbonylamino) propanoyl]hexahydropyridazine-3-carboxylic acid (compound T10, 433 mg, 454 μmol) in acetonitrile (51 mL) was added dropwise to the reaction mixture and then stirred at rt for 1 h. The solution was removed by reduce pressure under vacuum and then purified by silica gel chromatography to afford tert-butyl N-[(7S,13S)-23-benzyloxy-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaen-7-yl]carbamate (compound T11, 514 mg) as light brown oil. MS calc'd 934.4 (MH+), measured 934.4 (MH+).

Step 12: Preparation of (7S,13S)-7-amino-23-benzyloxy-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (intermediate T)

To a solution of tert-butyl N-[(7S,13S)-23-benzyloxy-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaen-7-yl]carbamate (compound T11, 300 mg, 321.15 μmol) in DCM (2 mL) was added TFA (2 mL) and the mixture was stirred at 20° C. for 1 h. After the reaction was completed, the reaction mixture was concentrated under vacuum to afford (7S,13S)-7-amino-23-benzyloxy-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (intermediate T, 300 mg) as light yellow oil. MS calc'd 834.4 (MH+), measured 834.4 (MH+).

Intermediate U (7S,13S)-7-amino-29-fluoro-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione

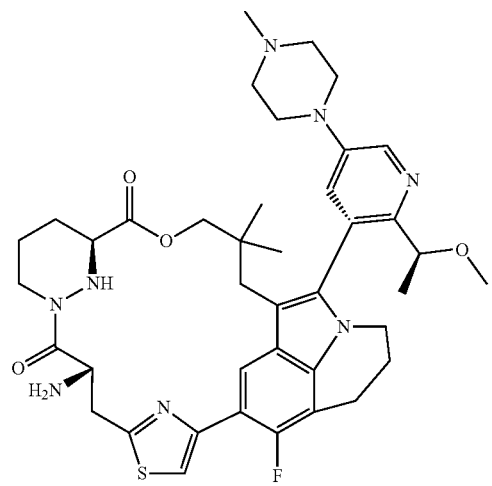

The title compound was prepared in analogy to the preparation of Intermediate E by using 6-bromo-5-fluoro-8-iodo-1,2,3,4-tetrahydroquinoline (intermediate D10) instead of 6-bromo-8-iodo-1,2,3,4-tetrahydroquinoline (Intermediate D1).

Intermediate V

Benzyl 4-[(5M)-5-[(7S,13S)-7-(tert-butoxycarbonylamino)-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-20-yl]-6-[(1S)-1-methoxyethyl]-3-pyridyl]piperazine-1-carboxylate

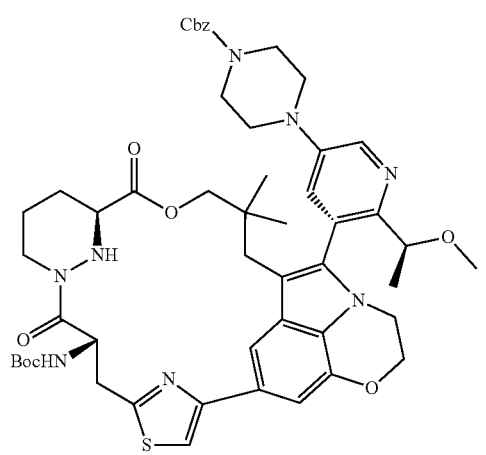

The title compound was prepared in analogy to the preparation of Intermediate E10 by using 7-bromo-5-iodo-3,4-dihydro-2H-1,4-benzoxazine (Intermediate D2) instead of 6-bromo-8-iodo-1,2,3,4-tetrahydroquinoline (Intermediate D1).

Example 1

(1S,2S)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-methyl-cyclopropanecarboxamide

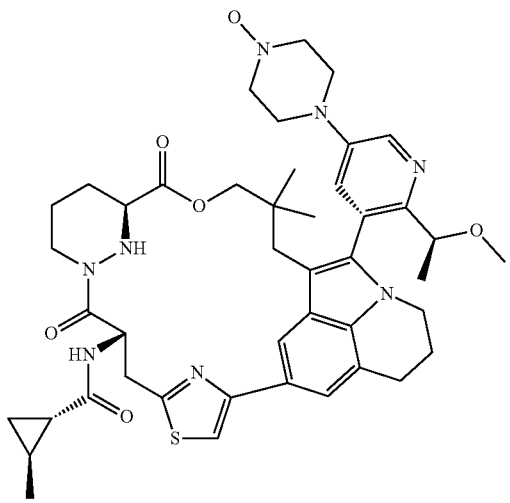

To a solution of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate F, 32.13 mg, 0.12 mmol) and (1S,2S)-2-methylcyclopropanecarboxylic acid (33.0 mg, 0.33 mmol) in DMF (2 mL) were added DIEA (85.0 mg, 0.66 mmol), T$_3$P (67.0 mg, 0.11 mmol) at 0° C. After being stirred at 20° C. for 1 h, the reaction mixture was diluted with water (15 mL), extracted with EtOAc (15 mL, three times). The combined organic layer was washed with brine (20 mL), dried over Na$_2$SO$_4$, filtered and concentrated in vacuo to get a residue. The residue was purified by prep-HPLC to afford Example 1 (26.6 mg) as a yellow solid. MS calc'd 810.4 (MH$^+$), measured 810.4 (MH$^+$). $^1$H NMR (400 MHZ, METHANOL-d$_4$) δ=8.42 (s, 1H), 8.36 (d, J=2.8 Hz, 1H), 7.86 (d, J=2.4 Hz, 1H), 7.50 (s, 1H), 7.45 (s, 1H), 5.83-5.77 (m, 1H), 4.59-4.38 (m, 1H), 4.21-4.17 (m, 1H), 4.16-4.08 (m, 1H), 3.86 (t, J=4.8 Hz, 4H), 3.81-3.59 (m, 3H), 3.50-3.32 (m, 8H), 3.29-3.22 (m, 2H), 3.19-2.94 (m, 4H), 2.86-2.60 (m, 2H), 2.43-2.07 (m, 3H), 2.01-1.86 (m, 1H), 1.83-1.53 (m, 2H), 1.50-1.43 (m, 4H), 1.31-1.17 (m, 1H), 1.12 (d, J=6.0 Hz, 3H), 1.09-1.02 (m, 2H), 0.99 (s, 3H), 0.66-0.63 (m, 1H), 0.62 (s, 3H).

Example 2

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-methyl-cyclopropanecarboxamide

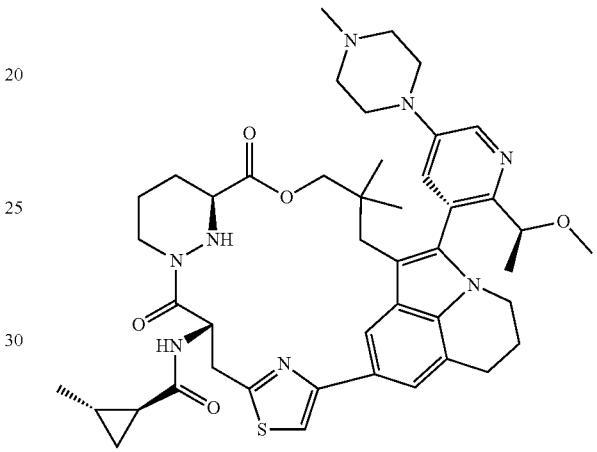

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate E) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate F). Example 2 (16.2 mg) was obtained as a yellow solid. MS calc'd 823.4 (MH$^+$), measured 823.4 (MH$^+$). $^1$H NMR (400 MHZ, Methanol-d$_4$) δ=8.49 (d, J=2.8 Hz, 1H), 8.39 (s, 1H), 7.67 (s, 1H), 7.49 (s, 1H), 7.43 (s, 1H), 5.83-5.73 (m, 1H), 4.85-4.77 (m, 1H), 4.54-4.40 (m, 2H), 4.25-4.16 (m, 2H), 3.85-3.67 (m, 3H), 3.66-3.57 (m, 2H), 3.46-3.33 (m, 6H), 3.30-3.22 (m, 2H), 3.18-2.92 (m, 7H), 2.82-2.71 (m, 1H), 2.67-2.58 (m, 1H), 2.39-2.25 (m, 1H), 2.23-2.13 (m, 2H), 1.98-1.89 (m, 1H), 1.84-1.69 (m, 1H), 1.66-1.53 (m, 1H), 1.51-1.43 (m, 4H), 1.37-1.15 (m, 2H), 1.14-1.10 (m, 3H), 1.09-1.04 (m, 1H), 0.98 (s, 3H), 0.67-0.61 (m, 1H), 0.56 (s, 3H).

Example 3

(1S,2S)-N-[(7S,13S)-(20M)-20-[2-[(1S)-1-methoxyethyl]-5-[4-(2,2,2-trifluoroethyl) piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-methyl-cyclopropanecarboxamide

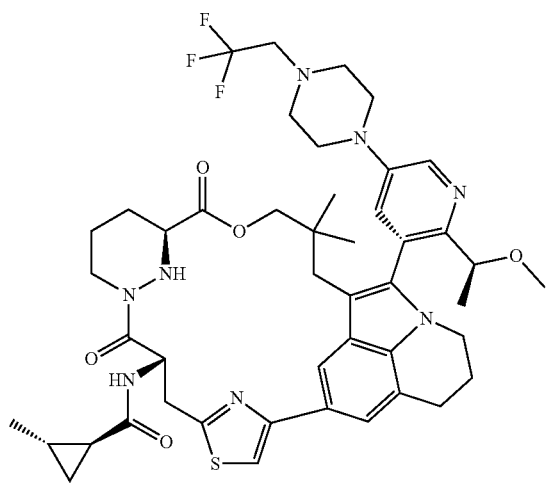

The title compound was prepared in analogy to the preparation of Example 1 by using (7S,13S)-7-amino-(20M)-20-[2-[(1S)-1-methoxyethyl]-5-[4-(2,2,2-trifluoroethyl) piperazin-1-yl]-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (intermediate G) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate F). Example 3 (27.6 mg) was obtained as a yellow solid. MS calc'd 891.4 (MH$^+$), measured 891.4 (MH$^+$). $^1$H NMR (400 MHZ, Methanol-d$_4$) δ=8.42 (s, 1H), 8.37 (d, J=2.8 Hz, 1H), 7.83 (d, J=2.8 Hz, 1H), 7.50 (s, 1H), 7.45 (s, 1H), 5.85-5.75 (m, 1H), 4.56-4.48 (m, 1H), 4.47-4.39 (m, 1H), 4.22 (dd, J=3.2, 11.8 Hz, 1H), 4.17-4.09 (m, 1H), 3.81-3.72 (m, 2H), 3.70-3.62 (m, 1H), 3.51-3.46 (m, 4H), 3.42 (s, 3H), 3.30-2.95 (m, 7H), 2.90-2.85 (m, 4H), 2.81-2.65 (m, 2H), 2.39-2.27 (m, 1H), 2.24-2.13 (m, 2H), 1.98-1.89 (m, 1H), 1.82-1.67 (m, 1H), 1.66-1.52 (m, 1H), 1.49-1.43 (m, 4H), 1.27-1.18 (m, 1H), 1.14-1.10 (m, 3H), 1.09-1.04 (m, 1H), 1.00 (s, 3H), 0.67-0.58 (m, 4H).

Example 5

(1S,2S)-N-[(7S,13S)-(20M)-20-[2-[(1S)-1-methoxyethyl]-5-[4-(2,2,2-trifluoroethyl) piperazin-1-yl]-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-methyl-cyclopropanecarboxamide

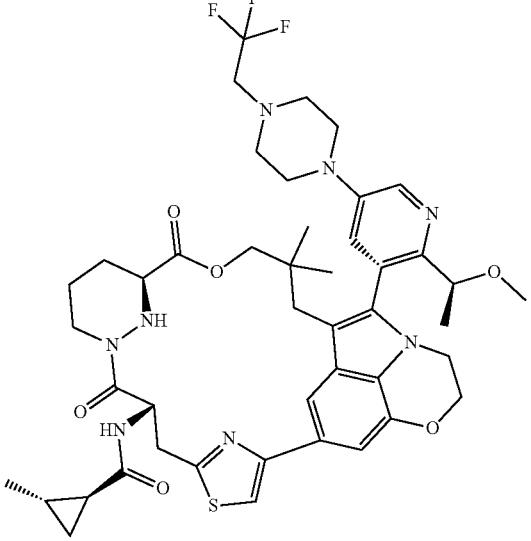

The title compound was prepared in analogy to the preparation of Example 1 by using (7S,13S)-7-amino-(20M)-20-[2-[(1S)-1-methoxyethyl]-5-[4-(2,2,2-trifluoroethyl) piperazin-1-yl]-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (intermediate I) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F). Example 5 (22.11 mg) was obtained as a light yellow solid. MS calc'd 893.4 (MH$^+$), measured 893.4 (MH$^+$). $^1$H NMR (400 MHZ, DMSO-d$_6$) δ=8.52 (d, J=8.8 Hz, 1H), 8.44 (d, J=2.7 Hz, 1H), 8.12 (s, 1H), 7.74 (s, 1H), 7.18 (d, J=2.8 Hz, 1H), 7.15 (s, 1H), 5.55 (t, J=9.0 Hz, 1H), 5.04 (d, J=12.1 Hz, 1H), 4.68-4.54 (m, 2H), 4.35-4.15 (m, 4H), 3.74-3.67 (m, 1H), 3.62-3.56 (m, 2H), 3.28-3.25 (m, 4H), 3.23 (s, 3H), 3.19-3.07 (m, 1H), 3.03-2.84 (m, 1H), 2.83-2.69 (m, 5H), 2.43 (s, 1H), 2.14-2.08 (m, 1H), 1.87-1.71 (m, 2H), 1.56-1.43 (m, 2H), 1.33 (d, J=6.1 Hz, 3H), 1.23 (s, 1H), 1.08-1.01 (m, 6H), 0.94 (s, 3H), 0.87-0.82 (m, 1H), 0.58-0.48 (m, 1H), 0.38 (s, 3H).

Example 6

(1S,2S)-2-(difluoromethyl)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1²,⁵.1⁹,¹³.0¹⁹,²⁷.0²¹,²⁶]hentriaconta-1 (28),2,5 (31), 19,25 (29),26-hexaen-7-yl]cyclopropanecarboxamide

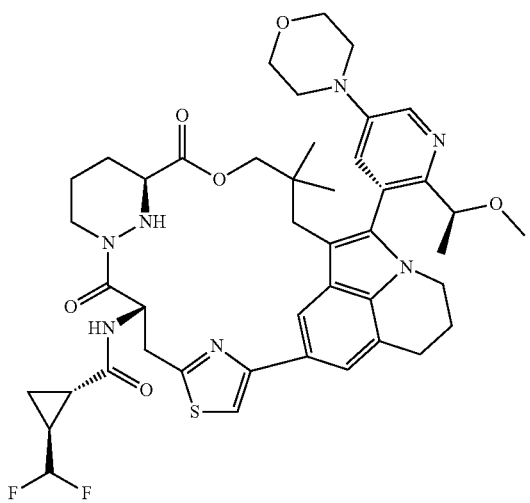

The title compound was prepared in analogy to the preparation of Example 1 by using (1S,2S)-2-(difluoromethyl)cyclopropanecarboxylic acid instead of (1S,2S)-2-methylcyclopropanecarboxylic acid. Example 6 (34.9 mg) was obtained as a yellow solid. MS calc'd 846.4 (MH⁺), measured 846.4 (MH⁺). $^1$H NMR (400 MHZ, METHANOL-$d_4$) δ=8.42 (s, 1H), 8.36 (d, J=2.80 Hz, 1H), 7.82 (d, J=2.80 Hz, 1H), 7.51 (s, 1H), 7.45 (s, 1H), 5.96-5.64 (m, 2H), 4.53 (q, J=6.40 Hz, 1H), 4.47-4.38 (m, 1H), 4.24-4.09 (m, 2H), 3.87 (t, J=4.80 Hz, 4H), 3.81-3.64 (m, 3H), 3.44-3.38 (m, 8H), 3.17-2.94 (m, 3H), 2.83-2.67 (m, 2H), 2.38-2.26 (m, 1H), 2.25-2.11 (m, 2H), 2.09-2.00 (m, 2H), 1.98-1.88 (m, 1H), 1.84-1.69 (m, 2H), 1.67-1.54 (m, 1H), 1.48 (d, J=6.40 Hz, 3H), 1.21-1.07 (m, 2H), 0.99 (s, 3H), 0.62 (s, 3H).

Example 7

(1S,5R,6r)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1²,⁵.1⁹,¹³.0¹⁹,²⁷.0²¹,²⁶]hentriaconta-1 (28),2,5 (31), 19,25 (29),26-hexaen-7-yl]-3-oxabicyclo[3.1.0]hexane-6-carboxamide

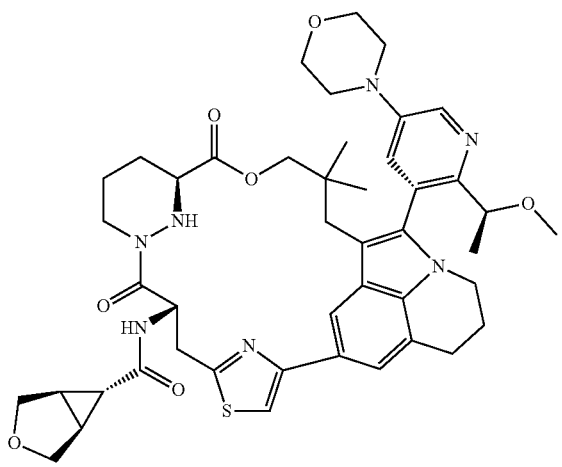

The title compound was prepared in analogy to the preparation of Example 1 by using (1S,5R,6r)-3-oxabicyclo[3.1.0]hexane-6-carboxylic acid instead of (1S,2S)-2-methylcyclopropanecarboxylic acid. Example 7 (29.3 mg) was obtained as a yellow solid. MS calc'd 838.4 (MH⁺), measured 838.4 (MH⁺). $^1$H NMR (400 MHZ, DMSO-$d_6$) δ=8.56 (d, J=8.8 Hz, 1H), 8.44 (d, J=2.8 Hz, 1H), 8.34 (s, 1H), 7.71 (s, 1H), 7.45 (s, 1H), 7.34 (s, 1H), 5.58 (t, J=8.80 Hz, 1H), 5.07 (d, J=12.4 Hz, 1H), 4.39-4.31 (m, 1H), 4.27-4.13 (m, 3H), 3.85-3.72 (m, 8H), 3.29-3.24 (m, 7H), 3.17-2.84 (m, 6H), 2.81-2.70 (m, 1H), 2.29-2.04 (m, 4H), 1.97-1.71 (m, 5H), 1.67-1.41 (m, 3H), 1.35 (d, J=6.40 Hz, 3H), 0.92 (s, 3H), 0.43 (s, 3H).

Example 8

(1S,2S)-N-[(7S,13S)-(20M)-20-[2-[(1S)-1-methoxyethyl]-5-morpholino-3-pyridyl]-17,17-dimethyl-8,14-dioxo-15,24-dioxa-4-thia-9,21,30,31-tetrazahexacyclo[23.3.1.1²,⁵.1⁹,¹³.0¹⁹,²⁷.0²¹,²⁶]hentriaconta-1 (28),2,5 (31), 19,25 (29),26-hexaen-7-yl]-2-methyl-cyclopropanecarboxamide

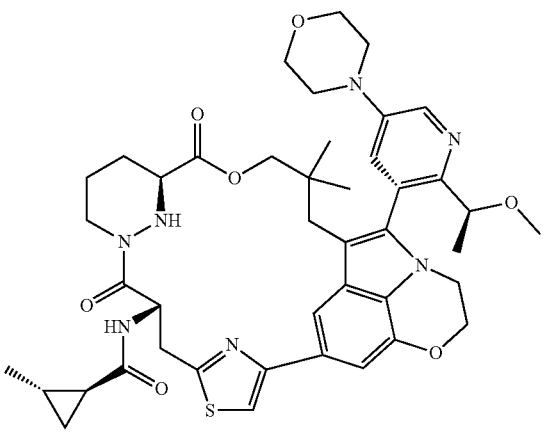

The title compound was prepared in analogy to the preparation of Example 1 by using (7S,13S)-7-amino-(20M)-20-[2-[(1S)-1-methoxyethyl]-5-morpholino-3-pyridyl]-17,17-dimethyl-15,24-dioxa-4-thia-9,21,30,31-tetrazahexacyclo[23.3.1.1²,⁵.1⁹,¹³.0¹⁹,²⁷.0²¹,²⁶]hentriaconta-1 (28),2,5 (31), 19,25 (29),26-hexaene-8,14-dione (intermediate J) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1²,⁵.1⁹,¹³.0¹⁹,²⁷.0²¹,²⁶]hentriaconta-1 (28),2,5 (31), 19,25 (29),26-hexaene-8,14-dione (Intermediate F). Example 8 (20 mg) was obtained as a light yellow solid. MS calc'd 812.4 (MH⁺), measured 812.4 (MH⁺). $^1$H NMR (400 MHZ, ACETONITRILE-$d_3$) δ=8.38 (d, J=2.9 Hz, 1H), 8.20 (s, 1H), 7.44 (s, 1H), 7.29 (d, J=2.8 Hz, 1H), 7.15-7.06 (m, 2H), 5.67 (t, J=8.9 Hz, 1H), 4.67-4.56 (m, 2H), 4.48 (d, J=6.2 Hz, 1H), 4.45-4.18 (m, 4H), 3.89-3.79 (m, 4H), 3.78-3.63 (m, 3H), 3.40-3.25 (m, 8H), 3.20-3.09 (m, 1H), 3.04 (br d, J=14.3 Hz, 1H), 2.77-2.65 (m, 1H), 2.58 (br d, J=14.3 Hz, 1H), 1.91 (br d, J=12.6 Hz, 1H), 1.85-1.74 (m, 1H), 1.62-1.51 (m, 1H), 1.44-1.36 (m, 4H), 1.29 (br d, J=6.0 Hz, 1H), 1.21-1.15 (m, 1H), 1.13-1.08 (m, 3H), 1.04-0.95 (m, 4H), 0.66-0.58 (m, 1H), 0.51 (s, 3H).

Example 9

(1S,2S)-2-(difluoromethyl)-N-[(7S,13S)-(20M)-20-[2-[(1S)-1-methoxyethyl]-5-morpholino-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]cyclopropanecarboxamide

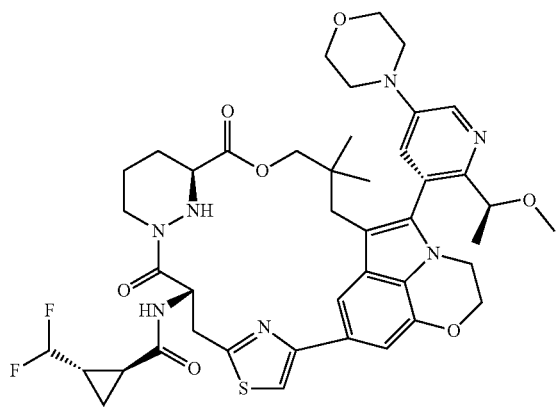

The title compound was prepared in analogy to the preparation of Example 1 by using (7S,13S)-7-amino-(20M)-20-[2-[(1S)-1-methoxyethyl]-5-morpholino-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (intermediate J) and (1S,2S)-2-(difluoromethyl)cyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate F) and (1S,2S)-2-methylcyclopropanecarboxylic acid. Example 9 (6 mg) was obtained as a light yellow solid. MS calc'd 848.4 (MH$^+$), measured 848.4 (MH$^+$). $^1$H NMR (400 MHZ, ACETONITRILE-d$_3$) δ=8.29 (d, J=3.0 Hz, 1H), 8.22 (d, J=0.8 Hz, 1H), 7.54 (d, J=3.0 Hz, 1H), 7.45 (s, 1H), 7.33-7.26 (m, 1H), 7.13 (d, J=1.0 Hz, 1H), 5.80-5.48 (m, 2H), 4.65-4.55 (m, 3H), 4.53-4.35 (m, 1H), 4.37-4.32 (m, 1H), 4.29-4.21 (m, 2H), 3.85-3.79 (m, 5H), 3.72 (d, J=6.8 Hz, 2H), 3.41-3.31 (m, 8H), 3.20-3.11 (m, 1H), 3.03 (br d, J=14.3 Hz, 1H), 2.73 (br d, J=3.0 Hz, 1H), 2.65 (br d, J=14.3 Hz, 1H), 1.83-1.74 (m, 2H), 1.63-1.52 (m, 1H), 1.41 (d, J=6.3 Hz, 3H), 1.32-1.25 (m, 3H), 1.12 (br s, 2H), 1.01 (s, 3H), 0.58 (s, 3H).

Example 10

(1S,5R,6r)-N-[(7S,13S)-(20M)-20-[2-[(1S)-1-methoxyethyl]-5-morpholino-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-3-oxabicyclo[3.1.0]hexane-6-carboxamide

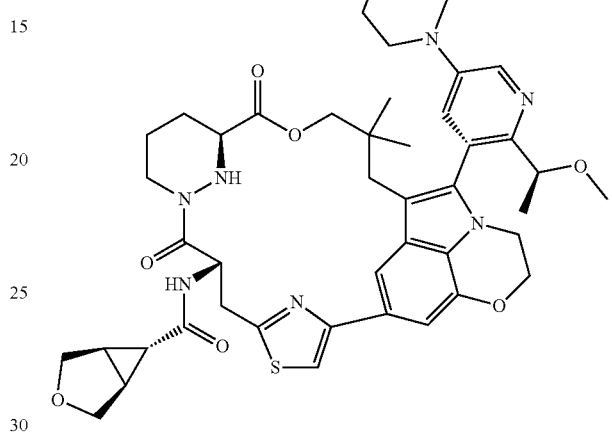

The title compound was prepared in analogy to the preparation of Example 1 by using (7S,13S)-7-amino-(20M)-20-[2-[(1S)-1-methoxyethyl]-5-morpholino-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (intermediate J) and (1S,5R,6r)-3-oxabicyclo[3.1.0]hexane-6-carboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate F) and (1S,2S)-2-methylcyclopropanecarboxylic acid. Example 10 (5.2 mg) was obtained as a light yellow solid. MS calc'd 840.4 (MH$^+$), measured 840.4 (MH$^+$). 1H NMR (400 MHZ, ACETONITRILE-d$_3$) δ=8.34 (d, J=3.0 Hz, 1H), 8.21 (s, 1H), 7.45 (s, 1H), 7.41 (d, J=2.8 Hz, 1H), 7.12 (d, J=1.0 Hz, 2H), 5.92-5.63 (m, 2H), 4.67-4.58 (m, 2H), 4.53 (d, J=6.3 Hz, 1H), 4.45-4.37 (m, 1H), 4.35-4.28 (m, 2H), 4.22 (br d, J=3.0 Hz, 1H), 3.88 (s, 2H), 3.85-3.79 (m, 4H), 3.76 (s, 1H), 3.74-3.66 (m, 4H), 3.39-3.29 (m, 8H), 3.17-3.10 (m, 1H), 3.04 (d, J=14.5 Hz, 1H), 2.75-2.68 (m, 1H), 2.64-2.60 (m, 1H), 2.03 (s, 1H), 2.01-1.99 (m, 1H), 1.94-1.87 (m, 1H), 1.84-1.73 (m, 1H), 1.56 (br t, J=3.3 Hz, 2H), 1.41 (d, J=6.3 Hz, 3H), 1.00 (s, 3H), 0.55 (s, 3H).

Example 11

(1S,2S)-2-(difluoromethyl)-N-[(7S,13S)-(20M)-20-[2-[(1S)-1-methoxyethyl]-5-[4-(2,2,2-trifluoroethyl) piperazin-1-yl]-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]cyclopropanecarboxamide

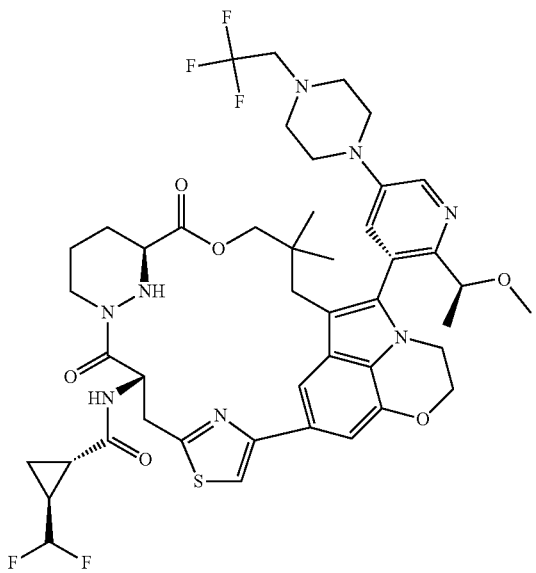

The title compound was prepared in analogy to the preparation of Example 1 by using (7S,13S)-7-amino-(20M)-20-[2-[(1S)-1-methoxyethyl]-5-[4-(2,2,2-trifluoroethyl) piperazin-1-yl]-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (intermediate I) and (1S,2S)-2-(difluoromethyl)cyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 11 (22.1 mg) was obtained as a light yellow solid. MS calc'd 929.4 (MH$^+$), measured 929.4 (MH$^+$). $^1$H NMR (400 MHZ, ACETONITRILE-d$_3$) δ=8.40 (d, J=2.8 Hz, 1H), 8.17 (s, 1H), 7.41 (s, 1H), 7.22-7.16 (m, 1H), 7.15-7.11 (m, 1H), 7.07-7.03 (m, 1H), 5.77-5.66 (m, 1H), 4.66-4.52 (m, 2H), 4.44-4.34 (m, 3H), 4.33-4.18 (m, 2H), 3.76-3.63 (m, 3H), 3.37 (d, J=15.5 Hz, 1H), 3.30-3.24 (m, 7H), 3.19-3.06 (m, 4H), 3.00 (d, J=15.0 Hz, 1H), 2.83-2.79 (m, 4H), 2.74-2.63 (m, 2H), 2.58-2.49 (m, 2H), 1.79-1.76 (m, 2H), 1.60-1.52 (m, 2H), 1.37 (d, J=6.1 Hz, 3H), 1.13-1.06 (m, 2H), 0.96 (s, 3H), 0.47 (s, 3H).

Example 12

(1S,5R,6r)-N-[(7S,13S)-(20M)-20-[2-[(1S)-1-methoxyethyl]-5-[4-(2,2,2-trifluoroethyl) piperazin-1-yl]-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-3-oxabicyclo[3.1.0]hexane-6-carboxamide

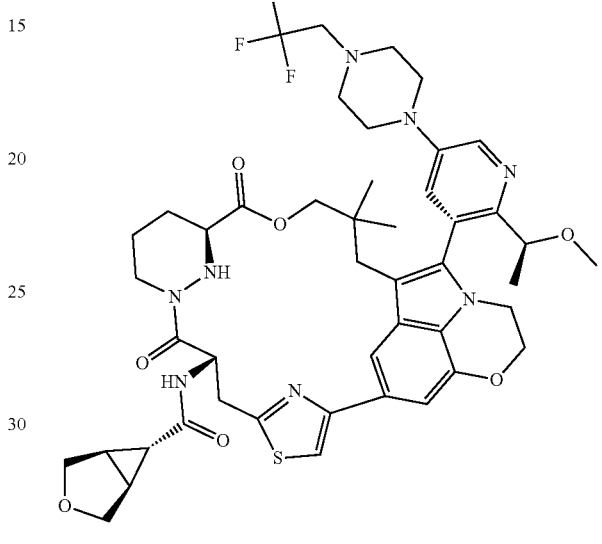

The title compound was prepared in analogy to the preparation of Example 1 by using (7S,13S)-7-amino-(20M)-20-[2-[(1S)-1-methoxyethyl]-5-[4-(2,2,2-trifluoroethyl) piperazin-1-yl]-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (intermediate I) and (1S,5R,6r)-3-oxabicyclo[3.1.0]hexane-6-carboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 12 (13.4 mg) was obtained as a white solid. MS calc'd 921.4 (MH$^+$), measured 921.4 (MH$^+$). $^1$H NMR (400 MHZ, ACETONITRILE-d$_3$) δ=8.44-8.37 (m, 1H), 8.20-8.14 (m, 1H), 7.44-7.38 (m, 1H), 7.16-7.12 (m, 1H), 7.06 (d, J=1.0 Hz, 1H), 7.02-6.97 (m, 1H), 5.71-5.60 (m, 1H), 4.61-4.52 (m, 2H), 4.40-4.36 (m, 2H), 4.30-4.19 (m, 2H), 3.89-3.82 (m, 2H), 3.75-3.66 (m, 4H), 3.41-3.32 (m, 2H), 3.30-3.24 (m, 7H), 3.17-3.05 (m, 4H), 3.00 (d, J=13.9 Hz, 1H), 2.83-2.79 (m, 4H), 2.74-2.65 (m, 2H), 2.56-2.52 (m, 1H), 2.00 (s, 1H), 1.78-1.75 (m, 1H), 1.55-1.50 (m, 2H), 1.37 (d, J=6.1 Hz, 3H), 1.30-1.26 (m, 1H), 1.00-0.93 (m, 3H), 0.92-0.87 (m, 1H), 0.51-0.41 (m, 3H).

Example 13

(1S,5R,6r)-N-[(7S,13S)-(20M)-20-[2-[(1S)-1-methoxyethyl]-5-[4-(2,2,2-trifluoroethyl) piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-3-oxabicyclo[3.1.0]hexane-6-carboxamide

Example 14

(1S,2S)-2-(difluoromethyl)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]cyclopropanecarboxamide

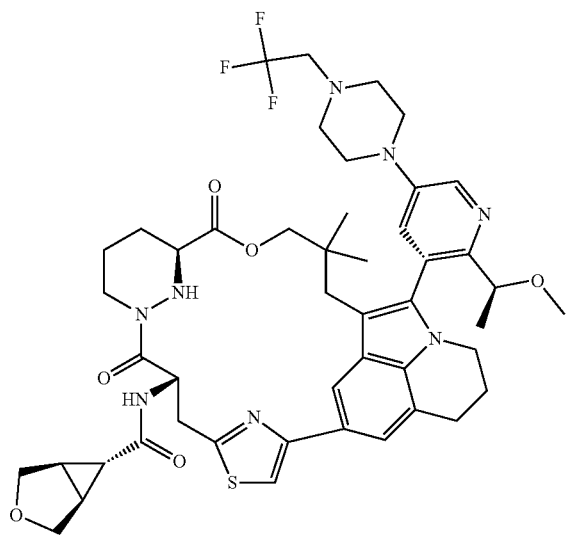

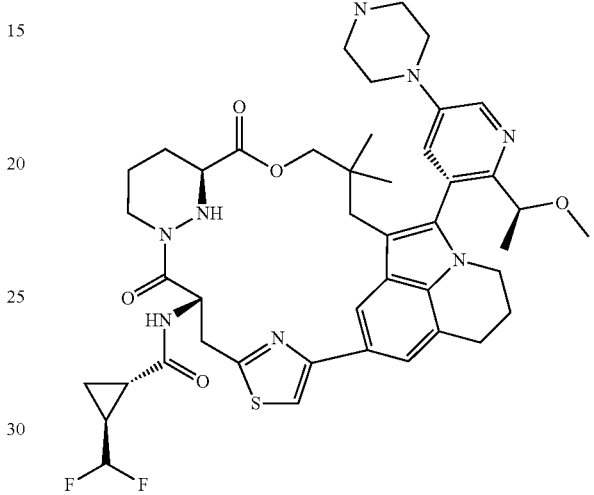

The title compound was prepared in analogy to the preparation of Example 1 by using (7S,13S)-7-amino-(20M)-20-[2-[(1S)-1-methoxyethyl]-5-[4-(2,2,2-trifluoroethyl) piperazin-1-yl]-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (intermediate G) and (1S,5R,6r)-3-oxabicyclo[3.1.0]hexane-6-carboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 13 (11.9 mg) was obtained as a yellow solid. MS calc'd 919.4 (MH$^+$), measured 919.4 (MH$^+$). $^1$H NMR (400 MHZ, METHANOL-d$_4$) δ=8.45-8.33 (m, 2H), 7.84-7.83 (m, 1H), 7.54-7.43 (m, 2H), 5.81 (d, J=8.4 Hz, 1H), 4.52 (d, J=6.4 Hz, 1H), 4.43 (d, J=1.6 Hz, 1H), 4.25-4.17 (m, 1H), 4.17-4.08 (m, 1H), 3.92 (t, J=8.8 Hz, 2H), 3.81-3.67 (m, 5H), 3.52-3.38 (m, 8H), 3.25-2.99 (m, 6H), 2.91-2.85 (m, 4H), 2.82-2.66 (m, 2H), 2.37-2.15 (m, 3H), 2.13-2.04 (m, 2H), 1.98-1.88 (m, 1H), 1.81-1.57 (m, 3H), 1.48 (d, J=6.0 Hz, 3H), 1.05-0.95 (m, 3H), 0.66-0.57 (m, 3H).

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate E) and (1S,2S)-2-(difluoromethyl)cyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S, 2S)-2-methylcyclopropanecarboxylic acid. Example 14 (28.7 mg) was obtained as a yellow solid. MS calc'd 859.4 (MH$^+$), measured 859.5 (MH$^+$). $^1$H NMR (400 MHZ, METHANOL-d$_4$) δ=8.47 (d, J=2.8 Hz, 1H), 8.38 (s, 1H), 7.51-7.47 (m, 2H), 7.41 (s, 1H), 5.82-5.79 (m, 2H), 4.44 (m, 2H), 4.26-4.19 (m, 2H), 4.12-4.02 (m, 1H), 3.80-3.68 (m, 3H), 3.65-3.49 (m, 2H), 3.45-3.40 (m, 2H), 3.38-3.33 (m, 5H), 3.29-3.26 (m, 1H), 3.15-3.01 (m, 3H), 3.01-2.97 (m, 4H), 2.73-2.81 (m, 1H), 2.64-2.57 (m, 1H), 2.35-2.26 (m, 1H), 2.21-2.14 (m, 2H), 2.12-1.94 (m, 2H), 1.83-1.73 (m, 2H), 1.66-1.58 (m, 1H), 1.45 (d, J=6.0 Hz, 3H), 1.34-1.28 (m, 1H), 1.18-1.09 (m, 2H), 0.96 (s, 3H), 0.55 (s, 3H).

Example 15

(1S,5R,6r)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-3-oxabicyclo[3.1.0]hexane-6-carboxamide

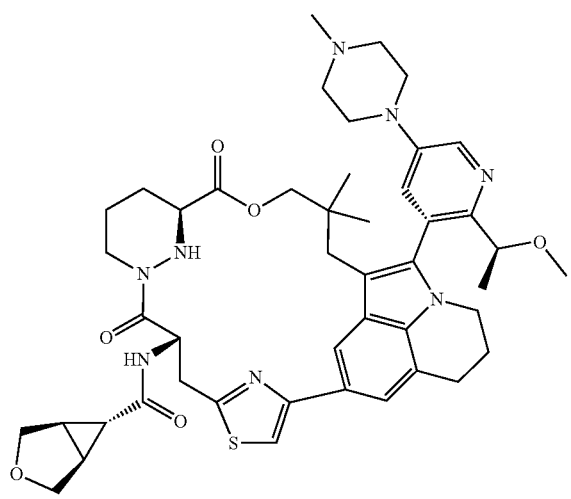

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate E) and (1S,5R,6r)-3-oxabicyclo[3.1.0]hexane-6-carboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 15 (26.8 mg) was obtained as a yellow solid. MS calc'd 851.4 (MH$^+$), measured 851.4 (MH$^+$). $^1$H NMR (400 MHZ, Methanol-d$_4$) δ=8.48 (d, J=2.8 Hz, 1H), 8.39 (s, 1H), 7.59 (d, J=2.8 Hz, 1H), 7.50 (s, 1H), 7.43 (s, 1H), 5.77 (d, J=8.0 Hz, 1H), 4.90-4.88 (m, 1H), 4.50-4.41 (m, 2H), 4.25-4.18 (m, 2H), 4.14-4.01 (m, 1H), 3.99-3.86 (m, 3H), 3.81-3.70 (m, 5H), 3.66-3.52 (m, 3H), 3.45-3.39 (m, 2H), 3.38 (s, 3H), 3.28-3.24 (m, 1H), 3.14-3.07 (m, 2H), 2.99 (s, 4H), 2.81-2.74 (m, 1H), 2.62 (d, J=14.4 Hz, 1H), 2.36-2.27 (m, 1H), 2.21-2.14 (m, 2H), 2.12-2.09 (m, 1H), 2.08-2.04 (m, 1H), 1.97-1.90 (m, 1H), 1.82-1.73 (m, 1H), 1.69 (t, J=2.8 Hz, 1H), 1.65-1.57 (m, 1H), 1.46 (d, J=6.4 Hz, 3H), 1.39-1.25 (m, 1H), 0.97 (s, 3H), 0.56 (s, 3H).

Example 16

(1R,2S)-2-cyclopropyl-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]cyclopropanecarboxamide

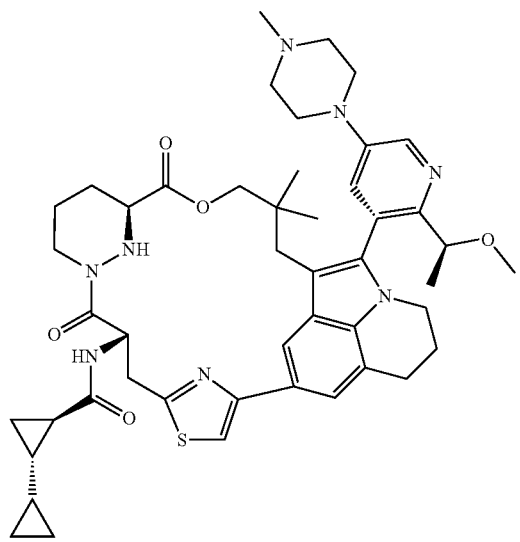

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate E) and (1R,2S)-2-cyclopropylcyclopropanecarboxylic acid instead of (7S, 13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 16 (8 mg) was obtained as a yellow solid. MS calc'd 849.4 (MH$^+$), measured 849.4 (MH$^+$). $^1$H NMR (400 MHZ, METHA-NOL-d$_4$) δ=8.48 (d, J=3.2 Hz, 1H), 8.39 (d, J=2.4 Hz, 1H), 7.63 (d, J=2.8 Hz, 1H), 7.50 (d, J=8.0 Hz, 1H), 7.43 (d, J=2.8 Hz, 1H), 5.77 (d, J=8.4 Hz, 1H), 4.53-4.39 (m, 2H), 4.28-4.05 (m, 3H), 3.83-3.66 (m, 3H), 3.65-3.50 (m, 3H), 3.47-3.34 (m, 6H), 3.29-3.24 (m, 1H), 3.15-2.93 (m, 7H), 2.82-2.72 (m, 1H), 2.61 (d, J=14.4 Hz, 1H), 2.38-2.27 (m, 1H), 2.23-2.13 (m, 2H), 1.98-1.90 (m, 1H), 1.83-1.70 (m, 1H), 1.66-1.54 (m, 1H), 1.46 (d, J=6.4 Hz, 3H), 1.33-1.28 (m, 1H), 1.09-0.71 (m, 6H), 0.71-0.63 (m, 1H), 0.61-0.50 (m, 3H), 049-0.39 (m, 2H), 0.20-0.13 (m, 2H).

Example 17

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2-methyl-cyclopropanecarboxamide

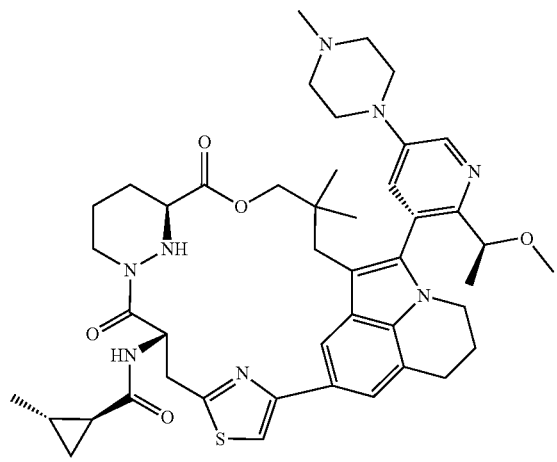

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate H) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate F). Example 17 (4.8 mg) was obtained as a white solid. MS calc'd 825.4 (MH$^+$), measured 825.4 (MH$^+$). $^1$H NMR (400 MHz, ACETONITRILE-d$_3$) δ=8.42 (d, J=3.0 Hz, 1H), 8.24-8.10 (m, 1H), 7.46-7.37 (m, 1H), 7.14 (d, J=3.1 Hz, 1H), 7.08-6.94 (m, 2H), 5.64 (s, 1H), 4.67-4.53 (m, 2H), 4.52-4.34 (m, 3H), 4.31-4.15 (m, 2H), 3.77-3.61 (m, 3H), 3.60-3.44 (m, 1H), 3.40 (s, 5H), 3.26 (s, 3H), 3.17-3.07 (m, 1H), 3.05-2.97 (m, 1H), 2.95-2.85 (m, 4H), 2.73-2.63 (m, 2H), 2.55 (s, 4H), 1.77 (td, J=2.6, 4.9 Hz, 1H), 1.59-1.47 (m, 2H), 1.37 (d, J=6.1 Hz, 3H), 1.30-1.25 (m, 1H), 1.19-1.13 (m, 1H), 1.10-1.06 (m, 3H), 0.97 (s, 3H), 0.63-0.56 (m, 1H), 0.46 (s, 3H).

Example 18

(1S,2S)-N-[(7S,13S)-23,23-difluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2-methyl-cyclopropanecarboxamide

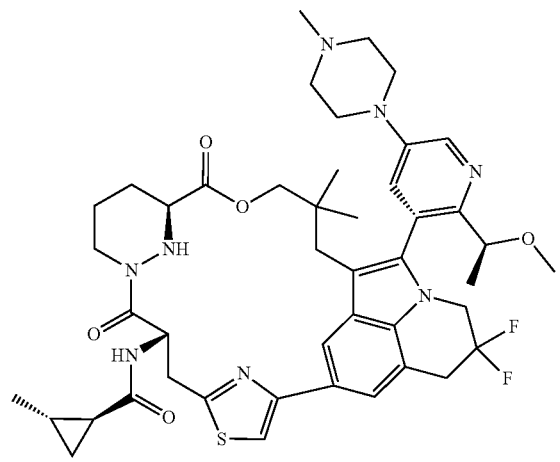

The title compound was prepared in analogy to the preparation of Example 1 by using (7S,13S)-7-amino-23,23-difluoro-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (intermediate K) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate F). Example 18 (11.2 mg) was obtained as a yellow solid. MS calc'd 859.4 (MH$^+$), measured 859.4 (MH$^+$). $^1$H NMR (400 MHZ, Methanol-d$_4$) δ=8.55-8.46 (m, 2H), 7.56 (s, 2H), 7.53 (d, J=2.8 Hz, 1H), 5.82-5.73 (m, 1H), 4.63-4.38 (m, 3H), 4.24 (dd, J=11.6, 2.8 Hz, 1H), 4.18-3.85 (m, 3H), 3.82-3.68 (m, 3H), 3.68-3.45 (m, 5H), 3.45-3.39 (m, 2H), 3.37 (s, 3H), 3.30-3.24 (m, 2H), 3.14-3.08 (m, 1H), 2.98 (s, 3H), 2.82-2.72 (m, 1H), 2.65-2.57 (m, 1H), 2.23-2.12 (m, 1H), 2.01-1.87 (m, 1H), 1.85-1.71 (m, 1H), 1.68-1.54 (m, 1H), 1.52-1.45 (m, 4H), 1.28-1.18 (m, 1H), 1.16-1.11 (m, 3H), 1.09-1.04 (m, 1H), 0.98 (s, 3H), 0.67-0.61 (m, 1H), 0.56 (s, 3H).

Example 19

2,2-difluoro-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-1-methyl-cyclopropanecarboxamide

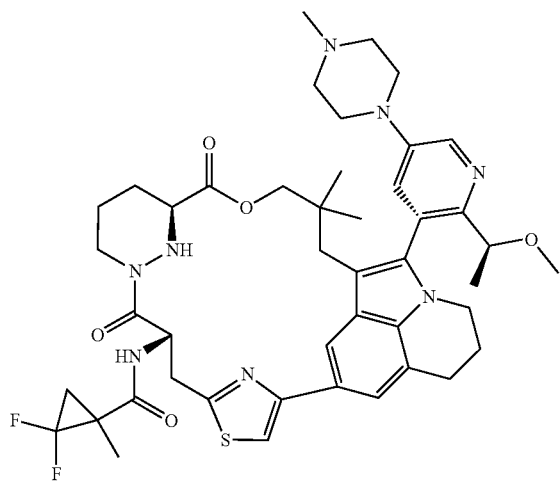

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate E) and 2,2-difluoro-1-methyl-cyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 19 (11 mg) was obtained as a yellow solid. MS calc'd 859.4 (MH$^+$), measured 859.6 (MH$^+$). $^1$H NMR (400 MHz, METHANOL-d$_4$) δ=8.49 (d, J=2.8 Hz, 1H), 8.39 (d, J=6.4 Hz, 1H), 7.66-7.57 (m, 1H), 7.53-7.47 (m, 1H), 7.43 (s, 1H), 5.85-5.70 (m, 1H), 4.53-4.46 (m 1H), 4.42 (d, J=12.4 Hz, 1H), 4.29-4.18 (m, 2H), 4.15-4.04 (m, 1H), 3.77-3.73 (m, 2H), 3.66-3.52 (m, 3H), 3.47-3.39 (m, 6H), 3.38-3.33 (m, 3H), 3.15-3.08 (m, 2H), 3.01-2.95 (m, 4H), 2.82-2.73 (m, 1H), 2.59 (d, J=14.4 Hz, 1H), 2.34-2.26 (m, 1H), 2.23-2.14 (m, 2H), 2.13-2.02 (m, 1H), 1.98-1.90 (m, 1H), 1.85-1.73 (m, 1H), 1.57 (s, 4H), 1.46 (d, J=6.4 Hz, 3H), 1.41-1.28 (m, 2H), 0.99 (s, 3H), 0.54 (s, 3H).

Example 21

(1S,2S)-2-(difluoromethyl)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]cyclopropanecarboxamide

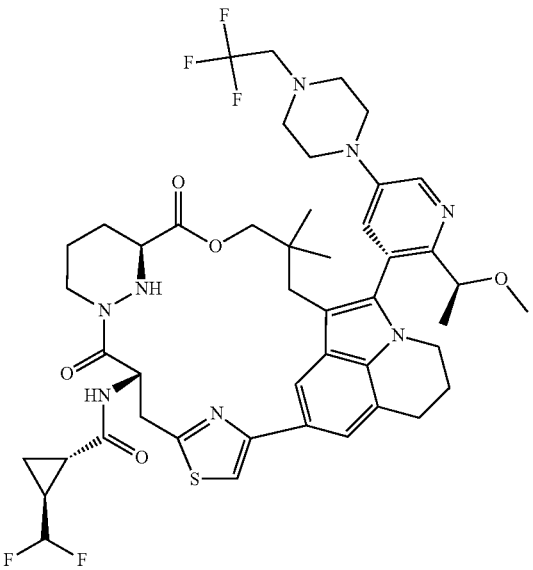

The title compound was prepared in analogy to the preparation of Example 1 by using (7S,13S)-7-amino-(20M)-20-[2-[(1S)-1-methoxyethyl]-5-[4-(2,2,2-trifluoroethyl) piperazin-1-yl]-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (intermediate G) and (1S,2S)-2-(difluoromethyl) cyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 21 (7.3 mg) was obtained as a yellow solid. MS calc'd 927.4 (MH$^+$), measured 927.4 (MH$^+$). $^1$H NMR (400 MHZ, METHANOL-d$_4$) δ=8.42 (s, 1H), 8.37 (d, J=2.8 Hz, 1H), 7.80 (d, J=2.8 Hz, 1H), 7.50 (s, 1H), 7.45 (s, 1H), 5.94-5.66 (m, 2H), 4.54-4.48 (m, 1H), 4.42 (d, J=11.6 Hz, 1H), 4.21 (dd, J=2.8, 12.4 Hz, 1H), 4.16-4.10 (m, 1H), 3.80-3.72 (m, 2H), 3.49-3.45 (m, 4H), 3.42-3.40 (m, 3H), 3.29-3.23 (m, 1H), 3.21-3.11 (m, 3H), 3.11-3.00 (m, 3H), 2.89-2.85 (m, 4H), 2.81-2.74 (m, 1H), 2.73-2.67 (m, 1H), 2.36-2.29 (m, 1H), 2.21-2.13 (m, 2H), 2.07-2.02 (m, 1H), 1.95-1.89 (m, 1H), 1.81-1.72 (m, 2H), 1.65-1.57 (m, 1H), 1.47 (d, J=6.4 Hz, 3H), 1.30-1.27 (m, 1H), 1.16-1.08 (m, 2H), 0.99 (s, 3H), 0.62 (s, 3H).

Example 22

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-phenyl-cyclopropanecarboxamide

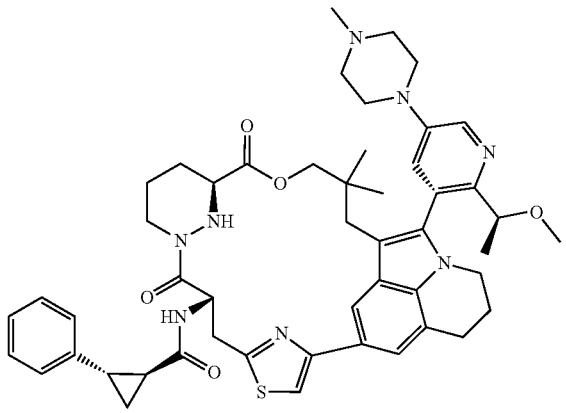

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate E) and (1S,2S)-2-phenylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 22 (21.7 mg) was obtained as a yellow solid. MS calc'd 885.4 (MH$^+$), measured 885.4 (MH$^+$). $^1$H NMR (400 MHZ, Methanol-d$_4$) δ=8.48 (d, J=2.8 Hz, 1H), 8.40 (s, 1H), 7.58 (d, J=2.8 Hz, 1H), 7.51 (s, 1H), 7.43 (s, 1H), 7.29-7.24 (m, 2H), 7.20-7.13 (m, 3H), 5.82 (d, J=7.2 Hz, 1H), 4.92-4.87 (m, 1H), 4.50-4.40 (m, 2H), 4.26-4.19 (m, 2H), 4.15-3.81 (m, 2H), 3.76 (d, J=1.6 Hz, 2H), 3.65-3.51 (m, 3H), 3.45-3.40 (m, 2H), 3.38 (s, 3H), 3.29-3.22 (m, 2H), 3.18-3.05 (m, 3H), 2.99 (s, 4H), 2.82-2.75 (m, 1H), 2.62 (d, J=14.0 Hz, 1H), 2.38-2.30 (m, 2H), 2.23-2.15 (m, 2H), 2.08-2.04 (m, 1H), 1.97-1.91 (m, 1H), 1.81-1.72 (m, 1H), 1.66-1.58 (m, 1H), 1.54-1.49 (m, 1H), 1.46 (d, J=6.4 Hz, 3H), 1.32-1.28 (m, 1H), 0.97 (s, 3H), 0.56 (s, 3H).

Example 24

(1r,2R,3S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2,3-dimethyl-cyclopropanecarboxamide

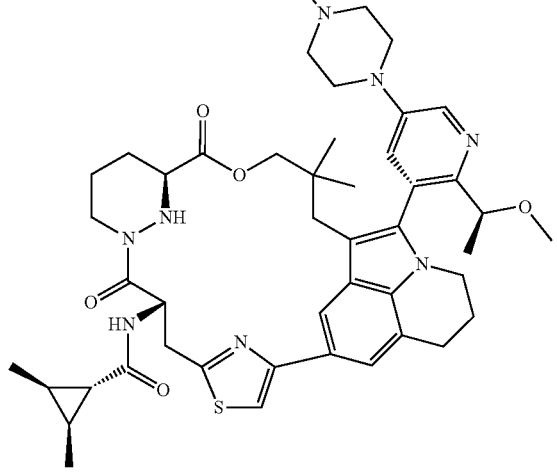

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29), 26-hexaene-8,14-dione (Intermediate E) and (1r,2S,3R)-2,3-dimethylcyclopropanecarboxylic acid (CAS 34669-51-7) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate F) and (1S,2S)-2-methylcyclopropanecarboxylic acid. Example 24 (7.3 mg) was obtained as a white solid. MS calc'd 837.4 (MH$^+$), measured 837.4 (MH$^+$). $^1$H NMR (400 MHZ, Methanol-d$_4$) δ=8.33-8.25 (m, 2H), 7.37 (s, 1H), 7.29 (s, 1H), 7.17 (d, J=2.8 Hz, 1H), 5.72-5.64 (m, 1H), 4.47 (br s, 2H), 4.36-4.24 (m, 2H), 4.17-4.08 (m, 2H), 3.66-3.62 (m, 2H), 3.54-3.45 (m, 1H), 3.34-3.26 (m, 5H), 3.18-3.13 (m, 1H), 3.02-2.85 (m, 3H), 2.73-2.61 (m, 5H), 2.50 (br d, J=14.3 Hz, 1H), 2.38 (s, 3H), 2.25-2.15 (m, 1H), 2.12-2.02 (m, 2H), 1.82 (br d, J=13.3 Hz, 1H), 1.71-1.58 (m, 1H), 1.49 (dq, J=3.6, 12.5 Hz, 1H), 1.36-1.31 (m, 3H), 1.30-1.21 (m, 2H), 1.08-0.94 (m, 8H), 0.86-0.81 (m, 3H), 0.46-0.40 (m, 3H).

Example 25

(1S,2S)-N-[(7S,13S)-(20M)-20-[5-[(9αS)-3,4,6,7,9,9a-hexahydro-1H-pyrazino[2,1-c][1,4]oxazin-8-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2-methyl-cyclopropanecarboxamide

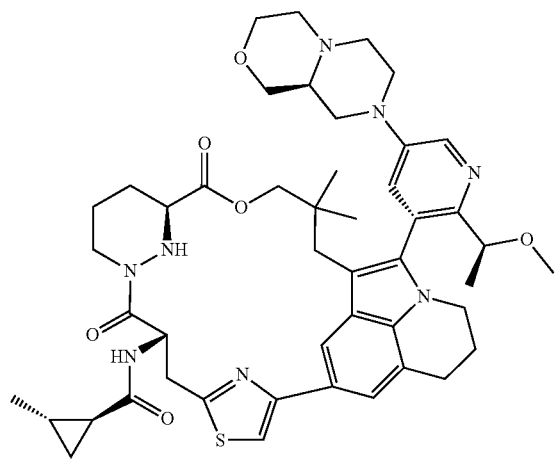

The title compound was prepared in analogy to the preparation of Example 1 by using (7S,13S)-(20M)-20-[5-[(9αS)-3,4,6,7,9,9a-hexahydro-1H-pyrazino[2,1-c][1,4]oxazin-8-yl]-2-[(1S)-1-methoxyethyl]-3-pyridyl]-7-amino-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate L) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate F). Example 25 (35.4 mg) was obtained as a yellow solid. MS calc'd 865.4 (MH$^+$), measured 865.5 (MH$^+$). $^1$H NMR (400 MHZ, METHANOL-d$_4$) δ=8.48 (s, 1H), 8.39 (s, 1H), 7.71-7.59 (m, 1H), 7.50 (s, 1H), 7.43 (s, 1H), 5.77 (d, J=8.4 Hz, 1H), 4.51-4.40 (m, 2H), 4.31-4.15 (m, 3H), 4.11-3.92 (m, 4H), 3.89-3.84 (m, 1H), 3.84-3.68 (m, 3H), 3.67-3.58 (m, 4H), 3.51-3.45 (m, 1H), 3.43-3.40 (m, 1H), 3.39-3.29 (m, 3H), 3.27-3.19 (m, 1H), 3.17-3.05 (m, 3H), 3.05-2.94 (m, 2H), 2.81-2.72 (m, 1H), 2.61-2.43 (m, 1H), 2.37-2.28 (m, 1H), 2.17-1.98 (m, 2H), 1.94-1.88 (m, 1H), 1.82-1.73 (m, 1H), 1.66-1.56 (m, 1H), 1.50-1.45 (m, 4H), 1.27-1.19 (m, 1H), 1.12 (d, J=6.0 Hz, 3H), 1.10-1.01 (m, 1H), 0.98 (s, 3H), 0.66-0.61 (m, 1H), 0.56 (s, 3H).

Example 28 and Example 29

(1R,2R)-2-(2-fluorophenyl)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]cyclopropanecarboxamide and (1S,2S)-2-(2-fluorophenyl)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]cyclopropanecarboxamide

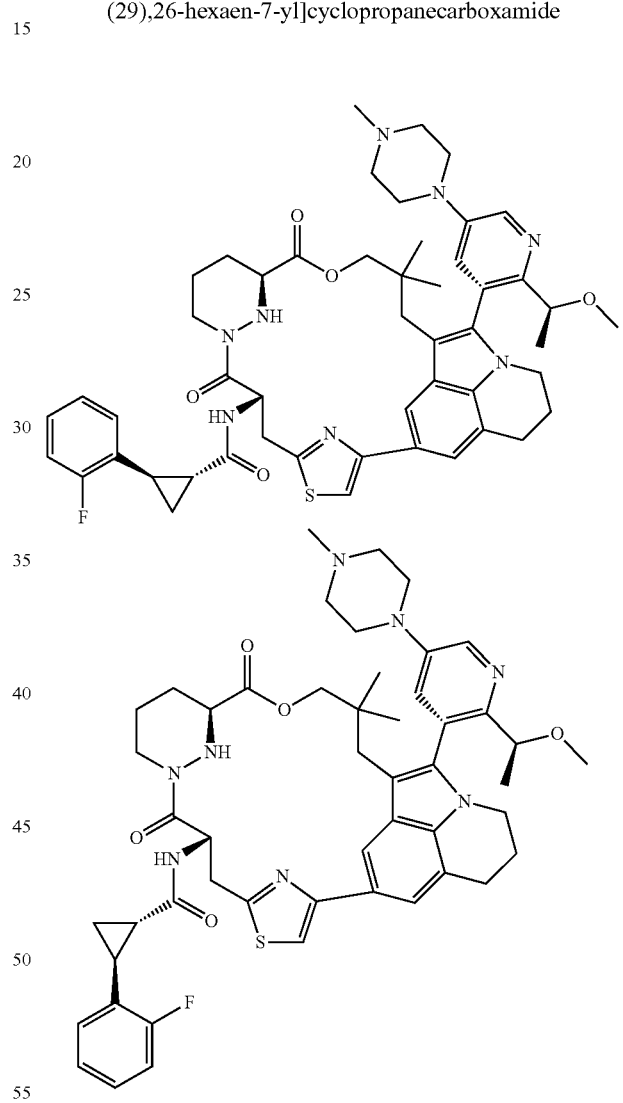

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate E) and trans-2-(2-fluorophenyl)cyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]

hentriaconta-1 (28),2,5 (31), 19,25 (29),26-hexaene-8,14-dione (Intermediate F) and (1S,2S)-2-methylcyclopropanecarboxylic acid and then purified by prep-HPLC and SFC.

SFC conditions: Instrument: SFC 150 Mgm; Column: TCI Chiral MB-S 250×30 mm I.D., 5 μm. Mobile phase: A for $CO_2$ and B for IPA (0.1% $NH_3H_2O$); Gradient: B 35%; Flow rate: 80 mL/min; Back pressure: 100 bar Column temperature: 35° C.

Example 28 (4.8 mg, SFC, slower eluted) was obtained as a yellow solid. MS calc'd 903.4 ($MH^+$), measured 903.4 ($MH^+$). $^1$H NMR (400 MHZ, Methanol-$d_4$) δ=8.47 (d, J=3.2 Hz, 1H), 8.40 (s, 1H), 7.52-7.48 (m, 2H), 7.42 (s, 1H), 7.26-7.20 (m, 1H), 7.14-7.04 (m, 3H), 5.87-5.81 (m, 1H), 4.48-4.42 (m, 2H), 4.28-3.97 (m, 4H), 3.76 (s, 3H), 3.62-3.55 (m, 2H), 3.46-3.41 (m, 2H), 3.39-3.37 (m, 3H), 3.28-3.25 (m, 1H), 3.13-3.08 (m, 2H), 2.99 (s, 5H), 2.82-2.75 (m, 1H), 2.61-2.52 (m, 2H), 2.35-2.28 (m, 1H), 2.27-2.00 (m, 4H), 1.97-1.91 (m, 1H), 1.82-1.73 (m, 1H), 1.65-1.58 (m, 1H), 1.50-1.43 (m, 4H), 1.42-1.23 (m, 2H), 1.00-0.95 (m, 3H), 0.57-0.51 (m, 3H).

Example 29 (5.3 mg, SFC, faster eluted) was obtained as a white solid. MS calc'd 903.4 ($MH^+$), measured 903.4 ($MH^+$). $^1$H NMR (400 MHZ, Methanol-$d_4$) δ=8.47-8.39 (m, 2H), 7.56-7.49 (m, 1H), 7.46-7.39 (m, 1H), 7.30-7.20 (m, 2H), 7.19-7.02 (m, 3H), 5.93-5.83 (m, 1H), 4.73-4.50 (m, 6H), 4.47-4.36 (m, 1H), 4.31-4.21 (m, 1H), 3.80-3.57 (m, 3H), 3.51-3.41 (m, 1H), 3.32-3.27 (m, 3H), 3.17-2.97 (m, 2H), 2.86-2.75 (m, 1H), 2.70-2.60 (m, 4H), 2.58-2.51 (m, 1H), 2.41-2.29 (m, 3H), 2.25-2.12 (m, 3H), 1.98-1.90 (m, 1H), 1.84-1.69 (m, 1H), 1.66-1.58 (m, 1H), 1.56-1.50 (m, 1H), 1.48-1.41 (m, 3H), 1.38-1.34 (m, 1H), 1.33-1.27 (m, 3H), 1.00-0.94 (m, 3H), 0.93-0.84 (m, 1H), 0.61-0.50 (m, 3H).

Example 30

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2-(2-pyridyl)cyclopropanecarboxamide The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate E) and trans-2-(2-pyridyl)cyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid and then purified by prep-HPLC and SFC.

SFC conditions: Instrument: SFC 150 Mgm; Column: TCI Chiral MB-S 250×30 mm I.D., 5 μm. Mobile phase: A for $CO_2$ and B for IPA (0.1% $NH_3H_2O$); Gradient: B 35%; Flow rate: 80 mL/min; Back pressure: 100 bar Column temperature: 35° C.

Example 30 (3.2 mg, SFC, faster eluted) was obtained as a yellow solid. MS calc'd 886.4 ($MH^+$), measured 886.4 ($MH^+$). $^1$H NMR (400 MHZ, Methanol-$d_4$) δ=8.33-8.26 (m, 3H), 7.64-7.56 (m, 1H), 7.41-7.37 (m, 1H), 7.31-7.28 (m, 1H), 7.25-7.21 (m, 1H), 7.16-7.13 (m, 1H), 7.13-7.07 (m, 1H), 5.76-5.68 (m, 1H), 4.53-4.42 (m, 6H), 4.34-4.25 (m, 2H), 4.16-4.09 (m, 2H), 3.69-3.63 (m, 2H), 3.54-3.47 (m, 1H), 3.35-3.29 (m, 1H), 3.04-2.89 (m, 3H), 2.73-2.62 (m, 1H), 2.57-2.48 (m, 5H), 2.44-2.37 (m, 1H), 2.28-2.17 (m, 5H), 2.14-2.03 (m, 2H), 1.86-1.79 (m, 1H), 1.71-1.42 (m, 5H), 1.37-1.32 (m, 3H), 0.89-0.75 (m, 4H), 0.49-0.41 (m, 3H).

Example 31

(1S,2S)-N-[(7S,13S)-23,23-difluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (29),2,5 (31), 19,25,27-hexaen-7-yl]-2-(difluoromethyl)cyclopropanecarboxamide

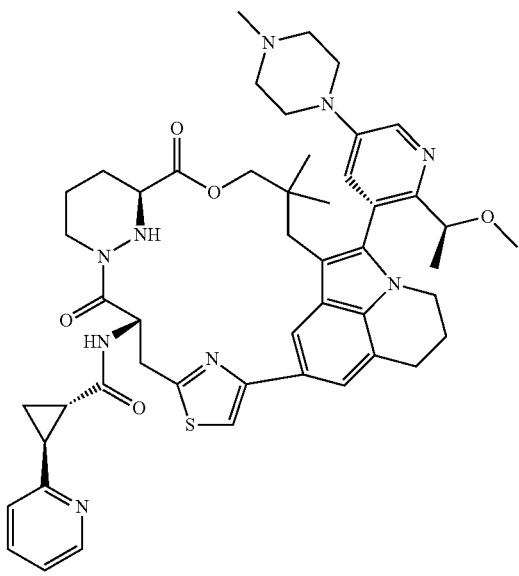

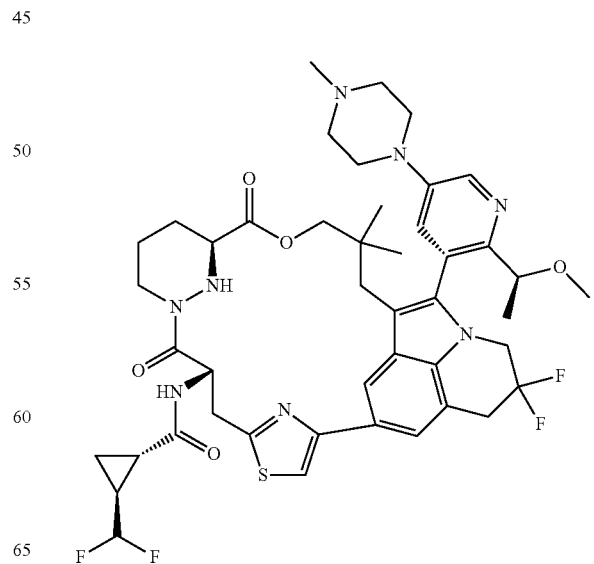

The title compound was prepared in analogy to the preparation of Example 1 by using (7S,13S)-7-amino-23, 23-difluoro-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$] hentriaconta-1 (28), 2,5 (31), 19,25 (29),26-hexaene-8,14-dione (intermediate K) and (1S,2S)-2-(difluoromethyl) cyclopropanecarboxylic acid instead of (7S,13S)-7-amino-(20M)-20-[2-[(1S)-1-methoxyethyl]-5-(4-methylpiperazino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$] hentriaconta-1 (28),2,5 (31), 19,25 (29),26-hexaene-8,14-dione (Intermediate F) and (1S,2S)-2-methylcyclopropanecarboxylic acid. Example 31 (5.1 mg) was obtained as a yellow solid. MS calc'd 895.4 (MH$^+$), measured 895.4 (MH$^+$). $^1$H NMR (400 MHZ, METHANOL-d$_4$) δ=8.51-8.48 (m, 2H), 7.58-7.55 (m, 2H), 7.39 (d, J=2.8 Hz, 1H), 5.84-5.65 (m, 2H), 4.61-4.55 (m, 1H), 4.49-4.41 (m, 2H), 4.25 (dd, J=2.8, 12.0 Hz, 1H), 4.10-3.99 (m, 2H), 3.94-3.86 (m, 1H), 3.81-3.68 (m, 3H), 3.66-3.56 (m, 3H), 3.53-3.40 (m, 3H), 3.35 (s, 4H), 3.28 (s, 1H), 3.14-3.11 (m, 1H), 2.99 (s, 3H), 2.82-2.76 (m, 1H), 2.62-2.56 (m, 1H), 2.21-2.15 (m, 1H), 2.08-2.03 (m, 1H), 1.97-1.92 (m, 1H), 1.83-1.74 (m, 2H), 1.65-1.59 (m, 1H), 1.46 (d, J=6.0 Hz, 3H), 1.32-1.28 (m, 1H), 1.19-1.10 (m, 2H), 0.97 (s, 3H), 0.55 (s, 3H).

Example 33

(1S,2R)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$] hentriaconta-1 (28),2,5 (31),19,25 (29),26-hexaen-7-yl]-2-methyl-cyclopropanecarboxamide

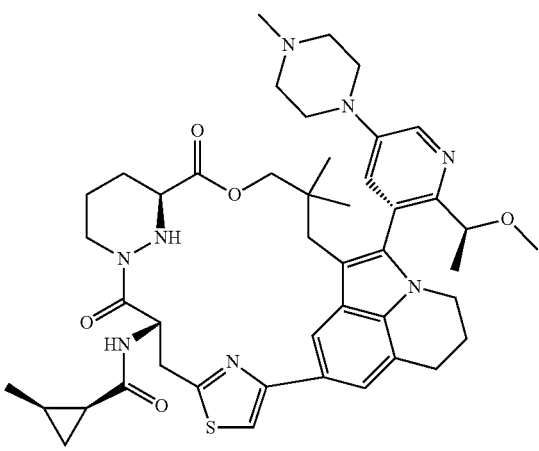

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$] hentriaconta-1 (28), 2,5 (31), 19,25 (29), 26-hexaene-8,14-dione (Intermediate E) and (1S,2R)-2-methylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$] hentriaconta-1 (28),2,5 (31), 19,25 (29),26-hexaene-8,14-dione (Intermediate F) and (1S,2S)-2-methylcyclopropanecarboxylic acid. Example 33 (12.5 mg) was obtained as a white solid. MS calc'd 824.4 (MH$^+$), measured 824.4 (MH$^+$). $^1$H NMR (400 MHZ, METHANOL-d$_4$) δ=8.40-8.36 (m, 1H), 8.32-8.28 (m, 1H), 7.46-7.43 (m, 1H), 7.42-7.38 (m, 1H), 7.35-7.30 (m, 1H), 5.71-5.66 (m, 1H), 4.40-4.35 (m, 1H), 4.34-4.28 (m, 1H), 4.18-4.07 (m, 2H), 4.03-3.85 (m, 1H), 3.72-3.55 (m, 3H), 3.54-3.45 (m, 2H), 3.40-3.35 (m, 1H), 3.34-3.31 (m, 1H), 3.31-3.24 (m, 6H), 3.17 (br d, J=8.8 Hz, 2H), 3.04-2.97 (m, 2H), 2.93-2.87 (m, 4H), 2.72-2.63 (m, 1H), 2.52-2.47 (m, 1H), 2.27-2.16 (m, 1H), 2.13-2.04 (m, 2H), 1.89-1.81 (m, 1H), 1.75-1.61 (m, 2H), 1.56-1.45 (m, 1H), 1.39-1.33 (m, 3H), 1.21-1.13 (m, 1H), 1.02-0.98 (m, 3H), 0.89-0.86 (m, 3H), 0.86-0.80 (m, 1H), 0.76-0.70 (m, 1H), 0.47-0.42 (m, 3H).

Example 34

(1S,2S)-2-(difluoromethyl)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]cyclopropanecarboxamide

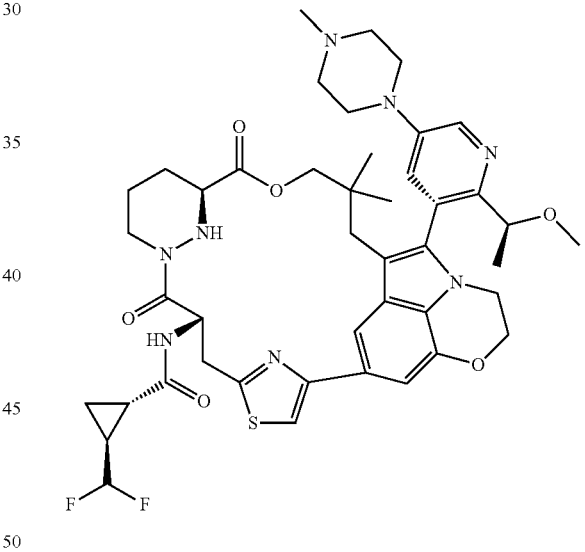

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15,24-dioxa-4-thia-9,21, 30,31-tetrazahexacyclo[23.3.1.1$^{2,5}$.1$^{9,13}$.0$^{19,27}$.0$^{21,26}$] hentriaconta-1 (28), 2,5 (31), 19,25 (29),26-hexaene-8,14-dione (Intermediate H) and (1S,2S)-2-(difluoromethyl) cyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$] hentriaconta-1 (28),2,5 (31), 19,25 (29),26-hexaene-8,14-dione (Intermediate F) and (1S,2S)-2-methylcyclopropanecarboxylic acid. Example 34 (38.2 mg) was obtained as a light yellow solid. MS calc'd 861.4 (MH$^+$), measured 861.4 (MH$^+$). $^1$H NMR (400 MHZ, METHANOL-d$_4$) δ=8.48 (d, J=2.9 Hz, 1H), 8.24-8.15 (m, 1H), 7.61-7.52 (m, 1H), 7.49 (s, 1H), 7.10 (s, 1H), 5.99-5.62 (m, 2H), 4.66-4.57 (m, 2H), 4.51 (q, J=6.3 Hz, 1H), 4.43 (d, J=12.5 Hz, 1H), 4.33-4.23 (m, 2H), 4.18-3.89 (m, 2H), 3.80-3.64 (m, 4H), 3.63-3.49 (m, 2H), 3.47-3.35 (m, 6H), 3.29-3.23 (m, 2H), 3.16-3.10 (m, 1H), 2.99 (s, 3H), 2.83-2.72 (m, 1H), 2.59 (d, J=14.5 Hz, 1H), 2.25-2.16 (m, 1H), 2.09-2.02 (m, 1H), 1.95 (d, J=12.6 Hz, 1H), 1.87-1.71 (m, 2H), 1.68-1.55 (m, 1H), 1.46 (d, J=6.3 Hz, 3H), 1.21-1.08 (m, 2H), 1.00 (s, 3H), 0.53 (s, 3H).

Example 35

(1S,5R,6r)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-3-oxabicyclo[3.1.0]hexane-6-carboxamide

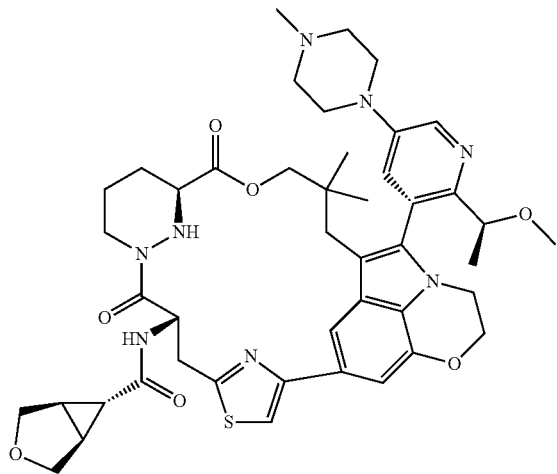

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate H) and (1S,5R,6r)-3-oxabicyclo[3.1.0]hexane-6-carboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 35 (42.0 mg) was obtained as a light yellow solid. MS calc'd 853.4 (MH$^+$), measured 853.4 (MH$^+$). $^1$H NMR (400 MHZ, METHANOL-d$_4$) δ=8.48 (d, J=2.8 Hz, 1H), 8.19 (s, 1H), 7.51-7.48 (m, 2H), 7.09 (d, J=0.9 Hz, 1H), 5.73 (d, J=7.6 Hz, 1H), 4.64-4.57 (m, 2H), 4.52-4.40 (m, 2H), 4.35-4.23 (m, 2H), 3.99-3.98 (m, 1H), 4.21-3.97 (m, 1H), 3.93 (d, J=8.6, 11.6 Hz, 2H), 3.80-3.67 (m, 6H), 3.58 (d, J=6.0 Hz, 2H), 3.45-3.34 (m, 6H), 3.30-3.19 (m, 4H), 3.12 (d, J=14.3 Hz, 1H), 2.78 (t, J=2.8, 13.0 Hz, 1H), 2.58 (d, J=14.5 Hz, 1H), 2.26-2.16 (m, 1H), 2.14-2.09 (m, 1H), 2.09-1.99 (m, 2H), 1.99-1.91 (m, 1H), 1.87-1.73 (m, 1H), 1.69 (t, J=3.1 Hz, 1H), 1.67-1.55 (m, 1H), 1.46 (d, J=6.1 Hz, 3H), 1.00 (s, 3H), 0.52 (s, 3H).

Example 37

(1R,2S)-2-cyclopropyl-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (29),2,5 (31),19,25,27-hexaen-7-yl]cyclopropanecarboxamide

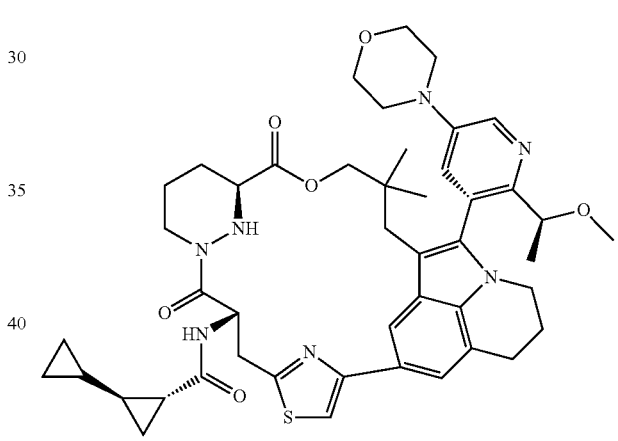

The title compound was prepared in analogy to the preparation of Example 1 by using (1R,2S)-2-cyclopropyl-cyclopropanecarboxylic acid instead of (1S,2S)-2-methyl-cyclopropanecarboxylic acid. Example 37 (23.1 mg) was obtained as a yellow solid. MS calc'd 836.4 (MH$^+$), measured 836.6 (MH$^+$). $^1$H NMR (400 MHZ, METHANOL-d$_4$) δ=8.41 (d, J=2.4 Hz, 1H), 8.37 (d, J=2.8 Hz, 1H), 7.73 (d, J=2.4 Hz, 1H), 7.50 (d, J=8.4 Hz, 1H), 7.44 (d, J=4.0 Hz, 1H), 5.80 (d, J=7.2 Hz, 1H), 4.55-4.48 (m, 1H), 4.42 (d, J=13.2 Hz, 1H), 4.25-4.18 (m, 1H), 4.18-4.11 (m, 1H), 3.86 (t, J=4.8 Hz, 4H), 3.75 (d, J=6.4 Hz, 2H), 3.70-3.64 (m, 1H), 3.61 (d, J=6.8 Hz, 1H), 3.42-3.37 (m, 8H), 3.28-3.23 (m, 1H), 3.11-3.03 (m, 2H), 2.81-2.72 (m, 1H), 2.71-2.64 (m, 1H), 2.22-2.14 (m, 2H), 1.97-1.89 (m, 1H), 1.80-1.70 (m, 1H), 1.64-1.54 (m, 2H), 1.47 (d, J=6.0 Hz, 3H), 1.34-1.29 (m, 1H), 1.20-1.16 (m, 1H), 1.01-0.94 (m, 4H), 0.91-0.86 (m, 1H), 0.70-0.64 (m, 1H), 0.60 (s, 3H), 0.49-0.39 (m, 2H), 0.20-0.14 (m, 2H).

Example 38

(1S,2S)-N-[(7S,13S)-(20M)-20-[2-[(1S)-1-methoxyethyl]-5-morpholino-3-pyridyl]-17,17,23,23-tetramethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2-methyl-cyclopropanecarboxamide

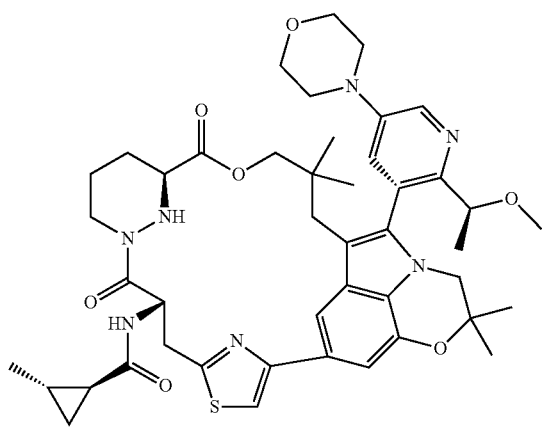

The title compound was prepared in analogy to the preparation of Example 1 by using (7S,13S)-7-amino-(20M)-20-[2-[(1S)-1-methoxyethyl]-5-morpholino-3-pyridyl]-17,17,23,23-tetramethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate M) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate F). Example 38 (8.3 mg) was obtained as a white solid. MS calc'd 840.4 (MH$^+$), measured 840.4 (MH$^+$). $^1$H NMR (400 MHZ, METHANOL-d$_4$) δ=8.37 (d, J=2.8 Hz, 1H), 8.21 (s, 1H), 7.75 (s, 1H), 7.48 (s, 1H), 7.08 (s, 1H), 5.82-5.80 (m, 1H), 4.74-4.60 (m, 1H), 4.50-4.38 (m, 1H), 4.28-4.16 (m, 1H), 4.03-3.92 (d, J=12.4 Hz 1H), 3.90-3.82 (t, J=4.8, 5H), 3.81-3.74 (s, 2H), 3.64 (d, J=12.4 Hz, 1H), 3.42-3.38 (m, 7H), 3.14-3.01 (m, 1H), 2.83-2.73 (m, 1H), 2.69 (d, J=14.3 Hz, 1H), 2.20 (m, 1H), 2.01-1.88 (m, 1H), 1.81-1.69 (m, 1H), 1.68-1.56 (m, 1H), 1.53-1.48 (m, 6H), 1.48-1.44 (m, 1H), 1.35 (s, 3H), 1.31-1.18 (m, 2H), 1.12 (d, J=6.0 Hz, 3H), 1.09-1.03 (m, 1H), 1.02-0.97 (s, 3H), 0.69-0.60 (m, 4H).

Example 40

(1S,5R,6r)-N-[(7S,13S)-(20M)-20-[5-[(9αS)-3,4,6,7,9,9a-hexahydro-1H-pyrazino[2,1-c][1,4]oxazin-8-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-3-oxabicyclo[3.1.0]hexane-6-carboxamide

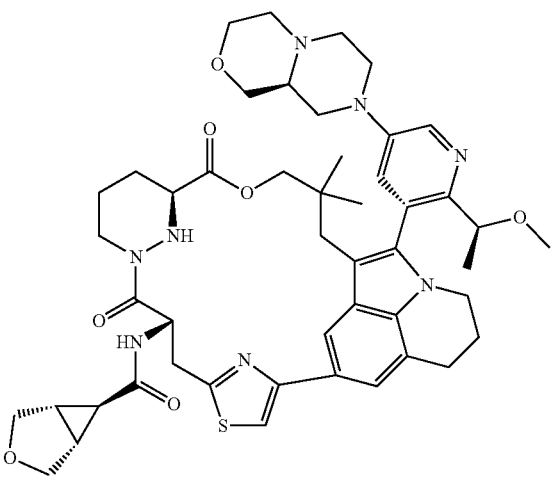

The title compound was prepared in analogy to the preparation of Example 1 by using (7S,13S)-(20M)-20-[5-[(9αS)-3,4,6,7,9,9a-hexahydro-1H-pyrazino[2,1-c][1,4]oxazin-8-yl]-2-[(1S)-1-methoxyethyl]-3-pyridyl]-7-amino-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate L) and (1S,5R,6r)-3-oxabicyclo[3.1.0]hexane-6-carboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 40 (17.1 mg) was obtained as a yellow solid. MS calc'd 893.4 (MH$^+$), measured 893.4 (MH$^+$). $^1$H NMR (400 MHZ, Methanol-d$_4$) δ=8.49 (d, J=2.8 Hz, 1H), 8.40 (s, 1H), 7.54-7.50 (m, 2H), 7.44 (s, 1H), 5.78 (d, J=8.0 Hz, 1H), 4.87-4.83 (m, 1H), 4.49-4.42 (m, 2H), 4.28-4.20 (m, 2H), 4.16-4.05 (m, 4H), 3.98-3.92 (m, 2H), 3.90-3.83 (m, 1H), 3.80-3.74 (m, 4H), 3.65-3.57 (m, 4H), 3.53-3.48 (m, 1H), 3.46-3.40 (m, 2H), 3.39 (s, 3H), 3.29-3.25 (m, 1H), 3.15-3.08 (m, 2H), 3.05-2.90 (m, 2H), 2.84-2.76 (m, 1H), 2.61 (d, J=14.0 Hz, 1H), 2.37-2.29 (m, 1H), 2.24-2.17 (m, 2H), 2.15-2.07 (m, 2H), 1.99-1.91 (m, 1H), 1.85-1.75 (m, 1H), 1.71 (t, J=3.2 Hz, 1H), 1.66-1.57 (m, 1H), 1.47 (d, J=6.0 Hz, 3H), 1.38-1.28 (m, 1H), 0.98 (s, 3H), 0.57 (s, 3H).

Example 41

(1S,2S)-N-[(7S,13S)-(20M)-20-[5-[(9αS)-3,4,6,7,9,9a-hexahydro-1H-pyrazino[2,1-c][1,4]oxazin-8-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-(difluoromethyl)cyclopropanecarboxamide

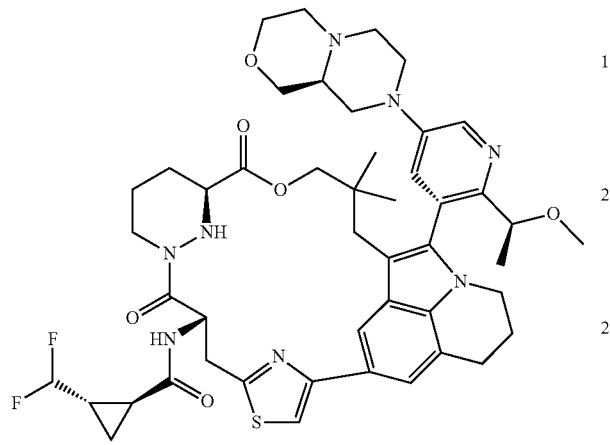

The title compound was prepared in analogy to the preparation of Example 1 by using (7S,13S)-(20M)-20-[5-[(9αS)-3,4,6,7,9,9a-hexahydro-1H-pyrazino[2,1-c][1,4]oxazin-8-yl]-2-[(1S)-1-methoxyethyl]-3-pyridyl]-7-amino-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1(28), 2,5(31), 19,25(29),26-hexaene-8,14-dione (Intermediate L) and (1S,2S)-2-(difluoromethyl)cyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 41 (16.4 mg) was obtained as a yellow solid. MS calc'd 901.4 (MH$^+$), measured 901.4 (MH$^+$). $^1$H NMR (400 MHZ, Methanol-d$_4$) δ=8.47 (d, J=2.8 Hz, 1H), 8.39 (s, 1H), 7.52-7.49 (m, 2H), 7.42 (s, 1H), 5.96-5.66 (m, 2H), 4.85-4.81 (m, 1H), 4.47-4.40 (m, 2H), 4.26-4.19 (m, 2H), 4.14-4.04 (m, 4H), 3.89-3.83 (m, 1H), 3.78-3.73 (m, 2H), 3.64-3.56 (m, 4H), 3.53-3.43 (m, 2H), 3.43-3.38 (m, 2H), 3.37 (s, 3H), 3.27-3.25 (m, 1H), 3.12-3.05 (m, 2H), 3.02-2.90 (m, 2H), 2.82-2.74 (m, 1H), 2.60 (d, J=14.4 Hz, 1H), 2.35-2.28 (m, 1H), 2.21-2.14 (m, 2H), 2.08-2.04 (m, 1H), 1.97-1.91 (m, 1H), 1.82-1.74 (m, 2H), 1.65-1.56 (m, 1H), 1.45 (d, J=6.0 Hz, 3H), 1.19-1.10 (m, 2H), 0.96 (s, 3H), 0.55 (s, 3H).

Example 42

(1R,5S,6s)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-3-oxabicyclo[3.1.0]hexane-6-carboxamide

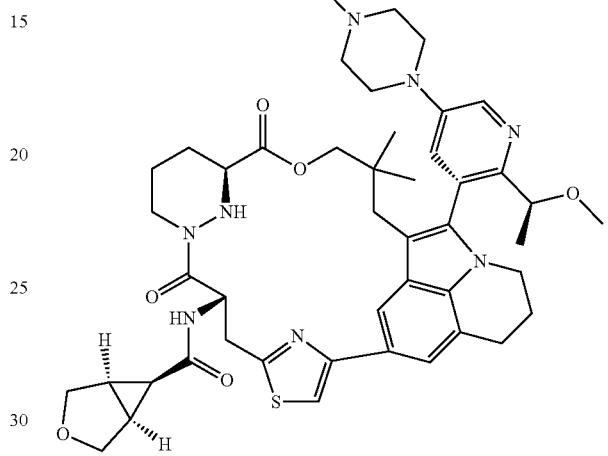

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate E) and (1R,5S,6s)-3-oxabicyclo[3.1.0]hexane-6-carboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 42 (9 mg) was obtained as a white solid. MS calc'd 851.4 (MH$^+$), measured 851.6 (MH$^+$). $^1$H NMR (400 MHZ, METHANOL-d$_4$) δ=8.48 (br s, 1H), 8.39 (s, 1H), 7.56 (br s, 1H), 7.49 (s, 1H), 7.41 (s, 1H), 5.78 (br d, J=7.0 Hz, 1H), 4.51-4.38 (m, 2H), 4.29-4.14 (m, 2H), 3.90 (br d, J=12.3 Hz, 3H), 3.82-3.67 (m, 5H), 3.66-3.54 (m, 3H), 3.36 (s, 7H), 3.28-3.22 (m, 1H), 3.17-3.02 (m, 3H), 2.97 (s, 4H), 2.83-2.71 (m, 1H), 2.69-2.56 (m, 1H), 2.17 (br d, J=12.0 Hz, 3H), 2.12-2.01 (m, 2H), 1.98-1.85 (m, 1H), 1.83-1.54 (m, 3H), 1.45 (d, J=6.1 Hz, 3H), 0.96 (s, 3H), 0.55 (s, 3H).

Example 43 (1S,2S)-N-[(7S,13S)-(20M)-20-[2-[(1S)-1-methoxyethyl]-5-morpholino-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (29),2,5 (31), 19,25,27-hexaen-7-yl]-2-phenyl-cyclopropanecarboxamide

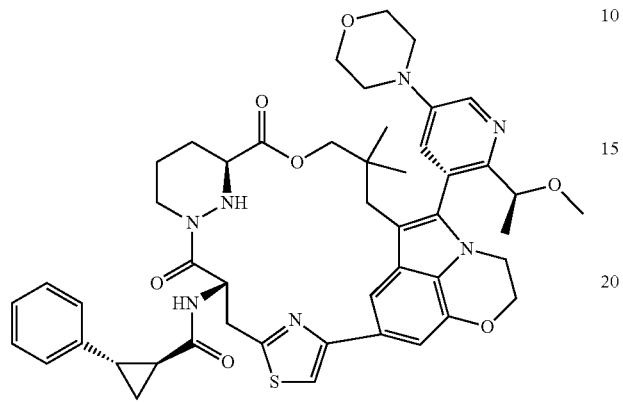

The title compound was prepared in analogy to the preparation of Example 1 by using (7S,13S)-7-amino-(20M)-20-[2-[(1S)-1-methoxyethyl]-5-morpholino-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (intermediate J) and (1S,2S)-2-phenylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate F) and (1S,2S)-2-methylcyclopropanecarboxylic acid. Example 43 (14.54 mg) was obtained as a light yellow solid. MS calc'd 874.4 (MH$^+$), measured 874.4 (MH$^+$). $^1$H NMR (400 MHZ, METHANOL-d$_4$) δ=8.37 (d, J=3.0 Hz, 1H), 8.23 (s, 1H), 7.81 (br d, J=0.9 Hz, 1H), 7.51 (s, 1H), 7.29-7.25 (m, 2H), 7.19 (d, J=7.5 Hz, 1H), 7.16-7.13 (m, 3H), 5.81 (br d, J=7.8 Hz, 1H), 4.68-4.55 (m, 4H), 4.45-4.40 (m, 1H), 4.26 (br d, J=8.4 Hz, 2H), 3.91-3.84 (m, 5H), 3.77 (d, J=3.8 Hz, 2H), 3.43 (s, 5H), 3.40 (br s, 3H), 3.17-3.13 (m, 1H), 2.67 (br d, J=14.1 Hz, 1H), 2.39-2.32 (m, 1H), 2.20 (br d, J=12.6 Hz, 1H), 2.06-2.02 (m, 1H), 1.99-1.91 (m, 1H), 1.85-1.73 (m, 1H), 1.69-1.59 (m, 1H), 1.49 (d, J=6.1 Hz, 4H), 1.33-1.28 (m, 2H), 1.03 (s, 3H), 0.59 (s, 3H).

Example 44

(1S,2S)-N-[(7S,13S)-(20M)-20-[2-[(1S)-1-methoxyethyl]-5-[4-(2,2,2-trifluoroethyl) piperazin-1-yl]-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (29),2,5 (31),19,25,27-hexaen-7-yl]-2-phenyl-cyclopropanecarboxamide

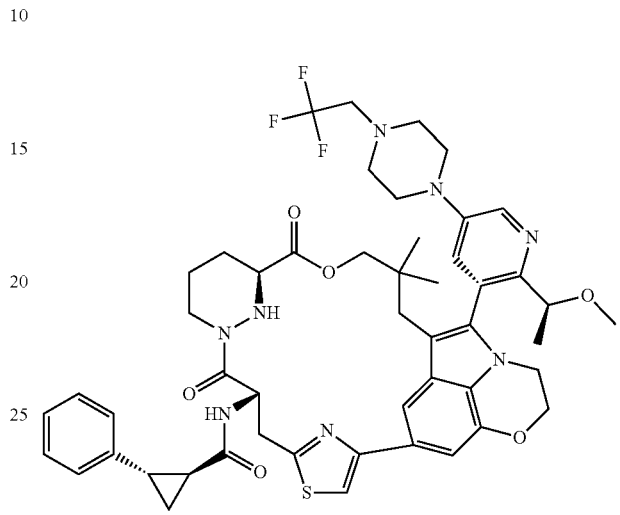

The title compound was prepared in analogy to the preparation of Example 1 by using (7S,13S)-7-amino-(20M)-20-[2-[(1S)-1-methoxyethyl]-5-[4-(2,2,2-trifluoroethyl) piperazin-1-yl]-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (intermediate I) and (1S,2S)-2-phenylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 44 (21.3 mg) was obtained as a light yellow solid. MS calc'd 955.4 (MH$^+$), measured 955.4 (MH$^+$). $^1$H NMR (400 MHZ, METHANOL-d$_4$) δ=8.37 (d, J=2.8 Hz, 1H), 8.22 (s, 1H), 7.66 (d, J=2.9 Hz, 1H), 7.50 (s, 1H), 7.29-7.25 (m, 2H), 7.19 (d, J=7.3 Hz, 1H), 7.14 (d, J=7.4 Hz, 2H), 7.12 (s, 1H), 5.84-5.78 (m, 1H), 4.61 (br d, J=3.9 Hz, 2H), 4.54 (br d, J=6.3 Hz, 1H), 4.43 (br d, J=10.5 Hz, 1H), 4.26 (dd, J=2.6, 12.1 Hz, 2H), 3.76 (s, 3H), 3.44 (dt, 5H), 3.40 (s, 3H), 3.28-3.22 (m, 1H), 3.19-3.11 (m, 3H), 2.88 (br t, J=4.8 Hz, 4H), 2.79 (dt, J=2.9, 13.0 Hz, 1H), 2.65 (d, J=14.6 Hz, 1H), 2.39-2.32 (m, 1H), 2.24-2.17 (m, 1H), 2.09-2.04 (m, 1H), 1.99-1.91 (m, 1H), 1.78 (br d, J=11.9 Hz, 1H), 1.62 (br dd, J=3.9, 12.2 Hz, 1H), 1.54-1.50 (m, 1H), 1.47 (d, J=6.3 Hz, 3H), 1.33-1.28 (m, 1H), 1.02 (s, 3H), 0.57 (s, 3H).

Example 45

(1r,2S,3R)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31),19,25 (29),26-hexaen-7-yl]-2,3-dimethyl-cyclopropanecarboxamide

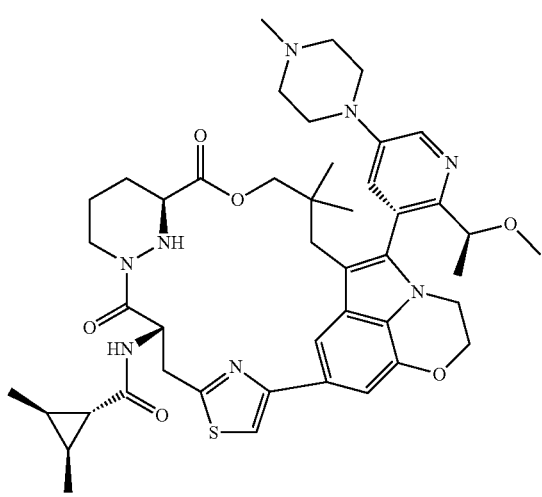

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate H) and (1r,2S,3R)-2,3-dimethylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 45 (32.0 mg) was obtained as a light yellow solid. MS calc'd 839.4 (MH$^+$), measured 839.4 (MH$^+$). $^1$H NMR (400 MHZ, METHANOL-d$_4$) δ=8.47 (d, J=2.8 Hz, 1H), 8.19 (s, 1H), 7.56-7.44 (m, 2H), 7.09 (d, J=1.0 Hz, 1H), 5.73 (d, J=7.5 Hz, 1H), 4.86-4.83 (m, 1H), 4.66-4.57 (m, 2H), 4.51-4.39 (m, 2H), 4.37-4.23 (m, 2H), 4.04 (d, J=2.9 Hz, 2H), 3.79-3.69 (m, 3H), 3.61 (d, J=7.0 Hz, 2H), 3.37 (s, 4H), 3.28-3.08 (m, 4H), 2.99 (s, 3H), 2.82-2.72 (m, 1H), 2.62-2.53 (m, 1H), 2.20 (d, J=2.8, 12.8 Hz, 1H), 2.00-1.91 (m, 1H), 1.86-1.72 (m, 1H), 1.68-1.55 (m, 1H), 1.45 (d, J=6.3 Hz, 3H), 1.42-1.27 (m, 3H), 1.19-1.09 (m, 7H), 1.04-0.96 (m, 3H), 0.52 (s, 3H).

Example 46

(1S,2S)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (29),2,5 (31), 19,25,27-hexaen-7-yl]-2-phenyl-cyclopropanecarboxamide

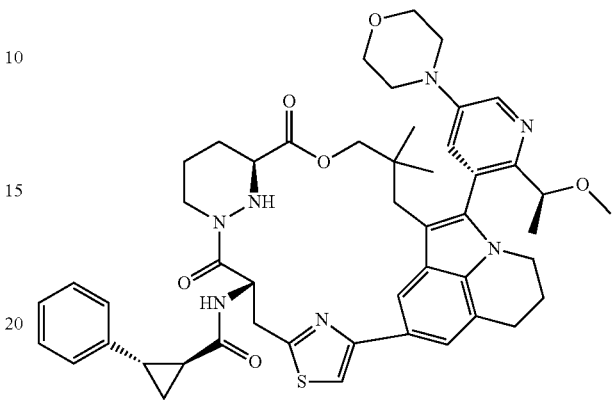

The title compound was prepared in analogy to the preparation of Example 1 by using (1S,2S)-2-phenylcyclopropanecarboxylic acid instead of (1S,2S)-2-methylcyclopropanecarboxylic acid. Example 46 (8 mg) was obtained as a yellow solid. MS calc'd 872.4 (MH$^+$), measured 872.6 (MH$^+$). $^1$H NMR (400 MHZ, METHANOL-d$_4$) δ=8.38 (s, 2H), 7.49 (s, 1H), 7.40 (s, 1H), 7.30-7.23 (m, 3H), 7.21-7.12 (m, 3H), 5.92-5.74 (m, 1H), 4.45-4.37 (m, 2H), 4.28-4.21 (m, 2H), 3.86 (t, J=4.4 Hz, 4H), 3.76 (s, 2H), 3.62-3.56 (m, 1H), 3.46-3.42 (m, 1H), 3.14-2.97 (m, 4H), 2.82-2.74 (m, 1H), 2.65-2.59 (m, 1H), 2.39-2.29 (m, 2H), 2.23-2.16 (m, 2H), 2.08-2.03 (m, 1H), 1.96-1.90 (m, 1H), 1.80-1.72 (m, 1H), 1.67-1.54 (m, 2H), 1.54-1.49 (m, 1H), 1.44 (d, J=6.0 Hz, 3H), 1.34-1.27 (m, 6H), 0.96 (s, 3H), 0.92-0.87 (m, 1H), 0.55 (s, 3H).

Example 47

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-pyrimidin-5-yl-cyclopropanecarboxamide

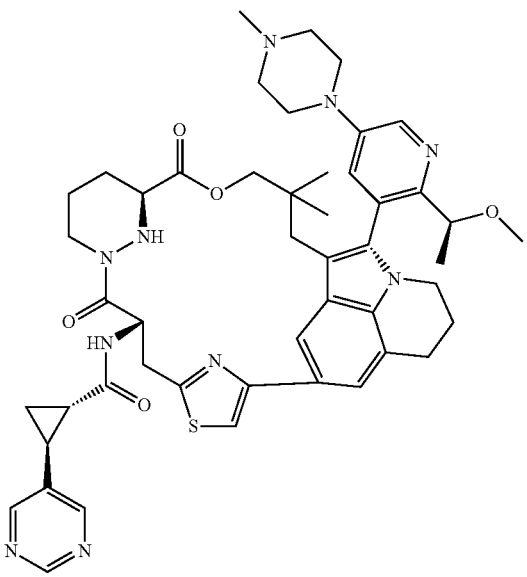

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate E) and trans-2-pyrimidin-5-ylcyclopropanecarboxylic acid (Intermediate R1) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate F) and (1S,2S)-2-methylcyclopropanecarboxylic acid and then purified by prep-HPLC and SFC.

SFC conditions: Column DAICEL CHIRALPAK IC (250 mm×30 mm, 10 μm); Condition: CO$_2$-EtOH (0.1% NH$_3$H$_2$O); Begin B 70 End B 70; Gradient Time (min) 6.8 100% B Hold; Flow Rate: (mL/min) 100.

Example 47 (13 mg, SFC, faster eluted) was obtained as a yellow solid. MS calc'd 887.4 (MH$^+$), measured 887.6 (MH$^+$). $^1$H NMR (400 MHZ, METHANOL-d$_4$) δ=8.91 (s, 1H), 8.60-8.50 (s, 2H), 8.38-8.24 (d, J=30 Hz, 2H), 7.45-7.37 (s, 1H), 7.33-7.25 (d, J=11.2 Hz, 2H), 5.75-5.66 (m, 1H), 4.36-4.30 (m, 2H), 4.16-4.11 (m, 2H), 4.03-3.97 (m, 1H), 3.68-3.64 (s, 2H), 3.49-3.43 (m, 2H), 3.39-3.35 (m, 1H), 3.34-3.31 (s, 1H), 3.23-3.22 (m, 1H), 3.04-2.95 (m, 3H), 2.90-2.86 (s, 4H), 2.74-2.65 (m, 1H), 2.52-2.39 (m, 2H), 2.34-2.27 (m, 1H), 2.25-2.16 (m, 1H), 2.13-2.08 (m, 4H), 1.88-1.82 (m, 1H), 1.71-1.64 (m, 1H), 1.56-1.51 (m, 2H), 1.36-1.31 (d, J=6.4 Hz, 4H), 1.28-1.24 (d, J=6.8 Hz, 2H), 1.20-1.18 (s, 2H), 0.88-0.83 (s, 3H), 0.82-0.77 (m, 1H), 0.47-0.40 (s, 3H).

Example 48

(1S,5R)-3,3-difluoro-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]bicyclo[3.1.0]hexane-6-carboxamide

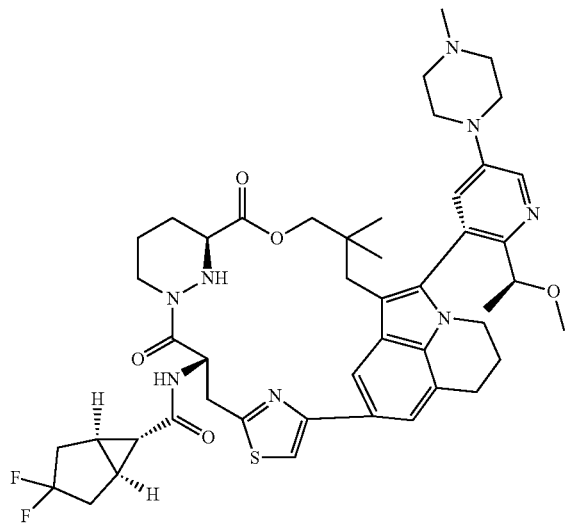

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$] hentriaconta-1 (28), 2,5 (31), 19,25 (29), 26-hexaene-8,14-dione (Intermediate E) and (1S,5R)-3,3-difluorobicyclo[3.1.0]hexane-6-carboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$] hentriaconta-1 (28), 2,5 (31), 19,25 (29), 26-hexaene-8,14-dione (Intermediate F) and (1S,2S)-2-methylcyclopropanecarboxylic acid. Example 48 (18.1 mg) was obtained as a yellow solid. MS calc'd 885.4 (MH$^+$), measured 885.6 (MH$^+$). 1H NMR (400 MHz, Methanol-d$_4$) δ=8.47 (d, J=2.8 Hz, 1H), 8.38 (s, 1H), 7.52-7.48 (m, 2H), 7.42 (s, 1H), 5.77-5.71 (m, 1H), 4.89 (s, 1H), 4.48-4.40 (m, 2H), 4.26-4.19 (m, 2H), 4.17-3.85 (m, 2H), 3.75 (s, 2H), 3.67-3.52 (m, 3H), 3.37 (s, 3H), 3.28-3.24 (m, 1H), 3.12-3.06 (m, 2H), 2.99 (s, 4H), 2.81-2.73 (m, 1H), 2.60 (d, J=14.4 Hz, 1H), 2.57-2.40 (m, 3H), 2.33-2.14 (m, 6H), 1.97-1.83 (m, 4H), 1.82-1.73 (m, 2H), 1.64-1.57 (m, 1H), 1.45 (d, J=6.0 Hz, 3H), 1.34-1.29 (m, 1H), 0.96 (s, 3H), 0.55 (s, 3H).

Example 49

(1S,2S)-N-[(7S,13S)-(20M)-20-[5-[(9αR)-1,3,4,6,7,8,9,9a-octahydropyrido[1,2-a]pyrazin-2-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-methyl-cyclopropanecarboxamide

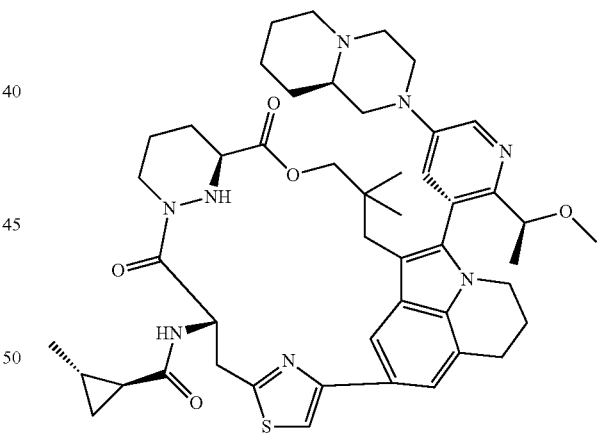

The title compound was prepared in analogy to the preparation of Example 1 by using (7S,13S)-(20M)-20-[5-[(9αR)-1,3,4,6,7,8,9,9a-octahydropyrido[1,2-a]pyrazin-2-yl]-2-[(1S)-1-methoxyethyl]-3-pyridyl]-7-amino-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate L2) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$] hentriaconta-1 (28), 2,5 (31), 19,25 (29),26-hexaene-8,14-dione (Intermediate F). Example 49 (29.8 mg) was obtained as a yellow solid. MS calc'd 863.5 (MH$^+$), measured 863.6

(MH+). ¹H NMR (400 MHZ, Methanol-d₄) δ=8.50 (d, J=2.8 Hz, 1H), 8.39 (s, 1H), 7.66 (s, 1H), 7.50 (s, 1H), 7.43 (s, 1H), 5.79-5.74 (m, 1H), 4.52-4.47 (m, 1H), 4.43 (d, J=10.8 Hz, 1H), 4.23 (dd, J=3.0, 12.0 Hz, 1H), 4.21-4.07 (m, 3H), 3.78-3.72 (m, 2H), 3.64-3.52 (m, 3H), 3.39 (s, 5H), 3.36-3.33 (m, 1H), 3.30-3.22 (m, 2H), 3.14-3.06 (m, 3H), 3.04-2.95 (m, 2H), 2.81-2.73 (m, 1H), 2.61 (d, J=14.4 Hz, 1H), 2.37-2.28 (m, 1H), 2.22-2.14 (m, 2H), 2.07-1.92 (m, 4H), 1.87-1.74 (m, 2H), 1.68-1.56 (m, 3H), 1.51-1.45 (m, 4H), 1.27-1.20 (m, 1H), 1.12 (d, J=6.0 Hz, 3H), 1.09-1.05 (m, 1H), 0.98 (s, 3H), 0.66-0.61 (m, 1H), 0.56 (s, 3H).

Example 50

(1S,2S)-N-[(7S,13S)-(20M)-20-[2-[(1S)-1-methoxy-ethyl]-5-(4-methylpiperazin-1-yl)-3-pyridyl]-17,17-dimethyl-8,14-dioxo-15-oxa-4-thia-9,21,30,31-tetrazahexacyclo[23.3.1.1²,⁵.1⁹,¹³.0¹⁹,²⁷.0²¹,²⁶]hentriaconta-1 (28),2,5 (31), 19,25 (29),26-hexaen-7-yl]-2-pyrimidin-4-yl-cyclopropanecarboxamide

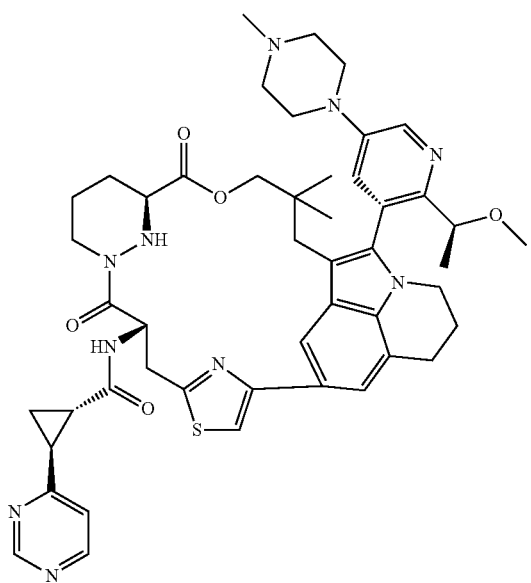

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1²,⁵.1⁹,¹³.0¹⁹,²⁷.0²¹,²⁶]hentriaconta-1 (28), 2,5 (31), 19,25 (29),26-hexaene-8,14-dione (Intermediate E) and 2-pyrimidin-4-ylcyclopropanecarboxylic acid (Intermediate R3) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1²,⁵.1⁹,¹³.0¹⁹,²⁷.0²¹,²⁶]hentriaconta-1 (28), 2,5 (31), 19,25 (29), 26-hexaene-8,14-dione (Intermediate F) and (1S,2S)-2-methylcyclopropanecarboxylic acid and then purified by prep-HPLC and SFC.

SFC conditions: Column: Chiralpak IG-3 50×4.6 mm I.D., 3 μm; Mobile phase: Phase A for CO₂, and Phase B for EtOH+ACN (0.05% DEA); Gradient elution: 60% EtOH+ACN (0.05% DEA) in CO₂, Flow rate: 3 mL/min; Detector: PDA; Column Temp: 35C; Back Pressure: 100 Bar Example 50 (16.9 mg, SFC, faster eluted) was obtained as a white solid. MS calc'd 887.4 (MH+), measured 887.5 (MH+). ¹H NMR (400 MHz, METHANOL-d₄) δ=8.89 (s, 1H), 8.54-8.43 (d, J=5.2 Hz 1H), 8.35-8.23 (m, 2H), 7.44-7.38 (d, J=4.4 Hz, 1H), 7.35 (s, 1H), 7.28 (s, 1H), 7.19-7.14 (d, J=2.4 Hz, 1H), 5.81-5.69 (d, J=8.8 Hz, 1H), 4.37-4.23 (m, 2H), 4.18-4.07 (m, 2H), 4.03-3.96 (m, 3H), 3.60 (s, 2H), 3.52-3.45 (m, 1H), 3.27 (s, 3H), 2.98-2.90 (m, 2H), 2.63 (s, 3H), 2.55-2.48 (m, 1H), 2.42-2.39 (m, 1H), 2.36-2.28 (m, 3H), 2.13-2.07 (m, 3H), 1.87-1.80 (m, 1H), 1.71-1.59 (m, 1H), 1.56-1.46 (m, 3H), 1.30-1.35 (d, J=6.0 Hz, 3H), 1.27 (s, 2H), 1.25 (s, 2H), 1.19 (s, 3H), 0.85 (s, 3H), 0.49-0.39 (m, 3H).

Example 51

(1S,2S)-N-[(7S,13S)-(20M)-20-[2-[(1S)-1-methoxy-ethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1²,⁵.1⁹,¹³.0¹⁹,²⁷.0²¹,²⁶]hentriaconta-1 (29),2,5 (31), 19,25,27-hexaen-7-yl]-2-phenyl-cyclopropanecarboxamide The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15,24-dioxa-4-thia-9,21,30,31-tetrazahexacyclo[23.3.1.1²,⁵.1⁹,¹³.0¹⁹,²⁷.0²¹,²⁶]hentriaconta-1 (28), 2,5 (31), 19,25 (29), 26-hexaene-8,14-dione (Intermediate H) and (1S,2S)-2-phenylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1²,⁵.1⁹,¹³.0¹⁹,²⁷.0²¹,²⁶]hentriaconta-1 (28),2,5 (31), 19,25 (29),26-hexaene-8,14-dione (Intermediate F) and (1S,2S)-2-methylcyclopropanecarboxylic acid. Example 51 (19.1 mg) was obtained as a light yellow solid. MS calc'd 887.4 (MH+), measured 887.4 (MH+). ¹H NMR (400 MHZ, METHANOL-d₄) δ=8.49 (d, J=2.4 Hz, 1H), 8.21 (s, 1H), 7.64 (d, J=2.6 Hz, 1H), 7.50 (s, 1H), 7.31-7.22 (m, 1H), 7.39-7.00 (m, 5H), 5.78 (d, J=8.5 Hz, 1H), 4.64-4.52 (m, 3H), 4.42 (d, J=11.8 Hz, 1H), 4.34-4.24 (m, 2H), 4.21-3.92 (m, 2H), 3.76 (s, 4H), 3.68-3.52 (m, 2H), 3.44-3.37 (m, 6H), 3.28-3.21 (m, 2H), 3.14 (d, J=14.6 Hz, 1H), 2.98 (s, 3H), 2.78 (d, J=2.6 Hz, 1H), 2.60 (d, J=14.3 Hz, 1H), 2.35 (d, J=2.8, 6.1 Hz, 1H), 2.21 (d, J=10.0 Hz, 1H), 2.09-2.03 (m, 1H), 1.99-1.89 (m, 1H), 1.85-1.73 (m, 1H), 1.66-1.56 (m, 1H), 1.54-1.45 (m, 4H), 1.32-1.26 (m, 1H), 1.02 (s, 3H), 0.54 (s, 3H).

Example 52

(1R,5S,6s)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-3-oxabicyclo[3.1.0]hexane-6-carboxamide

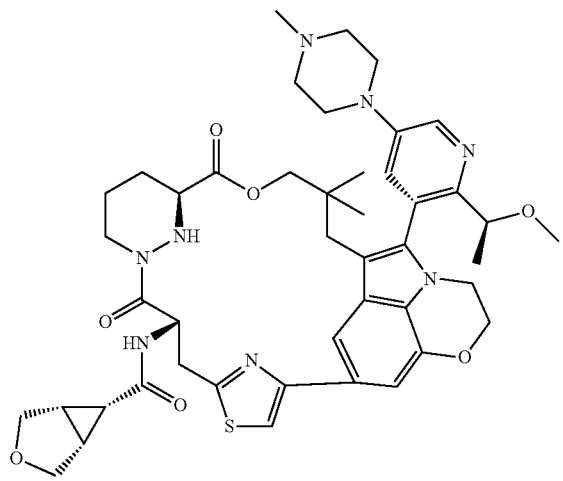

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate H) and (1R,5S,6s)-3-oxabicyclo[3.1.0]hexane-6-carboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 52 (28.2 mg) was obtained as a light yellow solid. MS calc'd 853.4 (MH$^+$), measured 853.4 (MH$^+$). $^1$H NMR (400 MHZ, METHANOL-d$_4$) δ=8.51 (d, J=2.8 Hz, 1H), 8.22 (s, 1H), 7.68-7.57 (m, 1H), 7.51 (s, 1H), 7.12 (s, 1H), 5.75 (d, J=8.3 Hz, 1H), 4.71-4.59 (m, 2H), 4.54 (q, J=5.9 Hz, 1H), 4.49-4.41 (m, 1H), 4.38-4.25 (m, 2H), 4.24-4.01 (m, 2H), 4.00-3.86 (m, 3H), 3.84-3.71 (m, 6H), 3.70-3.54 (m, 2H), 3.52-3.38 (m, 6H), 3.28 (d, J=5.8 Hz, 1H), 3.17-3.12 (m, 1H), 3.01 (s, 3H), 2.84-2.75 (m, 1H), 2.68-2.55 (m, 1H), 2.29-2.18 (m, 1H), 2.16-2.05 (m, 2H), 2.02-1.92 (m, 1H), 1.89-1.75 (m, 1H), 1.71 (t, J=3.1 Hz, 1H), 1.64 (d, J=3.2, 12.7 Hz, 1H), 1.55-1.44 (m, 3H), 1.03 (s, 3H), 0.55 (s, 3H).

Example 53

(1S,2S)-N-[(7S,13S,22S)-(20M)-20-[2-[(1S)-1-methoxyethyl]-5-morpholino-3-pyridyl]-17,17,22-trimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-methyl-cyclopropanecarboxamide

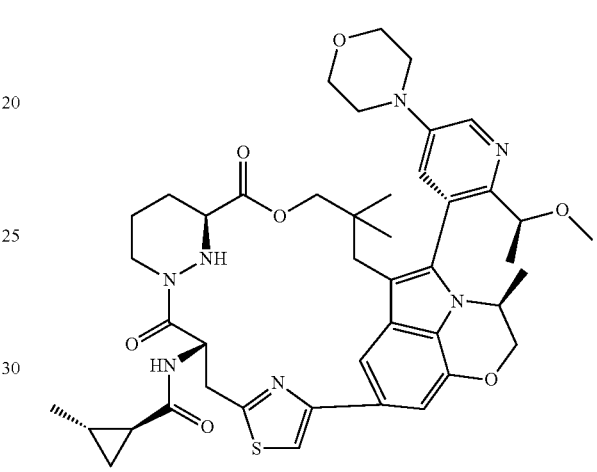

The title compound was prepared in analogy to the preparation of Example 1 by using (7S,13S,22S)-7-amino-(20M)-20-[2-[(1S)-1-methoxyethyl]-5-morpholino-3-pyridyl]-17,17,22-trimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate N) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate F). Example 53 (11 mg) was obtained as a white solid. MS calc'd 826.4 (MH$^+$), measured 826.4 (MH$^+$). $^1$H NMR (400 MHZ, METHANOL-d$_4$) δ=8.44-8.41 (d, J=2.8 Hz, 1H), 8.26 (s, 1H), 7.44-7.40 (m, 2H), 7.09-7.05 (m, 1H), 6.38 (t, J=6.8 Hz, 1H), 4.52-4.36 (m, 5H), 3.92-3.85 (m, 5H), 3.83-3.76 (m, 2H), 3.38-3.35 (m, 1H), 3.31-3.24 (m, 4H), 3.20-3.15 (d, J=8.4 Hz, 1H), 3.10-3.05 (m, 3H), 2.80-2.71 (m, 1H), 2.43-2.36 (d, J=14.8 Hz, 1H), 1.79-1.67 (m, 2H), 1.63-1.58 (m, 3H), 1.53-1.44 (m, 1H), 1.42-1.29 (m, 3H), 1.26-1.20 (m, 1H), 1.19-1.15 (d, 6.8 Hz, 3H), 1.13-1.08 (m, 3H), 1.05-0.98 (m, 1H), 0.97-0.91 (m, 3H), 0.60-0.54 (m, 2H), 0.53 (s, 2H).

Example 54

2,2-difluoro-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (29),2,5 (31), 19,25,27-hexaen-7-yl]-1-methyl-cyclopropanecarboxamide

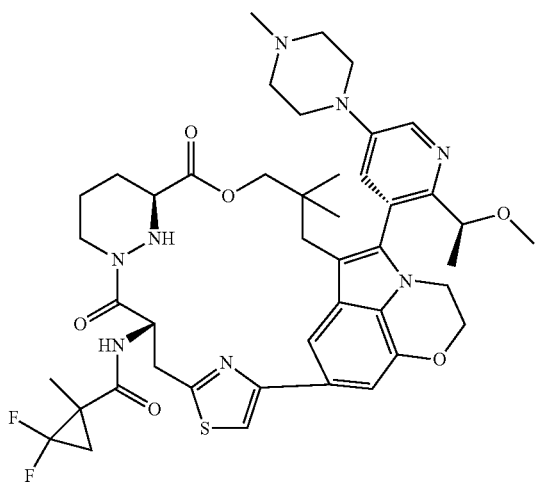

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate H) and 2,2-difluoro-1-methyl-cyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 54 (34 mg) was obtained as a light yellow solid. MS calc'd 861.4 (MH$^+$), measured 861.4 (MH$^+$). $^1$H NMR (400 MHZ, METHANOL-d$_4$) δ=8.55-8.46 (m, 1H), 8.20 (br d, J=6.1 Hz, 1H), 7.62 (br s, 1H), 7.49 (s, 1H), 7.10 (s, 1H), 5.88-5.63 (m, 1H), 4.67-4.50 (m, 4H), 4.43 (br d, J=11.1 Hz, 1H), 4.36-4.23 (m, 2H), 4.20-3.89 (m, 2H), 3.78-3.69 (m, 3H), 3.67-3.52 (m, 2H), 3.40 (s, 7H), 3.16 (br d, J=14.4 Hz, 2H), 2.99 (s, 3H), 2.85-2.73 (m, 1H), 2.58 (br d, J=14.0 Hz, 1H), 2.23 (br d, J=11.4 Hz, 1H), 2.15-1.90 (m, 2H), 1.89-1.73 (m, 1H), 1.69-1.54 (m, 4H), 1.52-1.36 (m, 4H), 1.02 (s, 3H), 0.52 (s, 3H).

Example 55

N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (29),2,5 (31), 19,25,27-hexaen-7-yl]-1,2-dimethyl-cyclopropanecarboxamide

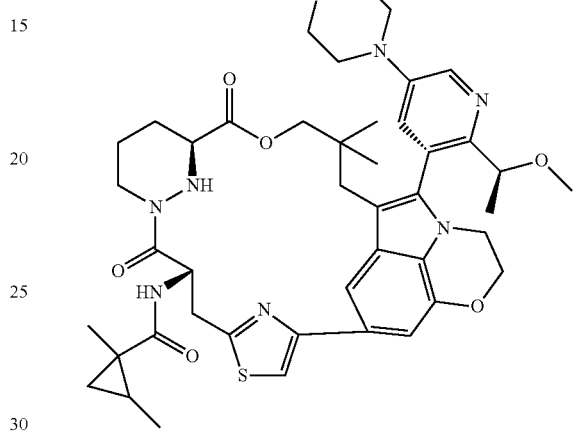

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate H) and 1,2-dimethylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 55 (19.8 mg) was obtained as a light yellow solid. MS calc'd 839.4 (MH$^+$), measured 839.4 (MH$^+$). $^1$H NMR (400 MHZ, METHANOL-d$_4$) δ=8.57 (s, 1H), 8.26 (s, 1H), 7.66 (s, 1H), 7.52 (s, 1H), 7.16 (s, 1H), 5.80-5.65 (m, 1H), 4.74-4.46 (m, 4H), 4.46-4.38 (m, 1H), 4.37-4.22 (m, 2H), 4.20-3.91 (m, 2H), 3.75 (s, 4H), 3.68-3.53 (m, 2H), 3.52-3.34 (m, 8H), 3.21-3.08 (m, 2H), 2.84-2.71 (m, 1H), 2.64-2.50 (m, 1H), 2.31-2.15 (m, 1H), 2.03-1.91 (m, 1H), 1.89-1.75 (m, 1H), 1.65-1.54 (m, 1H), 1.49-1.24 (m, 9H), 1.16 (t, J=5.3 Hz, 3H), 1.02 (s, 3H), 0.52 (s, 3H), 0.32 (s, 1H).

Example 56

(1S,2S)-N-[(7S,13S)-(20M)-20-[2-[(1S)-1-methoxy-ethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-(3-pyridyl)cyclopropanecarboxamide

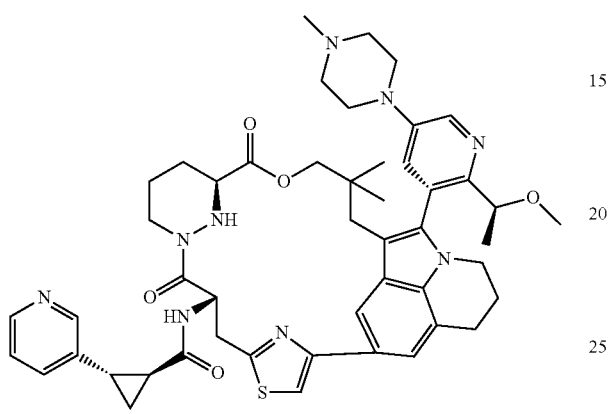

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate E) and (1S,2S)-2-(3-pyridyl)cyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1,2S)-2-methylcyclopropanecarboxylic acid. Example 56 (11.6 mg) was obtained as a yellow solid. MS calc'd 886.4 (MH$^+$), measured 886.6 (MH$^+$). $^1$H NMR (400 MHZ, Methanol-d$_4$) δ=8.78 (s, 1H), 8.68 (d, J=5.2 Hz, 1H), 8.48 (d, J=3.2 Hz, 1H), 8.40 (s, 1H), 8.33 (d, J=7.6 Hz, 1H), 7.96 (dd, J=8.0, 6.0 Hz, 1H), 7.55-7.49 (m, 2H), 7.43 (s, 1H), 5.86-5.76 (m, 1H), 4.89 (s, 1H), 4.48-4.41 (m, 2H), 4.27-4.19 (m, 2H), 4.17-3.88 (m, 2H), 3.76 (s, 3H), 3.70-3.55 (m, 3H), 3.51-3.42 (m, 3H), 3.37 (s, 3H), 3.28-3.24 (m, 1H), 3.14-3.07 (m, 2H), 2.99 (s, 4H), 2.84-2.76 (m, 1H), 2.66-2.57 (m, 2H), 2.34-2.16 (m, 4H), 1.99-1.92 (m, 1H), 1.86-1.75 (m, 1H), 1.74-1.69 (m, 1H), 1.67-1.59 (m, 1H), 1.58-1.54 (m, 1H), 1.46 (d, J=6.4 Hz, 3H), 0.97 (s, 3H), 0.56 (s, 3H).

Example 57 and Example 58

(1S,2S)-N-[(7S,13S)-(20M)-20-[2-[(1S)-1-methoxy-ethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-(4-pyridyl)cyclopropanecarboxamide and (1R,2R)-N-[(7S,13S)-(20M)-20-[2-[(1S)-1-methoxy-ethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2-(4-pyridyl)cyclopropanecarboxamide

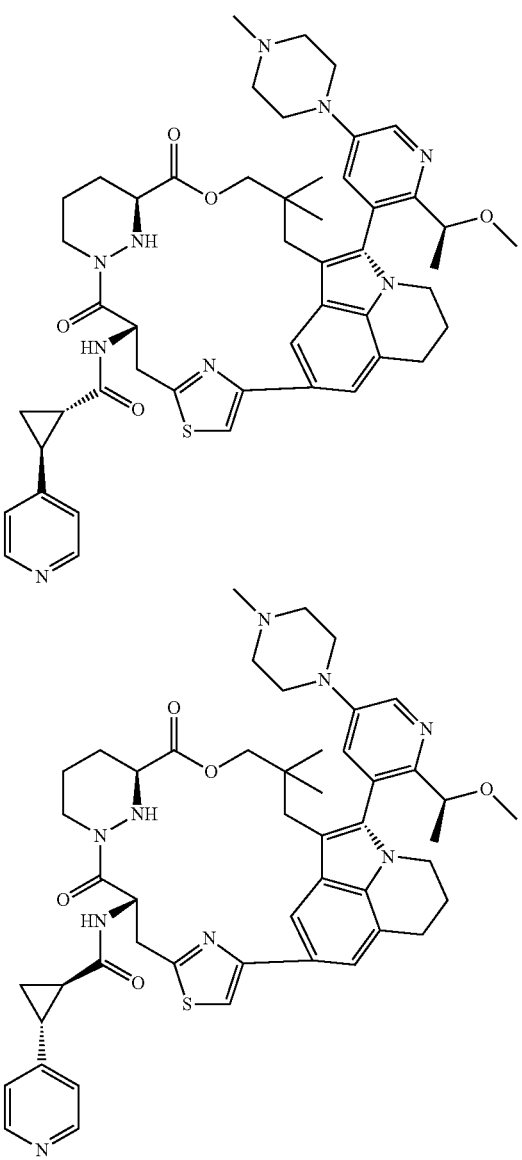

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]

hentriaconta-1 (28), 2,5 (31), 19,25 (29), 26-hexaene-8,14-dione (Intermediate E) and trans-2-(4-pyridyl)cyclopropanecarboxylic acid (Intermediate R4) instead of (7S,13S)-7-amino-(20M)-20-[2-[(1S)-1-methoxyethyl]-5-morpholino-3-pyridyl]-17,17-dimethyl-15-oxa-4-thia-9,21, 30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate F) and (1S,2S)-2-methylcyclopropanecarboxylic acid and then purified by prep-HPLC and SFC.

SFC conditions: Column DAICEL CHIRALCEL OJ (250 mm×30 mm, 10 μm); Condition CO$_2$-EtOH (0.1% NH$_3$H$_2$O); Begin B 30 End 30; Gradient Time (min) 4 100% B Hold; Flow Rate (mL/min) 120

Example 57 (6.5 mg, SFC, faster eluted) was obtained as a white solid. MS calc'd 886.4 (MH$^+$), measured 886.4 (MH$^+$). $^1$H NMR (400 MHZ, Methanol-d$_4$) δ=8.43-8.35 (m, 4H), 7.49 (s, J=2.0 Hz, 1H), 7.40 (s, 1H), 7.28-7.19 (m, 3H), 5.81 (d, J=8.8 Hz, 1H), 4.45-4.35 (m, 2H), 4.27-4.18 (m, 2H), 3.75 (s, 2H), 3.64-3.54 (m, 1H), 3.43 (d, J=15.2 Hz, 1H), 3.38-3.34 (m, 2H), 3.29-3.20 (m, 2H), 3.14-2.91 (m, 4H), 2.78 (t, J=12.8 Hz, 1H), 2.67-2.60 (m, 5H), 2.40-2.35 (m, 4H), 2.32-2.25 (m, 1H), 2.23-2.13 (m, 3H), 1.98-1.89 (m, 1H), 1.80-1.69 (m, 1H), 1.66-1.57 (m, 2H), 1.43 (d, J=6.0 Hz, 4H), 1.38-1.22 (m, 2H), 1.03-0.82 (m, 4H), 0.55 (s, 3H).

Example 58 (7.6 mg, SFC, slower eluted) was obtained as a white solid. MS calc'd 886.4 (MH$^+$), measured 886.4 (MH$^+$). $^1$H NMR (400 MHZ, Methanol-d$_4$) δ=8.45-8.35 (m, 4H), 7.48 (s, 1H), 7.39 (s, 1H), 7.33-7.27 (m, 1H), 7.25 (d, J=5.2 Hz, 2H), 5.84 (d, J=9.2 Hz, 1H), 4.47-4.34 (m, 2H), 4.28-4.19 (m, 2H), 3.76 (s, 2H), 3.64-3.54 (m, 1H), 3.49-3.41 (m, 4H), 3.27-3.22 (m, 1H), 3.13-2.97 (m, 4H), 2.95-2.90 (m, 2H), 2.82-2.75 (m, 1H), 2.64-2.51 (m, 4H), 2.46-2.38 (m, 1H), 2.34-2.26 (m, 1H), 2.23-2.16 (m, 3H), 1.99-1.89 (m, 1H), 1.83-1.72 (m, 1H), 1.69-1.49 (m, 2H), 1.44 (d, J=6.0 Hz, 4H), 1.36-1.21 (m, 2H), 1.03-0.93 (m, 4H), 0.54 (s, 3H).

Example 59

2-(4-fluorophenyl)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (29),2,5 (31),19,25,27-hexaen-7-yl]cyclopropanecarboxamide

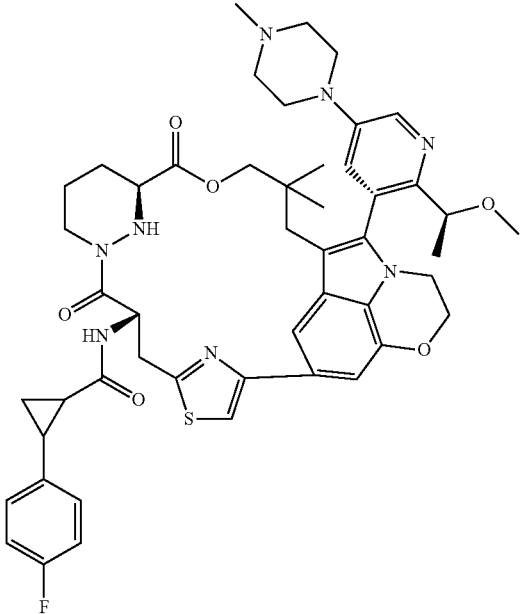

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15,24-dioxa-4-thia-9,21, 30,31-tetrazahexacyclo[23.3.1.1$^{2,5}$.1$^{9,13}$.0$^{19,27}$.0$^{21,26}$] hentriaconta-1 (28), 2,5 (31), 19,25 (29), 26-hexaene-8,14-dione (Intermediate H) and 2-(4-fluorophenyl)cyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$] hentriaconta-1 (28),2,5 (31), 19,25 (29),26-hexaene-8,14-dione (Intermediate F) and (1S,2S)-2-methylcyclopropanecarboxylic acid. Example 59 (37.8 mg) was obtained as a light yellow solid. MS calc'd 905.4 (MH$^+$), measured 905.5 (MH$^+$). $^1$H NMR (400 MHZ, METHANOL-d$_4$) δ=8.50 (d, J=2.8 Hz, 1H), 8.28 (s, 1H), 7.72 (s, 1H), 7.49 (d, J=3.4 Hz, 1H), 7.24-6.97 (m, 5H), 5.86-5.72 (m, 1H), 4.71-4.51 (m, 3H), 4.43 (br d, J=12.4 Hz, 1H), 4.34-4.22 (m, 2H), 4.21-3.85 (m, 2H), 3.76 (s, 3H), 3.63-3.55 (m, 1H), 3.46-3.36 (m, 6H), 3.29-3.21 (m, 2H), 3.14 (br d, J=14.8 Hz, 1H), 2.98 (s, 3H), 2.78 (br t, J=12.4 Hz, 1H), 2.60 (br d, J=14.3 Hz, 1H), 2.44-2.31 (m, 1H), 2.21 (br d, J=10.9 Hz, 1H), 2.01-1.90 (m, 2H), 1.81-1.16 (m, 9H), 1.01 (s, 3H), 0.54 (s, 3H).

Example 60

(1S,5R,6r)-N-[(7S,13S)-23,23-difluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-3-oxabicyclo[3.1.0]hexane-6-carboxamide

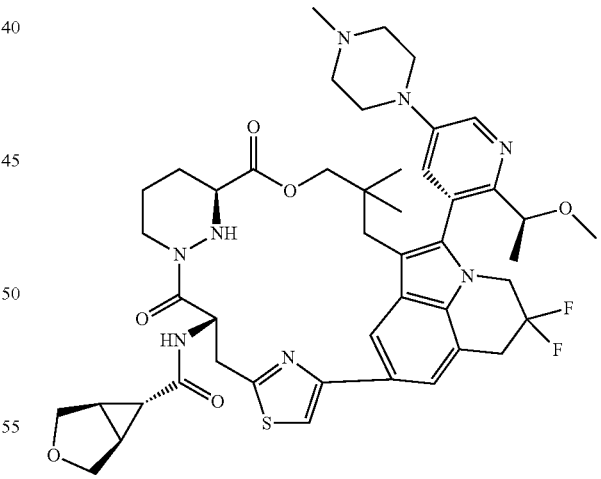

The title compound was prepared in analogy to the preparation of Example 1 by using (7S,13S)-7-amino-23,23-difluoro-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$] hentriaconta-1 (28), 2,5 (31), 19,25 (29), 26-hexaene-8,14-dione (intermediate K) and (1S,5R,6r)-3-oxabicyclo[3.1.0] hexane-6-carboxylic acid instead of (7S,13S)-7-amino-(20M)-20-[2-[(1S)-1-methoxyethyl]-5-morpholino-3- pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate F) and (1S,2S)-2-methylcyclopropanecarboxylic acid. Example 60 (19.3 mg) was obtained as a white solid. MS calc'd 887.4 (MH$^+$), measured 887.4 (MH$^+$), $^1$H NMR (400 MHZ, Methanol-d$_4$) δ=8.48 (s, 1H), 8.43 (d, J=2.8 Hz, 1H), 7.57-7.51 (m, 2H), 7.28-7.24 (m, 1H), 5.80-5.72 (m, 1H), 4.67-4.55 (m, 1H), 4.45-4.39 (m, 2H), 4.24 (dd, J=3.2, 12.0 Hz, 1H), 3.98-3.87 (m, 3H), 3.78-3.70 (m, 4H), 3.67-3.45 (m, 3H), 3.40-3.33 (m, 6H), 3.29-3.22 (m, 1H), 3.11-3.04 (m, 1H), 2.81-2.72 (m, 1H), 2.70-2.65 (m, 4H), 2.64-2.58 (m, 1H), 2.39 (s, 3H), 2.21-2.15 (m, 1H), 2.12-2.03 (m, 2H), 1.97-1.89 (m, 1H), 1.82-1.72 (m, 1H), 1.70-1.68 (m, 1H), 1.65-1.56 (m, 1H), 1.44 (d, J=6.0 Hz, 3H), 1.29 (s, 1H), 0.98-0.94 (m, 3H), 0.55 (s, 3H).

Example 61

(1r,2R,3S)-N-[(7S,13S)-(20M)-20-[2-[(1S)-1-methoxyethyl]-5-morpholino-3-pyridyl]-17,17,23,23-tetramethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2,3-dimethyl-cyclopropanecarboxamide

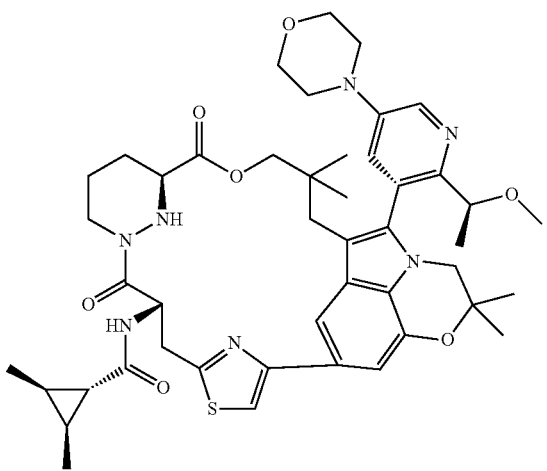

The title compound was prepared in analogy to the preparation of Example 1 by using (7S,13S)-7-amino-(20M)-20-[2-[(1S)-1-methoxyethyl]-5-morpholino-3-pyridyl]-17,17,23,23-tetramethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate M) and (1r,2R,3S)-2,3-dimethylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 61 (18 mg) was obtained as a white solid. MS calc'd 854.4 (MH$^+$), measured 854.5 (MH$^+$). $^1$H NMR (400 MHZ, Methanol-d$_4$) δ=8.45-8.36 (d, J=3.2 Hz, 1H), 8.25-8.20 (s, 1H), 7.85-7.77 (d, J=2.8 Hz, 1H), 7.53-7.46 (s, 1H), 7.15-7.8 (s, 1H), 5.86-5.79 (d, J=6.8 Hz, 1H), 4.74-4.64 (d, J=6.4 Hz, 1H), 4.49-4.40 (d, J=11.6 Hz, 1H), 4.37-4.20 (dd, J=3.2 Hz, 12 Hz, 1H), 4.03-3.93 (d, J=12.4 Hz, 1H), 3.91-3.84 (t, J=4.8 Hz, 5H), 3.84-3.79 (s, 2H), 3.73-3.62 (d, J=12.4 Hz, 1H), 3.47-3.43 (s, 3H), 3.41-3.37 (m, 1H), 3.30-3.24 (m, 1H), 3.12-3.05 (d, J=13.6 Hz, 1H), 2.85-2.67 (m, 2H), 2.21-2.21 (dd, J=2 Hz, 13.2 Hz, 1H), 1.98-1.89 (d, J=11.6 Hz, 1H), 1.81-1.60 (m, 2H), 1.57-1.49 (m, 7H), 1.45-1.29 (m, 6H), 1.20-1.11 (m, 8H), 1.05-0.95 (s, 3H), 0.72-0.68 (s, 3H).

Example 63

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-pyridazin-3-yl-cyclopropanecarboxamide

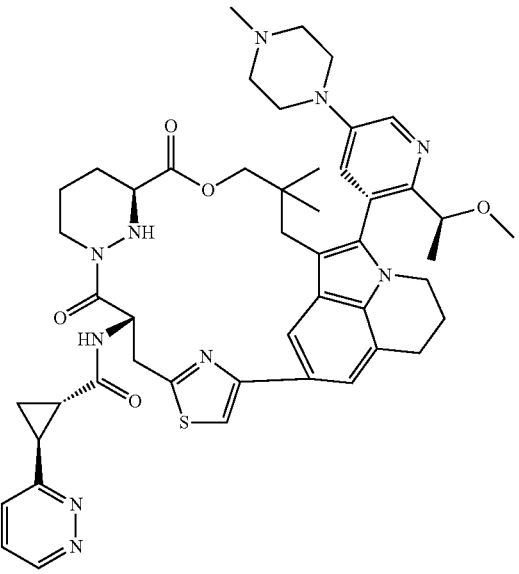

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate E) and trans-2-pyridazin-3-ylcyclopropanecarboxylic acid (Intermediate R2) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate F) and (1S,2S)-2-methylcyclopropanecarboxylic acid. Example 63 (6.0 mg) was obtained as a yellow solid. MS calc'd 887.4 (MH$^+$), measured 887.5 (MH$^+$). $^1$H NMR (400 MHZ, Methanol-d$_4$) δ=9.10-9.04 (m, 1H), 8.53-8.46 (m, 1H), 8.44-8.36 (m, 1H), 7.77-7.66 (m, 2H), 7.60 (d, J=2.8 Hz, 1H), 7.50 (s, 1H), 7.43 (s, 1H), 5.87-5.81 (m, 1H), 4.49-4.39 (m, 2H), 4.26-4.16 (m, 2H), 3.78-3.72 (m, 2H), 3.67-3.58 (m, 2H), 3.48-3.39 (m, 3H), 3.39-3.35 (m, 4H), 3.28-3.23 (m, 1H), 3.16-3.04 (m, 3H), 3.02-2.97 (m, 4H), 2.87-2.74 (m, 2H), 2.74-2.67 (m, 1H), 2.66-2.60 (m, 1H), 2.59-2.53 (m, 1H), 2.38-2.26 (m, 1H), 2.24-2.13 (m, 2H), 1.99-1.90 (m, 1H), 1.81-1.58 (m, 4H), 1.50 (d, J=6.4 Hz, 4H), 1.35-1.28 (m, 1H), 1.05-0.96 (m, 3H), 0.64-0.57 (m, 3H)

Example 64

(1R,2S)-2-cyclopropyl-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (29),2,5 (31), 19,25,27-hexaen-7-yl]cyclopropanecarboxamide

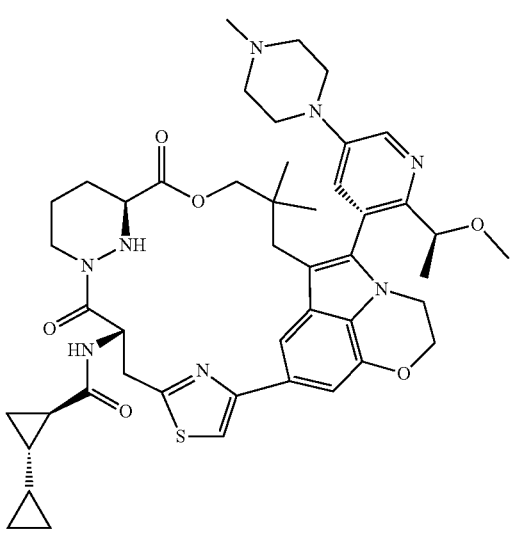

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate H) and (1R,2S)-2-cyclopropylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 64 (45.0 mg) was obtained as a light yellow solid. MS calc'd 851.4 (MH$^+$), measured 851.4 (MH$^+$). $^1$H NMR (400 MHZ, METHANOL-d$_4$) δ=8.29 (d, J=2.6 Hz, 1H), 8.01 (d, J=3.0 Hz, 1H), 7.35 (d, J=2.8 Hz, 1H), 7.28 (d, J=8.0 Hz, 1H), 6.90 (d, J=3.3 Hz, 1H), 5.57 (d, J=8.8 Hz, 1H), 4.56 (s, 3H), 4.46-4.37 (m, 2H), 4.32 (q, J=6.5 Hz, 1H), 4.24 (d, J=13.3 Hz, 1H), 4.14-4.04 (m, 2H), 3.62-3.46 (m, 4H), 3.39-3.22 (m, 4H), 3.18 (d, J=1.5 Hz, 4H), 3.07 (d, J=5.9 Hz, 1H), 2.93 (d, J=12.6 Hz, 1H), 2.79 (s, 3H), 2.64-2.52 (m, 1H), 2.39 (d, J=14.5 Hz, 1H), 2.06-1.95 (m, 1H), 1.80-1.71 (m, 1H), 1.68-1.52 (m, 1H), 1.48-1.35 (m, 2H), 1.27 (d, J=6.1 Hz, 3H), 1.16-1.07 (m, 1H), 0.85-0.74 (m, 4H), 0.73-0.65 (m, 1H), 0.48 (dd, J=7.0 Hz, 11.0 Hz, 1H), 0.34 (s, 3H), 0.29-0.17 (m, 2H), 0.05-0.09 (m, 2H).

Example 65

3,3-difluoro-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]cyclopentanecarboxamide

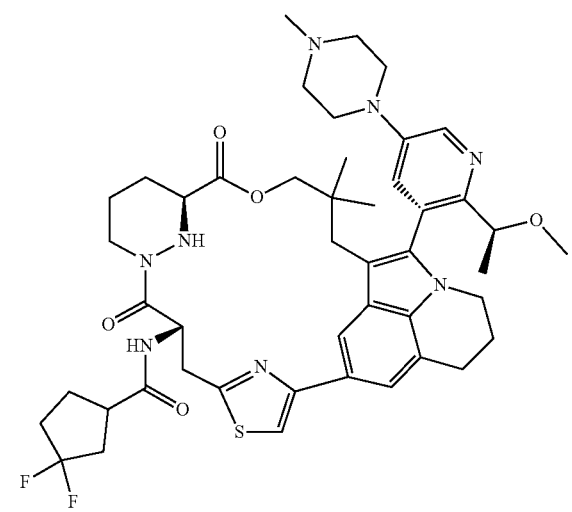

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate E) and 3,3-difluorocyclopentanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 65 (13.9 mg) was obtained as a light yellow solid. MS calc'd 873.4 (MH$^+$), measured 873.5 (MH$^+$). $^1$H NMR (400 MHZ, METHANOL-d$_4$) δ=8.49-8.42 (m, 1H), 8.36 (d, J=2.5 Hz, 1H), 8.29 (s, 1H), 7.39 (s, 1H), 7.34-7.30 (m, 2H), 5.65 (br t, J=8.1 Hz, 1H), 4.36-4.29 (m, 2H), 4.15 (br d, J=10.4 Hz, 2H), 3.66 (s, 2H), 3.54-3.43 (m, 3H), 3.31 (br s, 2H), 3.27 (s, 4H), 3.18-3.13 (m, 2H), 3.05-2.94 (m, 4H), 2.89 (s, 4H), 2.74-2.64 (m, 1H), 2.48 (br d, J=14.6 Hz, 1H), 2.31-2.17 (m, 3H), 2.14-2.05 (m, 3H), 2.03-1.81 (m, 4H), 1.74-1.63 (m, 1H), 1.58-1.49 (m, 1H), 1.34 (d, J=6.1 Hz, 3H), 1.24-1.17 (m, 1H), 0.87 (s, 3H), 0.43 (s, 3H).

Example 66

N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaen-7-yl]-2-oxabicyclo[2.1.1]hexane-1-carboxamide

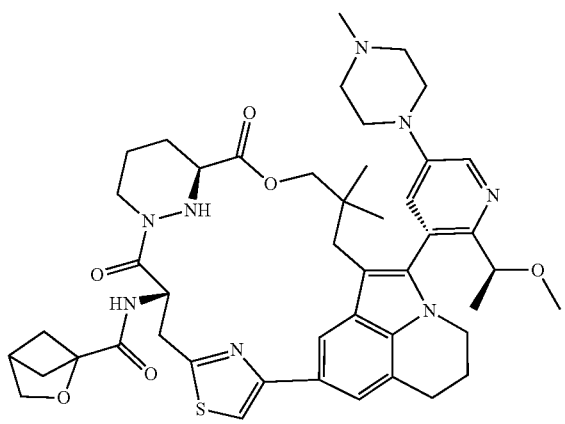

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate E) and 2-oxabicyclo[2.1.1]hexane-1-carboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 66 (13.4 mg) was obtained as a white solid. MS calc'd 851.4 (MH$^+$), measured 851.5 (MH$^+$). $^1$H NMR (400 MHZ, METHANOL-d$_4$) δ=8.36 (br s, 1H), 8.30 (br s, 1H), 7.46 (br s, 1H), 7.38 (d, J=3.1 Hz, 1H), 7.32 (br s, 1H), 5.86-5.76 (m, 1H), 4.39-4.30 (m, 2H), 4.18-4.05 (m, 3H), 3.88-3.81 (m, 2H), 3.67 (br s, 2H), 3.55-3.47 (m, 3H), 3.34-3.30 (m, 2H), 3.29-3.25 (m, 5H), 3.04-2.94 (m, 3H), 2.89 (br d, J=3.1 Hz, 5H), 2.69 (br t, J=12.7 Hz, 1H), 2.52 (br d, J=14.4 Hz, 1H), 2.26-2.18 (m, 1H), 2.15-2.02 (m, 4H), 1.90-1.81 (m, 1H), 1.73-1.64 (m, 1H), 1.63-1.48 (m, 4H), 1.40-1.33 (m, 3H), 1.19 (br s, 1H), 0.86 (br s, 3H), 0.47 (br s, 3H).

Example 67

(1S,2S)-N-[(7S,13S)-23,23-difluoro-(20M)-20-[2-[(1S)-1-methoxyethyl]-5-[4-(2,2,2-trifluoroethyl)piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2-methyl-cyclopropanecarboxamide

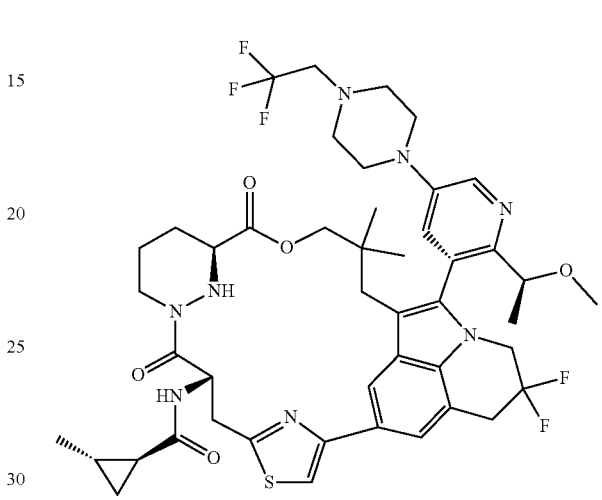

The title compound was prepared in analogy to the preparation of Example 1 by using (7S,13S)-7-amino-23,23-difluoro-(20M)-20-[2-[(1S)-1-methoxyethyl]-5-[4-(2,2,2-trifluoroethyl) piperazin-1-yl]-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate O) instead of (7S, 13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$] hentriaconta-1 (28), 2,5 (31), 19,25 (29),26-hexaene-8,14-dione (Intermediate F). Example 67 (22.8 mg) was obtained as a yellow solid. MS calc'd 927.4 (MH$^+$), measured 927.6 (MH$^+$), $^1$H NMR (400 MHZ, METHANOL-d$_4$) δ=8.51 (s, 1H), 8.40 (d, J=2.8 Hz, 1H), 7.65 (d, J=2.8 Hz, 1H), 7.60-7.54 (m, 2H), 5.79 (dd, J=1.2, 8.8 Hz, 1H), 4.57-4.38 (m, 3H), 4.23 (dd, J=3.2, 12.0 Hz, 1H), 4.06-3.94 (m, 1H), 3.82-3.48 (m, 5H), 3.47-3.43 (m, 4H), 3.39 (s, 3H), 3.29-3.24 (m, 1H), 3.21-3.08 (m, 3H), 2.91-2.85 (m, 4H), 2.82-2.73 (m, 1H), 2.71-2.64 (m, 1H), 2.21-2.13 (m, 1H), 1.98-1.89 (m, 1H), 1.82-1.70 (m, 1H), 1.65-1.55 (m, 1H), 1.50-1.45 (m, 4H), 1.27-1.18 (m, 1H), 1.15-1.10 (m, 3H), 1.09-1.04 (m, 1H), 1.00 (s, 3H), 0.67-0.56 (m, 4H).

Example 68

(1r,2R,3S)-N-[(7S,13S)-(20M)-20-[2-[(1S)-1-methoxyethyl]-5-morpholino-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (29),2,5 (31),19,25,27-hexaen-7-yl]-2,3-dimethyl-cyclopropanecarboxamide

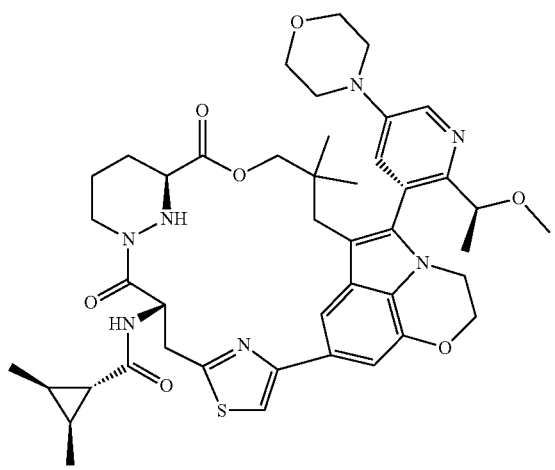

The title compound was prepared in analogy to the preparation of Example 1 by using (7S,13S)-7-amino-(20M)-20-[2-[(1S)-1-methoxyethyl]-5-morpholino-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (intermediate J) and (1r,2S,3R)-2,3-dimethylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate F) and (1S,2S)-2-methylcyclopropanecarboxylic acid. Example 68 (50 mg) was obtained as a yellow solid. MS calc'd 826.4 (MH$^+$), measured 826.6 (MH$^+$). 1H NMR (400 MHZ, METHANOL-d$_4$) δ=8.41 (d, J=2.6 Hz, 1H), 8.24 (s, 1H), 7.90 (d, J=2.8 Hz, 1H), 7.48 (s, 1H), 7.14 (s, 1H), 5.77 (br d, J=8.4 Hz, 1H), 4.71-4.52 (m, 3H), 4.45-4.40 (m, 1H), 4.25 (br d, J=9.0 Hz, 2H), 3.91-3.80 (m, 5H), 3.76 (br d, J=5.9 Hz, 2H), 3.42 (s, 7H), 3.37 (s, 1H), 3.30-3.21 (m, 1H), 3.16 (br d, J=14.4 Hz, 1H), 2.80-2.62 (m, 2H), 2.26-2.12 (m, 1H), 1.99-1.86 (m, 1H), 1.85-1.68 (m, 1H), 1.65-1.55 (m, 1H), 1.50 (d, J=6.3 Hz, 3H), 1.43-1.29 (m, 2H), 1.20-1.10 (m, 7H), 1.04 (s, 3H), 0.60 (s, 3H).

Example 69

(1r,2S,3R)-N-[(7S,13S)-(20M)-20-[2-[(1S)-1-methoxyethyl]-5-(4-methylpiperazin-1-yl)-3-pyridyl]-17,17,23,23-tetramethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2,3-dimethyl-cyclopropanecarboxamide

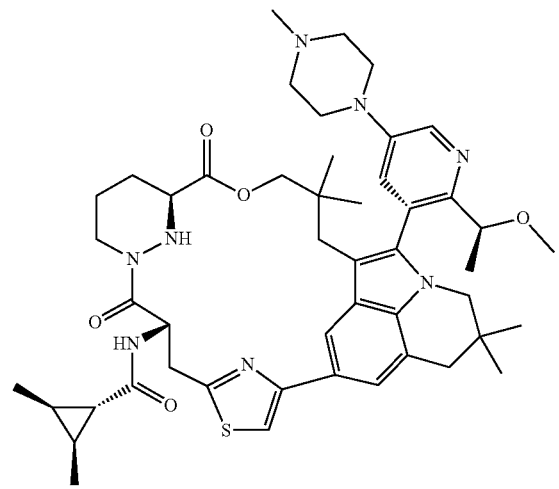

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17,23,23-tetramethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate P) and (1r,2S,3R)-2,3-dimethylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 69 (6 mg) was obtained as a white solid. MS calc'd 865.5 (MH$^+$), measured 865.5 (MH$^+$). $^1$H NMR (400 MHZ, METHANOL-d$_4$) δ=8.49 (br d, J=2.4 Hz, 1H), 8.41 (s, 1H), 7.52 (d, J=2.6 Hz, 1H), 7.49 (s, 1H), 7.41 (s, 1H), 5.83 (dd, J=1.9, 8.4 Hz, 1H), 4.57-4.47 (m, 2H), 4.45-4.35 (m, 1H), 4.24-4.15 (m, 1H), 3.84-3.74 (m, 3H), 3.67-3.34 (m, 8H), 3.29-3.21 (m, 2H), 3.08-3.00 (m, 1H), 2.99-2.95 (m, 3H), 2.94-2.87 (m, 1H), 2.81-2.71 (m, 2H), 2.70-2.62 (m, 1H), 2.17-2.06 (m, 1H), 1.95-1.84 (m, 1H), 1.76-1.68 (m, 1H), 1.66 (d, J=7.0 Hz, 3H), 1.60 (br s, 1H), 1.47 (d, J=6.1 Hz, 3H), 1.42-1.27 (m, 3H), 1.17-1.10 (m, 9H), 0.92 (s, 3H), 0.88-0.84 (m, 3H), 0.61 (s, 3H).

Example 70 trans-N-[(7S,13S)-(20M)-20-[2-[(1S)-1-methoxy-ethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (29),2,5 (31),19,25,27-hexaen-7-yl]-4-(1-methyltetrazol-5-yl)cyclohexanecarboxamide

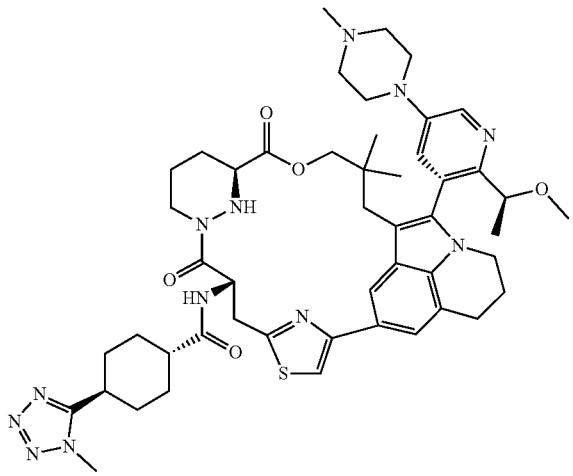

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate E) and trans-4-(1-methyltetrazol-5-yl)cyclohexanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate F) and (1S,2S)-2-methylcyclopropanecarboxylic acid. Example 70 (8 mg) was obtained as a white solid. MS calc'd 933.5 (MH$^+$), measured 933.5 (MH$^+$). $^1$H NMR (400 MHZ, METHANOL-d$_4$) δ=8.44-8.35 (m, 2H), 7.46 (s, 1H), 7.38 (s, 1H), 7.26 (d, J=2.9 Hz, 1H), 5.85-5.66 (m, 1H), 4.48-4.34 (m, 2H), 4.30-4.21 (m, 2H), 4.04 (s, 3H), 3.80-3.69 (m, 2H), 3.62-3.51 (m, 1H), 3.47-3.40 (m, 1H), 3.40-3.35 (m, 4H), 3.35-3.32 (m, 3H), 3.28-3.22 (m, 1H), 3.15-2.90 (m, 4H), 2.86-2.70 (m, 4H), 2.65 (s, 1H), 2.59 (d, J=14.4 Hz, 1H), 2.52-2.47 (m, 1H), 2.44 (s, 3H), 2.35-2.23 (m, 1H), 2.23-2.13 (m, 2H), 2.12-1.98 (m, 4H), 1.98-1.86 (m, 1H), 1.84-1.55 (m, 6H), 1.43 (d, J=6.1 Hz, 3H), 0.96 (s, 3H), 0.52 (s, 3H).

Example 71 trans-4-hydroxy-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-4-methyl-cyclohexanecarboxamide

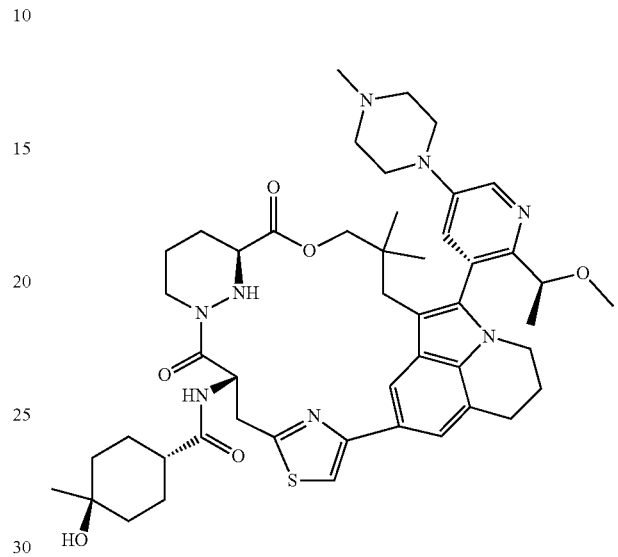

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate E) and trans-4-hydroxy-4-methyl-cyclohexanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 71 (12.3 mg) was obtained as a white solid. MS calc'd 881.5 (MH$^+$), measured 881.5 (MH$^+$). $^1$H NMR (400 MHZ, METHANOL-d$_4$) δ=8.34-8.26 (m, 2H), 7.37 (s, 1H), 7.29 (s, 1H), 7.15 (d, J=2.8 Hz, 1H), 5.64 (br d, J=8.3 Hz, 1H), 4.47 (br s, 1H), 4.35-4.25 (m, 2H), 4.15 (br dd, J=2.6, 11.9 Hz, 2H), 3.65 (s, 2H), 3.57-3.42 (m, 2H), 3.30-3.26 (m, 4H), 3.24 (s, 2H), 3.18-3.12 (m, 1H), 3.03-2.94 (m, 2H), 2.93-2.83 (m, 1H), 2.71-2.61 (m, 5H), 2.49 (br d, J=14.4 Hz, 1H), 2.33 (s, 3H), 2.30-2.14 (m, 3H), 2.13-2.05 (m, 2H), 1.87-1.79 (m, 2H), 1.76-1.68 (m, 2H), 1.67-1.61 (m, 2H), 1.58-1.49 (m, 3H), 1.47-1.39 (m, 2H), 1.33 (d, J=6.1 Hz, 3H), 1.14 (s, 3H), 0.86 (s, 3H), 0.43 (s, 3H).

Example 72

N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaen-7-yl]tricyclo[3.1.1.0$^{3,6}$]heptane-6-carboxamide

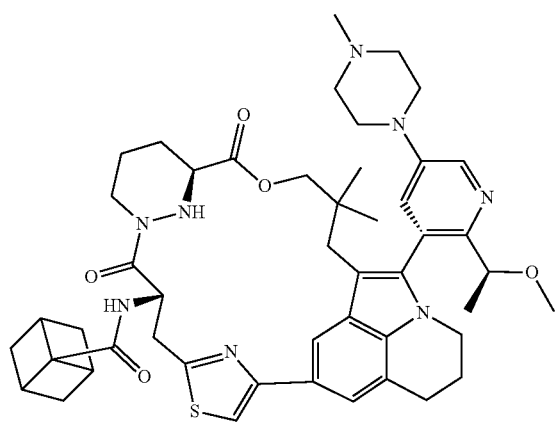

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$] hentriaconta-1 (28), 2,5 (31), 19,25 (29),26-hexaene-8,14-dione (Intermediate E) and tricyclo[3.1.1.0$^{3,6}$]heptane-6-carboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo [23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 72 (6.7 mg) was obtained as a white solid. MS calc'd 861.4 (MH$^+$), measured 861.4 (MH$^+$). $^1$H NMR (400 MHZ, METHANOL-d$_4$) δ=8.29 (s, 2H), 7.37 (s, 1H), 7.29 (s, 1H), 7.15 (s, 1H), 5.71 (dd, J=2.8, 6.8 Hz, 1H), 4.47 (s, 1H), 4.37-4.25 (m, 2H), 4.18-4.10 (m, 2H), 3.66 (s, 2H), 3.52-3.43 (m, 1H), 3.34-3.30 (m, 2H), 3.24 (s, 5H), 3.09-3.02 (m, 3H), 3.01-2.86 (m, 6H), 2.73-2.65 (m, 1H), 2.61 (br s, 3H), 2.50 (br d, J=14.5 Hz, 1H), 2.31 (s, 3H), 2.17 (br d, J=11.3 Hz, 4H), 2.13-2.05 (m, 2H), 1.88-1.81 (m, 1H), 1.72-1.63 (m, 1H), 1.57-1.46 (m, 1H), 1.35-1.31 (m, 3H), 1.24-1.13 (m, 1H), 0.86 (s, 3H), 0.82-0.68 (m, 1H), 0.43 (s, 3H).

Example 73

(1r,2S,3R)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$] hentriaconta-1 (28),2,5 (31), 19,25 (29),26-hexaen-7-yl]-2,3-dimethyl-cyclopropanecarboxamide

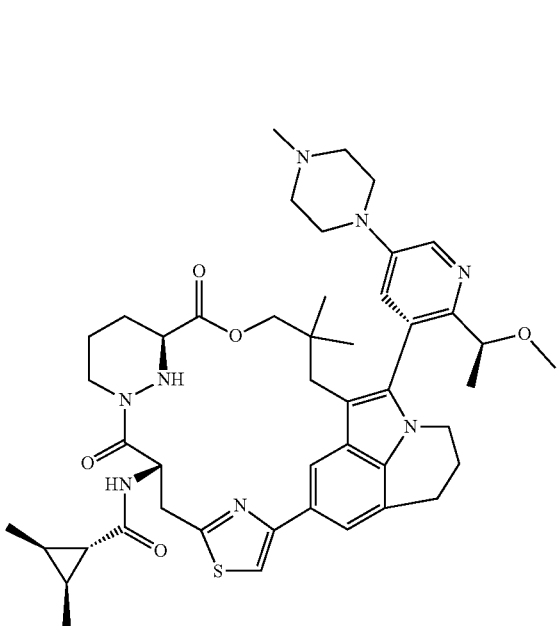

The title compound was prepared in analogy to the preparation of Example 1 by using (1r,2S,3R)-2,3-dimethylcyclopropanecarboxylic acid instead of (1S,2S)-2-methylcyclopropanecarboxylic acid. Example 73 (28 mg) was obtained as a yellow solid. MS calc'd 824.4 (MH$^+$), measured 824.6 (MH$^+$). $^1$H NMR (400 MHZ, Methanol-d$_4$) δ=8.42 (s, 1H), 8.36 (d, J=2.8 Hz, 1H), 7.89-7.83 (m, 1H), 7.51 (s, 1H), 7.45 (s, 1H), 5.84-5.78 (m, 1H), 4.58-4.50 (m, 1H), 4.43 (d, J=11.6 Hz, 1H), 4.25-4.17 (m, 1H), 4.16-4.09 (m, 1H), 3.86 (t, J=4.4 Hz, 4H), 3.79-3.72 (m, 2H), 3.71-3.65 (m, 1H), 3.43 (s, 7H), 3.38 (s, 1H), 3.29-3.22 (m, 1H), 3.14-3.01 (m, 3H), 2.80-2.67 (m, 2H), 2.37-2.29 (m, 1H), 2.23-2.12 (m, 2H), 1.97-1.88 (m, 1H), 1.80-1.69 (m, 1H), 1.65-1.55 (m, 1H), 1.48 (d, J=6.4 Hz, 3H), 1.40-1.32 (m, 2H), 1.17-1.11 (m, 7H), 0.99 (s, 3H), 0.62 (s, 3H).

Example 75

(1S,2S)-N-[(7S,13S)-23,23-difluoro-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2-methyl-cyclopropanecarboxamide

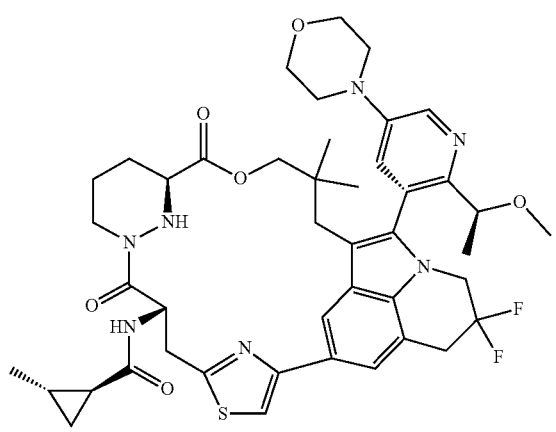

The title compound was prepared in analogy to the preparation of Example 1 by using (7S,13S)-7-amino-23,23-difluoro-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate Q) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate F). Example 75 (19.5 mg) was obtained as a yellow solid. MS calc'd 846.4 (MH$^+$), measured 846.4 (MH$^+$). $^1$H NMR (400 MHZ, METHANOL-d$_4$) δ=8.52 (s, 1H), 8.40 (d, J=2.8 Hz, 1H), 7.77 (s, 1H), 7.58 (d, J=7.2 Hz, 2H), 5.80 (d, J=8.4 Hz, 1H), 4.57-4.41 (m, 3H), 4.22 (d, J=8.8 Hz, 1H), 4.04 (d, J=14.4 Hz, 1H), 3.86 (d, J=4.4 Hz, 4H), 3.82-3.71 (m, 2H), 3.69-3.47 (m, 3H), 3.45-3.39 (m, 8H), 3.26 (d, J=8.8 Hz, 1H), 3.11 (d, J=15.2 Hz, 1H), 2.82-2.67 (m, 2H), 2.17 (d, J=11.6 Hz, 1H), 1.94 (d, J=12.8 Hz, 1H), 1.75 (s, 1H), 1.61 (d, J=15.2 Hz, 1H), 1.49 (d, J=6.4 Hz, 3H), 1.23-1.03 (m, 6H), 1.01 (s, 3H), 0.62 (s, 3H).

Example 76

(1r,2S,3R)-N-[(7S,13S)-23,23-difluoro-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2,3-dimethyl-cyclopropanecarboxamide

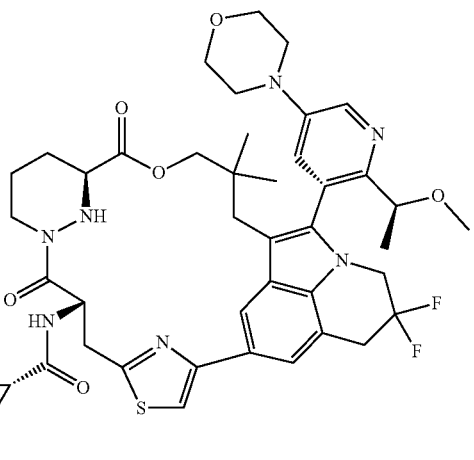

The title compound was prepared in analogy to the preparation of Example 1 by using (7S,13S)-7-amino-23,23-difluoro-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate Q) and (1r,2S,3R)-2,3-dimethylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 76 (16.7 mg) was obtained as a yellow solid. MS calc'd 860.4 (MH$^+$), measured 860.4 (MH$^+$). $^1$H NMR (400 MHZ, METHANOL-d$_4$) δ=8.52 (s, 1H), 8.40 (d, J=3.2 Hz, 1H), 7.66 (s, 1H), 7.59-7.56 (m, 2H), 5.79 (d, J=7.6 Hz, 1H), 4.56-4.49 (m, 2H), 4.46-4.40 (m, 1H), 4.25-4.20 (m, 1H), 4.05-3.95 (m, 1H), 3.86 (t, J=4.4 Hz, 4H), 3.81-3.77 (m, 1H), 3.74-3.70 (m, 1H), 3.69-3.58 (m, 2H), 3.57-3.48 (m, 1H), 3.41-3.37 (m, 7H), 3.28-3.23 (m, 1H), 3.10 (d, J=14.4 Hz, 1H), 2.81-2.73 (m, 1H), 2.68 (d, J=14.4 Hz, 1H), 2.21-2.14 (m, 1H), 1.97-1.89 (m, 1H), 1.81-1.70 (m, 1H), 1.64-1.56 (m, 1H), 1.48 (d, J=6.4 Hz, 3H), 1.40-1.33 (m, 2H), 1.16-1.11 (m, 7H), 1.00 (s, 3H), 0.61 (s, 3H).

Example 77

N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31),19,25 (29),26-hexaen-7-yl]tetrahydropyran-4-carboxamide

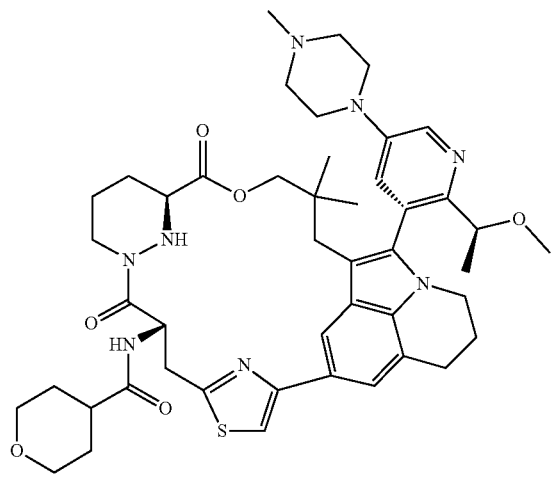

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$] hentriaconta-1 (28), 2,5 (31), 19,25 (29), 26-hexaene-8,14-dione (Intermediate E) and tetrahydropyran-4-carboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$. 0$^{19,27}$.0$^{21,26}$]hentriaconta-1 (28),2,5 (31), 19,25 (29),26-hexaene-8,14-dione (Intermediate F) and (1S,2S)-2-methyl-cyclopropanecarboxylic acid. Example 77 (11.4 mg) was obtained as a light yellow solid. MS calc'd 853.4 (MH$^+$), measured 853.5 (MH$^+$). $^1$H NMR (400 MHZ, METHANOL-d$_4$) δ=8.37 (d, J=2.9 Hz, 1H), 8.30 (s, 1H), 7.44 (d, J=2.9 Hz, 1H), 7.39 (s, 1H), 7.32 (s, 1H), 5.65 (br d, J=7.5 Hz, 1H), 4.46-4.29 (m, 2H), 4.18-4.08 (m, 2H), 3.89 (tdd, J=3.3, 7.0, 10.8 Hz, 3H), 3.66 (s, 2H), 3.59-3.33 (m, 7H), 3.32-3.26 (m, 5H), 3.19-3.13 (m, 2H), 3.05-2.96 (m, 2H), 2.89 (s, 4H), 2.72-2.64 (m, 1H), 2.57-2.46 (m, 2H), 2.26-2.17 (m, 1H), 2.13-2.04 (m, 2H), 1.88-1.80 (m, 1H), 1.75-1.68 (m, 3H), 1.67-1.60 (m, 2H), 1.57-1.47 (m, 2H), 1.36 (d, J=6.1 Hz, 3H), 0.88 (s, 3H), 0.45 (s, 3H).

Example 78

(1S,2S)-N-[(7S,13S)-23,23-difluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$. 0$^{19,27}$.0$^{21,26}$]hentriaconta-1 (28),2,5 (31), 19,25 (29),26-hexaen-7-yl]-2-phenyl-cyclopropanecarboxamide

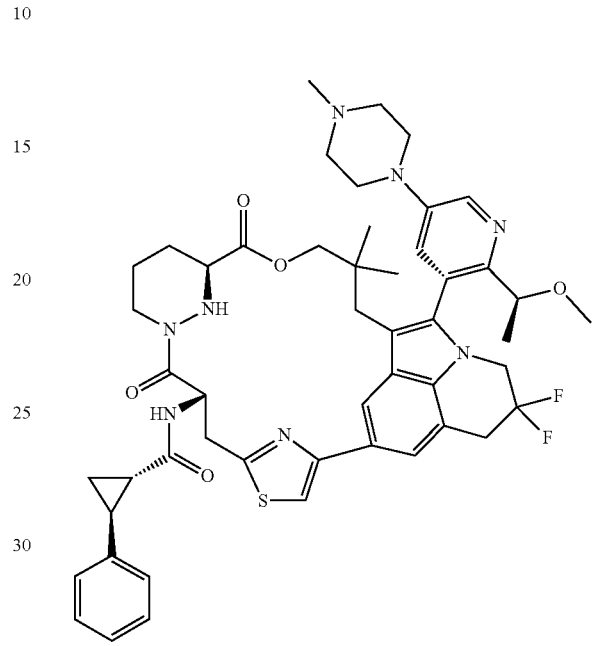

The title compound was prepared in analogy to the preparation of Example 1 by using (7S,13S)-7-amino-23,23-difluoro-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$] hentriaconta-1 (28), 2,5 (31), 19,25 (29), 26-hexaene-8,14-dione (intermediate K) and (1S,2S)-2-phenylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$] hentriaconta-1 (28),2,5 (31), 19,25 (29),26-hexaene-8,14-dione (Intermediate F) and (1S,2S)-2-methylcyclopropanecarboxylic acid. Example 78 (25.9 mg) was obtained as a yellow solid. MS calc'd 921.4 (MH$^+$), measured 921.6 (MH$^+$). $^1$H NMR (400 MHZ, Methanol-d$_4$) δ=8.53-8.48 (m, 2H), 7.61-7.55 (m, 2H), 7.42 (d, J=2.8 Hz, 1H), 7.30-7.24 (m, 2H), 7.21-7.12 (m, 3H), 5.85-5.78 (m, 1H), 4.87-4.85 (m, 1H), 4.63-4.53 (m, 1H), 4.51-4.39 (m, 2H), 4.25 (dd, J=12.0, 2.8 Hz, 1H), 4.18-3.83 (m, 3H), 3.81-3.72 (m, 2H), 3.68-3.44 (m, 5H), 3.41 (s, 1H), 3.35 (s, 5H), 3.26 (d, J=8.8 Hz, 1H), 3.13-3.08 (m, 1H), 2.99 (s, 3H), 2.83-2.75 (m, 1H), 2.60 (d, J=15.2 Hz, 1H), 2.39-2.33 (m, 1H), 2.22-2.15 (m, 1H), 2.08-2.03 (m, 1H), 1.97-1.91 (m, 1H), 1.82-1.71 (m, 1H), 1.68-1.59 (m, 1H), 1.54-1.49 (m, 1H), 1.47 (d, J=6.4 Hz, 3H), 1.32-1.28 (m, 1H), 0.97 (s, 3H), 0.56 (s, 3H).

Example 79

(1S,2S)-N-[(7S,13S)-23,23-difluoro-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2-phenyl-cyclopropanecarboxamide

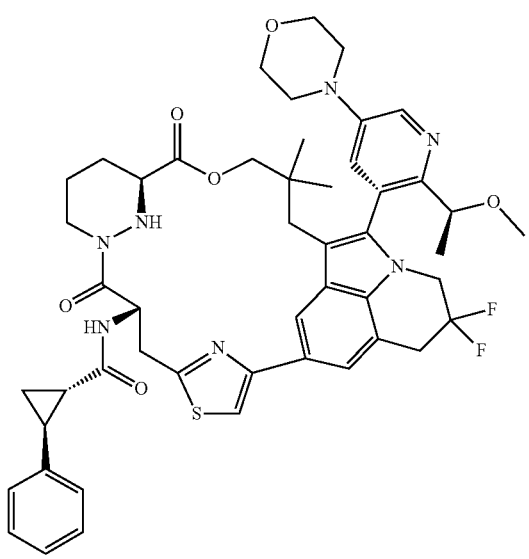

The title compound was prepared in analogy to the preparation of Example 1 by using (7S,13S)-7-amino-23,23-difluoro-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate Q) and (1S,2S)-2-phenylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 79 (20 mg) was obtained as a yellow solid. MS calc'd 908.4 (MH$^+$), measured 908.6 (MH$^+$). $^1$H NMR (400 MHZ, Methanol-d$_4$) δ=8.54 (s, 1H), 8.40 (d, J=2.8 Hz, 1H), 7.78 (d, J=2.8 Hz, 1H), 7.60-7.58 (m, 2H), 7.28-7.24 (m, 2H), 7.18-7.13 (m, 3H), 5.87-5.83 (m, 1H), 4.88-4.85 (m, 1H), 4.55 (d, J=6.4 Hz, 1H), 4.51-4.40 (m, 2H), 4.23 (dd, J=12.0, 2.8 Hz, 1H), 4.07-3.99 (m, 1H), 3.87 (t, J=4.8 Hz, 4H), 3.77 (d, J=17.6 Hz, 2H), 3.65-3.52 (m, 2H), 3.43-3.40 (m, 7H), 3.30-3.24 (m, 1H), 3.13-3.07 (m, 1H), 2.83-2.76 (m, 1H), 2.71 (d, J=14.0 Hz, 1H), 2.38-2.34 (m, 1H), 2.20-2.14 (m, 1H), 2.08-2.03 (m, 1H), 1.96-1.91 (m, 1H), 1.81-1.72 (m, 1H), 1.68-1.52 (m, 2H), 1.51-1.49 (m, 3H), 1.32-1.27 (m, 1H), 1.01 (s, 3H), 0.63 (s, 3H).

Example 80 and Example 81

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-pyrimidin-2-yl-cyclopropanecarboxamide and (1R,2R)-N-[(7S,13S)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2-pyrimidin-2-yl-cyclopropanecarboxamide

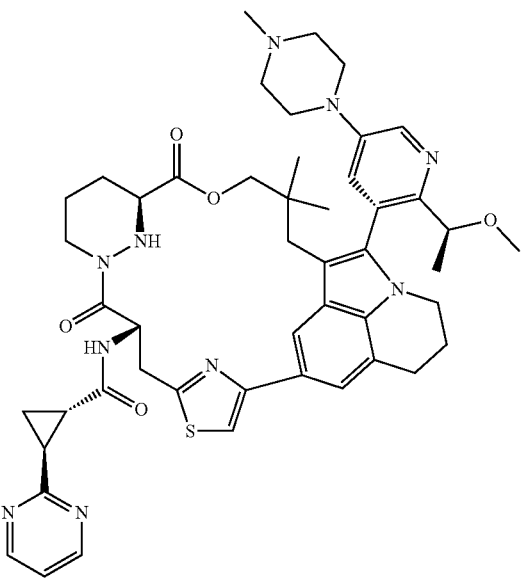

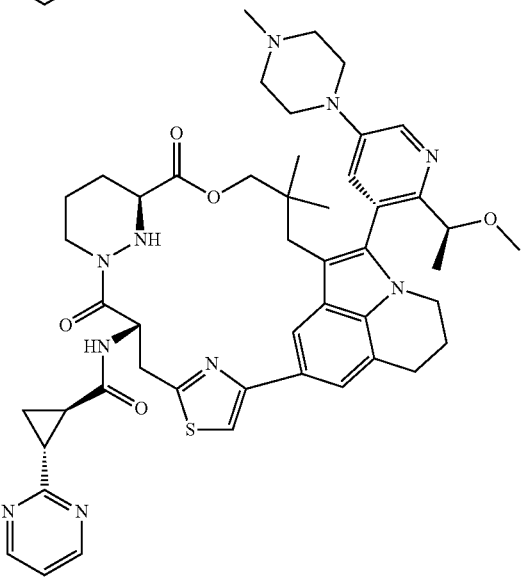

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]

hentriaconta-1 (28),2,5 (31), 19,25 (29),26-hexaene-8,14-dione (Intermediate E) and 2-pyrimidin-2-ylcyclopropanecarboxylic acid (Intermediate R5) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate F) and (1S,2S)-2-methylcyclopropanecarboxylic acid and then purified by prep-HPLC and SFC.

SFC conditions: Column DAICEL CHIRALCEL IG (250 mm×30 mm, 10 μm); Condition CO$_2$-EtOH (0.1% NH$_3$H$_2$O); Begin B 75 End 75 Gradient Time (min) 3.3 100% B Hold; Flow Rate (mL/min) 100.

Example 80 (13.4 mg, SFC, faster eluted) was obtained as a white solid. MS calc'd 887.4 (MH$^+$), measured 887.4 (MH$^+$). $^1$H NMR (400 MHZ, Methanol-d$_4$) δ=8.67 (d, J=4.8 Hz, 2H), 8.44 (s, 1H), 8.38 (s, 1H), 7.46 (s, 1H), 7.39 (s, 1H), 7.33 (s, 1H), 7.30 (t, J=5.0 Hz, 1H), 5.81 (d, J=8.4 Hz, 1H), 4.45-4.39 (m, 2H), 4.26-4.21 (m, 2H), 3.76 (s, 2H), 3.58-3.49 (m, 5H), 3.43 (m, 1H), 3.39 (s, 1H), 3.26-3.21 (m, 2H), 3.13-3.04 (m, 2H), 3.01-2.93 (m, 1H), 2.81 (s, 5H), 2.71-2.65 (m, 1H), 2.59 (m, 1H), 2.50-2.44 (m, 1H), 2.34-2.26 (m, 1H), 2.21-2.15 (m, 2H), 1.96-1.91 (m, 1H), 1.77 (m, 1H), 1.64-1.54 (m, 4H), 1.44 (d, J=6.8 Hz, 3H), 1.29 (s, 3H), 0.95 (s, 3H), 0.55 (s, 3H).

Example 81 (7.6 mg, SFC, slower eluted) was obtained as a white solid. MS calc'd 887.4 (MH$^+$), measured 887.4 (MH$^+$). $^1$H NMR (400 MHZ, Methanol-d$_4$) δ=8.65 (d, J=4.8 Hz, 2H), 8.41-8.37 (m, 2H), 8.37 (s, 2H), 7.30-7.24 (m, 2H), 5.84 (d, J=8.8 Hz, 1H), 4.44-4.35 (m, 2H), 4.28-4.20 (m, 2H), 3.76 (s, 2H), 3.64-3.56 (m, 1H), 3.49-3.35 (m, 4H), 3.25 (m, 1H), 3.15-2.94 (m, 4H), 2.81-2.74 (m, 1H), 2.69-2.61 (m, 6H), 2.49 (m, 2H), 2.37 (s, 3H), 2.34-2.13 (m, 4H), 1.95-1.89 (m, 1H), 1.73 (s, 1H), 1.63-1.57 (m, 3H), 1.44 (d, J=6.0 Hz, 3H), 1.32-1.28 (m, 1H), 0.95 (s, 3H), 0.55 (s, 3H).

Example 83

(1r,2S,3R)-N-[(7S,13S)-23,23-difluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (29),2,5 (31), 19,25,27-hexaen-7-yl]-2,3-dimethyl-cyclopropanecarboxamide The title compound was prepared in analogy to the preparation of Example 1 by using (7S,13S)-7-amino-23,23-difluoro-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (intermediate K) and (1r,2S,3R)-2,3-dimethylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 83 (16 mg) was obtained as a yellow solid. MS calc'd 873.4 (MH$^+$), measured 873.6 (MH$^+$). $^1$H NMR (400 MHZ, Methanol-d$_4$) δ=8.52-8.48 (m, 2H), 7.58-7.55 (m, 2H), 7.48 (d, J=2.8 Hz, 1H), 5.80-5.74 (m, 1H), 4.91-4.87 (m, 1H), 4.58-4.41 (m, 3H), 4.24 (dd, J=12.0, 3.2 Hz, 1H), 4.13-3.86 (m, 3H), 3.82-3.68 (m, 3H), 3.68-3.53 (m, 4H), 3.45-3.38 (m, 2H), 3.36 (s, 3H), 3.27-3.24 (m, 1H), 3.11 (d, J=14.4 Hz, 1H), 2.99 (s, 3H), 2.81-2.74 (m, 1H), 2.60 (d, J=14.4 Hz, 1H), 2.20-2.14 (m, 1H), 1.97-1.91 (m, 1H), 1.82-1.73 (m, 1H), 1.66-1.58 (m, 1H), 1.47 (d, J=6.4 Hz, 3H), 1.40-1.33 (m, 2H), 1.19-1.09 (m, 8H), 0.98 (s, 3H), 0.56 (s, 3H).

Example 85

(1r,2S,3R)-N-[(7S,13S)-(20M)-20-[2-[(1S)-1-methoxyethyl]-5-[4-(2,2,2-trifluoroethyl) piperazin-1-yl]-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2,3-dimethyl-cyclopropanecarboxamide

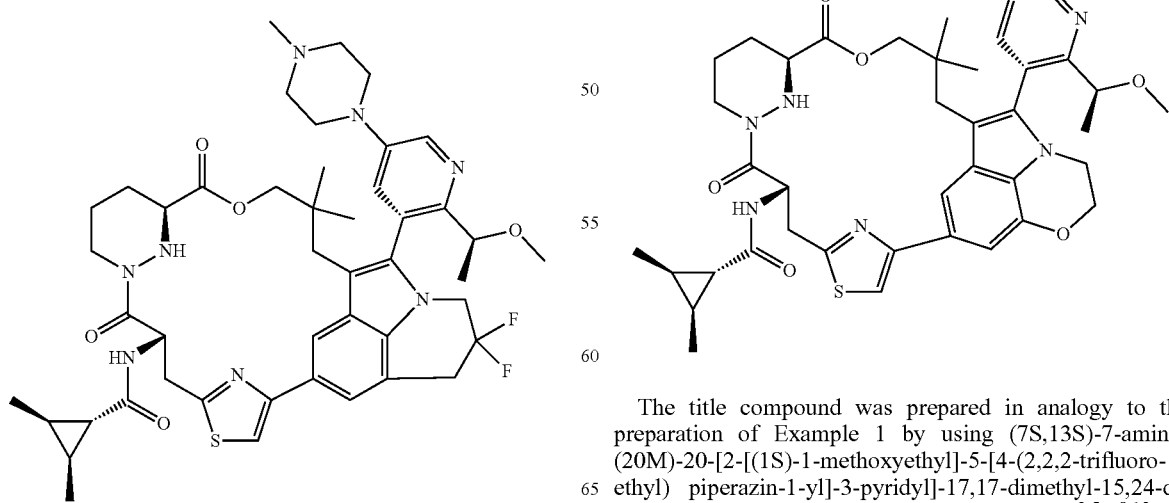

The title compound was prepared in analogy to the preparation of Example 1 by using (7S,13S)-7-amino-(20M)-20-[2-[(1S)-1-methoxyethyl]-5-[4-(2,2,2-trifluoroethyl) piperazin-1-yl]-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26- hexaene-8,14-dione (intermediate I) and (1r,2S,3R)-2,3-dimethylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 85 (22.2 mg) was obtained as a yellow solid. MS calc'd 907.4 (MH$^+$), measured 907.5 (MH$^+$). $^1$H NMR (400 MHZ, METHANOL-d$_4$) δ=8.39 (d, J=3.0 Hz, 1H), 8.24 (s, 1H), 7.91 (d, J=2.9 Hz, 1H), 7.52 (s, 1H), 7.15 (d, J=1.0 Hz, 1H), 5.78 (d, J=7.4 Hz, 1H), 4.72-4.57 (m, 3H), 4.45 (d, J=12.0 Hz, 1H), 4.32-4.20 (m, 2H), 3.87-3.73 (m, 3H), 3.56-3.49 (m, 4H), 3.47-3.39 (m, 4H), 3.31-3.14 (m, 5H), 2.96-2.86 (m, 4H), 2.79 (t, J=2.8, 12.9 Hz, 1H), 2.69 (d, J=14.4 Hz, 1H), 2.27-2.16 (m, 1H), 2.00-1.92 (m, 1H), 1.86-1.73 (m, 1H), 1.69-1.57 (m, 1H), 1.51 (d, J=6.3 Hz, 3H), 1.42-1.34 (m, 2H), 1.18-1.13 (m, 6H), 1.05 (s, 3H), 0.62 (s, 3H).

Example 86

(1r,2R,3S)-N-[(7S,13S)-(20M)-20-[2-[(1S)-1-methoxyethyl]-5-[4-(2,2,2-trifluoroethyl) piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2,3-dimethyl-cyclopropanecarboxamide

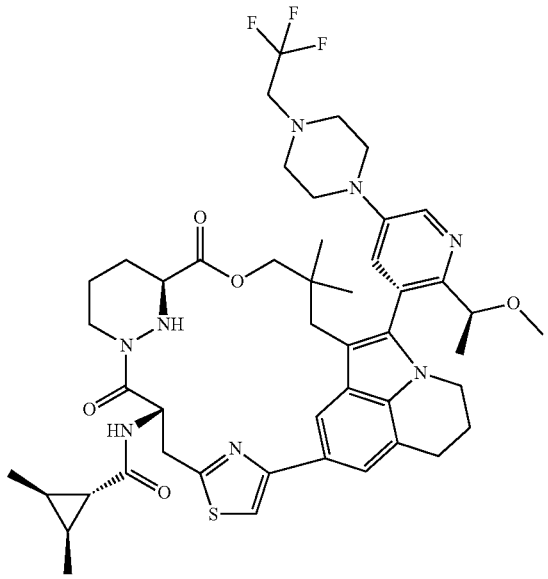

The title compound was prepared in analogy to the preparation of Example 1 by using (7S,13S)-7-amino-(20M)-20-[2-[(1S)-1-methoxyethyl]-5-[4-(2,2,2-trifluoroethyl) piperazin-1-yl]-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (intermediate G) and (1r,2S,3R)-2,3-dimethylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 86 (30.1 mg) was obtained as a light yellow solid. MS calc'd 905.4 (MH$^+$), measured 905.6 (MH$^+$). $^1$H NMR (400 MHZ, METHANOL-d$_4$) δ=8.45-8.40 (m, 1H), 8.39-8.32 (m, 1H), 7.94-7.87 (m, 1H), 7.54-7.49 (m, 1H), 7.46 (s, 1H), 5.80 (br d, J=7.5 Hz, 1H), 4.54 (q, J=6.3 Hz, 1H), 4.47-4.38 (m, 1H), 4.23-4.16 (m, 1H), 4.15-4.06 (m, 1H), 3.79-3.66 (m, 3H), 3.50-3.36 (m, 9H), 3.28-2.96 (m, 8H), 2.89 (br s, 3H), 2.81-2.64 (m, 4H), 2.32 (br d, J=4.4 Hz, 1H), 2.23-2.12 (m, 2H), 1.96-1.89 (m, 1H), 1.82-1.68 (m, 1H), 1.66-1.55 (m, 1H), 1.42-1.31 (m, 2H), 1.15-1.09 (m, 6H), 1.00 (s, 3H), 0.63 (s, 3H).

Example 87

(1r,2S,3R)-N-[(7S,13S)-23,23-difluoro-(20M)-20-[2-[(1S)-1-methoxyethyl]-5-[4-(2,2,2-trifluoroethyl) piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2,3-dimethyl-cyclopropanecarboxamide

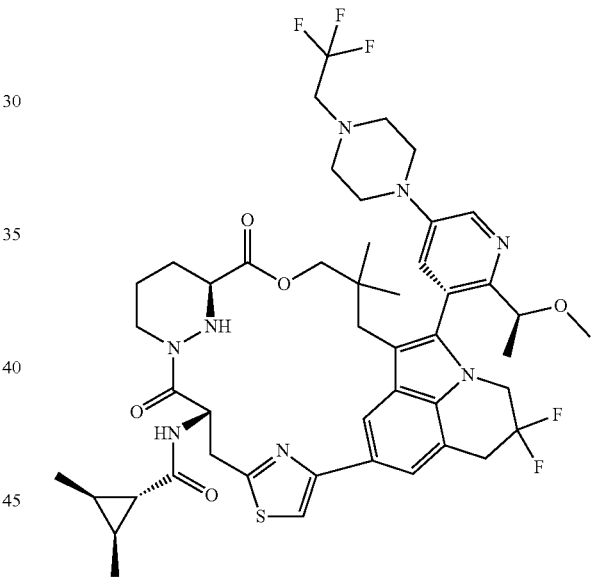

The title compound was prepared in analogy to the preparation of Example 1 by using (7S,13S)-7-amino-23,23-difluoro-(20M)-20-[2-[(1S)-1-methoxyethyl]-5-[4-(2,2,2-trifluoroethyl) piperazin-1-yl]-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate O) and (1r,2S,3R)-2,3-dimethylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 87 (32.4 mg) was obtained as a light yellow solid. MS calc'd 941.4 (MH$^+$), measured 941.4 (MH$^+$). $^1$H NMR (400 MHZ, METHANOL-d$_4$) δ=8.53 (s, 1H), 8.44-8.38 (m, 1H), 7.83-7.78 (m, 1H), 7.62-7.57 (m, 2H), 5.80 (br d, J=7.0 Hz, 1H), 4.55-4.40 (m, 3H), 4.22 (dd, J=2.9, 12.0 Hz, 1H), 4.09-3.98 (m, 1H), 3.83-3.76 (m, 1H), 3.75-3.69 (m, 1H), 3.68-3.56 (m, 2H), 3.51-3.46 (m, 4H), 3.44-3.38 (m, 4H), 3.28-3.08 (m, 4H), 2.92-2.86 (m, 4H), 2.80-2.67 (m, 2H), 2.23-2.11 (m, 1H), 1.96-1.91 (m, 1H), 1.83-1.70 (m, 1H), 1.67-1.57 (m, 1H), 1.49 (d, J=6.3 Hz, 3H), 1.39-1.31 (m, 2H), 1.16-1.11 (m, 7H), 1.01 (s, 3H), 0.63 (s, 3H).

Example 88

(1S,2S)-N-[(7S,13S)-(20M)-20-[2-[(1S)-1-methoxyethyl]-5-morpholino-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-pyrimidin-5-yl-cyclopropanecarboxamide

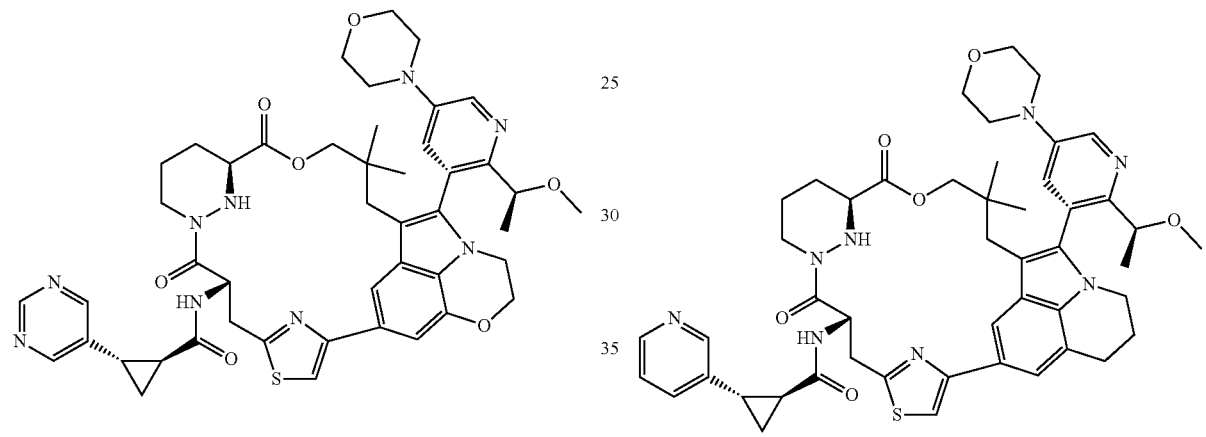

The title compound was prepared in analogy to the preparation of Example 1 by using (7S,13S)-7-amino-(20M)-20-[2-[(1S)-1-methoxyethyl]-5-morpholino-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (intermediate J) and trans-2-pyrimidin-5-ylcyclopropanecarboxylic acid (Intermediate R1) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate F) and (1S,2S)-2-methylcyclopropanecarboxylic acid and then purified by prep-HPLC. Example 88 (30 mg, prep-HPLC, faster eluted) was obtained as a light yellow solid. MS calc'd 876.4 (MH$^+$), measured 876.4 (MH$^+$). $^1$H NMR (400 MHZ, METHANOL-d$_4$) δ=9.0 (s, 1H), 8.67 (s, 2H), 8.42-8.33 (d, J=3.2 Hz, 1H), 8.28-8.20 (s, 1H), 7.90-7.80 (d, J=2.8 Hz, 1H), 7.52 (s, 1H), 7.18 (s, 1H), 5.87-5.68 (d, J=7.6 Hz, 1H), 4.70-4.57 (m, 3H), 4.50-4.39 (m, 1H), 4.32-4.19 (m, 2H), 3.90-3.85 (m, 4H), 3.79-3.74 (m, 2H), 3.50-3.45 (m, 1H), 3.45-3.40 (m, 8H), 3.28-3.22 (m, 1H), 3.19-3.10 (m, 1H), 2.86-2.73 (m, 1H), 2.72-2.62 (d, J=14.4 Hz 1H), 2.44-2.36 (m, 1H), 2.27-2.16 (m, 2H), 1.99-1.90 (m, 1H), 1.87-1.73 (m, 1H), 1.69-1.59 (m, 2H), 1.52-1.45 (m, 4H), 1.04 (s, 3H), 0.60 (s, 3H).

Example 89

(1S,2S)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-(3-pyridyl)cyclopropanecarboxamide

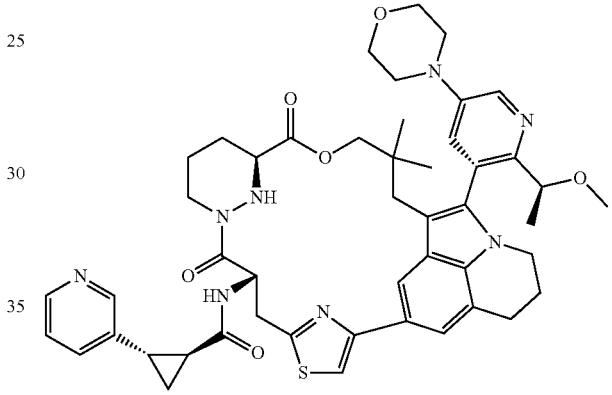

The title compound was prepared in analogy to the preparation of Example 1 by using (1S,2S)-2-(3-pyridyl)cyclopropanecarboxylic acid instead of (1S,2S)-2-methylcyclopropanecarboxylic acid. Example 89 (17.8 mg) was obtained as a yellow solid. MS calc'd 873.4 (MH$^+$), measured 873.4 (MH$^+$). $^1$H NMR (400 MHZ, METHANOL-d$_4$) δ=8.79 (s, 1H), 8.69 (d, J=5.2 Hz, 1H), 8.43 (s, 1H), 8.39-8.34 (m, 2H), 7.97 (dd, J=6.0, 8.0 Hz, 1H), 7.86 (d, J=2.4 Hz, 1H), 7.52 (s, 1H), 7.46 (s, 1H), 5.84 (d, J=7.6 Hz, 1H), 4.54 (q, J=6.0 Hz, 1H), 4.47-4.41 (m, 1H), 4.23 (dd, J=2.8, 11.6 Hz, 1H), 4.17-4.10 (m, 1H), 3.86 (t, J=4.8 Hz, 4H), 3.77 (s, 2H), 3.69 (m, 1H), 3.43 (s, 6H), 3.28-3.23 (m, 1H), 3.18-2.96 (m, 4H), 2.83-2.75 (m, 1H), 2.74-2.68 (m, 1H), 2.63-2.57 (m, 1H), 2.37-2.31 (m, 1H), 2.29-2.24 (m, 1H), 2.22-2.15 (m, 2H), 1.97-1.91 (m, 1H), 1.82-1.74 (m, 1H), 1.73-1.68 (m, 1H), 1.65-1.59 (m, 1H), 1.57-1.52 (m, 1H), 1.49 (d, J=6.4 Hz, 3H), 1.37-1.27 (m, 1H), 1.00 (s, 3H), 0.64 (s, 3H).

Example 90

(1S,2S)-N-[(7S,13S)-(20M)-20-[2-[(1S)-1-methoxyethyl]-5-[4-(2,2,2-trifluoroethyl) piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-(3-pyridyl)cyclopropanecarboxamide

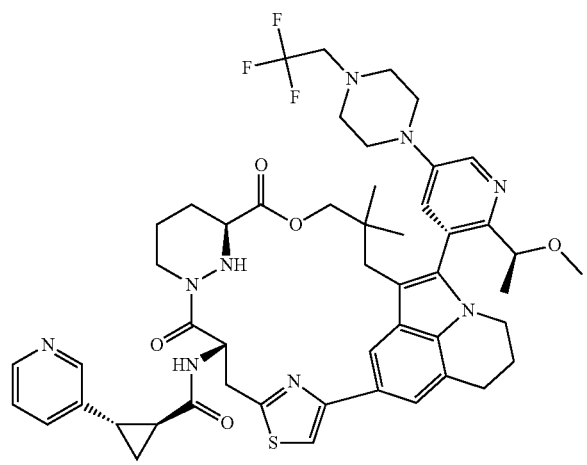

The title compound was prepared in analogy to the preparation of Example 1 by using (7S,13S)-7-amino-(20M)-20-[2-[(1S)-1-methoxyethyl]-5-[4-(2,2,2-trifluoroethyl) piperazin-1-yl]-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (intermediate G) and (1S,2S)-2-(3-pyridyl)cyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 90 (26.0 mg) was obtained as a yellow solid. MS calc'd 954.4 (MH$^+$), measured 954.4 (MH$^+$). $^1$H NMR (400 MHZ, METHANOL-d$_4$) δ=8.79 (s, 1H), 8.69 (d, J=5.2 Hz, 1H), 8.44 (s, 1H), 8.39-8.34 (m, 2H), 7.97 (dd, J=6.0, 8.0 Hz, 1H), 7.88 (s, 1H), 7.53 (s, 1H), 7.46 (s, 1H), 5.84 (d, J=7.6 Hz, 1H), 4.54 (q, J=6.0 Hz, 1H), 4.46-4.40 (m, 1H), 4.23 (dd, J=2.8, 11.6 Hz, 1H), 4.16-4.10 (m, 1H), 3.77-3.76 (m, 1H), 3.72-3.67 (m, 1H), 3.63-3.58 (m, 2H), 3.51-3.49 (m, 3H), 3.43 (s, 3H), 3.18 (q, J=9.6 Hz, 3H), 3.13-3.06 (m, 2H), 2.90-2.88 (m, 3H), 2.83-2.76 (m, 1H), 2.73-2.68 (m, 1H), 2.63-2.58 (m, 1H), 2.36-2.30 (m, 1H), 2.28-2.24 (m, 1H), 2.21-2.17 (m, 1H), 1.98-1.92 (m, 1H), 1.83-1.74 (m, 1H), 1.73-1.68 (m, 1H), 1.62 (dd, J=3.2, 12.4 Hz, 1H), 1.58-1.54 (m, 1H), 1.48 (d, J=6.4 Hz, 3H), 1.33-1.29 (m, 1H), 1.18 (t, J=7.2 Hz, 3H), 1.01 (s, 3H), 0.64 (s, 3H).

Example 91

(1S,2S)-N-[(7S,13S)-23,23-difluoro-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2-(3-pyridyl)cyclopropanecarboxamide

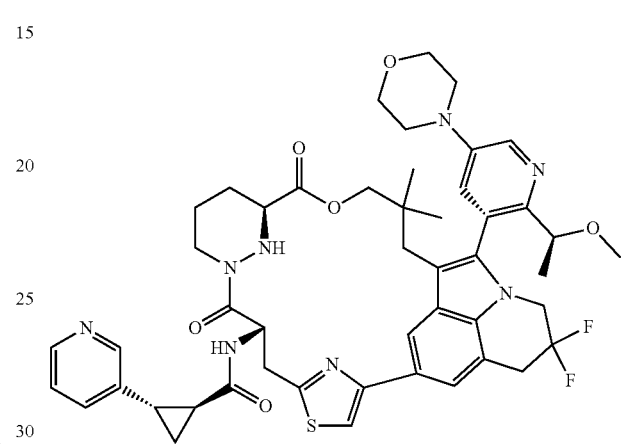

The title compound was prepared in analogy to the preparation of Example 1 by using (7S,13S)-7-amino-23,23-difluoro-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate Q) and (1S,2S)-2-(3-pyridyl)cyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 91 (24.6 mg) was obtained as a yellow solid. MS calc'd 909.4 (MH$^+$), measured 909.4 (MH$^+$). $^1$H NMR (400 MHZ, METHANOL-d$_4$) δ=8.78 (s, 1H), 8.68 (d, J=4.8 Hz, 1H), 8.53 (s, 1H), 8.42 (d, J=2.8 Hz, 1H), 8.33 (d, J=8.0 Hz, 1H), 7.95 (dd, J=6.0, 8.0 Hz, 1H), 7.70 (d, J=2.8 Hz, 1H), 7.60 (s, 2H), 5.82 (d, J=8.0 Hz, 1H), 4.57-4.49 (m, 2H), 4.46-4.41 (m, 1H), 4.25 (dd, J=2.8, 11.6 Hz, 1H), 4.06-3.97 (m, 1H), 3.86 (t, J=4.8 Hz, 4H), 3.81-3.72 (m, 2H), 3.64-3.58 (m, 2H), 3.51-3.42 (m, 2H), 3.40 (s, 3H), 3.29-3.24 (m, 1H), 3.12-3.04 (m, 1H), 2.83-2.76 (m, 1H), 2.73-2.67 (m, 1H), 2.62-2.57 (m, 1H), 2.28-2.23 (m, 1H), 2.22-2.17 (m, 1H), 1.98-1.92 (m, 1H), 1.85-1.75 (m, 1H), 1.73-1.68 (m, 1H), 1.65-1.60 (m, 1H), 1.57-1.52 (m, 1H), 1.49 (d, J=6.4 Hz, 3H), 1.33-1.29 (m, 1H), 1.18 (t, J=7.2 Hz, 2H), 1.01 (s, 3H), 0.62 (s, 3H).

Example 92

(1S,2S)-N-[(7S,13S)-23,23-difluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2-(3-pyridyl)cyclopropanecarboxamide

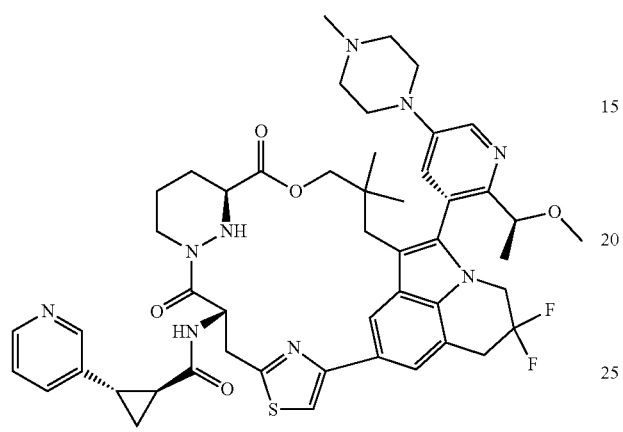

The title compound was prepared in analogy to the preparation of Example 1 by using (7S,13S)-7-amino-23,23-difluoro-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (intermediate K) and (1S,2S)-2-(3-pyridyl)cyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 92 (23.3 mg) was obtained as a yellow solid. MS calc'd 922.4 (MH$^+$), measured 922.4 (MH$^+$). $^1$H NMR (400 MHZ, METHANOL-d$_4$) δ=8.78 (s, 1H), 8.68 (d, J=5.2 Hz, 1H), 8.52-8.49 (m, 2H), 8.32 (d, J=8.4 Hz, 1H), 7.95 (dd, J=5.6, 8.0 Hz, 1H), 7.59 (s, 1H), 7.57 (s, 1H), 7.47 (d, J=2.8 Hz, 1H), 5.80 (d, J=8.4 Hz, 1H), 4.62-4.54 (m, 1H), 4.51-4.42 (m, 2H), 4.26 (dd, J=3.2, 12.4 Hz, 1H), 4.00-3.87 (m, 2H), 3.82-3.71 (m, 3H), 3.61 (q, J=7.2 Hz, 3H), 3.46 (d, J=14.8 Hz, 2H), 3.36 (s, 3H), 3.13-3.08 (m, 1H), 2.99 (s, 3H), 2.83-2.76 (m, 1H), 2.63-2.57 (m, 2H), 2.29-2.24 (m, 1H), 2.21-2.17 (m, 1H), 1.96 (d, J=13.2 Hz, 1H), 1.85-1.76 (m, 1H), 1.73-1.69 (m, 1H), 1.63 (dd, J=3.2, 12.4 Hz, 1H), 1.57-1.52 (m, 1H), 1.47 (d, J=6.0 Hz, 3H), 1.34-1.29 (m, 3H), 1.18 (t, J=7.2 Hz, 2H), 0.99 (s, 3H), 0.57 (s, 3H).

Example 93

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-pyrimidin-5-yl-cyclopropanecarboxamide

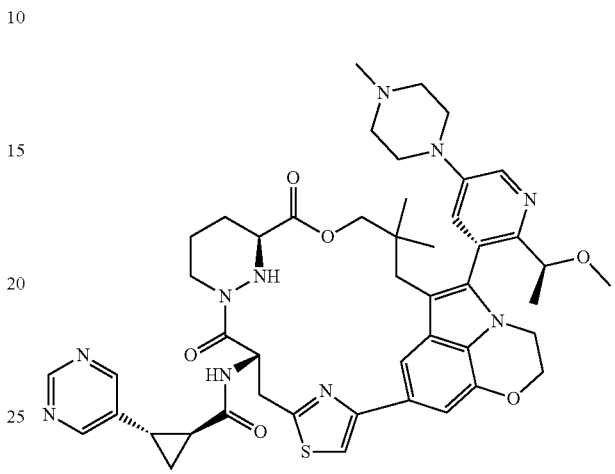

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate H) and trans-2-pyrimidin-5-ylcyclopropanecarboxylic acid (Intermediate R1) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate F) and (1S,2S)-2-methylcyclopropanecarboxylic acid and then purified by prep-HPLC. Example 93 (36.6 mg, prep-HPLC, faster eluted) was obtained as a light yellow solid. MS calc'd 889.4 (MH$^+$), measured 889.6 (MH$^+$). $^1$H NMR (400 MHZ, METHANOL-d$_4$) δ=9.00 (s, 1H), 8.65 (s, 2H), 8.50 (d, J=3.2 Hz, 1H), 8.24 (s, 1H), 7. (d, J=4.4 Hz, 1H), 7.52 (s, 1H), 7.10 (s, 1H), 5.76 (d, J=8.0 Hz, 1H), 4.65 (m, 2H), 4.53 (m, 1H), 4.47-4.40 (m, 1H), 4.33-4.25 (m, 2H), 4.20-3.93 (m, 2H), 3.79-3.72 (m, 3H), 3.67-3.52 (m, 2H), 3.48-3.41 (m, 2H), 3.39-3.37 (m, 3H), 3.29-3.23 (m, 2H), 3.16-3.10 (m, 1H), 3.07-2.86 (m, 4H), 2.82-2.73 (m, 1H), 2.64-2.57 (m, 1H), 2.42-2.35 (m, 1H), 2.26-2.16 (m, 2H), 1.98-1.89 (m, 1H), 1.80 (q, J=12.8 Hz, 1H), 1.60 (td, J=4.9, 9.4 Hz, 2H), 1.54-1.14 (m, 5H), 1.05-0.97 (m, 3H), 0.59-0.48 (m, 3H).

Example 94

(1S,2S)-N-[(7S,13S)-(20M)-20-[2-[(1S)-1-methoxy-ethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2-pyrimidin-5-yl-cyclopropanecarboxamide

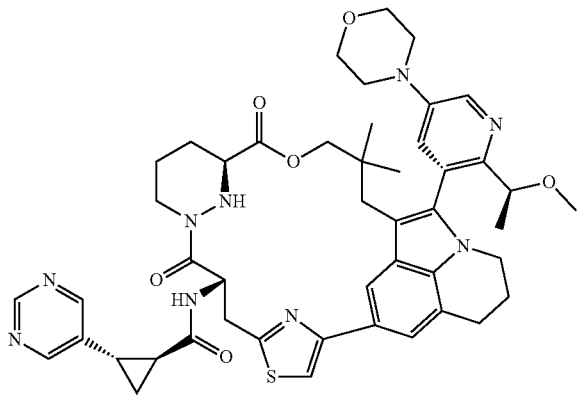

The title compound was prepared in analogy to the preparation of Example 1 by using trans-2-pyrimidin-5-ylcyclopropanecarboxylic acid (Intermediate R1) instead of (1S,2S)-2-methylcyclopropanecarboxylic acid and then purified by prep-HPLC. Example 94 (15 mg, prep-HPLC, slower eluted) was obtained as a light yellow solid. MS calc'd 874.4 (MH$^+$), measured 874.4 (MH$^+$). $^1$H NMR (400 MHZ, METHANOL-d$_4$) δ=9.01 (s, 1H), 8.66 (s, 2H), 8.44 (s, 1H), 8.37 (d, J=2.8 Hz, 1H), 7.86 (d, J=2.8 Hz, 1H), 7.52 (s, 1H), 7.46 (s, 1H), 5.84 (dd, J=0.8, 8.4 Hz, 1H), 4.54 (q, J=6.4 Hz, 1H), 4.44 (d, J=11.6 Hz, 1H), 4.22 (dd, J=2.8, 11.6 Hz, 1H), 4.16-4.09 (m, 1H), 3.87 (t, J=4.8 Hz, 4H), 3.77 (d, J=4.4 Hz, 2H), 3.72-3.66 (m, 1H), 3.43 (s, 7H), 3.29-3.23 (m, 1H), 3.22-2.87 (m, 4H), 2.84-2.75 (m, 1H), 2.71 (d, J=14.4 Hz, 1H), 2.43-2.38 (m, 1H), 2.37-2.29 (m, 1H), 2.23-2.15 (m, 3H), 1.98-1.90 (m, 1H), 1.82-1.71 (m, 1H), 1.65-1.57 (m, 2H), 1.49 (d, J=6.4 Hz, 3H), 1.47-1.42 (m, 1H), 1.00 (s, 3H), 0.64 (s, 3H).

Example 95

(1S,2S)-N-[(7S,13S)-23,23-difluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-pyrimidin-5-yl-cyclopropanecarboxamide

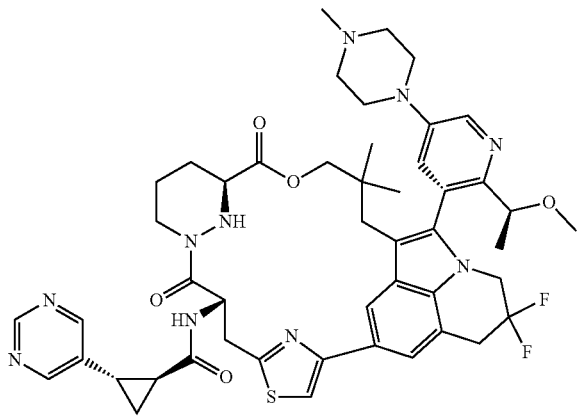

The title compound was prepared in analogy to the preparation of Example 1 by using (7S,13S)-7-amino-23,23-difluoro-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (intermediate K) and trans-2-pyrimidin-5-ylcyclopropanecarboxylic acid (Intermediate R1) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate F) and (1S,2S)-2-methylcyclopropanecarboxylic acid and then purified by prep-HPLC. Example 95 (15 mg, prep-HPLC, slower eluted) was obtained as a light yellow solid. MS calc'd 923.4 (MH$^+$), measured 923.4 (MH$^+$). $^1$H NMR (400 MHZ, METHANOL-d$_4$) δ=9.01 (s, 1H), 8.67 (s, 2H), 8.53-8.50 (m, 2H), 7.59-7.56 (m, 2H), 7.54 (d, J=2.8 Hz, 1H), 5.80 (d, J=8.0 Hz, 1H), 4.59-4.52 (m, 1H), 4.50 (d, J=6.0 Hz, 1H), 4.44 (d, J=12.0 Hz, 1H), 4.26 (dd, J=3.2, 12.0 Hz, 1H), 4.01-3.87 (m, 2H), 3.82-3.70 (m, 3H), 3.65-3.51 (m, 4H), 3.46 (d, J=14.8 Hz, 2H), 3.37 (s, 4H), 3.29-3.25 (m, 2H), 3.15-3.03 (m, 3H), 2.99 (s, 3H), 2.83-2.76 (m, 1H), 2.62 (d, J=14.0 Hz, 1H), 2.43-2.38 (m, 1H), 2.24-2.17 (m, 2H), 1.95 (d, J=12.8 Hz, 1H), 1.83-1.75 (m, 1H), 1.65-1.59 (m, 2H), 1.48 (d, J=6.0 Hz, 3H), 1.46-1.43 (m, 1H), 0.99 (s, 3H), 0.57 (s, 3H).

Example 96

(1S,2S)-N-[(7S,13S)-(20M)-20-[2-[(1S)-1-methoxy-ethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2-(3-pyridyl)cyclopropanecarboxamide

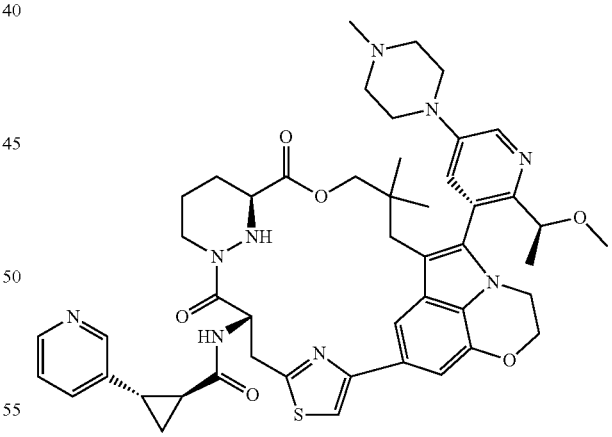

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (intermediate H) and (1S,2S)-2-(3-pyridyl)cyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31- tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 96 (14.9 mg) was obtained as a white solid. MS calc'd 888.4 (MH$^+$), measured 888.4 (MH$^+$). $^1$H NMR (400 MHZ, METHANOL-d$_4$) δ=8.44-8.36 (m, 3H), 8.19 (d, J=0.8 Hz, 1H), 7.65-7.57 (m, 1H), 7.47 (s, 1H), 7.41-7.34 (m, 1H), 7.29 (d, J=2.8 Hz, 1H), 7.07 (d, J=0.8 Hz, 1H), 5.78 (d, J=7.6 Hz, 1H), 4.60 (dd, J=2.8 Hz, 5.8 Hz, 2H), 4.46-4.39 (m, 2H), 4.38-4.25 (m, 2H), 3.78-3.71 (m, 3H), 3.39 (s, 3H), 3.34 (s, 3H), 3.27-3.22 (m, 1H), 2.75 (s, 4H), 2.63-2.53 (m, 1H), 2.47-2.43 (m, 3H), 2.23-2.19 (m, 1H), 2.17-2.11 (m, 1H), 1.97-1.90 (m, 1H), 1.64-1.56 (m, 2H), 1.44 (d, J=6.4 Hz, 3H), 1.41-1.34 (m, 7H), 0.994 (s, 3H), 0.516 (s, 3H).

Example 97

(1S,2S)-N-[(7S,13S)-(20M)-20-[2-[(1S)-1-methoxyethyl]-5-morpholino-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$,]hentriaconta-1 (28),2,5 (31), 19,25 (29),26-hexaen-7-yl]-2-(3-pyridyl)cyclopropanecarboxamide

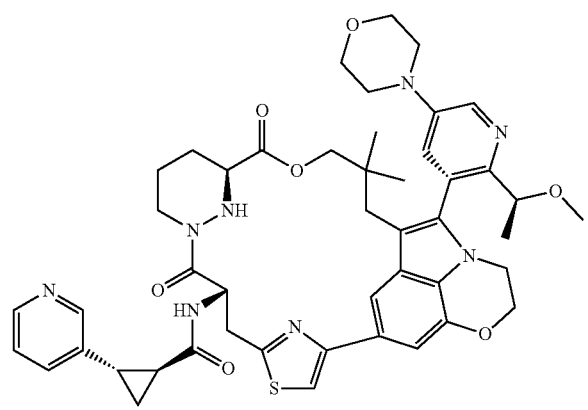

The title compound was prepared in analogy to the preparation of Example 1 by using (7S,13S)-7-amino-(20M)-20-[2-[(1S)-1-methoxyethyl]-5-morpholino-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (intermediate J) and (1S,2S)-2-(3-pyridyl)cyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate F) and (1S,2S)-2-methylcyclopropanecarboxylic acid. Example 97 (26 mg) was obtained as a white solid. MS calc'd 875.4 (MH$^+$), measured 875.4 (MH$^+$). $^1$H NMR (400 MHZ, METHANOL-d$_4$) δ=8.77 (d, J=1.6 Hz, 1H), 8.67 (d, J=5.6 Hz, 1H), 8.39 (d, J=3.2 Hz, 1H), 8.3 (d, J=8.4 Hz, 1H) 8.22 (s, 1H), 7.94-7.92 (m, 1H), 7.71-7.7 (m, 1H), 7.50 (s, 1H), 7.12 (s, 1H), 5.81-5.77 (m, 1H), 4.62-4.56 (m, 3H), 4.29 (d, J=3.6 Hz, 1H), 4.28-4.25 (m, 2H), 3.86-3.76 (m, 7H), 3.43-3.42 (m, 8H), 3.39-3.37 (m, 1H), 3.26-3.12 (m, 1H), 2.82-2.72 (m, 1H), 2.67-2.64 (m, 1H), 2.61-2.52 (m, 1H), 2.26-2.24 (m, 2H), 2.05-1.90 (m, 1H), 1.89-1.81 (m, 1H), 1.80-1.75 (m, 1H), 1.69-1.68 (m, 1H), 1.67-1.66 (m, 1H), 1.54 (d, J=6.4 Hz, 3H), 1.03 (s, 3H), 0.57 (s, 3H).

Example 98

(1S,2S)-N-[(7S,13S)-(20M)-20-[2-[(1S)-1-methoxyethyl]-5-[4-(2,2,2-trifluoroethyl) piperazin-1-yl]-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2-(3-pyridyl)cyclopropanecarboxamide

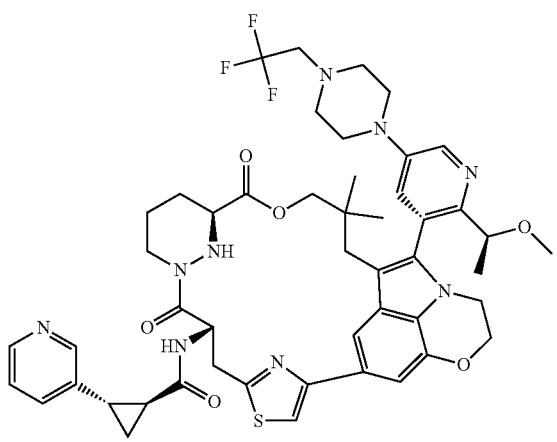

The title compound was prepared in analogy to the preparation of Example 1 by using (7S,13S)-7-amino-(20M)-20-[2-[(1S)-1-methoxyethyl]-5-[4-(2,2,2-trifluoroethyl) piperazin-1-yl]-3-pyridyl]-17,17-dimethyl-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (intermediate I) and (1S,2S)-2-(3-pyridyl)cyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 98 (24.8 mg) was obtained as a light yellow solid. MS calc'd 956.4 (MH$^+$), measured 956.4 (MH$^+$). $^1$H NMR (400 MHZ, METHANOL-d$_4$) δ=8.79 (s, 1H), 8.69 (d, J=5.4 Hz, 1H), 8.41-8.31 (m, 2H), 8.23 (s, 1H), 8.01-7.93 (m, 1H), 7.88-7.74 (m, 1H), 7.51 (s, 1H), 7.13 (s, 1H), 5.79 (d, J=8.0 Hz, 1H), 4.66-4.56 (m, 3H), 4.48-4.39 (m, 1H), 4.31-4.20 (m, 2H), 3.86-3.73 (m, 3H), 3.60-3.32 (m, 5H), 3.42 (s, 3H), 3.28-3.14 (m, 4H), 2.92-2.86 (m, 4H), 2.84-2.75 (m, 1H), 2.70-2.57 (m, 2H), 2.30-2.18 (m, 2H), 2.00-1.92 (m, 1H), 1.88-1.76 (m, 1H), 1.74-1.66 (m, 1H), 1.65-1.53 (m, 2H), 1.49 (d, J=6.4 Hz, 3H), 1.04 (s, 3H), 0.59 (s, 3H).

Example 99

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-pyrazin-2-yl-cyclopropanecarboxamide

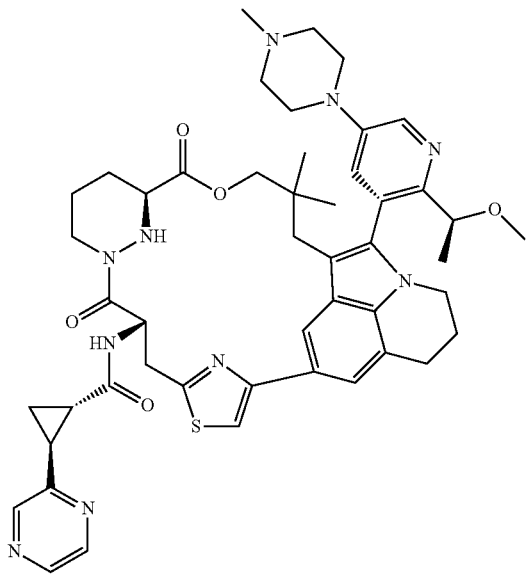

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (intermediate E) and trans-(1S,2S)-2-pyrazin-2-ylcyclopropanecarboxylic acid (intermediate R6) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate F) and (1S,2S)-2-methylcyclopropanecarboxylic acid and then purified by reversed phase chromatography and Prep-HPLC. Example 99 (1 mg, slower eluted) was obtained as a white solid. MS calc'd 887.4 (MH$^+$), measured 887.4 (MH$^+$). $^1$H NMR (400 MHZ, METHANOL-d$_4$) δ=8.62 (d, J=1.6 Hz, 1H), 8.53-8.51 (m, 1H), 8.44-8.40 (m, 3H), 7.52 (s, 1H), 7.44-7.38 (m, 1H), 7.28 (d, J=2.8 Hz, 1H), 5.86-5.79 (m, 1H), 4.48-4.38 (m, 2H), 4.30-4.23 (m, 2H), 3.76 (s, 2H), 3.67-3.59 (m, 1H), 3.52-3.41 (m, 2H), 3.36 (s, 4H), 3.28-3.25 (m, 1H), 3.15-3.00 (m, 3H), 2.84-2.75 (m, 1H), 2.68-2.64 (m, 5H), 2.62-2.58 (m, 2H), 2.48-2.43 (m, 1H), 2.38 (s, 3H), 2.26-2.18 (m, 2H), 1.95 (s, 1H), 1.81-1.73 (m, 1H), 1.66-1.58 (m, 3H), 1.44 (d, J=6.4 Hz, 3H), 1.39-1.30 (m, 2H), 0.97 (s, 3H), 0.56 (s, 3H).

Example 100

(1r,2R,3S)-N-[(7S,13S)-(20M)-20-[2-[(1S)-1-methoxyethyl]-5-(4-methylpiperazin-1-yl)-3-pyridyl]-17,17-dimethyl-8,14-dioxo-15,25-dioxa-4-thia-9,21,31,32-tetrazahexacyclo[24.3.1.1$^{2,5}$.1$^{9,13}$.0$^{19,28}$.0$^{21,27}$]dotriaconta-1 (29),2,5 (32),19,26 (30),27-hexaen-7-yl]-2,3-dimethyl-cyclopropanecarboxamide

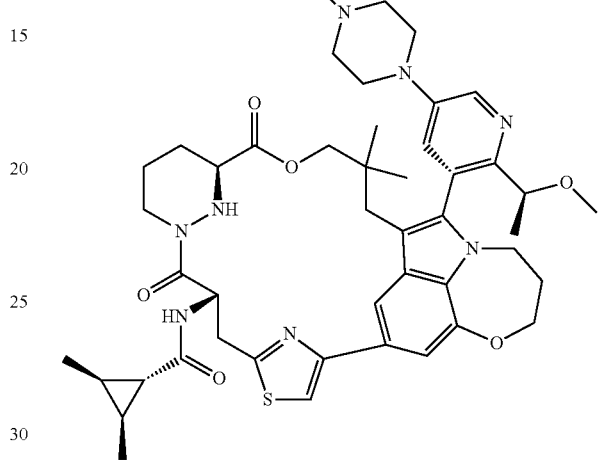

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15,25-dioxa-4-thia-9,21,31,32-tetrazahexacyclo[24.3.1.1$^{2,5}$.1$^{9,13}$.0$^{19,28}$.0$^{21,27}$]dotriaconta-1 (29),2,5 (32), 19,26 (30), 27-hexaene-8,14-dione (intermediate S) and (1r,2S,3R)-2,3-dimethylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 100 (17.2 mg) was obtained as a yellow solid. MS calc'd 853.4 (MH$^+$), measured 853.4 (MH$^+$). $^1$H NMR (400 MHZ, METHANOL-d$_4$) δ=8.47 (d, J=2.8 Hz, 1H), 8.22 (s, 1H), 7.56-7.49 (m, 2H), 7.28 (s, 1H), 5.75 (d, J=7.6 Hz, 1H), 4.59-4.52 (m, 1H), 4.51-4.41 (m, 2H), 4.25-4.08 (m, 3H), 4.05-3.90 (m, 2H), 3.71 (q, J=11.2 Hz, 6H), 3.45-3.35 (m, 6H), 3.29-3.22 (m, 2H), 3.07 (d, J=14.8 Hz, 1H), 3.00 (s, 3H), 2.77 (s, 1H), 2.61 (d, J=14.0 Hz, 1H), 2.46-2.32 (m, 1H), 2.27 (s, 1H), 2.15 (d, J=14.0 Hz, 1H), 1.91 (s, 1H), 1.82-1.68 (m, 1H), 1.61 (s, 1H), 1.49-1.29 (m, 6H), 1.14 (dd, J=6.0, 11.2 Hz, 6H), 0.93 (s, 3H), 0.50 (s, 3H).

Example 101

(1r,2S,3R)-N-[(7S,13S)-(20M)-20-[5-[(9αR)-1,3,4,6,7,8,9,9a-octahydropyrido[1,2-a]pyrazin-2-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2,3-dimethyl-cyclopropanecarboxamide

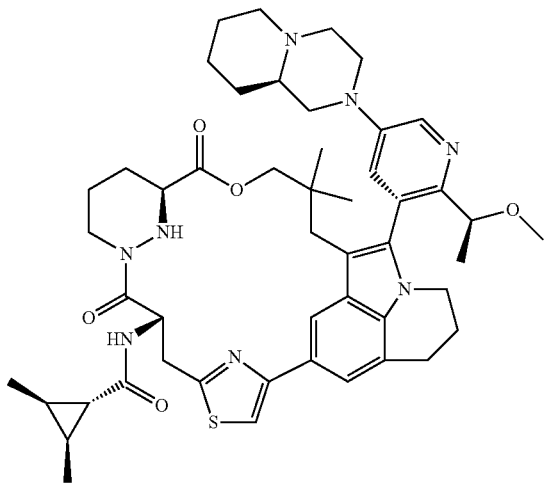

The title compound was prepared in analogy to the preparation of Example 1 by using (7S,13S)-(20M)-20-[5-[(9αR)-1,3,4,6,7,8,9,9a-octahydropyrido[1,2-a]pyrazin-2-yl]-2-[(1S)-1-methoxyethyl]-3-pyridyl]-7-amino-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (intermediate L2) and (1r,2S,3R)-2,3-dimethylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 101 (15.1 mg) was obtained as a yellow solid. MS calc'd 877.4 (MH$^+$), measured 877.4 (MH$^+$). $^1$H NMR (400 MHZ, METHANOL-d$_4$) δ=8.48 (d, J=2.8 Hz, 1H), 8.39 (s, 1H), 7.57 (s, 1H), 7.50 (s, 1H), 7.43 (s, 1H), 5.77 (d, J=7.2 Hz, 1H), 4.51-4.41 (m, 2H), 4.23 (dd, J=2.8, 11.6 Hz, 2H), 4.11 (d, J=13.6 Hz, 2H), 3.80-3.72 (m, 2H), 3.62-3.53 (m, 3H), 3.43-3.36 (m, 6H), 3.29-3.24 (m, 2H), 3.14-3.07 (m, 3H), 2.99 (d, J=11.2 Hz, 2H), 2.82-2.73 (m, 1H), 2.60 (d, J=14.4 Hz, 1H), 2.31 (d, J=4.0 Hz, 1H), 2.17 (d, J=12.8 Hz, 2H), 2.07-1.93 (m, 4H), 1.86-1.52 (m, 6H), 1.46 (d, J=6.0 Hz, 3H), 1.42-1.33 (m, 2H), 1.16-1.12 (m, 6H), 0.97 (s, 3H), 0.55 (s, 3H).

Example 102

(1S,2S)-N-[(7S,13S)-(20M)-20-[5-[(9αR)-1,3,4,6,7,8,9,9a-octahydropyrido[1,2-a]pyrazin-2-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2-(3-pyridyl)cyclopropanecarboxamide

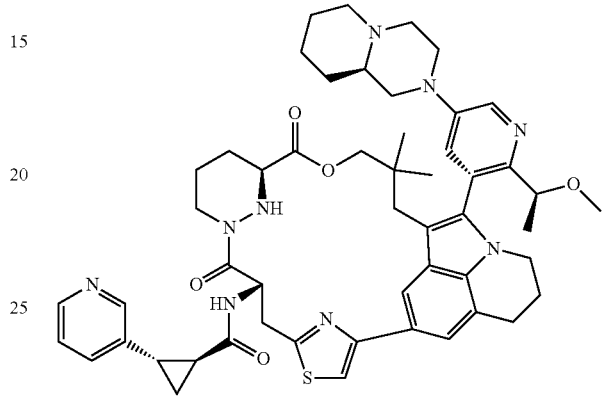

The title compound was prepared in analogy to the preparation of Example 1 by using (7S,13S)-(20M)-20-[5-[(9αR)-1,3,4,6,7,8,9,9a-octahydropyrido[1,2-a]pyrazin-2-yl]-2-[(1S)-1-methoxyethyl]-3-pyridyl]-7-amino-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (intermediate L2) and (1S,2S)-2-(3-pyridyl)cyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate F) and (1S,2S)-2-methylcyclopropanecarboxylic acid. Example 102 (24.3 mg) was obtained as a light yellow solid. MS calc'd 926.5 (MH$^+$), measured 926.5 (MH$^+$). $^1$H NMR (400 MHZ, METHANOL-d$_4$) δ=8.77 (s, 1H), 8.70-8.65 (m, 1H), 8.49 (d, J=3.2 Hz, 1H), 8.40 (s, 1H), 8.34-8.30 (m, 1H), 7.97-7.92 (m, 1H), 7.56 (d, J=3.2 Hz, 1H), 7.51 (s, 1H), 7.43 (s, 1H), 5.83-5.79 (m, 1H), 4.48-4.41 (m, 2H), 4.27-4.18 (m, 2H), 4.13-4.07 (m, 2H), 3.76 (s, 2H), 3.61-3.52 (m, 3H), 3.47-3.43 (m, 1H), 3.37 (s, 3H), 3.35-3.32 (m, 1H), 3.29-3.24 (m, 2H), 3.12-3.00 (m, 5H), 2.83-2.76 (m, 1H), 2.64-2.57 (m, 2H), 2.31-2.17 (m, 4H), 2.06-1.94 (m, 4H), 1.86-1.76 (m, 2H), 1.74-1.67 (m, 2H), 1.66-1.58 (m, 3H), 1.57-1.52 (m, 1H), 1.46 (d, J=6.0 Hz, 3H), 0.98 (s, 3H), 0.57 (s, 3H).

Example 103

(1S,2S)-N-[(7S,13S)-(20M)-20-[5-[(9αR)-1,3,4,6,7,
8,9,9a-octahydropyrido[1,2-a]pyrazin-2-yl]-2-[(1S)-
1-methoxyethyl]-3-pyridyl]-17,17-dimethyl-8,14-
dioxo-15-oxa-4-thia-9,21,30,31-tetrazahexacyclo
[23.3.1.1$^{2,5}$.1$^{9,13}$.0$^{19,27}$.0$^{21,26}$]hentriaconta-1 (28),2,5
(31),19,25 (29),26-hexaen-7-yl]-2-pyrimidin-5-yl-
cyclopropanecarboxamide

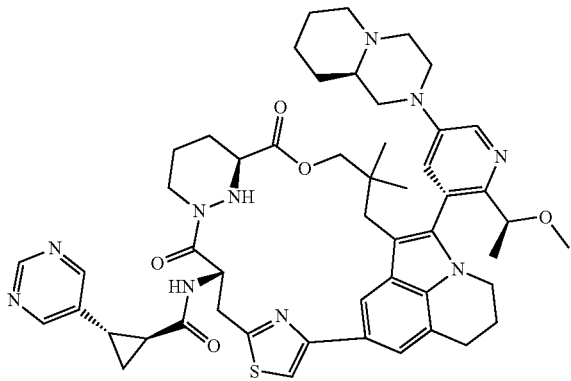

The title compound was prepared in analogy to the preparation of Example 1 by using (7S,13S)-(20M)-20-[5-[(9αR)-1,3,4,6,7,8,9,9a-octahydropyrido[1,2-a]pyrazin-2-yl]-2-[(1S)-1-methoxyethyl]-3-pyridyl]-7-amino-17,17-dimethyl-15-oxa-4-thia-9,21,30,31-tetrazahexacyclo [23.3.1.1$^{2,5}$.1$^{9,13}$.0$^{19,27}$.0$^{21,26}$]hentriaconta-1 (28), 2,5 (31), 19,25 (29), 26-hexaene-8,14-dione (intermediate L2) and trans-2-pyrimidin-5-ylcyclopropanecarboxylic acid (Intermediate R1) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo [23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate F) and (1S,2S)-2-methylcyclopropanecarboxylic acid and then purified by prep-HPLC. Example 103 (26.2 mg, prep-HPLC, slower eluted) was obtained as a yellow solid. MS calc'd 927.5 (MH$^+$), measured 927.5 (MH$^+$). $^1$H NMR (400 MHZ, METHANOL-d$_4$) δ=9.00 (s, 1H), 8.66 (s, 2H), 8.50 (d, J=2.8 Hz, 1H), 8.41 (s, 1H), 7.65 (d, J=2.8 Hz, 1H), 7.51 (s, 1H), 7.44 (s, 1H), 5.84-5.79 (m, 1H), 4.52-4.42 (m, 2H), 4.27-4.09 (m, 5H), 3.76 (s, 2H), 3.63-3.53 (m, 3H), 3.47-3.42 (m, 1H), 3.39 (s, 4H), 3.29-3.24 (m, 2H), 3.14-2.99 (m, 6H), 2.82-2.75 (m, 1H), 2.63 (d, J=14.4 Hz, 1H), 2.43-2.38 (m, 1H), 2.35-2.29 (m, 1H), 2.22-2.16 (m, 3H), 2.06-1.93 (m, 4H), 1.83-1.78 (m, 1H), 1.68-1.60 (m, 4H), 1.49-1.45 (m, 4H), 0.98 (s, 3H), 0.58 (s, 3H).

Example 104

(1S,2S)-N-[(7S,13S)-(20M)-20-[5-[(9αS)-3,4,6,7,9,
9a-hexahydro-1H-pyrazino[2,1-c][1,4]oxazin-8-yl]-
2-[(1S)-1-methoxyethyl]-3-pyridyl]-17,17-dimethyl-
8,14-dioxo-15-oxa-4-thia-9,21,30,31-
tetrazahexacyclo[23.3.1.1$^{2,5}$.1$^{9,13}$.0$^{19,27}$.0$^{21,26}$]
hentriaconta-1 (28),2,5 (31),19,25 (29),26-hexaen-
7-yl]-2-(3-pyridyl)cyclopropanecarboxamide

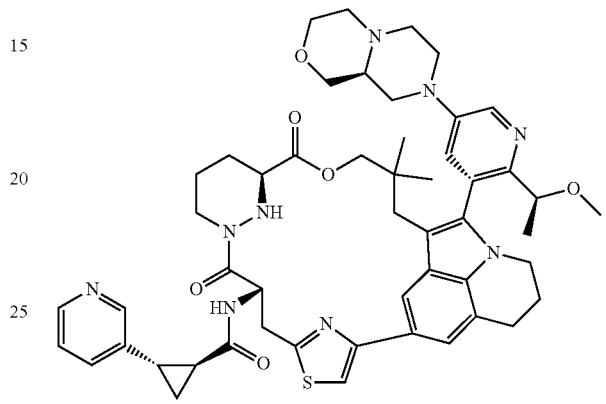

The title compound was prepared in analogy to the preparation of Example 1 by using (7S,13S)-(20M)-20-[5-[(9αS)-3,4,6,7,9,9a-hexahydro-1H-pyrazino[2,1-c][1,4] oxazin-8-yl]-2-[(1S)-1-methoxyethyl]-3-pyridyl]-7-amino-17,17-dimethyl-15-oxa-4-thia-9,21,30,31-tetrazahexacyclo [23.3.1.1$^{2,5}$.1$^{9,13}$.0$^{19,27}$.0$^{21,26}$]hentriaconta-1 (28), 2,5 (31), 19,25 (29),26-hexaene-8,14-dione (intermediate L1) and (1S,2S)-2-(3-pyridyl)cyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9, 21,30,31-tetrazahexacyclo[23.3.1.1$^{2,5}$.1$^{9,13}$.0$^{19,27}$.0$^{21,26}$] hentriaconta-1 (28),2,5 (31), 19,25 (29),26-hexaene-8,14-dione (Intermediate F) and (1S,2S)-2-methylcyclopropanecarboxylic acid. Example 104 (16.4 mg) was obtained as a light yellow solid. MS calc'd 928.4 (MH$^+$), measured 928.4 (MH$^+$). $^1$H NMR (400 MHZ, METHANOL-d$_4$) δ=8.87-8.72 (m, 1H), 8.71-8.58 (m, 1H), 8.49-8.45 (m, 1H), 8.39 (s, 1H), 8.20-8.13 (m, 1H), 7.89-7.79 (m, 1H), 7.51 (s, 1H), 7.45 (d, J=2.8 Hz, 1H), 7.42 (s, 1H), 5.83-5.78 (m, 1H), 4.45-4.40 (m, 2H), 4.27-4.21 (m, 2H), 4.12-3.99 (m, 5H), 3.89-3.84 (m, 1H), 3.76 (s, 2H), 3.62-3.54 (m, 4H), 3.49-3.42 (m, 3H), 3.36 (s, 3H), 3.27-3.23 (m, 2H), 3.14-2.99 (m, 4H), 2.82-2.76 (m, 1H), 2.63-2.55 (m, 2H), 2.34-2.28 (m, 1H), 2.25-2.17 (m, 3H), 1.97-1.91 (m, 1H), 1.69-1.59 (m, 2H), 1.52-1.49 (m, 1H), 1.45 (d, J=6.0 Hz, 3H), 1.33-1.28 (m, 1H), 0.97 (s, 3H), 0.55 (s, 3H).

Example 105

(1S,2S)-N-[(7S,13S)-(20M)-20-[5-[(9αS)-3,4,6,7,9,9a-hexahydro-1H-pyrazino[2,1-c][1,4]oxazin-8-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2-pyrimidin-5-yl-cyclopropanecarboxamide

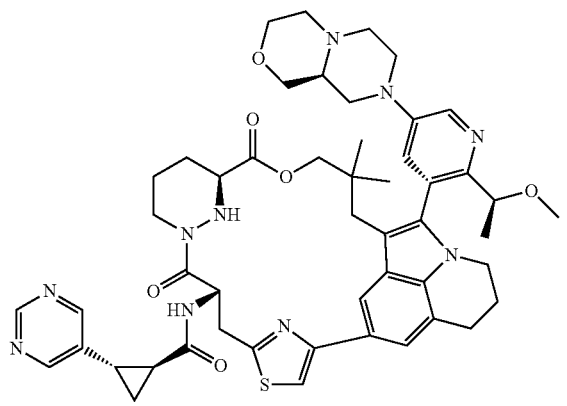

The title compound was prepared in analogy to the preparation of Example 1 by using (7S,13S)-(20M)-20-[5-[(9αS)-3,4,6,7,9,9a-hexahydro-1H-pyrazino[2,1-c][1,4]oxazin-8-yl]-2-[(1S)-1-methoxyethyl]-3-pyridyl]-7-amino-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaene-8,14-dione (intermediate L1) and trans-2-pyrimidin-5-ylcyclopropanecarboxylic acid (intermediate R1) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaene-8,14-dione (Intermediate F) and (1S,2S)-2-methylcyclopropanecarboxylic acid and then purified by prep-HPLC. Example 105 (22.4 mg, prep-HPLC, slower eluted) was obtained as a yellow solid. MS calc'd 929.4 (MH$^+$), measured 929.4 (MH$^+$). $^1$H NMR (400 MHZ, METHANOL-d$_4$) δ=9.00 (s, 1H), 8.67-8.65 (m, 2H), 8.48 (d, J=2.8 Hz, 1H), 8.40 (s, 1H), 7.59 (d, J=2.8 Hz, 1H), 7.52 (s, 1H), 7.44-7.42 (m, 1H), 5.82-5.78 (m, 1H), 4.49-4.42 (m, 2H), 4.28-4.20 (m, 2H), 4.15-4.03 (m, 5H), 3.91-3.85 (m, 1H), 3.76 (s, 2H), 3.65-3.58 (m, 4H), 3.47-3.42 (m, 2H), 3.38 (s, 3H), 3.29-3.24 (m, 2H), 3.13-3.07 (m, 2H), 3.03-2.96 (m, 2H), 2.82-2.76 (m, 1H), 2.64-2.59 (m, 1H), 2.43-2.38 (m, 1H), 2.35-2.29 (m, 1H), 2.27-2.14 (m, 4H), 1.97-1.92 (m, 1H), 1.83-1.75 (m, 1H), 1.65-1.59 (m, 2H), 1.46 (d, J=6.4 Hz, 4H), 0.98 (s, 3H), 0.56 (s, 3H).

Example 106

(1r,2R,3S)-N-[(7S,13S)-(20M)-20-[5-(4-cyclopropylpiperazin-1-yl)-2-[(1S)-1-methoxyethyl]-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2,3-dimethyl-cyclopropanecarboxamide

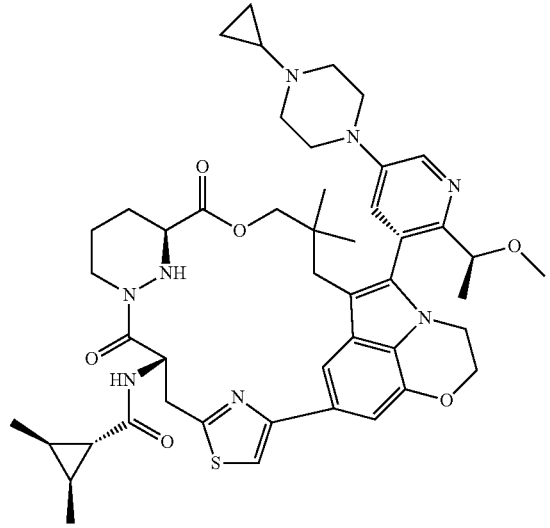

The compound was prepared according to the following scheme:

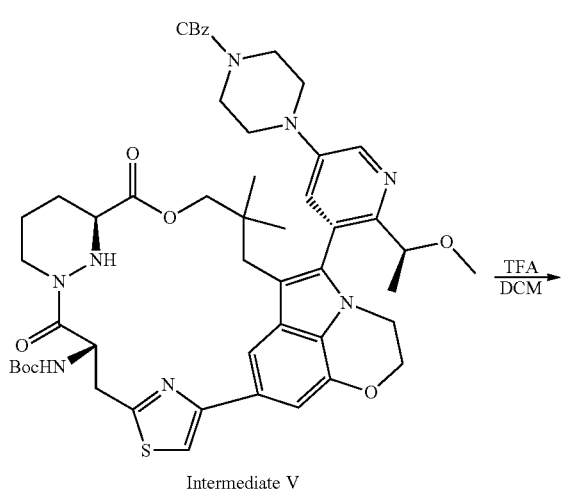

Intermediate V

-continued

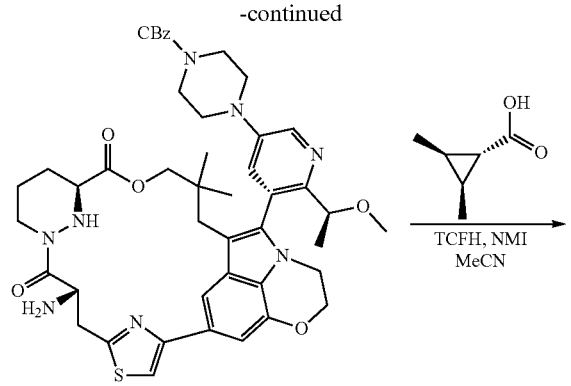

106-1

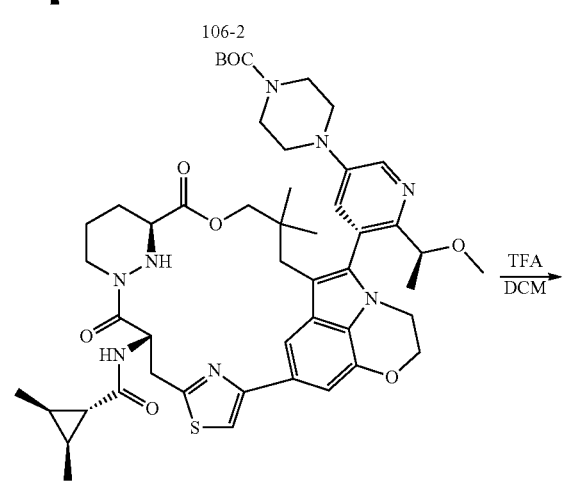

106-2

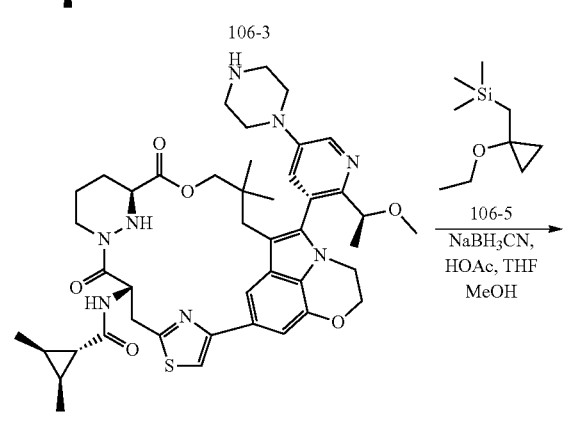

106-3

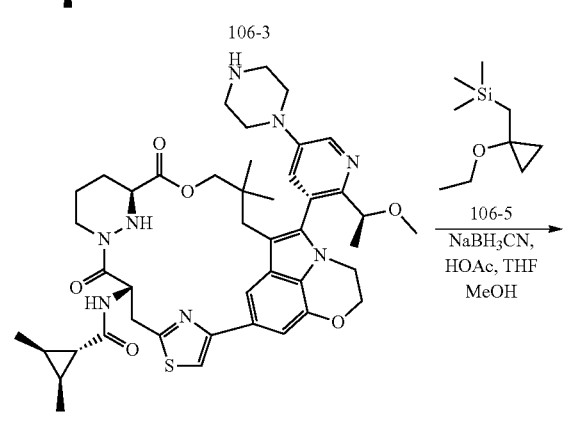

106-4

-continued

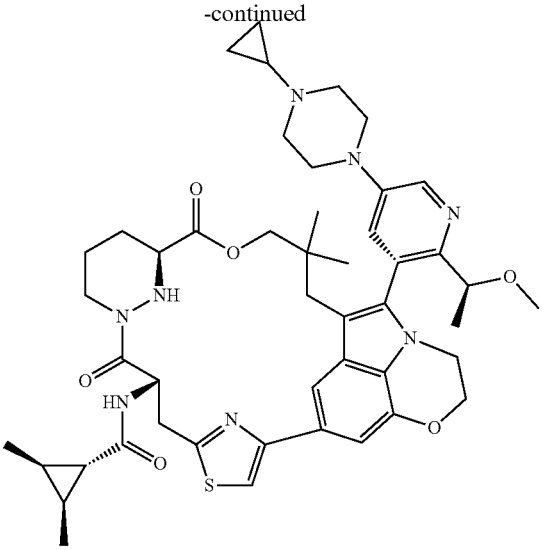

106

Step 1: Preparation of benzyl 4-[(5M)-5-[(7S,13S)-7-amino-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-20-yl]-6-[(1S)-1-methoxyethyl]-3-pyridyl]piperazine-1-carboxylate (compound 106-1)

To a solution of benzyl 4-[(5M)-5-[(7S,13S)-7-(tert-butoxycarbonylamino)-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-20-yl]-6-[(1S)-1-methoxyethyl]-3-pyridyl]piperazine-1-carboxylate (Intermediate V, 2.5 g, 1.3 mmol) in DCM (25 mL) was added TFA (15.0 mL) in one portion. After being stirred at 25° C. for 1 h, the reaction mixture was concentrated under vacuum to afford benzyl 4-[(5M)-5-[(7S, 13S)-7-amino-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaen-20-yl]-6-[(1S)-1-methoxyethyl]-3-pyridyl]piperazine-1-carboxylate (compound 106-1, 2.71 g) as light brown oil, which was used directly in the next step. MS calc'd 863.4 (MH$^+$), measured 863.4 (MH$^+$).

Step 2: Preparation of benzyl 4-[(5M)-5-[(7S,13S)-7-[[(1r,2S,3R)-2,3-dimethylcyclopropanecarbonyl]amino]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaen-20-yl]-6-[(1S)-1-methoxyethyl]-3-pyridyl]piperazine-1-carboxylate (compound 106-2)

To a solution of (1r,2S,3R)-2,3-dimethylcyclopropanecarboxylic acid (205. 8 mg, 1.8 mmol) in MeCN (11.8 mL) was added 1-methylimidazole (455.4 mg, 442 μL, 5.55 mmol) and TCFH (583.7 mg, 2.08 mmol) at rt. After being stirred at rt for 1 h, the reaction mixture was added with benzyl 4-[(5M)-5-[(7S,13S)-7-amino-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29), 26-hexaen-20-yl]-6-[(1S)-1-methoxyethyl]-3-pyridyl]piperazine-1-carboxylate; 2,2,2-trifluoroacetic acid (compound 106-1, 2.71 g, 1.39 mmol) and then stirred for another 2 hrs. The solvent was concentrated under vacuum and purified by silica gel chromatography to afford benzyl 4-[(5M)-5-[(7S, 13S)-7-[[(1r,2S,3R)-2,3-dimethylcyclopropanecarbonyl]

amino]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29), 26-hexaen-20-yl]-6-[(1S)-1-methoxyethyl]-3-pyridyl]piperazine-1-carboxylate (compound 106-2, 730 mg) as a light yellow powder. MS calc'd 959.4 (MH$^+$), measured 959.4 (MH$^+$).

Step 3: Preparation of tert-butyl 4-[(5M)-5-[(7S,13S)-7-[[(1r,2R,3S)-2,3-dimethylcyclopropanecarbonyl]amino]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29), 26-hexaen-20-yl]-6-[(1S)-1-methoxyethyl]-3-pyridyl]piperazine-1-carboxylate (compound 106-3)

To a solution of benzyl 4-[(5M)-5-[(7S,13S)-7-[[(1r,2S,3R)-2,3-dimethylcyclopropanecarbonyl]amino]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaen-20-yl]-6-[(1S)-1-methoxyethyl]-3-pyridyl]piperazine-1-carboxylate (compound 106-2, 730 mg, 0.76 mmol) and Boc$_2$O (332 mg, 1.52 mmol) in methanol (20 mL) was added Pd(OH)$_2$ on activated carbon (73 mg, 10% w/w) under nitrogen atmosphere. The reaction mixture was degassed and purged with H$_2$ for three times and then it was stirred at rt for 2 hrs under hydrogen atmosphere. After the reaction completed, the reaction mixture was filtered and the filtrate was concentrated under vacuum to give crude tert-butyl 4-[(5M)-5-[(7S,13S)-7-[[(1r,2R,3S)-2,3-dimethylcyclopropanecarbonyl]amino]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-20-yl]-6-[(1S)-1-methoxyethyl]-3-pyridyl]piperazine-1-carboxylate (compound 106-3, 1 g) as a yellow solid, which was used in the next step without purification. MS calc'd 925.5 (MH$^+$), measured 925.5 (MH$^+$).

Step 4: Preparation of (1r,2R,3S)-N-[(7S,13S)-(20M)-20-[2-[(1S)-1-methoxyethyl]-5-piperazin-1-yl-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaen-7-yl]-2,3-dimethyl-cyclopropanecarboxamide (compound 106-4)

To a solution of tert-butyl 4-[(5M)-5-[(7S,13S)-7-[[(1r,2R,3S)-2,3-dimethylcyclopropanecarbonyl]amino]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaen-20-yl]-6-[(1S)-1-methoxyethyl]-3-pyridyl]piperazine-1-carboxylate (compound 106-3, 1 g, 1.08 mmol) in DCM (10 mL) was added TFA (5.0 mL) in one portion. After being stirred at 25° C. for 1 h, the reaction mixture was concentrated under vacuum to afford a crude, which was purified by reversed-phase chromatography to afford (1r,2R,3S)-N-[(7S,13S)-(20M)-20-[2-[(1S)-1-methoxyethyl]-5-piperazin-1-yl-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29), 26-hexaen-7-yl]-2,3-dimethyl-cyclopropanecarboxamide (compound 106-4, 340 mg) as a light yellow powder. MS calc'd 825.4 (MH$^+$), measured 825.4 (MH$^+$).

Step 5: Preparation of (1r,2R,3S)-N-[(7S,13S)-(20M)-20-[5-(4-cyclopropylpiperazin-1-yl)-2-[(1S)-1-methoxyethyl]-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaen-7-yl]-2,3-dimethyl-cyclopropanecarboxamide (Example 106)

A solution of (1-ethoxycyclopropoxy)trimethylsilane (22.3 mg, 26 μL, 127.79 umol), (1r,2R,3S)-N-[(7S,13S)-(20M)-20-[2-[(1S)-1-methoxyethyl]-5-piperazin-1-yl-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaen-7-yl]-2,3-dimethyl-cyclopropanecarboxamide (compound 106-4, 40 mg, 42.6 μmol) and acetic acid (24 μL, 425.96 μmol) in methanol (extra dry, 400 μL)/tetrahydrofuran (extra dry, 400 μL) was stirred at 50° C. for 1 h under nitrogen atmosphere. The reaction mixture was added with NaBH$_3$CN (8.0 mg, 127.79 μmol) and then stirred at 50° C. for 3 hrs. The solvent was removed under vacuum and purified by prep-HPLC to afford (1r,2R,3S)-N-[(7S,13S)-(20M)-20-[5-(4-cyclopropylpiperazin-1-yl)-2-[(1S)-1-methoxyethyl]-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaen-7-yl]-2,3-dimethyl-cyclopropanecarboxamide (Example 106, 4 mg) as a white powder. MS calc'd 865.4 (MH$^+$), measured 865.4 (MH$^+$). $^1$H NMR (400 MHZ, METHANOL-d$_4$) δ=8.41 (br s, 1H), 8.20 (s, 1H), 7.48 (s, 1H), 7.28 (br s, 1H), 7.09 (d, J=1.0 Hz, 1H), 5.77 (br d, J=8.4 Hz, 1H), 4.59 (br s, 7H), 4.48-4.41 (m, 2H), 4.39-4.33 (m, 1H), 4.31-4.26 (m, 1H), 3.78-3.75 (m, 2H), 3.45-3.42 (m, 1H), 3.35 (br s, 3H), 3.28-3.23 (m, 1H), 3.15-3.07 (m, 1H), 2.88-2.82 (m, 4H), 2.80-2.70 (m, 1H), 2.61 (br d, J=13.8 Hz, 1H), 2.26-2.19 (m, 1H), 1.96 (br d, J=12.8 Hz, 1H), 1.86-1.74 (m, 2H), 1.68-1.58 (m, 1H), 1.45 (br d, J=5.9 Hz, 3H), 1.42-1.34 (m, 2H), 1.33-1.30 (m, 1H), 1.16 (br dd, J=5.6, 12.0 Hz, 7H), 1.00 (s, 3H), 0.58-0.49 (m, 6H).

Example 107

(1r,2R,3S)-N-[(7S,13S,23S)-23-hydroxy-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2,3-dimethyl-cyclopropanecarboxamide

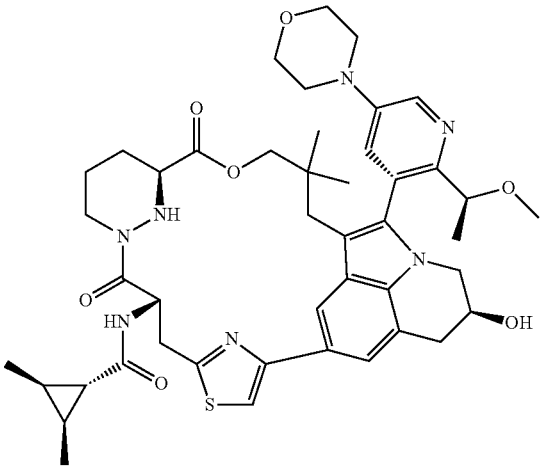

The compound was prepared according to the following scheme:

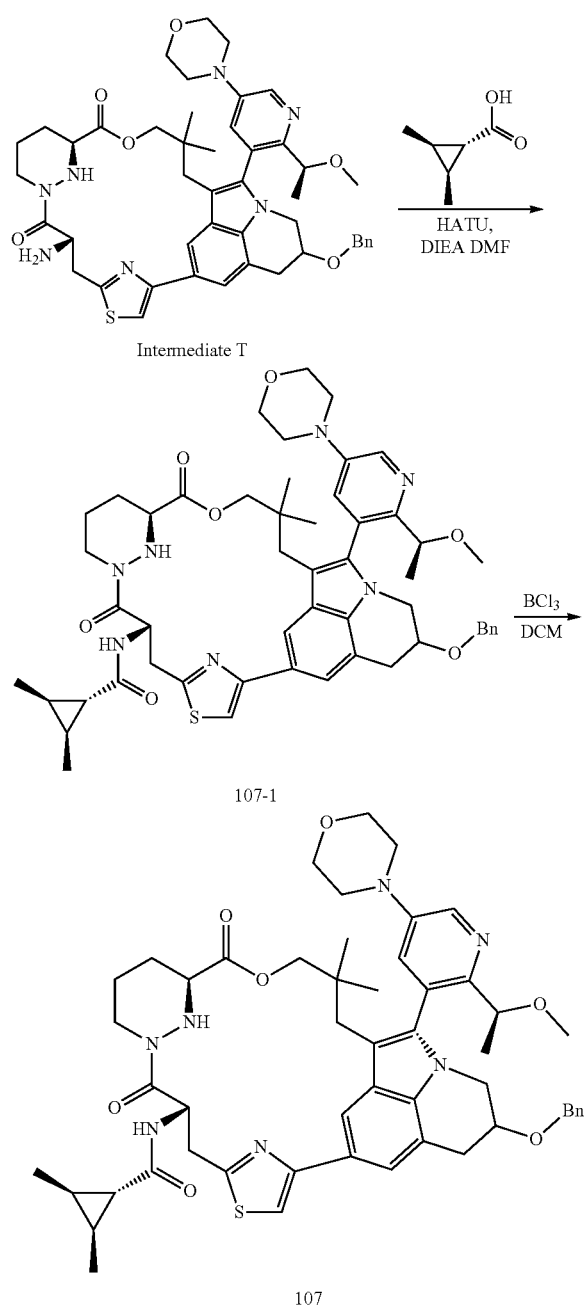

Step 1: Preparation of (1r,2R,3S)-N-[(7S,13S)-23-benzyloxy-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2,3-dimethyl-cyclopropanecarboxamide (compound 107-1)

To a solution of (1r,2S,3R)-2,3-dimethylcyclopropanecarboxylic acid (43 mg, 379.72 umol) in DMF (1 mL) was added HATU (156 mg, 411.37 μmol) and DIEA (332 μL, 1.9 mmol) at rt. After being stirred at rt for 1 h, the reaction mixture was added with (7S,13S)-7-amino-23-benzyloxy-20-[2-[(1S)-1-methoxyethyl]-5-morpholino-3-pyridyl]-17, 17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (Intermediate T, 300 mg, 0.316 mmol). After being stirred for another 2 hrs, the reaction mixture was concentrated under vacuum and then purified by reversed-phase chromatography to afford (1r,2R,3S)-N-[(7S,13S)-23-benzyloxy-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaen-7-yl]-2,3-dimethyl-cyclopropanecarboxamide (compound 107-1, 142 mg) as a light yellow powder. MS calc'd 930.5 (MH$^+$), measured 930.5 (MH$^+$).

Step 2: Preparation of (1r,2R,3S)-N-[(7S,13S,23S)-23-hydroxy-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31),19,25 (29),26-hexaen-7-yl]-2,3-dimethyl-cyclopropanecarboxamide (Example 107)

To a solution of (1r,2R,3S)-N-[(7S,13S)-23-benzyloxy-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaen-7-yl]-2,3-dimethyl-cyclopropanecarboxamide (compound 107-1, 120 mg, 129 μmol) in DCM (extra dry, 3 mL) at −78° C. was added dropwise 1 M boron trichloride (645 μL) under nitrogen atmosphere. The mixture was stirred for 1 hour at −78° C. and then was quenched by the addition of MeOH (8 mL) and then allowed to warm to room temperature. The solvent was removed under vacuum to get a residue. The resulting residue was purified by prep-HPLC to afford (1r,2R,3S)-N-[(7S,13S,23S)-23-hydroxy-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaen-7-yl]-2,3-dimethyl-cyclopropanecarboxamide (Example 107, 8.6 mg, slower eluted) as white powder. MS calc'd 840.4 (MH$^+$), measured 840.4 (MH$^+$). $^1$H NMR (400 MHZ, METHANOL-d$_4$) δ=8.45-8.42 (m, 1H), 8.42 (s, 1H), 7.53-7.48 (m, 2H), 7.47-7.45 (m, 1H), 7.31-7.26 (m, 1H), 5.86-5.79 (m, 1H), 5.73-5.66 (m, 1H), 4.58-4.49 (m, 1H), 4.49-4.37 (m, 2H), 4.34-4.19 (m, 1H), 3.90-3.86 (m, 6H), 3.82-3.78 (m, 1H), 3.78-3.75 (m, 2H), 3.51-3.39 (m, 2H), 3.16-3.06 (m, 2H), 2.91-2.87 (m, 1H), 2.83-2.74 (m, 1H), 2.32-2.25 (m, 1H), 2.20-2.12 (m, 1H), 1.98-1.90 (m, 1H), 1.63-1.57 (m, 1H), 1.52-1.48 (m, 2H), 1.47-1.43 (m, 2H), 1.39 (td, J=4.9, 9.4 Hz, 3H), 1.20-1.17 (m, 4H), 1.15 (dd, J=4.0, 6.1 Hz, 5H), 1.04-1.01 (m, 2H), 0.97-0.94 (m, 2H), 0.60-0.57 (m, 3H).

Example 108

(1r,2R,3S)-N-[(7S,13S)-(20M)-20-[2-[(1S)-1-methoxyethyl]-5-piperazin-1-yl-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2,3-dimethyl-cyclopropanecarboxamide

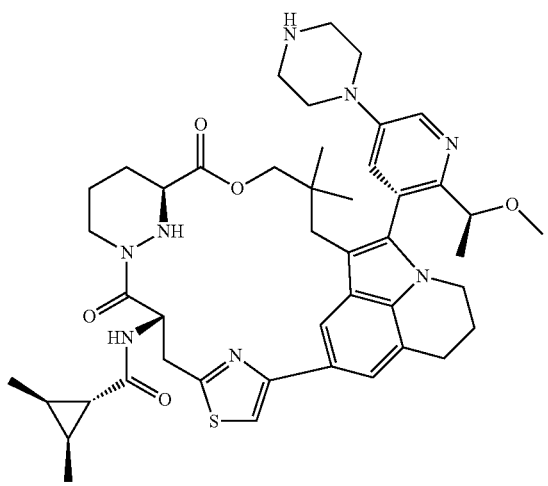

The title compound was prepared in analogy to the preparation of compound 106-4 by using benzyl 4-[(5M)-5-[(7S,13S)-7-(tert-butoxycarbonylamino)-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-20-yl]-6-[(1S)-1-methoxyethyl]-3-pyridyl]piperazine-1-carboxylate (compound E10) instead of benzyl 4-[(5M)-5-[(7S,13S)-7-(tert-butoxycarbonylamino)-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaen-20-yl]-6-[(1S)-1-methoxyethyl]-3-pyridyl]piperazine-1-carboxylate (Intermediate V). Example 108 (637 mg) was obtained as a light yellow solid. MS calc'd 823.4 (MH$^+$), measured 823.4 (MH$^+$). $^1$H NMR (400 MHZ, METHANOL-d$_4$) δ=8.49 (br d, J=1.4 Hz, 1H), 8.40 (s, 1H), 7.58 (br s, 1H), 7.52 (s, 1H), 7.44 (s, 1H), 5.80 (br d, J=8.4 Hz, 1H), 4.53-4.41 (m, 2H), 4.27-4.17 (m, 2H), 3.77 (br s, 2H), 3.69-3.59 (m, 5H), 3.44 (br s, 5H), 3.40 (s, 3H), 3.31-3.25 (m, 1H), 3.10 (br d, J=14.3 Hz, 2H), 3.05-2.96 (m, 1H), 2.79 (br t, J=12.3 Hz, 1H), 2.63 (br d, J=14.3 Hz, 1H), 2.39-2.28 (m, 1H), 2.18 (br d, J=11.5 Hz, 2H), 1.95 (br d, J=13.0 Hz, 1H), 1.83-1.71 (m, 1H), 1.68-1.58 (m, 1H), 1.48 (br d, J=6.1 Hz, 3H), 1.44-1.32 (m, 2H), 1.19-1.12 (m, 7H), 0.98 (s, 3H), 0.58 (s, 3H).

Example 109

(1r,2R,3S)-N-[(7S,13S)-20-[5-[4-(2,2-difluoroethyl)piperazin-1-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2,3-dimethyl-cyclopropanecarboxamide

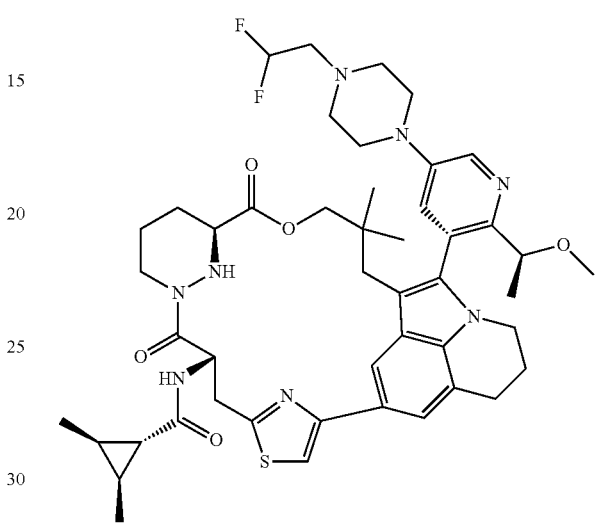

The compound was prepared according to the following scheme:

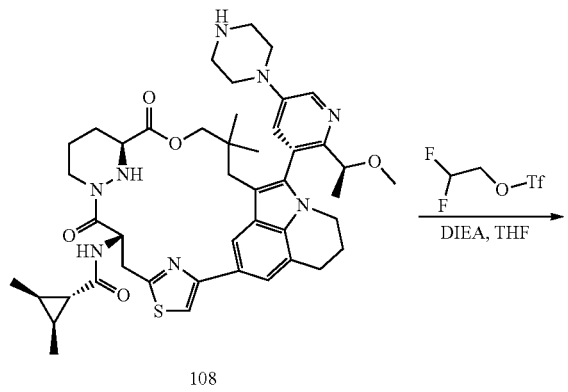

108

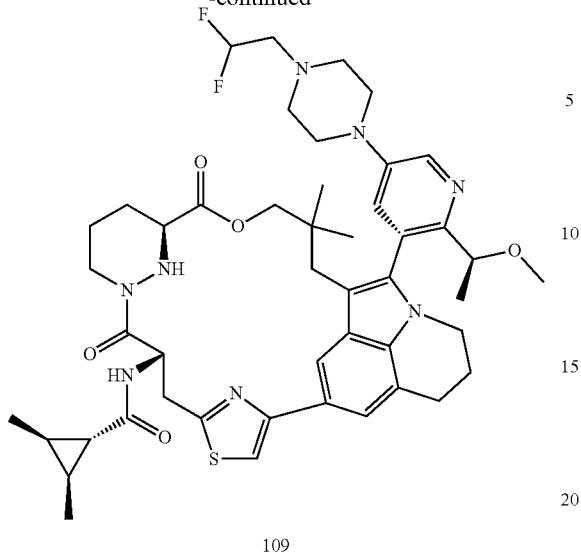

109

A suspension of (1r,2R,3S)-N-[(7S,13S)-(20M)-20-[5-(4-cyclopropylpiperazin-1-yl)-2-[(1S)-1-methoxyethyl]-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaen-7-yl]-2,3-dimethyl-cyclopropanecarboxamide (example 108, 30 mg, 32.01 umol), trifluoromethanesulfonic acid 2,2-difluoroethyl ester (10 mg, 7 μL, 48.02 μmol) and DIEA (13 mg, 17 μL, 96.04 μmol) in tetrahydrofuran (extra dry, 300 μL) was stirred at rt for 12 hrs. The solvent was concentrated and then purified by Prep-HPLC to afford (1r,2R,3S)-N-[(7S,13S)-20-[5-[4-(2,2-difluoroethyl) piperazin-1-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2,3-dimethyl-cyclopropanecarboxamide (example 109, 10 mg) as a white powder. MS calc'd 887.4 (MH$^+$), measured 887.4 (MH$^+$). $^1$H NMR (400 MHZ, METHANOL-d$_4$) δ=8.30-8.25 (m, 2H), 7.36 (s, 1H), 7.28 (s, 1H), 7.13 (d, J=2.9 Hz, 1H), 6.07-5.88 (m, 1H), 5.79-5.74 (m, 1H), 5.71-5.65 (m, 1H), 4.70 (br d, J=12.4 Hz, 2H), 4.54-4.41 (m, 2H), 4.35-4.23 (m, 2H), 4.17-4.08 (m, 2H), 3.64 (s, 2H), 3.47 (ddd, J=3.4, 8.6, 12.2 Hz, 1H), 3.33-3.28 (m, 1H), 3.19-3.12 (m, 2H), 3.02-2.85 (m, 3H), 2.77-2.64 (m, 7H), 2.50 (br d, J=14.3 Hz, 1H), 2.19 (tdd, J=4.2, 8.7, 13.1 Hz, 1H), 2.12-2.02 (m, 2H), 1.87-1.77 (m, 1H), 1.71-1.57 (m, 1H), 1.55-1.43 (m, 1H), 1.35-1.30 (m, 3H), 1.30-1.15 (m, 3H), 1.08-1.00 (m, 7H), 0.84 (s, 3H), 0.48-0.40 (m, 3H).

Example 110

(1r,2R,3S)-N-[(7S,13S)-(20M)-20-[5-[4-(2-fluoroethyl) piperazin-1-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2,3-dimethyl-cyclopropanecarboxamide

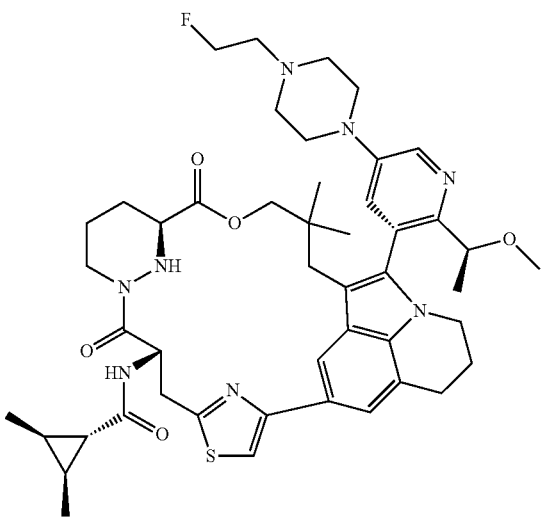

The title compound was prepared in analogy to the preparation of Example 109 by using 1-fluoro-2-iodo-ethane instead of trifluoromethanesulfonic acid 2,2-difluoroethyl ester. Example 110 (17 mg) was obtained as a white solid. MS calc'd 869.4 (MH$^+$), measured 869.4 (MH$^+$). 1H NMR (400 MHZ, METHANOL-d$_4$) δ=8.31-8.26 (m, 2H), 7.37 (s, 1H), 7.29 (s, 1H), 7.14 (d, J=2.9 Hz, 1H), 5.68 (dd, J=1.6, 8.5 Hz, 1H), 4.61-4.55 (m, 2H), 4.49-4.42 (m, 2H), 4.37-4.24 (m, 2H), 4.16-4.08 (m, 2H), 3.65 (s, 2H), 3.49 (ddd, J=3.5, 8.6, 12.2 Hz, 1H), 3.33-3.27 (m, 2H), 3.18-3.13 (m, 1H), 3.02-2.83 (m, 4H), 2.73-2.60 (m, 8H), 2.51 (br d, J=14.4 Hz, 1H), 2.26-2.15 (m, 1H), 2.13-2.02 (m, 2H), 1.82 (br d, J=12.6 Hz, 1H), 1.70-1.58 (m, 1H), 1.48 (dq, J=3.7, 12.5 Hz, 1H), 1.36-1.31 (m, 3H), 1.30-1.21 (m, 2H), 1.14-1.09 (m, 2H), 1.07-1.01 (m, 7H), 0.85 (s, 3H), 0.44 (s, 3H).

Example 111

(1r,2R,3S)-N-[(7S,13S)-(20M)-20-[5-[4-(3-hydroxy-propyl) piperazin-1-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2,3-dimethyl-cyclopropanecarboxamide

Example 112

(1R,2R)-N-[(7S,13S)-(20M)-20-[2-[(1S)-1-methoxy-ethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-(4-methylpyrimidin-5-yl)cyclopropanecarboxamide

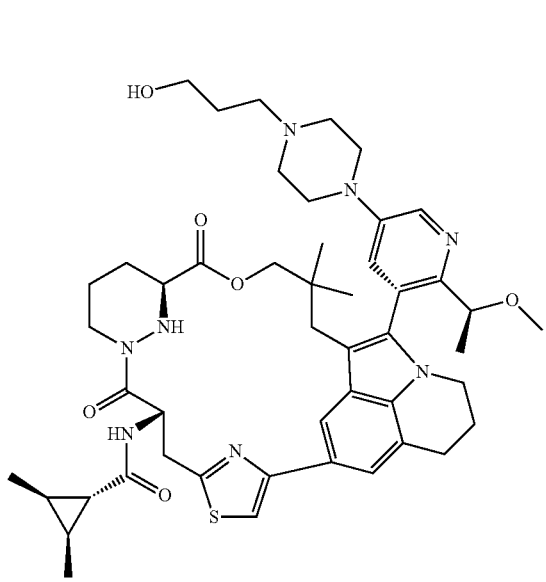

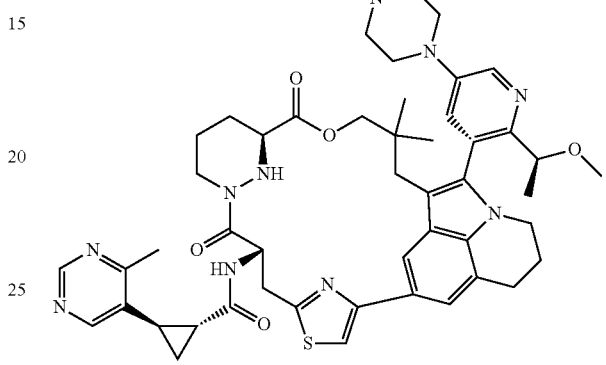

The title compound was prepared in analogy to the preparation of Example 109 by using 3-bromo-1-propanol and sodium iodide instead of trifluoromethanesulfonic acid 2,2-difluoroethyl ester. Example 111 (15 mg) was obtained as a white solid. MS calc'd 881.5 (MH$^+$), measured 881.5 (MH$^+$). $^1$H NMR (400 MHZ, METHANOL-d$_4$) δ=8.32-8.25 (m, 2H), 7.37 (s, 1H), 7.29 (d, J=0.9 Hz, 1H), 7.14 (d, J=2.9 Hz, 1H), 5.68 (dd, J=1.6, 8.5 Hz, 1H), 4.72-4.68 (m, 4H), 4.57-4.40 (m, 2H), 4.36-4.24 (m, 2H), 4.17-4.09 (m, 2H), 3.65 (s, 2H), 3.58-3.52 (m, 2H), 3.51-3.45 (m, 1H), 3.34-3.27 (m, 1H), 3.18-3.13 (m, 1H), 3.04-2.83 (m, 3H), 2.71-2.62 (m, 1H), 2.58 (br t, J=4.9 Hz, 4H), 2.51 (d, J=14.4 Hz, 1H), 2.47-2.42 (m, 2H), 2.25-2.14 (m, 1H), 2.13-2.03 (m, 2H), 1.86-1.78 (m, 1H), 1.72-1.65 (m, 2H), 1.64-1.58 (m, 1H), 1.55-1.43 (m, 1H), 1.33 (d, J=6.1 Hz, 3H), 1.30-1.20 (m, 2H), 1.19-1.10 (m, 1H), 1.07-1.00 (m, 7H), 0.84 (s, 3H), 0.44 (s, 3H).

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (intermediate E) and trans-(1S,2S)-2-(4-methylpyrimidin-5-yl)cyclopropanecarboxylic acid (intermediate R7) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate F) and (1S,2S)-2-methylcyclopropanecarboxylic acid and then purified by Prep-HPLC. Example 112 (4.5 mg, slower eluted) was obtained as a white solid. MS calc'd 901.5 (MH$^+$), measured 901.5 (MH$^+$). $^1$H NMR (400 MHZ, METHANOL-d$_4$) δ=8.90 (s, 1H), 8.49 (s, 1H), 8.45-8.38 (m, 2H), 7.51 (s, 1H), 7.42 (s, 1H), 7.29 (d, J=2.6 Hz, 1H), 5.85 (br d, J=8.3 Hz, 1H), 4.59 (s, 9H), 4.50-4.42 (m, 1H), 4.42-4.38 (m, 1H), 4.30-4.24 (m, 1H), 3.78 (s, 2H), 3.67-3.57 (m, 1H), 3.48 (br d, J=14.6 Hz, 1H), 3.40 (br d, J=4.0 Hz, 3H), 3.16-3.00 (m, 3H), 2.79 (br s, 4H), 2.66 (s, 3H), 2.48 (s, 3H), 2.43-2.38 (m, 1H), 2.35-2.28 (m, 1H), 2.22 (br d, J=12.3 Hz, 2H), 2.10-2.04 (m, 1H), 2.01-1.93 (m, 1H), 1.84-1.76 (m, 1H), 1.70-1.57 (m, 2H), 1.45 (d, J=6.1 Hz, 3H), 0.98 (s, 3H), 0.56 (s, 3H).

Example 113

(1r,2R,3S)-N-[(7S,13S)-(20M)-20-[5-(4-ethylpiperazin-1-yl)-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2,3-dimethyl-cyclopropanecarboxamide

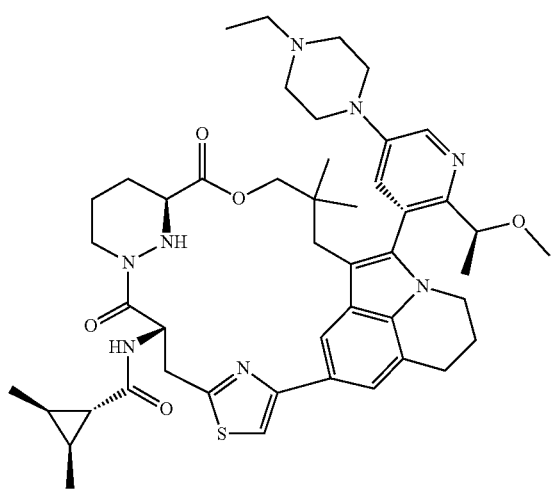

A solution of (1r,2R,3S)-N-[(7S,13S)-(20M)-20-[5-(4-cyclopropylpiperazin-1-yl)-2-[(1S)-1-methoxyethyl]-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaen-7-yl]-2,3-dimethyl-cyclopropanecarboxamide (example 108, 30 mg, 32.01 μmol), 5 M acetaldehyde (13 μL, 64.03 μmol) and acetic acid (18 μL, 320.14 μmol) in methanol (extra dry, 0.3 mL) was stirred at rt for 1 hour. The reaction mixture was added with NaBH$_3$CN (6.04 mg, 96.04 μmol) and then stirred at rt for 2 hrs. The solvent was removed under vacuum and then purified by prep-HPLC to afford (1r,2R,3S)-N-[(7S,13S)-(20M)-20-[5-(4-ethylpiperazin-1-yl)-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaen-7-yl]-2,3-dimethyl-cyclopropanecarboxamide (Example 113, 10.1 mg) as white powder. MS calc'd 851.5 (MH$^+$), measured 851.5 (MH$^+$). $^1$H NMR (400 MHZ, METHANOL-d$_4$) δ=8.44 (d, J=2.9 Hz, 1H), 8.39 (s, 1H), 7.50 (s, 1H), 7.41 (s, 1H), 7.32 (d, J=2.9 Hz, 1H), 5.80 (br d, J=7.1 Hz, 1H), 4.64-4.56 (m, 1H), 4.48-4.38 (m, 2H), 4.30-4.20 (m, 2H), 3.77 (s, 2H), 3.67-3.56 (m, 2H), 3.50-3.43 (m, 4H), 3.35 (s, 3H), 3.17-2.95 (m, 7H), 2.91-2.73 (m, 3H), 2.66-2.58 (m, 1H), 2.36-2.27 (m, 1H), 2.26-2.15 (m, 2H), 1.98-1.91 (m, 1H), 1.83-1.71 (m, 1H), 1.67-1.56 (m, 1H), 1.45 (d, J=6.1 Hz, 3H), 1.42-1.34 (m, 2H), 1.28 (t, J=7.3 Hz, 3H), 1.20-1.11 (m, 7H), 0.96 (s, 3H), 0.55 (s, 3H).

Example 114

(1R,2R)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-thiazol-4-yl-cyclopropanecarboxamide

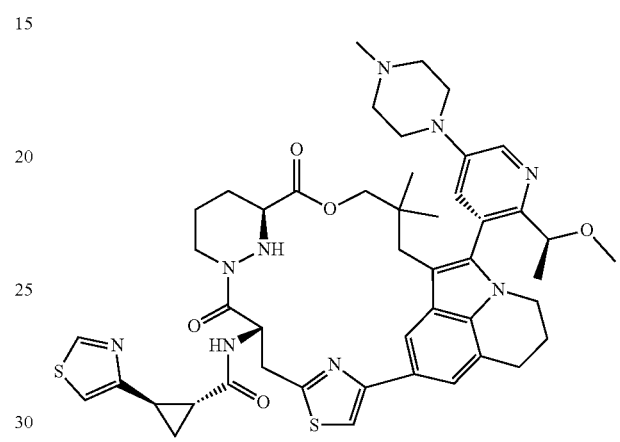

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaene-8,14-dione (intermediate E) and trans-(1S,2S)-2-thiazol-4-ylcyclopropanecarboxylic acid (intermediate R8) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaene-8,14-dione (Intermediate F) and (1S,2S)-2-methylcyclopropanecarboxylic acid and then purified by Prep-HPLC. Example 114 (1.5 mg, slower eluted) was obtained as a white solid. MS calc'd 892.4 (MH$^+$), measured 892.4 (MH$^+$). $^1$H NMR (400 MHZ, METHANOL-d$_4$) δ=8.79 (d, J=1.8 Hz, 1H), 8.38-8.35 (m, 1H), 8.30 (s, 1H), 7.41 (s, 1H), 7.33 (s, 1H), 7.21 (d, J=2.0 Hz, 1H), 5.76-5.71 (m, 1H), 4.16-3.94 (m, 1H), 3.68-3.65 (m, 1H), 3.57-3.47 (m, 3H), 3.39-3.32 (m, 1H), 3.31-3.27 (m, 4H), 3.15-3.10 (m, 1H), 3.05-2.95 (m, 2H), 2.93-2.87 (m, 4H), 2.73-2.53 (m, 1H), 2.53-2.42 (m, 1H), 2.29-2.16 (m, 2H), 2.12-2.02 (m, 2H), 1.95-1.92 (m, 2H), 1.88-1.79 (m, 1H), 1.69-1.59 (m, 1H), 1.57-1.43 (m, 2H), 1.39-1.34 (m, 4H), 1.30-1.25 (m, 1H), 1.23-1.16 (m, 5H), 1.11-1.00 (m, 2H), 0.89-0.85 (m, 3H), 0.81-0.76 (m, 1H), 0.50-0.44 (m, 3H).

Example 115

(1r,2S,3R)-N-[(7S,13S)-(20M)-20-[2-[(1S)-1-methoxyethyl]-5-[4-(2-methoxyethyl) piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2,3-dimethyl-cyclopropanecarboxamide

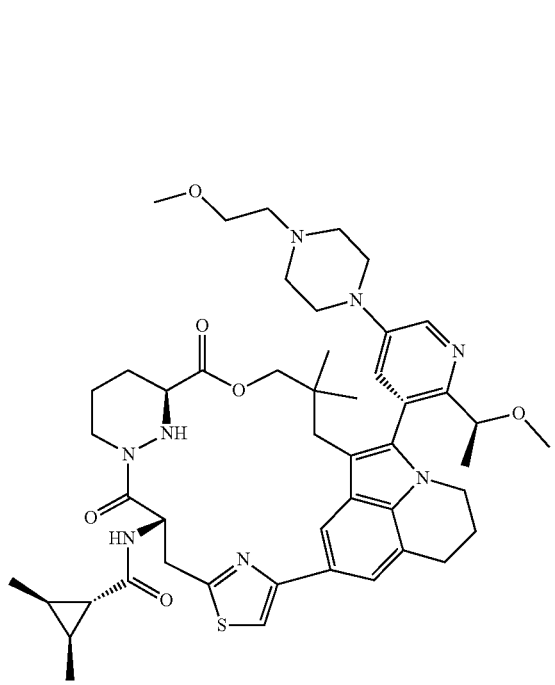

The title compound was prepared in analogy to the preparation of Example 109 by using 2-bromoethyl methyl ether and sodium iodide instead of trifluoromethanesulfonic acid 2,2-difluoroethyl ester. Example 115 (18 mg) was obtained as a white solid. MS calc'd 881.5 (MH$^+$), measured 881.5 (MH$^+$). $^1$H NMR (500 MHZ, METHANOL-d$_4$) δ=8.41-8.34 (m, 2H), 7.47 (s, 1H), 7.41-7.35 (m, 1H), 7.27-7.19 (m, 1H), 5.83-5.73 (m, 1H), 4.65-4.54 (m, 1H), 4.46-4.34 (m, 2H), 4.26-4.19 (m, 2H), 3.74 (s, 2H), 3.57 (s, 3H), 3.42-3.37 (m, 1H), 3.35 (s, 3H), 3.34-3.32 (m, 6H), 3.28-3.22 (m, 1H), 3.14-2.93 (m, 3H), 2.80-2.73 (m, 1H), 2.73-2.67 (m, 4H), 2.66-2.57 (m, 3H), 2.37-2.25 (m, 1H), 2.21-2.10 (m, 2H), 1.96-1.87 (m, 1H), 1.79-1.67 (m, 1H), 1.65-1.53 (m, 1H), 1.46-1.41 (m, 3H), 1.40-1.31 (m, 2H), 1.18-1.11 (m, 7H), 0.94 (s, 3H), 0.53 (s, 3H).

Example 116

(1R,2R)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2-(2-methyl-3-pyridyl) cyclopropanecarboxamide

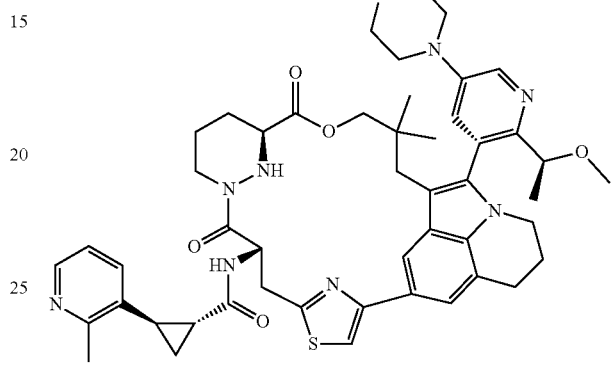

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (intermediate E) and trans-(1S,2S)-2-(2-methyl-3-pyridyl)cyclopropanecarboxylic acid (intermediate R9) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29),26-hexaene-8,14-dione (Intermediate F) and (1S,2S)-2-methyl-cyclopropanecarboxylic acid and then purified by Prep-HPLC. Example 116 (5 mg, slower eluted) was obtained as a white solid. MS calc'd 900.5 (MH$^+$), measured 900.5 (MH$^+$). $^1$H NMR (500 MHZ, METHANOL-d$_4$) δ=8.48-8.41 (m, 1H), 8.39 (s, 1H), 8.28-8.24 (m, 1H), 7.57-7.53 (m, 1H), 7.49 (s, 1H), 7.41 (s, 1H), 7.32 (d, J=2.9 Hz, 1H), 7.23 (dd, J=5.0, 7.7 Hz, 1H), 5.95-5.68 (m, 1H), 4.67-4.52 (m, 2H), 4.40 (br d, J=6.3 Hz, 2H), 4.30-4.20 (m, 2H), 3.76 (s, 2H), 3.62-3.53 (m, 1H), 3.49 (br s, 5H), 3.35 (s, 3H), 3.12 (br s, 6H), 3.02-2.92 (m, 1H), 2.84-2.74 (m, 1H), 2.72 (s, 3H), 2.62 (s, 3H), 2.45-2.38 (m, 1H), 2.35-2.25 (m, 1H), 2.23-2.14 (m, 2H), 1.99-1.89 (m, 2H), 1.84-1.70 (m, 1H), 1.67-1.58 (m, 1H), 1.58-1.51 (m, 1H), 1.44 (d, J=6.3 Hz, 3H), 1.39-1.33 (m, 1H), 0.96 (s, 3H), 0.54 (s, 3H).

Example 117

(1r,2R,3S)-N-[(7S,13S)-(20M)-20-[2-[(1S)-1-methoxyethyl]-5-(4-tetrahydropyran-4-ylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide

Example 118

(1r,2R,3S)-N-[(7S,13S)-(20M)-20-[2-[(1S)-1-methoxyethyl]-5-[4-(oxetan-3-yl)piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide

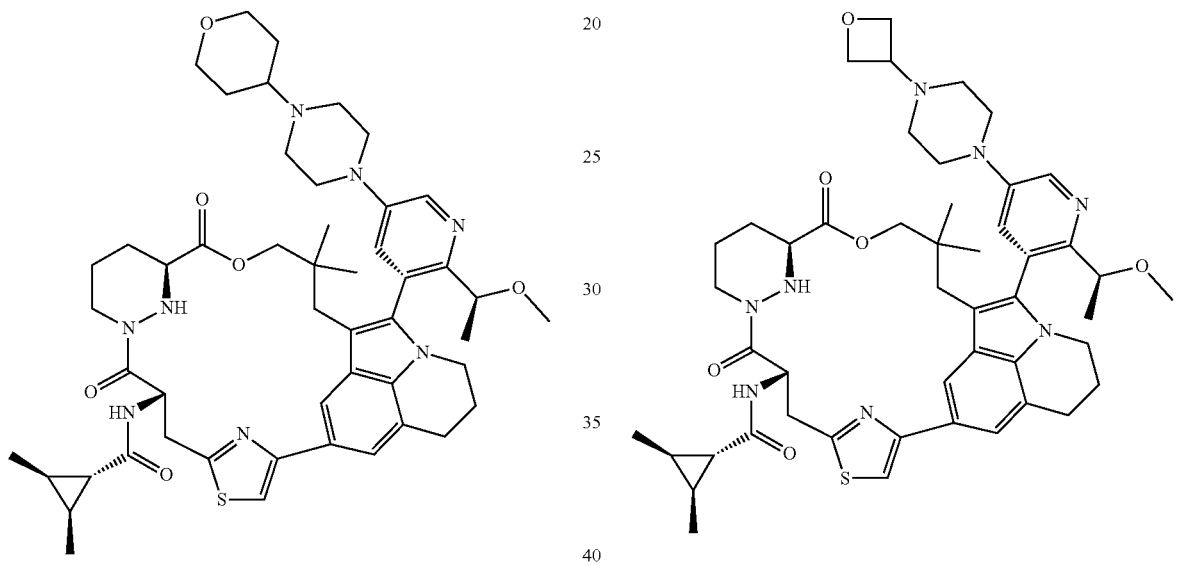

The title compound was prepared in analogy to the preparation of Example 113 by using tetrahydro-4h-pyran-4-one instead of acetaldehyde. Example 117 (16 mg) was obtained as a white solid. MS calc'd 907.5 (MH$^+$), measured 907.9 (MH$^+$). $^1$H NMR (500 MHZ, METHANOL-d$_4$) δ=8.52-8.46 (m, 1H), 8.42-8.39 (m, 1H), 8.38-8.35 (m, 1H), 7.48 (s, 1H), 7.42-7.36 (m, 1H), 7.30-7.24 (m, 1H), 5.86-5.71 (m, 1H), 5.49 (s, 1H), 4.47-4.35 (m, 2H), 4.28-4.17 (m, 2H), 4.08-3.99 (m, 2H), 3.75 (s, 2H), 3.63-3.54 (m, 1H), 3.47-3.37 (m, 6H), 3.33 (s, 3H), 3.27-3.22 (m, 1H), 3.13-3.03 (m, 2H), 3.01-2.90 (m, 4H), 2.70 (br s, 2H), 2.64-2.56 (m, 1H), 2.35-2.25 (m, 1H), 2.24-2.12 (m, 2H), 1.98-1.87 (m, 3H), 1.80-1.67 (m, 1H), 1.66-1.54 (m, 3H), 1.43 (d, J=6.3 Hz, 3H), 1.39-1.30 (m, 2H), 1.18-1.09 (m, 7H), 0.95 (s, 3H), 0.53 (s, 3H).

The title compound was prepared in analogy to the preparation of Example 113 by using 3-oxetanone instead of acetaldehyde. Example 118 (13 mg) was obtained as a white solid. MS calc'd 879.5 (MH$^+$), measured 879.5 (MH$^+$). $^1$H NMR (500 MHZ, METHANOL-d$_4$) δ=8.43-8.36 (m, 2H), 7.48 (s, 1H), 7.39 (d, J=0.8 Hz, 1H), 7.29 (d, J=2.7 Hz, 1H), 5.85-5.70 (m, 1H), 4.76 (s, 2H), 4.69-4.64 (m, 2H), 4.45-4.34 (m, 2H), 4.26-4.19 (m, 2H), 3.75 (s, 3H), 3.63-3.55 (m, 1H), 3.47-3.36 (m, 5H), 3.33 (s, 3H), 3.30-3.22 (m, 1H), 3.13-2.93 (m, 3H), 2.83-2.56 (m, 6H), 2.35-2.23 (m, 1H), 2.22-2.12 (m, 2H), 1.95-1.88 (m, 1H), 1.80-1.69 (m, 1H), 1.64-1.53 (m, 1H), 1.43 (d, J=6.3 Hz, 3H), 1.41-1.26 (m, 2H), 1.15 (d, J=6.1 Hz, 4H), 1.12 (d, J=6.1 Hz, 3H), 0.95 (s, 3H), 0.54 (s, 3H).

Example 119
(1r,2S,3R)-N-[(7S,13S)-(20M)-20-[2-[(1S)-1-methoxyethyl]-5-[4-[[(2S)-morpholin-2-yl]methyl]piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2,3-dimethyl-cyclopropanecarboxamide
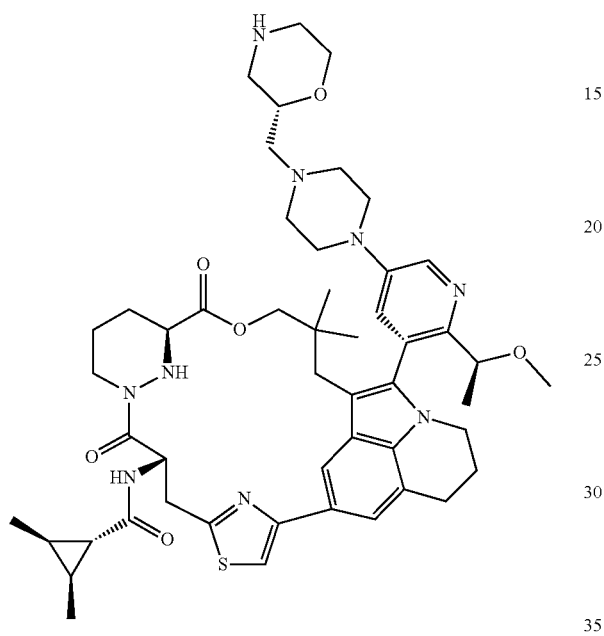
The compound was prepared according to the following scheme:
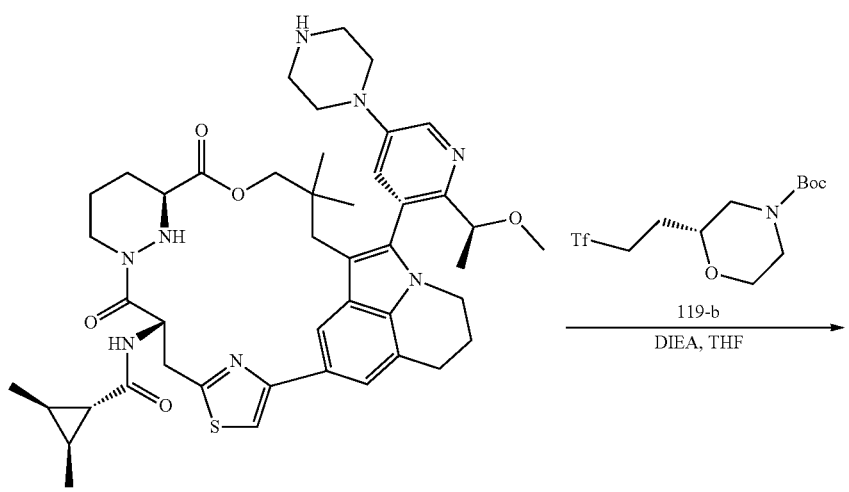

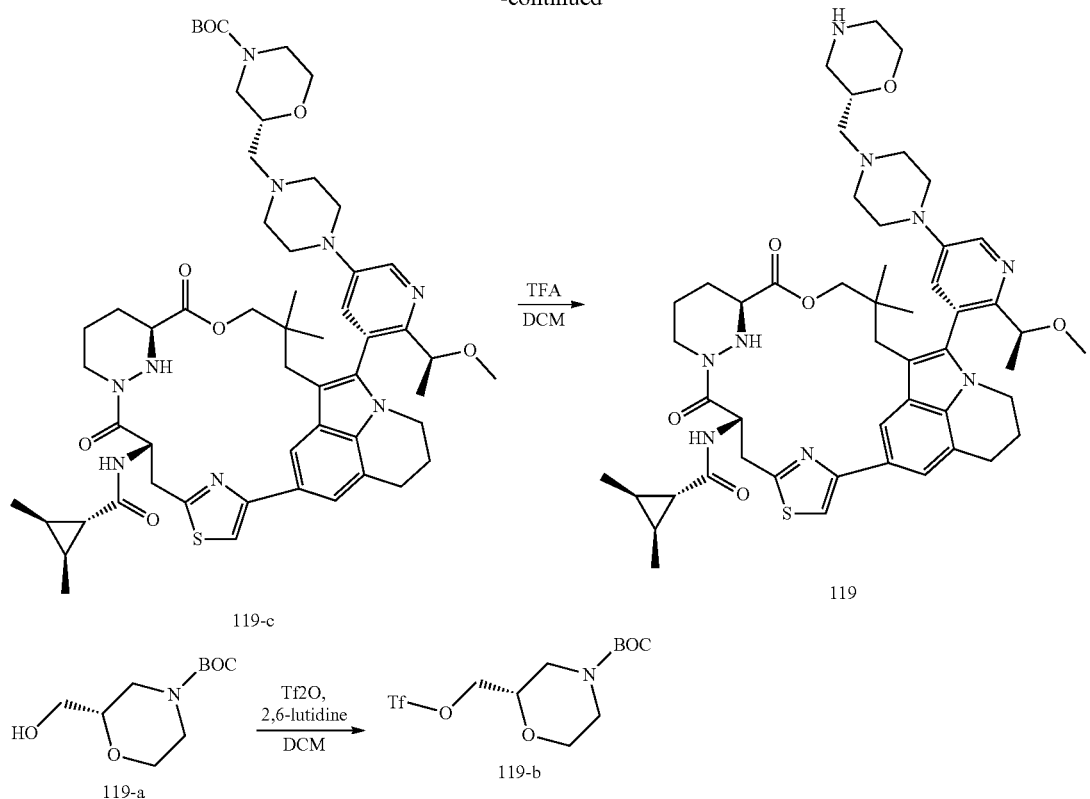

199-c

119

119-a → 119-b

Tf2O, 2,6-lutidine, DCM

Step 1: Preparation of tert-butyl (2S)-2-(trifluoromethylsulfonyloxymethyl) morpholine-4-carboxylate (compound 119-b)

To a solution of tert-butyl (2S)-2-(hydroxymethyl) morpholine-4-carboxylate (100 mg, 460.28 μmol) and 2,6-lutidine (107 μL, 920.56 μmol) in dichloromethane (2 mL) was added Tf$_2$O (93 μL, 552.33 μmol) at 0° C. The reaction mixture was stirred at 0° C. for 1 h. The reaction mixture was diluted with DCM (10 mL) and then washed with sat. NaHCO$_3$ aq. (10 mL), brine (5 mL). The organic layer was dried and then purified by silica gel chromatography to afford crude product tert-butyl (2S)-2-(trifluoromethylsulfonyloxymethyl) morpholine-4-carboxylate (compound 119-b, 100 mg) as light brown oil, which was used in the next step. MS calc'd 350.1 (MH$^+$), measured 293.9 (M-C$_4$H9+ H).

Step 2: Preparation of tert-butyl (2R)-2-[[4-[(5M)-5-[(7S,13S)-7-[[(1r,2S,3R)-2,3-dimethylcyclopropanecarbonyl] amino]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$] hentriaconta-1 (28),2,5 (31), 19,25 (29),26-hexaen-20-yl]-6-[(1S)-1-methoxyethyl]-3-pyridyl]piperazin-1-yl]methyl]morpholine-4-carboxylate (compound 119-c)

A suspension of (1r,2R,3S)-N-[(7S,13S)-(20M)-20-[5-(4-cyclopropylpiperazin-1-yl)-2-[(1S)-1-methoxyethyl]-3-pyridyl]-17,17-dimethyl-8,14-dioxo-15,24-dioxa-4-thia-9,21,30,31-tetrazahexacyclo[23.3.1.1$^{2,5}$.1$^{9,13}$.0$^{19,27}$.0$^{21,26}$] hentriaconta-1 (28), 2,5 (31), 19,25 (29),26-hexaen-7-yl]-2,3-dimethyl-cyclopropanecarboxamide (example 108, 30 mg, 32.01 μmol), tert-butyl (2S)-2-(trifluoromethylsulfonyloxymethyl) morpholine-4-carboxylate (compound 119-b, 100 mg) and DIEA (17 μL, 96.04 μmol) in tetrahydrofuran (extra dry, 300 μL) was stirred at rt for 2 hrs. The solvent was removed under vacuum to get a residue. The residue was purified by silica gel chromatography to afford tert-butyl (2R)-2-[[4-[(5M)-5-[(7S,13S)-7-[[(1r,2S,3R)-2,3-dimethylcyclopropanecarbonyl]amino]-17,17-dimethyl-8,14-dioxo-15-oxa-4-thia-9,21,30,31-tetrazahexacyclo[23.3.1.1$^{2,5}$.1$^{9,13}$. 0$^{19,27}$.0$^{21,26}$]hentriaconta-1 (28), 2,5 (31), 19,25 (29),26-hexaen-20-yl]-6-[(1S)-1-methoxyethyl]-3-pyridyl]piperazin-1-yl]methyl]morpholine-4-carboxylate (compound 119-c, 68 mg) as light brown oil. MS calc'd 1022.5 (MH$^+$), measured 1022.5 (MH$^+$).

Step 3: Preparation of (1r,2S,3R)-N-[(7S,13S)-(20M)-20-[2-[(1S)-1-methoxyethyl]-5-[4-[[(2S)-morpholin-2-yl]methyl] piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$. 0$^{19,27}$.0$^{21,26}$]hentriaconta-1 (28),2,5 (31), 19,25 (29),26-hexaen-7-yl]-2,3-dimethyl-cyclopropanecarboxamide (Example 119)

A solution of tert-butyl (2R)-2-[[4-[(5M)-5-[(7S,13S)-7-[[(1r,2S,3R)-2,3-dimethylcyclopropanecarbonyl]amino]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28), 2,5 (31), 19,25 (29), 26-hexaen-20-yl]-6-[(1S)-1-methoxyethyl]-3-pyridyl]piperazin-1-yl]methyl]morpholine-4-carboxylate (compound 119-c, 68 mg, 66.52 μmol) and TFA (1 mL) in dichloromethane (2 mL) was stirred at rt for 2 hrs. The solvent was removed under vacuum and then purified by prep-HPLC to afford (1r,2S,3R)-N-[(7S,13S)-(20M)-20-[2-[(1S)-1-methoxyethyl]-5-[4-[[(2S)-morpholin-2-yl] methyl]piperazin-1-yl]-3-pyridyl]-17,17-dimethyl-8,14-dioxo-15-oxa-4-thia-9,21,30,31-tetrazahexacyclo[23.3.1.1$^{2,5}$. 1$^{9,13}$.0$^{19,27}$.0$^{21,26}$]hentriaconta-1 (28), 2,5 (31), 19,25 (29), 26-hexaen-7-yl]-2,3-dimethyl-cyclopropanecarboxamide (Example 119, 18.4 mg) as light a yellow powder. MS calc'd 922.5 (MH⁺), measured 922.5 (MH⁺). ¹H NMR (400 MHZ, METHANOL-d₄) δ=8.48 (d, J=2.5 Hz, 1H), 8.40 (s, 1H), 7.53-7.49 (m, 2H), 7.43 (s, 1H), 5.79 (br d, J=8.6 Hz, 1H), 4.47 (br d, J=6.0 Hz, 1H), 4.44 (br s, 1H), 4.38-4.31 (m, 1H), 4.27-4.17 (m, 3H), 3.99-3.92 (m, 1H), 3.77 (br s, 2H), 3.71-3.61 (m, 5H), 3.54 (br s, 4H), 3.39 (s, 7H), 3.31-3.25 (m, 2H), 3.24-3.19 (m, 1H), 3.13-3.06 (m, 2H), 3.05-2.96 (m, 2H), 2.79 (br t, J=12.4 Hz, 1H), 2.62 (br d, J=14.3 Hz, 1H), 2.38-2.28 (m, 1H), 2.18 (br d, J=10.0 Hz, 2H), 1.96 (br d, J=13.5 Hz, 1H), 1.84-1.71 (m, 1H), 1.68-1.57 (m, 1H), 1.47 (br d, J=6.3 Hz, 3H), 1.43-1.34 (m, 2H), 1.19-1.13 (m, 7H), 0.98 (s, 3H), 0.57 (s, 3H).

Example 120

(1R,2R)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1²,⁵.1⁹,¹³.0¹⁹,²⁷.0²¹,²⁶]hentriaconta-1 (28),2,5 (31), 19,25 (29),26-hexaen-7-yl]-2-(5-methyl-3-pyridyl)cyclopropanecarboxamide

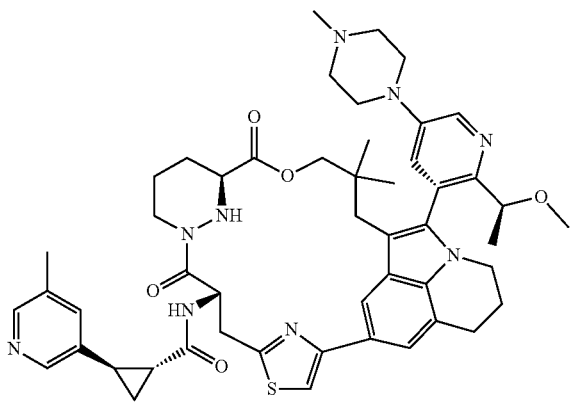

The title compound was prepared in analogy to the preparation of Example 1 by using (7S,13S)-7-amino-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1²,⁵.1⁹,¹³.0¹⁹,²⁷.0²¹,²⁶]hentriaconta-1 (28),2,5 (31), 19,25 (29),26-hexaene-8,14-dione (intermediate E) and trans-(1S,2S)-2-(5-methyl-3-pyridyl)cyclopropanecarboxylic acid (intermediate R10) instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1²,⁵.1⁹,¹³.0¹⁹,²⁷.0²¹,²⁶]hentriaconta-1 (28),2,5 (31), 19,25 (29),26-hexaene-8,14-dione (Intermediate F) and (1S,2S)-2-methylcyclopropanecarboxylic acid and then purified by Prep-HPLC. Example 120 (11.6 mg, slower eluted) was obtained as a yellow solid. MS calc'd 900.5 (MH⁺), measured 900.5 (MH⁺). ¹H NMR (500 MHZ, METHANOL-d₄) δ=8.61-8.57 (m, 1H), 8.55-8.51 (m, 1H), 8.48-8.46 (m, 1H), 8.39 (s, 1H), 8.18 (br d, J=7.0 Hz, 1H), 7.53-7.49 (m, 1H), 7.44 (br d, J=2.9 Hz, 1H), 7.41 (br s, 1H), 5.88-5.74 (m, 1H), 4.50-4.40 (m, 2H), 4.30-4.18 (m, 2H), 4.12-3.94 (m, 1H), 3.76 (s, 2H), 3.66-3.54 (m, 3H), 3.49-3.41 (m, 2H), 3.36 (s, 4H), 3.29-3.24 (m, 2H), 3.14-3.03 (m, 3H), 3.02-2.96 (m, 4H), 2.83-2.75 (m, 1H), 2.63-2.55 (m, 2H), 2.55-2.51 (m, 3H), 2.36-2.26 (m, 1H), 2.25-2.12 (m, 3H), 1.99-1.89 (m, 1H), 1.82-1.73 (m, 1H), 1.72-1.59 (m, 2H), 1.57-1.51 (m, 1H), 1.45 (d, J=6.3 Hz, 3H), 1.37-1.28 (m, 1H), 0.97 (s, 3H), 0.55 (s, 3H)

Example 121

(1r,2R,3S)-N-[(7S,13S)-(20M)-20-[2-[(1S)-1-methoxyethyl]-5-[4-[2-(2-oxopyrrolidin-1-yl)ethyl]piperazin-1-yl]-3-pyridyl]-17,17-dimethyl-8,14-dioxo-15-oxa-4-thia-9,21,30,31-tetrazahexacyclo[23.3.1.1²,⁵.1⁹,¹³.0¹⁹,²⁷.0²¹,²⁶]hentriaconta-1 (28),2,5 (31), 19,25 (29),26-hexaen-7-yl]-2,3-dimethyl-cyclopropanecarboxamide

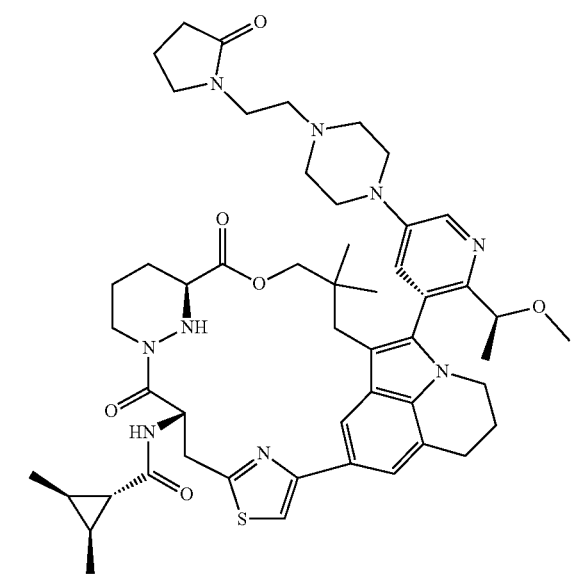

The title compound was prepared in analogy to the preparation of Example 109 by using 1-(2-bromoethyl)pyrrolidin-2-one and sodium iodide instead of trifluoromethanesulfonic acid 2,2-difluoroethyl ester. Example 121 (12 mg) was obtained as a white solid. MS calc'd 934.5 (MH⁺), measured 934.5 (MH⁺). ¹H NMR (400 MHZ, METHANOL-d₄) δ=8.43-8.35 (m, 2H), 7.47 (s, 1H), 7.39 (s, 1H), 7.25 (d, J=2.9 Hz, 1H), 5.84-5.73 (m, 1H), 4.63-4.52 (m, 1H), 4.48-4.33 (m, 2H), 4.29-4.18 (m, 2H), 3.75 (s, 2H), 3.64-3.56 (m, 1H), 3.55-3.46 (m, 4H), 3.33 (br s, 6H), 3.28-3.22 (m, 1H), 3.15-2.93 (m, 4H), 2.85-2.71 (m, 5H), 2.69-2.56 (m, 3H), 2.41-2.35 (m, 2H), 2.33-2.25 (m, 1H), 2.25-2.12 (m, 2H), 2.11-2.00 (m, 2H), 1.97-1.88 (m, 1H), 1.81-1.66 (m, 1H), 1.66-1.51 (m, 1H), 1.43 (d, J=6.1 Hz, 3H), 1.40-1.28 (m, 2H), 1.14 (dd, J=6.0, 11.3 Hz, 7H), 0.94 (s, 3H), 0.54 (s, 3H).

Example 122

(1r,2R,3S)-N-[(7S,13S)-(20M)-20-[2-[(1S)-1-methoxyethyl]-5-[4-(2-tetrahydrofuran-3-yloxyethyl)piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2,3-dimethyl-cyclopropanecarboxamide

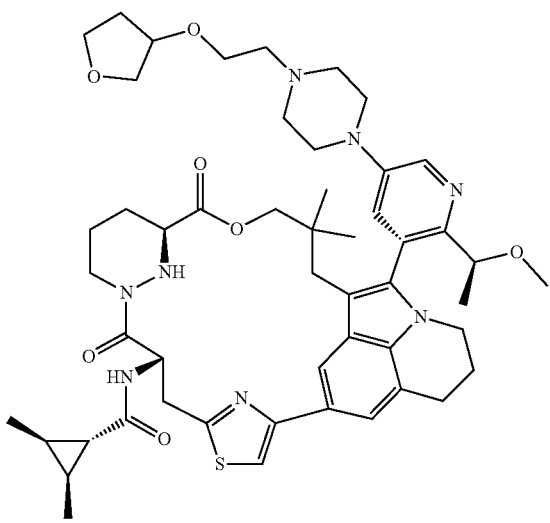

The title compound was prepared in analogy to the preparation of Example 109 by using 4-methylbenzenesulfonic acid 2-tetrahydrofuran-3-yloxyethyl ester and sodium iodide instead of trifluoromethanesulfonic acid 2,2-difluoroethyl ester. Example 122 (4 mg) was obtained as a white solid. MS calc'd 959.5 (MNa$^+$), measured 959.5 (MNa$^+$). $^1$H NMR (500 MHZ, METHANOL-d$_4$) δ=8.42-8.32 (m, 2H), 7.47 (s, 1H), 7.39 (s, 1H), 7.23 (d, J=2.9 Hz, 1H), 5.78 (br d, J=7.5 Hz, 1H), 4.80 (br d, J=12.2 Hz, 1H), 4.46-4.34 (m, 2H), 4.27-4.12 (m, 3H), 3.90-3.72 (m, 6H), 3.68-3.54 (m, 4H), 3.38 (s, 5H), 3.29-3.23 (m, 1H), 3.05 (br d, J=14.5 Hz, 3H), 2.79-2.69 (m, 5H), 2.65 (br t, J=5.5 Hz, 3H), 2.34-2.24 (m, 1H), 2.23-2.12 (m, 2H), 2.04-1.97 (m, 2H), 1.95-1.87 (m, 1H), 1.78-1.78 (m, 1H), 1.80-1.67 (m, 1H), 1.58 (dq, J=3.3, 12.5 Hz, 1H), 1.43 (d, J=6.1 Hz, 3H), 1.40-1.32 (m, 2H), 1.28-1.20 (m, 1H), 1.18-1.09 (m, 7H), 0.94 (s, 2H), 0.53 (s, 3H).

Example 123

(1r,2R,3S)-N-[(7S,13S)-(20M)-20-[2-[(1S)-1-methoxyethyl]-5-[4-(3-methoxy-3-methyl-butyl)piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2,3-dimethyl-cyclopropanecarboxamide

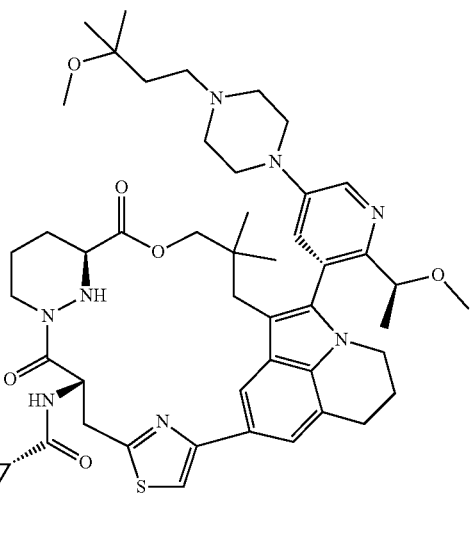

The title compound was prepared in analogy to the preparation of Example 109 by using 4-methylbenzenesulfonic acid (3-methoxy-3-methyl-butyl) ester and sodium iodide instead of trifluoromethanesulfonic acid 2,2-difluoroethyl ester. Example 123 (7.8 mg) was obtained as a white solid. MS calc'd 923.5 (MH$^+$), measured 923.5 (MH$^+$). $^1$H NMR (500 MHZ, METHANOL-d$_4$) δ=8.44-8.33 (m, 2H), 7.52-7.45 (m, 1H), 7.43-7.35 (m, 1H), 7.29-7.21 (m, 1H), 5.82-5.74 (m, 1H), 4.46-4.34 (m, 2H), 4.27-4.17 (m, 2H), 3.79-3.70 (m, 2H), 3.63-3.54 (m, 1H), 3.43-3.38 (m, 1H), 3.37-3.32 (m, 7H), 3.29-3.24 (m, 1H), 3.20 (s, 3H), 3.12-2.93 (m, 3H), 2.81-2.67 (m, 5H), 2.65-2.56 (m, 1H), 2.56-2.48 (m, 2H), 2.36-2.25 (m, 1H), 2.23-2.12 (m, 2H), 1.97-1.87 (m, 1H), 1.82-1.70 (m, 3H), 1.64-1.53 (m, 1H), 1.43 (d, J=6.1 Hz, 3H), 1.41-1.31 (m, 2H), 1.20 (s, 6H), 1.14 (dd, J=6.0, 14.2 Hz, 7H), 0.95 (s, 3H), 0.54 (s, 3H).

Example 124

(1r,2S,3R)-N-[(7S,13S)-29-fluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1 (28),2,5 (31), 19,25 (29),26-hexaen-7-yl]-2,3-dimethyl-cyclopropanecarboxamide

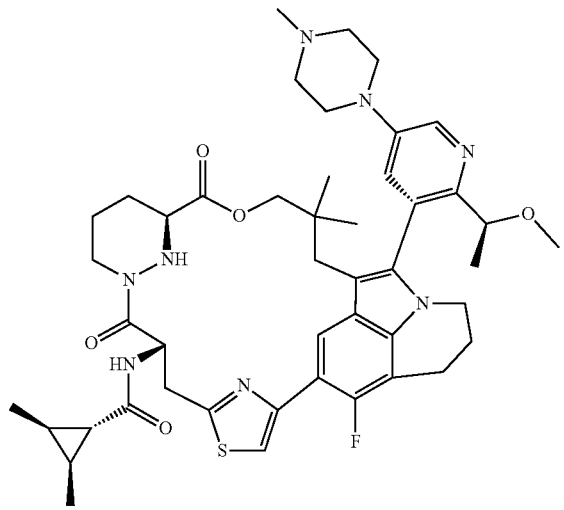

The title compound was prepared in analogy to the preparation of Example 1 by using (7S,13S)-7-amino-29-fluoro-(20M)-20-[2-[(1S)-1-methoxyethyl]-5-(4-methylpiperazin-1-yl)-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$] hentriaconta-1 (28), 2,5 (31), 19,25 (29), 26-hexaene-8,14-dione (intermediate U) and (1r,2S,3R)-2,3-dimethylcyclopropanecarboxylic acid instead of (7S,13S)-7-amino-(20M)-20-[2-[(1S)-1-methoxyethyl]-5-morpholino-3-pyridyl]-17,17-dimethyl-15-oxa-4-thia-9,21,30,31-tetrazahexacyclo[23.3.1.1$^{2,5}$.1$^{9,13}$.0$^{19,27}$.0$^{21,26}$] hentriaconta-1 (28),2,5 (31), 19,25 (29),26-hexaene-8,14-dione (Intermediate F) and (1S,2S)-2-methylcyclopropanecarboxylic acid. Example 124 (12.3 mg) was obtained as a yellow solid. MS calc'd 855.4 (MH$^+$), measured 855.4 (MH$^+$). $^1$H NMR (400 MHZ, METHANOL-d$_4$) δ=8.47 (s, 2H), 7.63-7.58 (m, 1H), 7.51-7.44 (m, 1H), 5.78 (d, J=9.2 Hz, 1H), 4.93-4.89 (m, 1H), 4.47-4.42 (m, 2H), 4.22-4.14 (m, 3H), 3.80-3.69 (m, 3H), 3.56 (s, 3H), 3.49-3.37 (m, 4H), 3.24 (s, 1H), 3.19-3.10 (m, 2H), 3.06-2.91 (m, 7H), 2.82-2.76 (m, 1H), 2.62 (d, J=14.0 Hz, 1H), 2.31-2.22 (m, 2H), 2.17 (d, J=13.6 Hz, 1H), 1.95 (d, J=12.4 Hz, 1H), 1.83-1.75 (m, 1H), 1.65-1.60 (m, 1H), 1.45 (d, J=6.0 Hz, 3H), 1.40-1.33 (m, 2H), 1.17-1.12 (m, 7H), 0.94 (s, 3H), 0.56 (s, 3H).

Example 125

(1S,2S)-N-[(7S,13S)-(20M)-20-[2-[(1S)-1-methoxyethyl]-5-morpholino-3-pyridyl]-17,17,22,22-tetramethyl-8,14-dioxo-15-oxa-4-thia-9,21,30,31-tetrazahexacyclo[23.3.1.1$^{2,5}$.1$^{9,13}$.0$^{19,27}$.0$^{21,26}$] hentriaconta-1 (29),2,5 (31),19,25,27-hexaen-7-yl]-2-methyl-cyclopropanecarboxamide

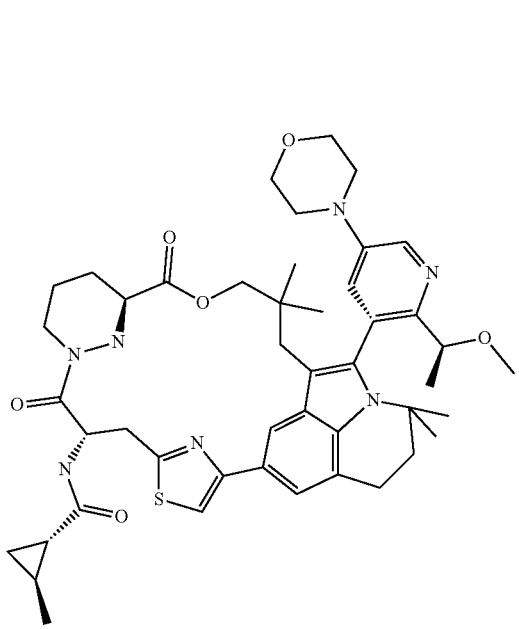

The title compound was prepared in analogy to the preparation of Example 38 by using 6-bromo-8-iodo-2,2-dimethyl-3,4-dihydro-1H-quinoline instead of 7-bromo-5-iodo-2,2-dimethyl-3,4-dihydro-1,4-benzoxazine (Intermediate D4). Example 125 (6.3 mg) was obtained as a white solid. MS calc'd 838.4 (MH$^+$), measured 838.4 (MH$^+$). $^1$H NMR (500 MHZ, CHLOROFORM-d) δ=8.37 (s, 1H), 8.06 (s, 1H), 7.35-7.30 (m, 1H), 7.24-7.23 (m, 1H), 7.20 (d, J=2.1 Hz, 1H), 6.86 (br d, J=6.9 Hz, 1H), 6.34-6.25 (m, 1H), 5.28-5.20 (m, 1H), 4.51 (br d, J=11.6 Hz, 1H), 4.21 (br d, J=10.5 Hz, 1H), 4.09-4.01 (m, 2H), 3.90 (br d, J=1.8 Hz, 4H), 3.69-3.61 (m, 2H), 3.57-3.49 (m, 2H), 3.41 (dd, J=3.2, 14.3 Hz, 1H), 3.32 (br dd, J=6.3, 16.3 Hz, 1H), 3.23 (br d, J=4.0 Hz, 4H), 3.16 (s, 2H), 3.11 (s, 3H), 3.08-2.97 (m, 4H), 2.61 (dt, J=2.7, 12.9 Hz, 1H), 2.25-2.15 (m, 2H), 1.97-1.86 (m, 2H), 1.82 (br dd, J=2.4, 13.0 Hz, 1H), 1.75-1.69 (m, 1H), 1.31 (s, 2H), 1.22 (s, 2H), 0.97 (s, 3H), 0.80 (s, 3H), 0.65 (s, 3H), 0.63 (s, 3H), 0.58-0.53 (m, 1H)

Example 126

(1r,2R,3S)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,31,32-tetrazahexacyclo[24.3.1.1$^{2,5}$.1$^{9,13}$.0$^{19,28}$.0$^{19,28}$.0$^{21,27}$]dotriaconta-1 (29),2,5 (32),19,26 (30),27-hexaen-7-yl]-2,3-dimethyl-cyclopropanecarboxamide

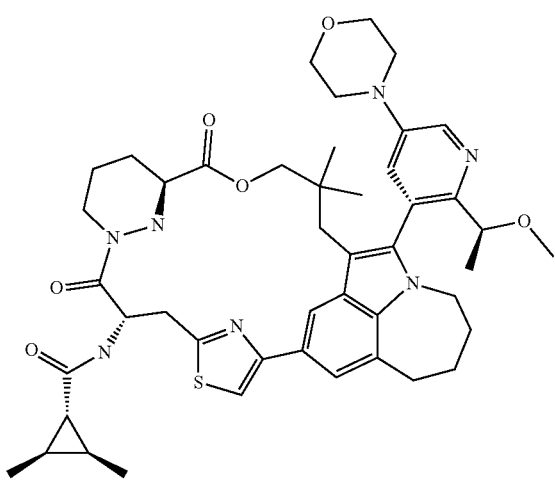

The title compound was prepared in analogy to the preparation of Example 73 by using 7-bromo-9-iodo-2,3,4,5-tetrahydro-1H-1-benzazepine instead of 6-bromo-8-iodo-1,2,3,4-tetrahydroquinoline (Intermediate D1). Example 126 (4 mg) was obtained as a yellow solid. MS calc'd 838.4 (MH$^+$), measured 838.4 (MH$^+$). $^1$H NMR (400 MHZ, Methanol-d$_4$) δ=8.43-8.38 (m, 1H), 7.70-7.63 (m, 1H), 7.56 (s, 1H), 7.53-7.45 (m, 1H), 5.79-5.74 (m, 1H), 4.57-4.49 (m, 4H), 4.47-4.38 (m, 1H), 4.21-4.14 (m, 1H), 4.13-4.03 (m, 1H), 3.93-3.81 (m, 4H), 3.74-3.61 (m, 3H), 3.43 (br s, 3H), 3.40-3.35 (m, 5H), 3.12-3.05 (m, 1H), 2.83-2.72 (m, 1H), 2.70-2.63 (m, 1H), 2.28-2.02 (m, 4H), 1.97-1.73 (m, 3H), 1.62-1.56 (m, 1H), 1.51-1.41 (m, 3H), 1.40-1.33 (m, 2H), 1.29-1.26 (m, 1H), 1.17-1.10 (m, 7H), 0.98-0.91 (m, 3H), 0.52 (s, 3H)

Example 127

(1r,2R,3S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,32,33-tetrazahexacyclo[25.3.1.1$^{2,5}$.1$^{9,13}$.0$^{19,29}$.0$^{21,28}$]tritriaconta-1 (30),2,5 (33),19,27 (31),28-hexaen-7-yl]-2,3-dimethyl-cyclopropanecarboxamide

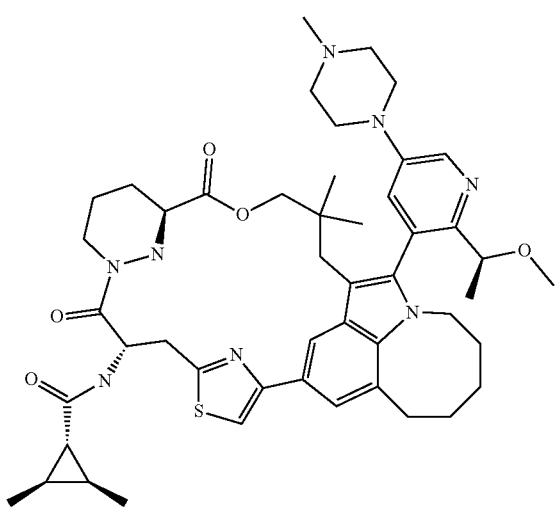

The title compound was prepared in analogy to the preparation of Example 24 by using 8-bromo-10-iodo-1,2,3,4,5,6-hexahydro-1-benzazocine instead of 6-bromo-8-iodo-1,2,3,4-tetrahydroquinoline (Intermediate D1). Example 127 (4 mg) was obtained as a white solid. MS calc'd 865.5 (MH$^+$), measured 865.5 (MH$^+$). $^1$H NMR (400 MHZ, Methanol-d$_4$) δ=8.40 (d, J=2.9 Hz, 1H), 8.37 (d, J=1.0 Hz, 1H), 7.51 (s, 1H), 7.35-7.24 (m, 2H), 5.91-5.79 (m, 1H), 4.65 (br t, J=11.3 Hz, 1H), 4.42 (br d, J=11.8 Hz, 1H), 4.27-4.16 (m, 2H), 4.14-4.07 (m, 1H), 3.82-3.68 (m, 3H), 3.44-3.34 (m, 6H), 3.29-3.23 (m, 4H), 3.06 (br dd, J=6.4, 13.1 Hz, 1H), 2.92 (br d, J=15.8 Hz, 1H), 2.80-2.59 (m, 6H), 2.41 (s, 3H), 2.08 (br d, J=12.1 Hz, 1H), 2.03-1.96 (m, 1H), 1.93-1.80 (m, 2H), 1.74-1.64 (m, 2H), 1.62-1.53 (m, 2H), 1.44 (d, J=6.1 Hz, 3H), 1.39-1.33 (m, 2H), 1.13 (dd, J=5.8, 9.3 Hz, 8H), 0.92-0.82 (m, 3H), 0.56 (s, 3H).

Biological Example

Compound A122 (page 70, Table. 1a) and Compound A252 (page 95, Table. 1a) from WO2022060836 were cited as reference compound for this invention.

(A122)

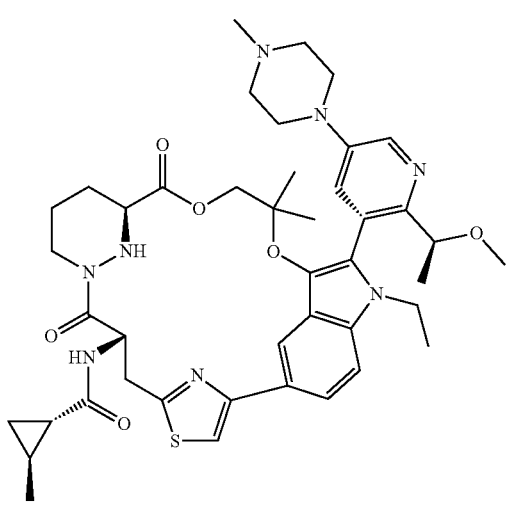

(A252)

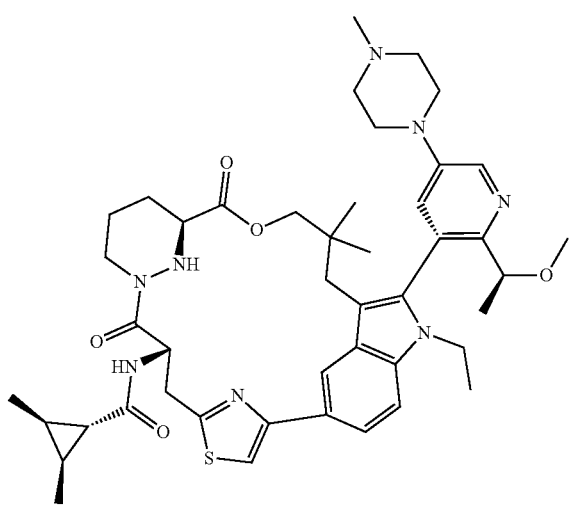

Example 128

Single Dose Pharmacokinetics (PK) Study in Female BALB/c Mice

The purpose of this study was to determine the pharmacokinetics of selected compounds following single intravenous bolus or oral gavage administration in female BALB/c mice. Briefly, two groups of female BALB/c mice (available from Shanghai Lingchang Biotechnology Co., Ltd) (N=3/group) were treated with a single dose of compound intravenously at 3 mg/kg (IV) or orally at 30 mg/kg (PO). Blood samples were collected at 5 min (only for IV), min, 30 min, 1 h, 2 h, 4 h, 7 h and 24 h post-dose. Blood samples were placed on ice until centrifugation to obtain plasma samples. The concentration of compound in plasma samples was determined using LC-MS/MS method. The pharmacokinetic parameters were calculated by non-compartmental analysis.

TABLE 1

Results of SDPK

| compound | 3 mg/kg, iv | 30 mg/kg, po | |
|---|---|---|---|
| | CL (mL/min/kg) | $C_{max}$ (ng/mL) | $AUC_{0\text{-}last}$ (h × ng/ml) |
| A122 | 33.9 | 2530 | 9760 |
| A252 | 37.8 | 2435 | 14642 |
| Example 24 | 5.3 | 10498 | 57240 |
| Example 73 | 5.8 | 15058 | 69514 |

From Table 1, it can be seen that Example 24 has excellent pharmacokinetic properties in mouse model. Especially Example 24 has 4.3-fold increase in $C_{max}$, 4-fold increase in $AUC_{0\text{-}last}$ and significant lower clearance compared with compound A252, and almost 4-fold increase in $C_{max}$, 6-fold-increase in $AUC_{0\text{-}last}$ and significant lower clearance compared with compound A122.

Similarly, Example 73 also has excellent pharmacokinetic properties in mouse model. Especially Example 73 exhibits 6.2-fold increase in $C_{max}$, 4.7-fold increase in $AUC^{0\text{-}last}$ and significant lower clearance compared with compound A252, and 5.9-fold increase in $C_{max}$, 7.1-fold increase in $AUC_{0\text{-}last}$ and significant lower clearance compared with compound A122.

Above improvement over reference compounds (A252 and A122) demonstrated that the compounds of this invention are more suitable for treating cancers with RAS mutation as an orally therapeutic active ingredient in clinic.

Example 129

Human Hepatocyte Stability Assay

The hepatocyte stability assay measures the rate of disappearance of a compound from incubations with cryopreserved suspension hepatocytes from human. Positive controls, including Midazolam, Raloxifene and Dextromethorphan, are included in every experiment. Incubations consist of 1 μM tested compound and suspension of human hepatocytes ($1\times10^6$ cells/mL) in supplemented Williams' E Medium with 10% FBS and 0.5% Penicillin-streptomycin. The hepatocyte suspension was incubated with intermittent shaking 900 rpm at 37° C., in a 5% $CO_2$ incubator. The reaction was stopped by adding methanol containing internal standard (2 μM Tolbutamide) at 2, 10, 20, 40, 60 and 120 minutes after compound addition, depletion of the parent compound was monitored by LC-MS/MS analysis.

TABLE 2

Human hepatocytes stability of Examples and Compounds of present invention

| Example | Hepatic clearance (Human) (mL/min/kg) |
|---|---|
| A122 | 9 |
| A252 | 9.2 |
| Example 24 | 3.4 |

Above result clearly shows that reference compounds (A122 and A252) had much higher clearance while Example 24 maintained the low clearance in human hepatocytes stability assay. Achieving low clearance is advantageous to improve in vivo performance of the compound, such as dose reduction, exposure enhancement, and half-life prolongation.

Example 130

In Vivo Xenograft Studies

The purpose of the study was to assess the anti-tumor activity in difficult KRAS mutated xenograft tumor model using SHP-77 (small cell lung cancer, SCLC; ATCC CRL-2195) by examining the time-dependent effects on MAPK pathway modulation and tumor suppression post-administration of Example 24 and reference compound A122.

Studies were conducted at Wuxi AppTec (Nantong, China). All CDX mouse studies and procedures related to animal handling, care and treatment were conducted in compliance with all applicable regulations and guidelines of the relevant Institutional Animal Care and Use Committee (IACUC). Mice were maintained under pathogen-free conditions, and food and water was provided ad libitum.

Female CB17-SCID mice at 6-8 weeks old from Vital River Co., LTD. were used for these studies. In order to generate subcutaneous xenograft tumors, each mouse was inoculated at the right flank with tumor cells in 100 µL of PBS and Matrigel matrix in the right hind flank with $1\times10^7$ cells. Mouse health was monitored daily, and caliper measurements began when tumors were palpable. Tumor volume measurements were determined utilizing the formula $0.5\times L\times W^2$ in which L refers to length and W refers to width of each tumor. When tumors reached an average tumor volume of approximately 100-200 mm$^3$ for efficacy study and 300-500 mm$^3$ for single-dose PK/PD study, mice were randomized into treatment groups.

Mice were treated by oral gavage at 10 mg/kg with either vehicle consisting of DMSO: Solutol HS15:water=10:10:80 (% v/v/v) or compounds (Example 24, A122) in vehicle at indicated doses. For efficacy studies, animals were orally administered daily, tumor volumes and body weights were measured 3 times per week. Study day on efficacy plots indicates the day after which compound treatment was initiated. For single-dose PK/PD study, at the indicated time points after a single dose of Example 24 at the indicated dose levels, tumor samples were collected for PD analysis. RNA extraction and analysis of DUSP6 levels by in tumor tissue were performed as described in Example 134.

Figure 5:
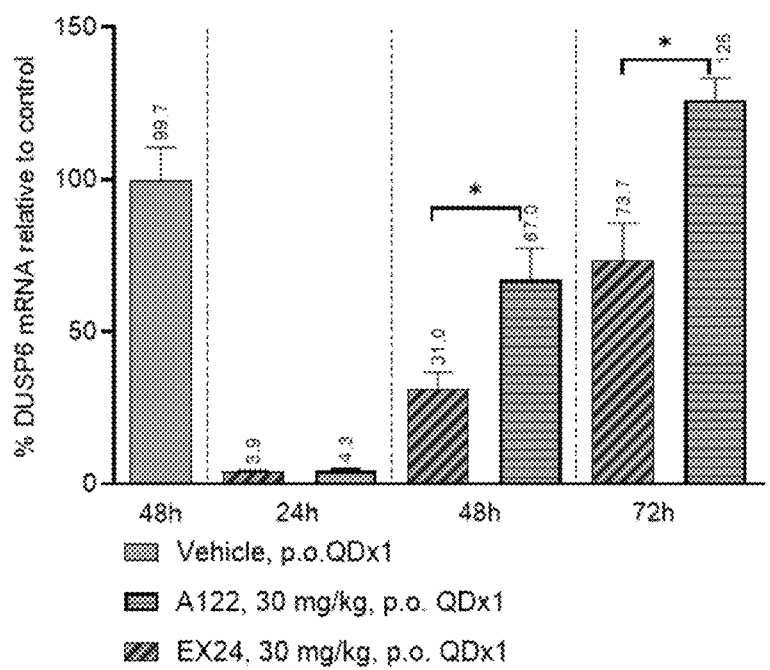
FIG. 5. DUSP6 express levels in tumor samples of SHP77 xenograft model. The differences of DUSP6 inhibition for EX24 group were determined to be statistically significant versus A122 group at both 48 h and 72 h post dosing, via two-tailed t test. * indicates p<0.05. Error bars represented Standard Error of Mean (SEM). All data were analyzed using Prism GraphPad software.

A single oral dose of 30 mg/kg Example 24 or A122 was sufficient to maximally suppress tumor DUSP6 levels at 24 h for both Example 24 (3.9% remaining) and A122 (4.3% remaining). Notably, the inhibitory effect of A122 to DUSP6 began to diminish after 48 hours (67% remaining) and vanish at 72 hours (126% remaining). In contrast, the inhibitory effect of Example 24 on DUSP6 expression was sustained at 48 hours (31% remaining) and remained effective at 72 hours (73.7% remaining) post-dose. (FIG. 5)

Figure 6:
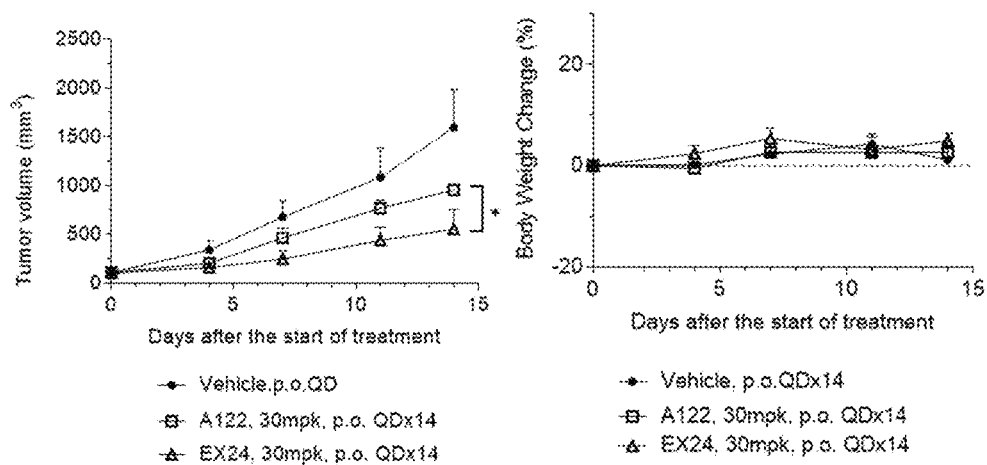
FIG. 6. Tumor volume changes and body weight change after administering vehicle or test articles to female CB-17 SCID mice bearing SHP-77 SCLC tumors. Data points represent mean±SEM. Tumor volumes at day 14 for EX24 group were determined to be statistically significant versus A122 group via two-tailed t test. * indicates P<0.05. p.o.: oral administration; QD: once a day.

Daily administration of Example 24 at 30 mg/kg was well-tolerated based on body weights (FIG. 6) and resulted in 70% mean tumor growth inhibition (TGI) following 14 days treatment in comparison to A122 that lead to only 43% TGI at same dose regiments. (FIG. 6)

Based on above comparison data, Example 24 exhibited longer and sustained pathway inhibition over treatment period (FIG. 5), and demonstrated significantly enhanced anti-tumor activities (FIG. 6) compared with reference compound that potentially could result in more durable anti-tumor responses in clinic.

Example 131

Cell Proliferation Analysis

The objective of this study was to evaluate the extent and degree to which Example 24 or A122 inhibits cell proliferation in a panel of 119 human cancer cell lines with RAS mutations or amplifications across various histological subtypes.

On Day-1, cells were plated in 384-well round-bottom ultra-low adhesion plates (cat. Corning 3830, with cell density adjusted according to Table 3. The assay plate was then centrifuged at 1000 rpm for 1 minute to ensure even distribution of cells. The plate was incubated at 37° C. in a 5% $CO_2$ atmosphere (It is worth noting that for SW1271 cell plate, it needs to be incubated in an incubator without additional $CO_2$).

On Day 0, Example 24 or A122 was added to each well using a Tecan HP D300E dispenser, with a 3-fold dilution across 9 doses. The final concentration of DMSO was normalized to 0.2%. The assay plate was then centrifuged at 1000 rpm for 1 minute and incubated for 7 days.

On Day 7, CellTiter-Glo (CTG) 3D reagent (Promega G9683) was dispensed into each well of a 384-well plate using a multi-drop dispenser (Thermo Scientific 66413). A liquid handling automation workstation (Bravo with a 384-well head) was used to mix the CTG reagents. Plates were left on a shaker for 30 minutes at 450 rpm, shielded from light. Following this, plates were incubated for an additional 10 minutes, also protected from light, before being read on an EnVision Luminometer.

For data analysis, the XL-fit software (Supplier: ID Business Solutions Ltd., Software version: XL fit 5.0) was utilized. The percentage of inhibition was calculated using the formula: Inhibition %=(Max-Sample value)/(Max-Min)×100. Curve fitting was performed as follows: For complete dose-response curves, the relative $IC_{50}$ was reported from the fit. For incomplete curves, if minimal inhibition was greater than 50%, an $IC_{50}$ less than the lowest compound concentration was reported. If minimal inhibition was between 20% and 50%, the bottom was locked at 0% and the $IC_{50}$ was reported. If maximal inhibition was less than 50%, an $IC_{50}$ greater than the highest compound concentration was reported. For maximal inhibition between 50% and 85%, the top was locked at 100% and the $IC_{50}$ was reported.

Figure 7:
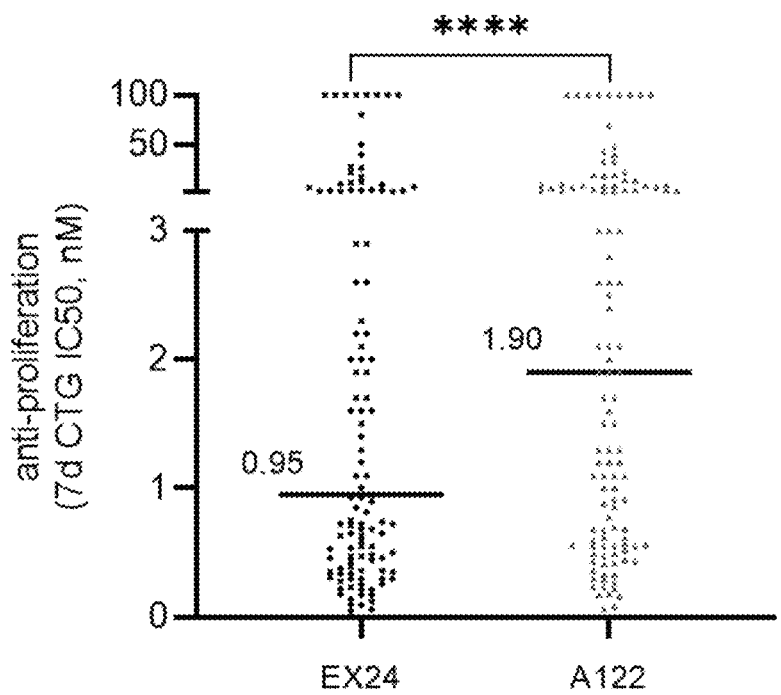
FIG. 7. Scatter plot of the IC50 values of RAS addicted cell panels (n=119) from Table 3. Median IC50 of EX24 group (0.95 nM) was determined to be statistically significant versus median IC50 of A122 group (1.90 nM) via two-tailed t test. * indicates P<0.0001

Results from in vitro cell proliferation assays statistically showed that Example 24 exhibited a more potent inhibitory effect on cell growth compared to A122, with a statistically significant difference (P<0.0001) (FIG. 7). The median $IC_{50}$ for Example 24 was 0.95 nM, which is twice effective compared to A122, that had a median $IC_{50}$ of 1.90 nM. This enhanced potency suggests that Example 24 could potentially have more effective anti-tumor effects in clinical settings.

TABLE 3

Anti-proliferation $IC_{50}$ Values of each cell line

| | Cell line | Example 24 $IC_{50}$ (nM) | A122 $IC_{50}$ (nM) | Mutation | Medium type | Cells per well |
|---|---|---|---|---|---|---|
| 1 | LS1034 | 12 | 7.3 | KRAS (A146T) | RPMI-1640 + 10% FBS | 1000 |

TABLE 3-continued

Anti-proliferation IC$_{50}$ Values of each cell line

| Cell line | Example 24 IC$_{50}$ (nM) | A122 IC$_{50}$ (nM) | Mutation | Medium type | Cells per well |
|---|---|---|---|---|---|
| 2 PL-21 | 1 | 2.1 | KRAS (A146V) | RPMI-1640 + 10% FBS | 1000 |
| 3 KMS-28BM | 0.63 | 0.88 | KRAS (G12A) | RPMI1640 + 10% FBS | 1000 |
| 4 NCI-H1573 | 0.82 | 1.2 | KRAS (G12A) | RPMI1640 + 10% FBS | 1000 |
| 5 MM.1S | 0.3 | 0.55 | KRAS (G12A) | RPMI1640 + 10% FBS | 1300 |
| 6 RPMI8226 | 0.38 | 0.52 | KRAS (G12A) | RPMI 1640 + 10% FBS | 1300 |
| 7 RERF-LC-Ad1 | 0.3 | 0.22 | KRAS (G12A) | RPMI1640 + 10% FBS | 1300 |
| 8 LU99 | 0.59 | 0.91 | KRAS (G12C) | RPMI1640 + 10% FBS | 1000 |
| 9 Mia-pa-ca-2 | 0.064 | 0.082 | KRAS (G12C) | RPMI1640 + 10% FBS | 1000 |
| 10 NCI-H1792 | 0.21 | 0.43 | KRAS (G12C) | RPMI1640 + 10% FBS | 1000 |
| 11 NCI-H2030 | 0.34 | 0.56 | KRAS (G12C) | RPMI1640 + 10% FBS | 1000 |
| 12 NCI-H2122 | 0.39 | 0.62 | KRAS (G12C) | RPMI1640 + 10% FBS | 1000 |
| 13 NCI-H23 | 0.17 | 0.33 | KRAS (G12C) | RPMI1640 + 10% FBS | 1000 |
| 14 NCI-H358 | 0.12 | 0.27 | KRAS (G12C) | RPMI1640 + 10% FBS | 1000 |
| 15 SW 837 | 0.22 | 0.67 | KRAS (G12C) | RPMI1640 + 10% FBS | 1000 |
| 16 AsPc-1 | 0.65 | 0.55 | KRAS (G12D) | RPMI 1640 + 10% FBS | 1000 |
| 17 PANC-1 | 0.95 | 0.68 | KRAS (G12D) | RPMI 1640 + 10% FBS | 1000 |
| 18 PK-59 | 0.44 | 0.62 | KRAS (G12D) | RPMI 1640 + 10% FBS | 1000 |
| 19 SK-LU-1 | 0.5 | 0.56 | KRAS (G12D) | EMEM + 10% FBS | 1300 |
| 20 SW 1990 | 1.6 | 1.5 | KRAS (G12D) | RPMI 1640 + 10% FBS | 1300 |
| 21 GP2d | 0.63 | 0.55 | KRAS (G12D) | DMEM + 10% FBS | 1000 |
| 22 HEC-1-A | 1.6 | 1.9 | KRAS (G12D) | McCoy's 5a + 10% FBS | 1000 |
| 23 LS513 | 0.68 | 0.47 | KRAS (G12D) | RPMI1640 + 10% FBS | 1000 |
| 24 GP5d | 0.48 | 0.41 | KRAS (G12D) | DMEM + 10% FBS | 1300 |
| 25 HPAC | 0.31 | 0.3 | KRAS (G12D) | RPMI 1640 + 10% FBS | 2000 |
| 26 Panc 02.03 | 3.2 | 5.2 | KRAS (G12D) | RPMI-1640 + 15% FBS + 10 Units/ml human recombinant insulin | 1000 |
| 27 NCI-H2291 | 0.55 | 1 | KRAS (G12F) | RPMI1640 + 10% FBS | 1000 |
| 28 CAL-62 | 1.1 | 8.8 | KRAS (G12R) | DMEM + 10% FBS | 1000 |
| 29 PSN-1 | 0.85 | 1.2 | KRAS (G12R) | RPMI1640 + 10% FBS | 1000 |
| 30 MDA-MB-134-VI | 1.5 | 2.6 | KRAS (G12R) | RPMI 1640 + 20% FBS | 2000 |
| 31 KP-2 | 0.35 | 0.43 | KRAS (G12R) | RPMI 1640 + 10% FBS | 1000 |
| 32 A549 | 0.72 | 1.1 | KRAS (G12S) | RPMI-1640 + 10% FBS | 1000 |
| 33 Capan-2 | 0.23 | 0.59 | KRAS (G12V) | McCoy's 5a + 10% FBS | 1000 |
| 34 COR-L23 | 0.53 | 0.78 | KRAS (G12V) | RPMI 1640 + 10% FBS | 1000 |
| 35 LCLC-97TM1 | 0.092 | 0.17 | KRAS (G12V) | RPMI 1640 + 20% FBS | 1000 |
| 36 SK-CO-1 | 0.18 | 0.33 | KRAS (G12V) | EMEM + 10% FBS | 1000 |
| 37 SW 480 | 1.2 | 2 | KRAS (G12V) | RPMI 1640 + 10% FBS | 1000 |

TABLE 3-continued

Anti-proliferation IC$_{50}$ Values of each cell line

| | Cell line | Example 24 IC$_{50}$ (nM) | A122 IC$_{50}$ (nM) | Mutation | Medium type | Cells per well |
|---|---|---|---|---|---|---|
| 38 | NCI-H2444 | 0.17 | 0.29 | KRAS (G12V) | RPMI1640 + 10% FBS | 1300 |
| 39 | SW 900 | 0.28 | 0.23 | KRAS (G12V) | RPMI1640 + 10% FBS | 1000 |
| 40 | NCI-H441 | 0.25 | 0.49 | KRAS (G12V) | RPMI1640 + 10% FBS | 1300 |
| 41 | CFPAC-1 | 0.54 | 1.1 | KRAS (G12V) | IMDM + 10% FBS | 1000 |
| 42 | RKN | 0.045 | 0.066 | KRAS (G12V) | Ham's F12 + 10% FBS | 1000 |
| 43 | NCI-H727 | 0.14 | 0.16 | KRAS (G12V) | RPMI 1640 + 10% FBS | 1000 |
| 44 | RCM-1 | 2.2 | 6.5 | KRAS (G12V) | RPMI 1640 + 10% FBS | 1300 |
| 45 | SW620 | 0.1 | 0.23 | KRAS (G12V) | RPMI1640 + 10% FBS | 1000 |
| 46 | NCI-H1355 | 22 | 33 | KRAS (G13C) | RPMI1640 + 10% FBS | 1000 |
| 47 | TOV-21G | 4.9 | 33 | KRAS (G13C) | DMEM + 10% FBS | 1000 |
| 48 | NCI-H1734 | 0.74 | 1.3 | KRAS (G13C) | RPMI1640 + 10% FBS | 2000 |
| 49 | HCT-15 | 100 | 100 | KRAS (G13D) | RPMI 1640 + 10% FBS | 1000 |
| 50 | HCT-116 | 1.9 | 1.9 | KRAS (G13D) | RPMI 1640 + 10% FBS | 1000 |
| 51 | MDA-MB-231 | 27 | 20 | KRAS (G13D) | RPMI1640 + 10% FBS | 1000 |
| 52 | DV-90 | 3.9 | 4.7 | KRAS (G13D) | RPMI1640 + 10% FBS | 1000 |
| 53 | HCT-8 | 80 | 69 | KRAS (G13D) | RPMI1640 + 10% FBS | 1000 |
| 54 | NCI-H1944 | 1.6 | 1.7 | KRAS (G13D) | RPMI1640 + 10% FBS | 1000 |
| 55 | LoVo | 0.55 | 0.36 | KRAS (G13D) | RPMI 1640 + 10% FBS | 1000 |
| 56 | Toledo | 100 | 100 | KRAS (G13D) | RPMI1640 + 10% FBS | 1000 |
| 57 | T84 | 100 | 100 | KRAS (G13D) | RPMI 1640 + 10% FBS | 1000 |
| 58 | NCI-H747 | 0.72 | 0.91 | KRAS (G13D) | RPMI-1640 + 10% FBS | 1300 |
| 59 | NOMO-1 | 0.47 | 0.86 | KRAS (G13D) | RPMI-1640 + 10% FBS | 1000 |
| 60 | DLD-1 | 18 | 20 | KRAS (G13D) | RPMI1640 + 10% FBS | 1000 |
| 61 | SKM-1 | 0.93 | 1.3 | KRAS (K117N) | RPMI1640 + 10% FBS | 1000 |
| 62 | NCI-H2347 | 2 | 4.2 | KRAS (L19F) | RPMI1640 + 10% FBS | 1000 |
| 63 | Hs-766T | 100 | 100 | KRAS (Q61H) | DMEM + 10% FBS | 1000 |
| 64 | SJSA-1 | 2.6 | 3.1 | KRAS (Q61H) | RPMI1640 + 10% FBS | 1000 |
| 65 | Calu-6 | 0.65 | 1.3 | KRAS (Q61K) | RPMI 1640 + 10% FBS | 1000 |
| 66 | SNU-668 | 2 | 4.3 | KRAS (Q61K) | RPMI1640 + 10% FBS | 1000 |
| 67 | SW 948 | 2.9 | 8.5 | KRAS (Q61L) | RPMI1640 + 10% FBS | 1300 |
| 68 | NCI-H650 | 2.3 | 9.6 | KRAS (Q61L) | RPMI 1640 + 10% FBS | 1000 |
| 69 | Panc 02.13 | 4 | 15 | KRAS (Q61R) | RPMI-1640 Medium + 15% FBS + 10 Units/ml human recombinant insulin | 1000 |
| 70 | KMS26 | 50 | 48 | KRAS (WT ampl) | RPMI1640 + 10% FBS | 1000 |
| 71 | CHL1 | 8.1 | 9.3 | KRAS (WT ampl) | DMEM + 10% FBS | 1000 |

TABLE 3-continued

Anti-proliferation IC$_{50}$ Values of each cell line

| Cell line | Example 24 IC$_{50}$ (nM) | A122 IC$_{50}$ (nM) | Mutation | Medium type | Cells per well |
|---|---|---|---|---|---|
| 72 MKN-1 | 28 | 40 | KRAS (WT ampl) | RPMI1640 + 10% FBS | 1000 |
| 73 TT | 2.9 | 5.9 | KRAS (WT ampl) | F-12K Medium + 10% FBS | 1500 |
| 74 UMC-11 | 100 | 100 | KRAS (WT ampl) | RPMI1640 + 10% FBS | 1000 |
| 75 KLE | 100 | 100 | KRAS (WT ampl) | DMEM:F12 + 10% FBS | 2000 |
| 76 BEN | 40 | 43 | KRAS (WT ampl) | DMEM + 10% FBS | 1000 |
| 77 KURAMOCHI | 100 | 100 | KRAS (WT ampl) | RPMI1640 + 10% FBS | 3000 |
| 78 NCI-H838 | 100 | 100 | KRAS (WT ampl) | RPMI 1640 + 10% FBS | 1000 |
| 79 MOLT-4 | 1000 | 1000 | NRAS (p.G12C) | RPMI 1640 + 10% FBS | 1000 |
| 80 THP-1 | 0.26 | 0.18 | NRAS (p.G12D) | RPMI 1640 + 10% FBS + 0.05 mM 2-mercaptoethanol | 1000 |
| 81 PA-1 | 0.46 | 0.42 | NRAS (p.G12D) | EMEM + 10% h.i. FBS | 1000 |
| 82 TYK-nu | 0.34 | 0.68 | NRAS (p.G12D and p.Q61K) | EMEM + 10% FBS | 1000 |
| 83 HAL-01 | 13 | 14 | NRAS (p.G12S) | RPMI 1640 + 10% h.i. FBS | 1000 |
| 84 GA-10 | 1000 | 1000 | NRAS (p.G12V) | RPMI 1640 + 10% FBS | 1000 |
| 85 Mino | 3.8 | 1000 | NRAS (p.G13D) | RPMI 1640+15% FBS | 1300 |
| 86 NCI-H929 | 7.3 | 8.7 | NRAS (p.G13D) | RPMI 1640 + 10% FBS + 2-mercaptoethanol (final conc.: 0.05 mM) | 2000 |
| 87 AML-193 | 1.1 | 2.1 | NRAS (p.G13V) | IMDM + 0.005 mg/ml insulin + 0.005 mg/ml transferrin + 5 ng/ml GM-CSF + 5% FBS | 1300 |
| 88 RD | 0.36 | 0.7 | NRAS (p.Q61H) | DMEM + 10% FBS | 1000 |
| 89 OCI-Ly19 | 1.9 | 2.4 | NRAS (p.Q61K) | MEM a + 20% FBS | 1000 |
| 90 NCI-H2087 | 0.21 | 0.44 | NRAS (p.Q61K) | RPMI 1640 + 5%FBS | 1300 |
| 91 HuT 78 | 0.3 | 0.55 | NRAS (p.Q61K) | IMDM+20%FBS | 1500 |
| 92 SNU-387 | 0.43 | 1.1 | NRAS (p.Q61K) | RPMI 1640 + 10% FBS | 2000 |
| 93 HCC-15 | 0.68 | 1.7 | NRAS (p.Q61K) | RPMI 1640 + 10% FBS | 1000 |
| 94 H9 | 0.72 | 1.6 | NRAS (p.Q61K) | RPMI 1640 + 10% FBS | 1000 |
| 95 CHP-212 | 0.35 | 1.1 | NRAS (p.Q61K) | EMEM:F12 Medium = 1:1 + 10% FBS | 1000 |
| 96 HT1080 | 0.36 | 0.49 | NRAS (p.Q61K) | EMEM + 10% FBS | 1000 |
| 97 NCI-H1299 | 0.93 | 1.5 | NRAS (p.Q61K) | RPMI 1640 + 10% FBS | 1000 |
| 98 SK-N-AS | 0.47 | 1.9 | NRAS (p.Q61K) | DMEM + 10% FBS + 0.1 mM NEAA | 1000 |
| 99 SK-N-SH | 1000 | 580 | NRAS (p.Q61K) | EMEM + 10% FBS | 1000 |
| 100 NCI-H2135 | 0.71 | 1.2 | NRAS (p.Q61K) | HITES medium supplemented with 5% fetal bovine serum | 1000 |

TABLE 3-continued

Anti-proliferation IC$_{50}$ Values of each cell line

| Cell line | Example 24 IC$_{50}$ (nM) | A122 IC$_{50}$ (nM) | Mutation | Medium type | Cells per well |
|---|---|---|---|---|---|
| 101 HepG2 | 2.1 | 5.5 | NRAS (p.Q61L) | EMEM + 10% FBS | 1300 |
| 102 GAK | 10 | 19 | NRAS (p.Q61L) | Ham's F12 + 10% FBS | 1300 |
| 103 MOLP8 | 11 | 22 | NRAS (p.Q61L) | RPMI 1640 + 20% h.i. FBS | 1500 |
| 104 OCI-AML-3 | 3.3 | 8.9 | NRAS (p.Q61L) | RPMI-1640 + 20%FBS | 1000 |
| 105 TF-1 | 130 | 100 | NRAS (p.Q61P) | RPMI 1640 + 10% FBS + 2 ng/ml GM-CSF | 1500 |
| 106 SK-MEL-2 | 2 | 3 | NRAS (p.Q61R) | EMEM + 10% FBS | 1000 |
| 107 KU1919 | 2.2 | 2.8 | NRAS (p.Q61R) | RPMI 1640 + 10% FBS | 1000 |
| 108 ONS-76 | 0.9 | 2.1 | NRAS (p.Q61R) | RPMI 1640 + 10% FBS | 1000 |
| 109 SW1271 | 1.7 | 3 | NRAS (p.Q61R) | Leibovitz's L-15 + 10% FBS | 1000 |
| 110 HT-1197 | 1.4 | 2.5 | NRAS (p.Q61R) | EMEM + 10% FBS | 1300 |
| 111 SUM 159PT | 4.5 | 3 | HRAS (p.G12D) | Ham's F-12 + 10 mM HEPES + 5 µg/ml Insulin + 1 µg/ml Hydrocortisone + 5% FBS | 1000 |
| 112 HS 578T | 1.7 | 3.1 | HRAS (p.G12D) | DMEM + 2mM Glutamine + 10 µg/ml Bovine Insulin + 10% FBS | 2000 |
| 113 T24 | 0.3 | 0.57 | HRAS (p.G12V) | McCoy's 5a + 10%FBS | 1000 |
| 114 RL95-2 | 1.3 | 2.6 | HRAS (p.Q61H) | DMEM:F-12 + 10% FBS + 0.005 mg/ml insulin | 1000 |
| 115 KNS-62 | 2.6 | 6.4 | HRAS (p.Q61L) | EMEM + 20% FBS | 1000 |
| 116 NCI-H1915 | 3.6 | 10 | HRAS (p.Q61L) | RPMI 1640 + 10% FBS | 1000 |
| 117 KYSE-30 | 0.46 | 1 | HRAS (p.Q61L) | RPMI-1640 + 10% FBS | 3000 |
| 118 NCI-H1876 | 3.1 | 3.6 | NRAS (p.Q61K) | DMEM:F12 + 0.005 mg/ml Insulin + 0.01 mg/ml Transferrin + 30 nM Sodium selenite + 10 nM Hydrocortisone + 10 nM beta-estradiol + 2 mM L-glutamine + 5% FBS | 2000 |
| 119 SW 1088 | 0.75 | 2.6 | NRAS (p.Q61K) | RPMI 1640 + 10% FBS | 2000 |

Example 132

Wild Type (WT) KRAS/HRAS/NRAS-BRAF with CYPA (500 nM) Interaction Assay for Selectivity Test The purpose of this test is to determine the selectivity of compounds of this invention.

In this example, TR-FRET was used to measure the compound or compound-CYPA dependent disruption of the KRAS G12V-BRAF complex to assess inhibition efficacy. The IC$_{50}$ ratio between WT KRAS/HRAS/NRAS and KRAS G12V mutant was calculated as selective index, which indicated tolerability and safety profile. Disruption of WT KRAS/HRAS/NRAS-BRAF complex by compounds was detected respectively. In assay buffer containing 25 mM HEPES (PH-7.4, 4-(2-hydroxyethyl)-1-piperazineethanesulfonic acid, Thermo, 15630080), 0.002% Tween20, 0.1% BSA, 100 mM NaCl, 5 mM MgCl$_2$, 10 µM GMPPNP (Guanosine 5'-[β,γ-imido]triphosphate trisodium salt hydrate, Sigma, G0635), tagless CYPA and GMPPNP loaded 6His-RAS proteins, and GST-BRAF$^{RBD}$ were mixed in a well of a 384-well assay plate at final concentrations of 50 nM, 6.25 nM and 1 nM, respectively. Compound was present in plate wells as a 16-point 3-fold dilution series starting at a final concentration of 10 µM and incubated for 3 hours. A mixture of MAb Anti-6His-XL665 (Cisbio, 61HISXLB) and Mab anti-GST-TB cryptate (Cisbio, 61GSTTLB) was then added at a final concentration of 6.67 nM and 0.21 nM, respectively, and the plate was incubated for an additional 1.5 hours. TR-FRET signal was read on a PHERstar FSX microplate reader (Ex320 nm, Em 665/615 nm). Compounds that facilitate disruption of the RAS-BRAF complex were identified as those eliciting a decrease in the TR-FRET ratio relative to DMSO control wells.

The G12V biochemical assay is very stable and robust, making it as a feasible representative mutant for most other RAS mutants.

TABLE 4

Activity and selective ratio of Examples and Compounds of present invention in WT KRAS/HRAS/NRAS-BRAF with CYPA (500 nM) interaction assay

|  |  | A122 | A252 | Example 24 |
|---|---|---|---|---|
| $IC_{50}$ (nM) | KRAS G12V | 8 | 9 | 7 |
|  | WT KRAS | 16 | 18 | 32 |
|  | WT HRAS | 10 | 23 | 38 |
|  | WT NRAS | 10 | 19 | 35 |
| Selectivity Index ($IC_{50}$ ratio) | WT KRAS/KRAS G12V | 2.0 | 2.0 | 4.6 |
|  | WT HRAS/KRAS G12V | 1.3 | 2.6 | 5.4 |
|  | WT NRAS/KRAS G12V | 1.3 | 2.1 | 5.0 |

Wild type (WT) KRAS/HRAS/NRAS inhibition could increase the risk of toxicity, Example 24 demonstrated much higher selectivity compared to A122 and A252, potentially indicating an improved tolerability and safety profile.

Example 133

Stable KRAS Mutant Cell Lines and Cell Viability Assay.

The aim of the study was to determine the potency and efficacy of compounds for cell proliferation using CellTiter-Glo® (CTG) Luminescent Cell Viability Assay (Promega Corp., Madison, WI). We cloned 14 $KRAS^{G12C}$ variant sequences with secondary mutations (V8A, V9Y, S17E, T58I, A59T, S65W, R68S, D69P, M72I, D92R, H95N, Y96D, Q99W and F156L) into the Miapaca-2. Totally 14 stable Miapaca-2 mutant cell lines were established through lentivirus infection. For the cell viability assay, cells were dosed with compounds in a 9-point dose-response using a 4 fold dilution series at a top dose of 10 µM. KRAS mutant cells were maintained in DMEM+10% FBS+2.5% HI Horse serum+1% PS+1 µg/mL Puromycin and seeded into 96-well plates at 800-1,500 cells per well 24 h before compound addition and then incubated with compound for 3 d before assaying viability (CellTiter-Glo, Promega). Assays were performed in biological duplicates. Nonlinear regression curves were fitted using Xfit. $IC_{50}$ (absolute $IC_{50}$) is the dose at which the estimated viability is 50% relative to untreated wells. Inhibition rate of the compound is calculated according to the formula below: % inhibition=100-100×(Luminescence value-HPE)/(ZPE-HPE).

HPE: Luminescence value from the wells with only medium
ZPE: Luminescence value from the wells with DMSO Example 134

Brain Metastasis Intracranial Model

The purpose of this assay is to determine whether brain exposure of the compounds of current invention was sufficient to mediate regression of tumors in experimental Brain Metastases (BM) models.

Cell Culture

NCI-H1373 cell line was purchased from the ATCC (CRL-5866). NCI-H1373-Luc cells were generated by WuXi AppTec. For generating NCI-H1373-Luc cell line, NCI-H1373 cells were transduced with GFP-Luc-puro lentivirus vector (HBLV-1014, HANBIO, carrying cDNA coding for firefly luciferase) and then selected with 1 µg/mL puromycin. All cells were authenticated by short tandem repeat fingerprinting, and periodically tested to be Mycoplasma free. H1373-luc cells were cultured in medium containing RPMI1640 (Thermo Fisher Scientific) plus 10% Fetal Bovine Serum (FBS, Thermo Fisher Scientific, 2.5 µg/mL puromycin and 1% Antibiotic-Antimycotic (Thermo Fisher Scientific), at 37° C. in an atmosphere of 5% $CO_2$ in air. The medium was renewed every 2 to 3 days and tumor cells were routinely sub-cultured at a confluence of 80-90%. Cells growing in an exponential growth phase were harvested and counted for inoculation.

In Vivo Efficacy and PD Studies

Example 24, formulated in 10% DMSO, 10% Solutol HS15, 80% water, was dosed orally to 7-9 weeks female BALB/c nude mice (Vital River Co., LTD.) in v at 30 mg/kg (dosing volume of 10 ml/kg) once daily for 14 days. Terminal tissue and blood harvest was performed at 6 hours after post last dose of test articles, using 4 mice per group. In brief, whole blood was collected into K2-EDTA tubes and subjected to centrifugation to separate plasma. Brains were collected, rinsed, and homogenized. Mice Brain were analyzed using qPCR using DUSP6 and ACTB TaqMan probes (ABI-4369016, ABI-4351370).

Murine studies were conducted at the WuXi AppTec and were performed in compliance with all applicable regulations and guidelines of the Institutional Animal Care and Use Committee (IACUC). Mice were maintained in a special pathogen-free environment and in individual ventilation cages, and food and water will be sterilized before use. 8 to 9 weeks female NU/NU nude mice (Charles River Lab.) were implanted intracarotid injection with 0.5×105 NCI-H1373-Luc cells in 100 µL serum-free media. When bioluminescence reached a mean of 1.28E+08 photons/second (range of 5.79E+07-2.685E+08 photons/second) at day 15 post inoculation, tumor-bearing mice were randomized into different groups with 4 mice in each group. The randomization date was denoted as treatment day 0. Afterwards, oral daily dosing of vehicle or Example 24 began and continued for 14 days. Baseline bioluminescent imaging (BLI) began 24 hours prior to initial dosing with vehicle or test articles,

TABLE 5 cell viability in mutant cells with KRAS G12C and other mutations

|  | G12C + V8A, $IC_{50}$ (nM) | G12C + V9Y, $IC_{50}$ (nM) | G12C + S17E, $IC_{50}$ (nM) | G12C + A59T, $IC_{50}$ (nM) | G12C + T58I, $IC_{50}$ (nM) | G12C + D69P, $IC_{50}$ (nM) | G12C + S65W, $IC_{50}$ (nM) | G12C + R68S, $IC_{50}$ (nM) | G12C + M72I, $IC_{50}$ (nM) | G12C + D92R, $IC_{50}$ (nM) | G12C + H95N, $IC_{50}$ (nM) | G12C + Y96D, $IC_{50}$ (nM) | G12C + Q99W, $IC_{50}$ (nM) | G12C + F156L, $IC_{50}$ (nM) |
|---|---|---|---|---|---|---|---|---|---|---|---|---|---|---|
| Example 24 | 1 | 1 | 3 | 6 | 2 | 0 | 1 | 2 | 1 | 2 | 1 | 2 | 5 | 1 |
| Example 73 | 1 | 1 | 1 | 4 | 2 | 1 | 1 | 2 | / | 2 | 1 | 2 | 3 | 2 | and additional imaging time points for all animals were measured twice a week by Xenogen machine (PerkinElmer IVIS Lumina II) between 0-14 days post grouping. Animals were injected intraperitoneally with luciferin (150 mg/kg, 0.01 mL/g) based on body weight and pre-anesthetized using 1%-2% isoflurane in oxygen at 1-2 L/minute, the animals were moved into the imaging chamber for bioluminescence measurements with IVIS in a complete anesthetic state. Images were acquired beginning at 15 minutes after luciferin injection.

Data Analysis of Efficacy Studies

For imaging analysis, region of interest (ROI) analysis was completed on BLI (bioluminescence imaging) images using Living image software. BLI images were generated by overlaying BLI signals for each animal onto their respective white-light images for anatomic reference. Brain ROIs were generated using a fixed-area circle, and were placed on the basis of the BLI signal in the relevant area, using the photographic anatomical reference images. BLI signals in images were scaled in units of radiance (photons per second per square millimeter per steradian). The BLI density was then used for calculations of T/C value. The T/C value (in percent) is an indication of antitumor effectiveness; T and C are the mean volumes of the treated and control groups, respectively, on a given day.

TGI (tumor growth inhibition) was calculated for each group using the formula: TGI (%)=[1−(Ti−T0)/(Vi−V0)]×100; Ti is the average tumor bioluminescence of a treatment group on a given day, T0 is the average tumor bioluminescence of the treatment group on the day of treatment start, Vi is the average tumor bioluminescence of the vehicle control group on the same day with Ti, and V0 is the average tumor bioluminescence of the vehicle group on the day of treatment start.

Summary statistics, including mean and the standard error of the mean (SEM), were provided for the tumor volume of each group at each time point. Statistical analysis of difference in tumor volume among the groups was conducted using the data obtained on day 14 (Intracranial inoculation). To compare individual groups of interest, data were analyzed using Student's One-tailed t test by Prism GraphPad 9.5.1 software. Statistical comparisons between two groups were considered significant when the adjusted P value was below 0.05.

Data Analysis for DUSP6

All the targets mRNA expression levels were normalized to the housekeeping gene, and the data were represented as fold-changes according to the 2-ΔΔCt method, where ΔCt-Ct target gene-Ct housekeeping gene and ΔΔCt=ΔCt treatment-ΔCt reference, ΔCt reference was chosen as the vehicle group. The data were interpreted by GraphPad Prism, and statistical analysis of difference in the each targets mRNA expression among the groups were conducted. For comparison between two groups, an independent sample t-test will be used. For comparison among three or more groups, a one-way ANOVA (Dunnett's multiple comparisons test) will be performed, p<0.05 was considered to be statistically significant.

Results

Figure 2:
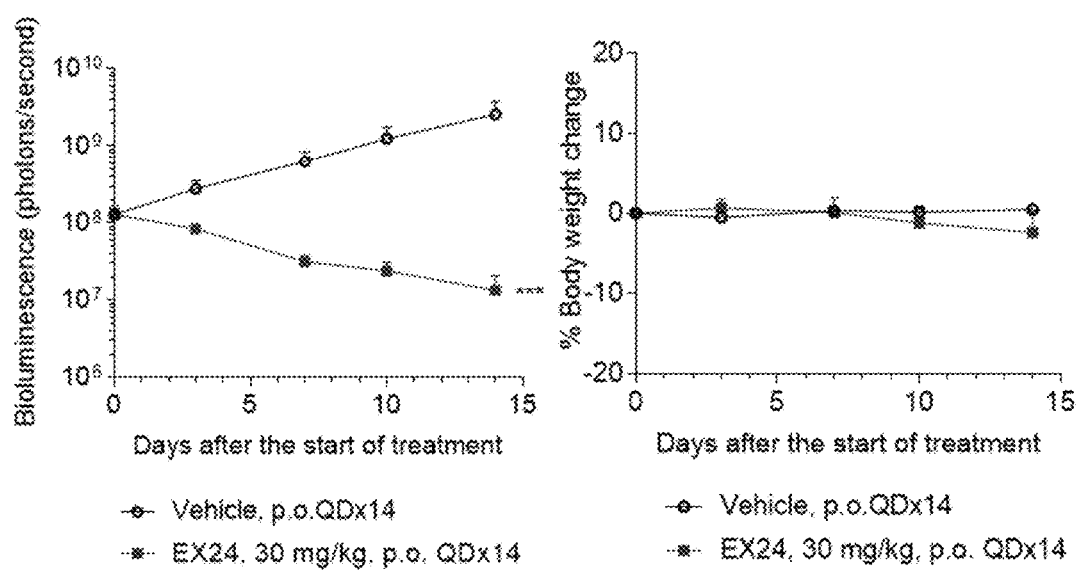
FIG. 2. Bioluminescence signal changes and body weight change after administering vehicle or test articles to female BALB/c nude mice bearing NCI-H1373-luc intracranial tumors. Data points represent mean±SEM.
Figure 3:
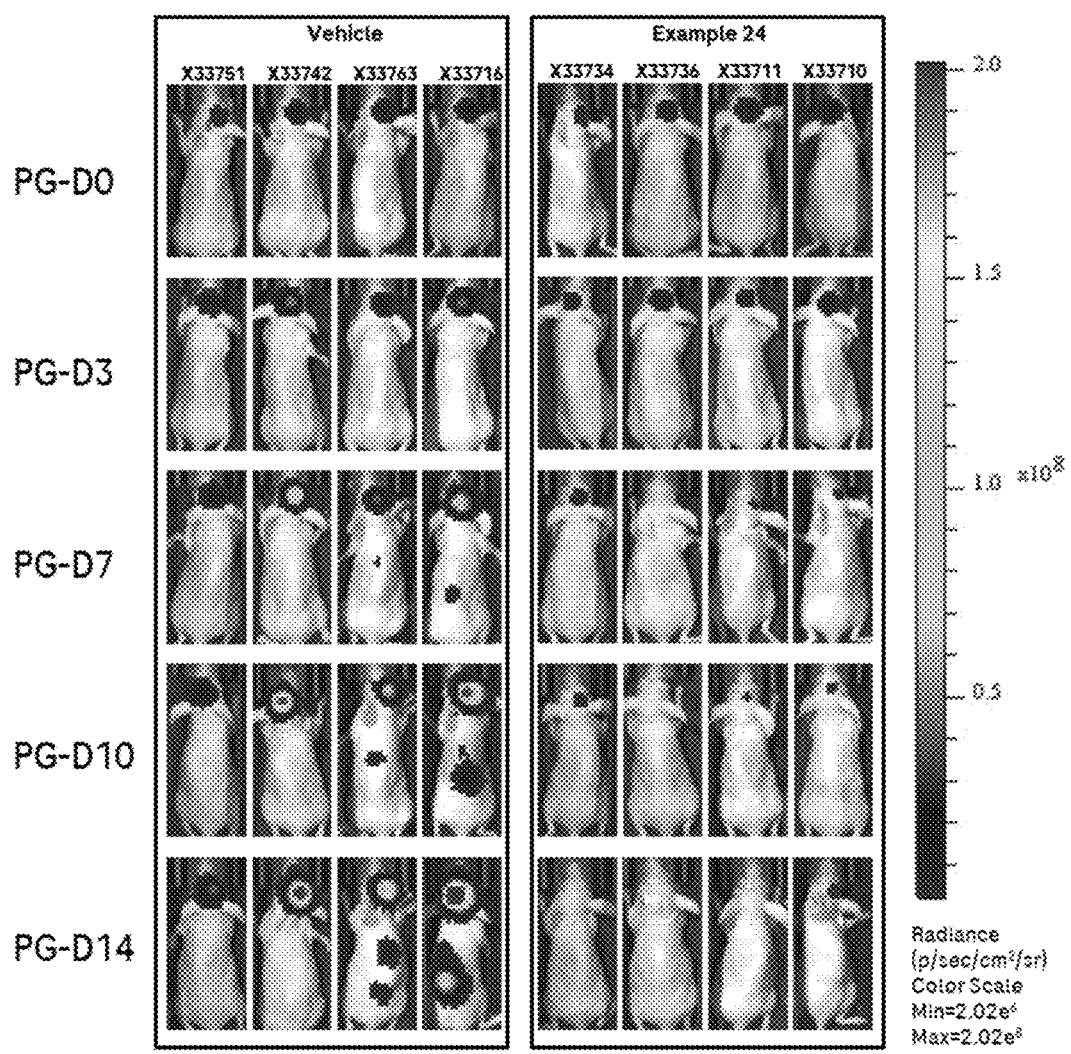
FIG. 3. Tumor bioluminescence picture of each group from FIG. 2.
Figure 4:
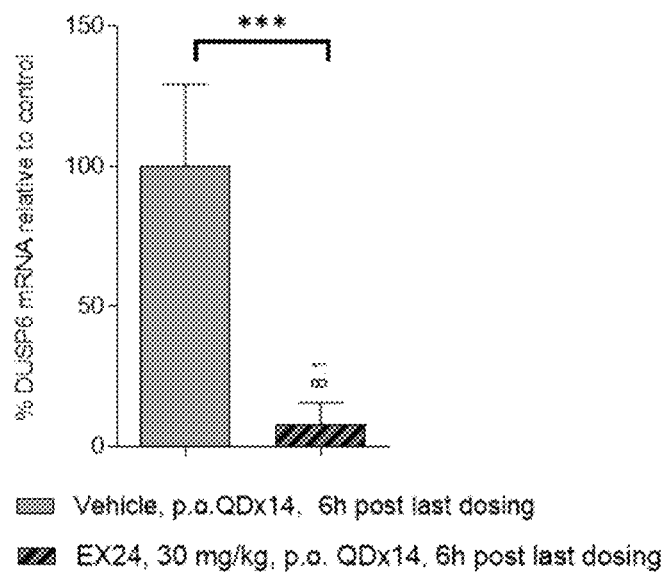
FIG. 4. DUSP6 express levels in brain samples of NCI-H1373-luc intracranial tumor model from FIG. 2. All data were analyzed using Prism GraphPad software. *** indicates p<0.001. Error bars represented Standard Error of Mean (SEM).

The result below showed significant inhibition of brain tumor growth (Table 6), meanwhile mice were well tolerated with no sign of overt toxicity or animal weight loss (FIG. 2 and FIG. 3). In line with these potent anti-BM effects, Example 24 significantly decreased MAPK activation (DUSP6) in the brain of the NCI-H1373-Luc model, providing critical on-target pharmacodynamic evidence (FIG. 4). Together, these data demonstrated target pathway inhibition and tumor regression in NSCLC BM mouse models treated with an efficacious dose of Example 24.

TABLE 6

Tumor growth inhibition analysis (T/C and TGI on day 14)

| Treatment | ROI ($\times 10^7$ photon/s) | T/C (%) | TGI (%) | p value (vs. Vehicle, t-test, One-tailed) |
|---|---|---|---|---|
| Vehicle | 259.21 ± 116.10 | — | — | — |
| Example 24 30 mg/kg, PO, QD | 1.34 ± 0.75 | 0.52 | 104.68 | p < 0.05 |

Example 135

Cell Viability Assay

The purpose of this cellular assay was to determine the effects of test compounds on the proliferation of human cancer cell lines NCI-H358 (ATCC-CRL5807) cells, AGS (ATCC-CRL-1739) cells, SW620 (ATCC-CCL-227) over a 3-day treatment period by quantifying the amount of NADPH present at endpoint using Cell Counting Kit-8.

Cells were seeded at 5,000 cells/well (NCI-H358), 2,000 cells/well (AGS) 2,000 cells/well (SW620) in 96-well assay plates (Corning-3699) and incubated overnight. On the day of the assay, diluted compounds were then added in a final concentration of 0.5% DMSO. After 72 hrs incubation, a tenth of the volume of cell counting kit 8 (Dnjindo-CK04) was added into each well. Read the signal (OD450 minus OD650) using EnVision after 2 hrs incubation. $IC_{50}$ was determined by fitting a 4-parameter sigmoidal concentration response model.

TABLE 7

Activity of Examples and Compounds of present invention in KRAS Cell viability assay

| Example | G12C $IC_{50}$ (nM) | G12D $IC_{50}$ (nM) | G12V $IC_{50}$ (nM) |
|---|---|---|---|
| Example 1 | 2.7 | 42.2 | 2.7 |
| Example 2 | 10.1 | 29.9 | 1.2 |
| Example 5 | 17.3 | 70.0 | 4.6 |
| Example 6 | 3.0 | 19.4 | 1.6 |
| Example 7 | 2.4 | 13.1 | 0.8 |
| Example 8 | 5.9 | 18.7 | 1.1 |
| Example 9 | 2.8 | 7.6 | <0.6 |
| Example 10 | 2.2 | 4.6 | <0.6 |
| Example 11 | 18.8 | 38.4 | 2.4 |
| Example 12 | 12.5 | 25.0 | 2.0 |
| Example 13 | 6.4 | 23.0 | 0.7 |
| Example 14 | 3.6 | 17.5 | 1.0 |
| Example 15 | 6.6 | 15.9 | 1.2 |
| Example 16 | 7.3 | 25.9 | 1.6 |
| Example 17 | 10.3 | 21.7 | 1.1 |
| Example 18 | 18.0 | 54.5 | 2.9 |
| Example 19 | 17.1 | 98.7 | 3.8 |
| Example 21 | 15.3 | 56.2 | 1.9 |
| Example 22 | 3.1 | 14.2 | 0.8 |
| Example 24 | 1.3 | 4.7 | 0.3 |
| Example 25 | 6.7 | 32.6 | 1.8 |
| Example 28 | 7.0 | 22.3 | 1.5 |
| Example 29 | 2.5 | 11.4 | 0.8 |
| Example 30 | 4.9 | 23.4 | 1.3 |
| Example 31 | 3.1 | 21.8 | <0.6 |
| Example 33 | 32.3 | 100.5 | 7.4 |
| Example 34 | 4.7 | 12.4 | 1.1 |
| Example 35 | 4.3 | 13.0 | 1.0 |
| Example 37 | 7.8 | 28.3 | 2.1 |
| Example 38 | 89.4 | 119.6 | 18.0 |
| Example 40 | 3.0 | 11.8 | 0.8 |

TABLE 7-continued

Activity of Examples and Compounds of present invention in KRAS Cell viability assay

| Example | G12C $IC_{50}$ (nM) | G12D $IC_{50}$ (nM) | G12V $IC_{50}$ (nM) |
|---|---|---|---|
| Example 41 | 3.6 | 14.0 | 0.9 |
| Example 42 | 5.4 | 22.4 | 1.3 |
| Example 43 | 3.6 | 11.9 | 0.9 |
| Example 44 | 16.8 | 33.9 | 3.1 |
| Example 45 | 1.8 | 3.6 | 0.2 |
| Example 46 | 8.1 | 32.2 | 2.4 |
| Example 47 | 2.5 | 10.2 | 0.9 |
| Example 48 | 9.5 | 26.5 | 1.7 |
| Example 49 | 9.7 | 29.1 | 1.7 |
| Example 50 | 24.1 | 72.6 | 3.8 |
| Example 51 | 5.9 | 13.3 | 1.4 |
| Example 52 | 7.0 | 12.0 | 1.1 |
| Example 54 | 12.1 | 36.8 | 3.0 |
| Example 55 | 48.3 | 69.1 | 5.6 |
| Example 56 | 1.2 | 5.2 | 0.3 |
| Example 57 | 5.4 | 27.6 | 1.5 |
| Example 58 | 7.6 | 38.5 | 2.0 |
| Example 59 | 33.7 | 87.2 | 7.4 |
| Example 60 | 8.2 | 32.0 | 1.7 |
| Example 61 | 22.6 | 33.4 | 3.0 |
| Example 63 | 10.6 | 78.0 | 4.2 |
| Example 64 | 8.0 | 21.9 | 1.3 |
| Example 68 | 3.2 | 7.8 | 0.5 |
| Example 69 | 19.2 | 75.4 | 4.4 |
| Example 70 | 24.7 | 98.7 | 17.9 |
| Example 73 | 2.2 | 7.4 | 0.3 |
| Example 75 | 20.2 | 58.7 | 3.6 |
| Example 76 | 2.1 | 4.9 | 0.3 |
| Example 78 | 9.8 | 30.6 | 2.3 |
| Example 79 | 13.2 | 57.0 | 3.2 |
| Example 81 | 5.3 | 23.4 | 0.8 |
| Example 83 | 3.1 | 9.2 | 0.5 |
| Example 85 | 9.0 | 13.0 | 1.0 |
| Example 86 | 14.1 | 45.2 | 2.5 |
| Example 87 | 30.0 | 58.0 | 4.0 |
| Example 88 | 2.0 | 4.0 | 0.4 |
| Example 89 | 1.5 | 6.0 | 0.3 |
| Example 90 | 3.3 | 16.8 | 0.8 |
| Example 91 | 2.8 | 9.7 | 0.6 |
| Example 92 | 2.5 | 8.8 | 0.7 |
| Example 93 | 3.0 | 5.0 | 1.0 |
| Example 94 | 2.3 | 6.9 | 0.5 |
| Example 95 | 4.0 | 8.7 | 1.3 |
| Example 96 | 1.0 | 1.7 | 0.2 |
| Example 97 | 1.9 | 2.6 | 0.3 |
| Example 98 | 4.0 | 8.1 | 0.6 |
| Example 99 | 2.1 | 7.8 | 0.4 |
| Example 100 | 2.7 | 8.2 | 0.7 |
| Example 101 | 1.8 | 6.9 | 0.3 |
| Example 102 | 1.2 | 4.9 | 0.4 |
| Example 103 | 1.3 | 5.2 | 0.4 |
| Example 104 | 0.8 | 3.8 | 0.2 |
| Example 105 | 1.5 | 6.8 | 0.6 |
| Example 106 | 4.4 | 8.7 | 0.4 |
| Example 107 | 8.4 | 5.4 | 1.2 |
| Example 108 | 2.2 | 1.8 | 0.5 |
| Example 109 | 2.8 | 5.1 | 0.6 |
| Example 110 | 1.8 | 2.6 | 0.4 |
| Example 111 | 1.0 | 0.8 | 0.2 |
| Example 112 | 2.2 | 3.4 | 0.8 |
| Example 113 | 2.1 | 1.5 | 0.3 |
| Example 114 | 4.5 | 5.1 | 1.3 |
| Example 115 | 1.7 | 3.4 | 0.4 |
| Example 116 | 1.4 | 3.5 | 0.5 |
| Example 117 | 1.5 | 2.5 | 0.2 |
| Example 118 | 1.1 | 1.3 | 0.2 |
| Example 119 | 3.5 | 4.4 | 0.8 |
| Example 120 | 1.4 | 2.2 | 0.4 |
| Example 121 | 1.6 | 2.4 | 0.3 |
| Example 122 | 1.8 | 3.4 | 0.5 |
| Example 123 | 3.0 | 5.1 | 0.6 |
| Example 124 | 8.9 | 13.8 | 1.6 |
| Example 125 | 1104 | 4716 | 208 |
| Example 126 | 40 | 757 | 7.0 |
| Example 127 | 1000 | 1000 | 27 |

Example 136

KRAS-BRAF with CYPA (500 nM) Interaction Assay

In this example, TR-FRET was also used to measure the compound or compound-CYPA dependent disruption of the KRAS G12C-BRAF complex. This protocol was also used to measure disruption of KRAS G12D or KRAS G12V binding to BRAF by a compound of the invention, respectively. In assay buffer containing 25 mM HEPES PH=7.4 (4-(2-hydroxyethyl)-1-piperazineethanesulfonic acid, Thermo, 15630080), 0.002% Tween20, 0.1% BSA, 100 mM NaCl, 5 mM $MgCl_2$, 10 μM GMPPNP (Guanosine 5'-[β,γ-imido]triphosphate trisodium salt hydrate, Sigma, G0635), tagless CYPA, GMPPNP loaded 6His-KRAS proteins, and GST-BRAF$^{RBD}$ were mixed in a well of a 384-well assay plate at final concentrations of 50 nM, 6.25 nM and 1 nM, respectively. Compound was present in plate wells as a 16-point 3-fold dilution series starting at a final concentration of 10 μM and incubated for 3 hours. A mixture of MAb Anti-6His-XL665 (Cisbio, 61HISXLB) and Mab anti-GST-TB cryptate (Cisbio, 61GSTTLB) was then added at a final concentration of 6.67 nM and 0.21 nM, respectively, and the plate was incubated for an additional 1.5 hours. TR-FRET signal was read on a PHERstar FSX microplate reader (Ex320 nm, Em 665/615 nm). Compounds that facilitate disruption of the KRAS-BRAF complex were identified as those eliciting a decrease in the TR-FRET ratio relative to DMSO control wells.

TABLE 8

Activity of Examples and Compounds of present invention in KRAS-BRAF with CYPA (500 nM) interaction assay

| Example | G12C $IC_{50}$ (nM) | G12D $IC_{50}$ (μM) | G12V $IC_{50}$ (μM) |
|---|---|---|---|
| Example 1 | 14.9 | 121.3 | 21.0 |
| Example 2 | 28.8 | 119.9 | 43.0 |
| Example 3 | 31.4 | 293.6 | 38.5 |
| Example 5 | 34.8 | 205.1 | 39.3 |
| Example 6 | 11.1 | 61.2 | 15.5 |
| Example 7 | 9.4 | 57.7 | 18.6 |
| Example 8 | 23.7 | 66.9 | 37.9 |
| Example 9 | 21.1 | 80.3 | 26.8 |
| Example 10 | 5.9 | 24.4 | 8.1 |
| Example 11 | 12.4 | 31.2 | 18.7 |
| Example 12 | 12.0 | 31.0 | 15.6 |
| Example 13 | 1.5 | 15.8 | 2.8 |
| Example 14 | 22.2 | 217.0 | 26.1 |
| Example 15 | 11.9 | 68.2 | 13.6 |
| Example 16 | 10.2 | 40.7 | 14.9 |
| Example 17 | 25.4 | 89.2 | 46.2 |
| Example 18 | 14.7 | 277.8 | 20.6 |
| Example 21 | 15.0 | 372.3 | 26.8 |
| Example 22 | 6.4 | 295.3 | 16.6 |
| Example 24 | 9.7 | 49.5 | 7.1 |
| Example 25 | 32.6 | 144.8 | 36.7 |
| Example 28 | 53.8 | 351.8 | 62.3 |
| Example 29 | 12.7 | 66.2 | 8.9 |
| Example 30 | 17.2 | 78.3 | 16.8 |
| Example 33 | 19.5 | 110.7 | 25.7 |

TABLE 8-continued

Activity of Examples and Compounds of present invention in
KRAS-BRAF with CYPA (500 nM) interaction assay

| Example | G12C IC$_{50}$ (nM) | G12D IC$_{50}$ (µM) | G12V IC$_{50}$ (µM) |
|---|---|---|---|
| Example 34 | 31.8 | 117.3 | 49.8 |
| Example 35 | 14.5 | 54.5 | 20.9 |
| Example 37 | 20.5 | 175.0 | 15.8 |
| Example 40 | 13.0 | 47.1 | 14.3 |
| Example 41 | 23.8 | 298.7 | 30.0 |
| Example 42 | 20.5 | 71.3 | 22.8 |
| Example 45 | 14.1 | 57.6 | 16.5 |
| Example 47 | 21.2 | 173.0 | 44.5 |
| Example 48 | 4.4 | 30.0 | 7.8 |
| Example 49 | 17.5 | 69.0 | 41.1 |
| Example 50 | 22.0 | 214.5 | 30.5 |
| Example 51 | 21.1 | 77.1 | 39.2 |
| Example 52 | 16.1 | 38.3 | 20.8 |
| Example 53 | 65.7 | 170.6 | 99.1 |
| Example 54 | 23.3 | 173.3 | 57.7 |
| Example 55 | 23.6 | 88.5 | 28.3 |
| Example 56 | 10.3 | 74.4 | 26.7 |
| Example 57 | 8.0 | 77.1 | 24.8 |
| Example 58 | 14.0 | 111.2 | 17.7 |
| Example 59 | 16.7 | 394.5 | 32.6 |
| Example 60 | 15.2 | 65.8 | 22.2 |
| Example 61 | 50.9 | 465.6 | 58.2 |
| Example 63 | 34.0 | 166.9 | 38.8 |
| Example 64 | 17.2 | 73.2 | 25.4 |
| Example 65 | 51.3 | 424 | 87.8 |
| Example 66 | 50.5 | 157.9 | 53.2 |
| Example 68 | 16.8 | 45.1 | 15.1 |
| Example 69 | 35.7 | 432.6 | 47.8 |
| Example 71 | 28.9 | 162.1 | 48.8 |
| Example 72 | 31.5 | 135.1 | 48.0 |
| Example 73 | 8.9 | 44.4 | 7.2 |
| Example 75 | 29.7 | 355.9 | 19.1 |
| Example 76 | 9.1 | 107.5 | 9.8 |
| Example 77 | 41.8 | 259.7 | 80.6 |
| Example 81 | 30.5 | 179.2 | 45.8 |
| Example 83 | 10.3 | 81.9 | 13.9 |
| Example 85 | 18.8 | 116.8 | 12.0 |
| Example 86 | 17.9 | 93.2 | 20.4 |
| Example 87 | 32.6 | 653.1 | 34.0 |
| Example 88 | 9.7 | 51.1 | 16.3 |
| Example 89 | 6.0 | 36.8 | 14.2 |
| Example 90 | 6.4 | 466.2 | 13.9 |
| Example 91 | 8.1 | 52.8 | 10.4 |
| Example 92 | 16.0 | 93.4 | 25.9 |
| Example 93 | 14.8 | 43.2 | 19.8 |
| Example 94 | 6.9 | 50.4 | 14.6 |
| Example 95 | 13.7 | 76.6 | 24.1 |
| Example 96 | 9.4 | 42.2 | 16.0 |
| Example 97 | 14.4 | 49.5 | 19.5 |
| Example 98 | 11.1 | 47.3 | 20.8 |
| Example 99 | 12.6 | 51.8 | 17.2 |
| Example 100 | 33.1 | 205.4 | 39.8 |
| Example 101 | 5.4 | 41.3 | 4.5 |
| Example 102 | 6.5 | 72.3 | 10.9 |
| Example 103 | 6.0 | 71.1 | 11.2 |
| Example 104 | 9.8 | 103.0 | 22.1 |
| Example 105 | 13.3 | 98.5 | 23.6 |
| Example 106 | 10.8 | 41.8 | 8.7 |
| Example 107 | 47.6 | 260.0 | 74.5 |
| Example 108 | 4.6 | 47.6 | 5.6 |
| Example 109 | 6.0 | 42.8 | 7.5 |
| Example 110 | 4.9 | 37.5 | 6.1 |
| Example 111 | 4.7 | 51.4 | 7.4 |
| Example 112 | 10.4 | 138.4 | 22.2 |
| Example 113 | 4.3 | 38.0 | 5.6 |
| Example 114 | 8.9 | 64.3 | 14.0 |
| Example 115 | 18.5 | 176.8 | 25.6 |
| Example 116 | 20.6 | 244.7 | 31.8 |
| Example 117 | 15.9 | 94.0 | 14.4 |
| Example 118 | 13.5 | 79.8 | 13.4 |
| Example 119 | 9.3 | 70.4 | 9.5 |
| Example 120 | 20.4 | 125.8 | 25.3 |
| Example 121 | 13.0 | 78.4 | 12.0 |
| Example 122 | 15.1 | 77.2 | 13.5 |
| Example 123 | 13.7 | 78.8 | 12.6 |
| Example 124 | 16.2 | 112.5 | 19.3 |
| Example 125 | 463 | 10000 | 1525 |
| Example 126 | 151 | 3346 | 465 |
| Example 127 | 1619 | 10000 | 3554 |

Example 137

PERK Inhibition Assay

This assay is to measure the ability of test compounds in inhibiting the phosphorylation of ERK, the downstream signaling of KRAS G12C in NCI-H358 cells, KRAS G12D in AGS cells, and KRAS G12V in SW620. NCI-H358 (ATCC-CRL5807) cells, AGS (ATCC-CRL-1739) cells, SW620 (ATCC-CCL-227) cells were all grown and maintained using RPMI-1640 medium (Thermo Fisher Scientific) with 10% fetal bovine serum and 1% penicillin/streptomycin. On the day prior to compound addition, cells were plated in tissue culture-treated 96 well plates (Corning-3699) at a density of 30,000 cell/well, 20,000 cell/well, 30,000 cell/well for NCI-H358, AGS and SW620 respectively, and allowed for attachment overnight. Diluted compounds were then added in a final concentration of 0.5% DMSO. After 4 hours of incubation, the medium was removed, 100 µL of 4% formaldehyde was added, and the assay plates were incubated at room temperature for 20 minutes. The plates were then washed once with phosphate buffered saline (PBS), and permeabilized with 100 µL of chilled methanol for 10 minutes. Non-specific antibody binding to the plates was blocked using 50 µL 1×BSA blocking buffer (Thermo-37520, 10-fold dilution by Phosphate-Buffered Saline Tween (PBST) for at least 1 hour at room temperature.

The amount of phosphor-ERK was determined using an antibody specific for phosphorylated form of ERK. Primary antibody (PERK, CST-4370, Cell Signaling Technology) was diluted 1:300 in blocking buffer, with 50 µL aliquoted to each well, and incubated overnight at 4° C. Cells was washed five times for 5 minutes with PBST. Secondary antibody (HRP-linked anti-rabbit IgG, CST-7074, Cell Signaling Technology) was diluted 1:1000 in blocking buffer, and 50 µL was added to each well and incubated 1-2 hrs at room temperature. Cells was washed times for 5 minutes with PBST, 100 µL TMB ELISA substrate (abcam-ab171523) were added and gently shake for 20 minutes. 50 µL stop solution (abcam-ab171529) were added, and then read the signal (OD450) by EnVision.

IC$_{50}$ was determined by fitting a 4-parameter sigmoidal concentration response model.

TABLE 9

Activity of Examples and Compounds of present
invention in KRAS pERK inhibition assay

| Example | G12C IC$_{50}$ (nM) | G12D IC$_{50}$ (nM) | G12V IC$_{50}$ (nM) |
|---|---|---|---|
| Example 1 | 3.2 | 10.2 | 1.5 |
| Example 2 | 3.4 | 3.0 | 1.4 |
| Example 3 | 5.1 | 24.3 | 3.6 |
| Example 5 | 6.2 | 21.2 | 2.8 |
| Example 6 | 1.4 | 5.6 | 0.8 |
| Example 7 | 1.6 | 7.9 | 1.2 |

TABLE 9-continued

Activity of Examples and Compounds of present invention in KRAS pERK inhibition assay

| Example | G12C IC$_{50}$ (nM) | G12D IC$_{50}$ (nM) | G12V IC$_{50}$ (nM) |
|---|---|---|---|
| Example 8 | 2.6 | 7.1 | 1.2 |
| Example 9 | 2.3 | 1.8 | 0.8 |
| Example 10 | 3.3 | 1.4 | 1.2 |
| Example 11 | 5.1 | 2.9 | 0.8 |
| Example 12 | 3.8 | 2.2 | 1.2 |
| Example 13 | 3.0 | 10.8 | 1.5 |
| Example 14 | 0.8 | 5.6 | 0.7 |
| Example 15 | 0.7 | 5.2 | 0.8 |
| Example 16 | 4.6 | 2.6 | 2.8 |
| Example 17 | 2.9 | 2.7 | 1.8 |
| Example 18 | 16.8 | 7.7 | 7.4 |
| Example 19 | 1.9 | 20.7 | 2.7 |
| Example 21 | 2.1 | 8.8 | 1.4 |
| Example 22 | 0.6 | 3.8 | 0.7 |
| Example 24 | <0.6 | 0.9 | <0.6 |
| Example 25 | 1.0 | 11.3 | 0.8 |
| Example 28 | 1.2 | 9.4 | 1.3 |
| Example 29 | <0.6 | 1.6 | <0.6 |
| Example 30 | 1.3 | 7.3 | <0.6 |
| Example 31 | 2.3 | 19.8 | 1.6 |
| Example 33 | 8.5 | 23.1 | 2.7 |
| Example 34 | <0.6 | 4.6 | <0.6 |
| Example 35 | 1.0 | 4.7 | <0.6 |
| Example 37 | 0.9 | 9.1 | 0.6 |
| Example 38 | 8.0 | 59.4 | 5.5 |
| Example 40 | 0.6 | 5.6 | 0.4 |
| Example 41 | 0.4 | 4.8 | 0.4 |
| Example 42 | 0.9 | 8.1 | 1.4 |
| Example 43 | 0.7 | 3.8 | 0.3 |
| Example 44 | 2.1 | 9.1 | 1.4 |
| Example 45 | 0.6 | 2.1 | 0.2 |
| Example 46 | 0.9 | 9.1 | 1.0 |
| Example 47 | 1.2 | 4.8 | 1.4 |
| Example 48 | 1.2 | 10.1 | 1.0 |
| Example 49 | 2.4 | 13.7 | 1.3 |
| Example 50 | 3.5 | 20.1 | 2.4 |
| Example 51 | 1.0 | 4.8 | 0.7 |
| Example 52 | 1.4 | 5.1 | 0.7 |
| Example 53 | 21.2 | 176.0 | 24.5 |
| Example 54 | 1.3 | 8.8 | 1.0 |
| Example 55 | 4.9 | 18.1 | 3.1 |
| Example 56 | 0.8 | 2.7 | 0.6 |
| Example 57 | 1.1 | 6.1 | 1.3 |
| Example 58 | 6.4 | 20.5 | 4.9 |
| Example 59 | 8.8 | 21.3 | 3.0 |
| Example 60 | 2.3 | 8.2 | 0.9 |
| Example 61 | 8.5 | 10.3 | 1.1 |
| Example 63 | 5.1 | 18.3 | 3.0 |
| Example 64 | 1.2 | 3.7 | 0.6 |
| Example 65 | 2.3 | 31.7 | 5.0 |
| Example 66 | 2.6 | 40.2 | 3.3 |
| Example 67 | 2.4 | 31.8 | 3.2 |
| Example 68 | 0.2 | 3.9 | 0.3 |
| Example 69 | 1.5 | 11.3 | 1.5 |
| Example 70 | 1.8 | 27.9 | 5.5 |
| Example 71 | 3.6 | 51.5 | 6.5 |
| Example 72 | 2.3 | 41.5 | 4.8 |
| Example 73 | 0.7 | 4.5 | 0.4 |
| Example 75 | 4.9 | 23.6 | 2.6 |
| Example 76 | 0.7 | 3.9 | 0.2 |
| Example 77 | 4.4 | 26.1 | 4.0 |
| Example 78 | 2.0 | 10.1 | 1.1 |
| Example 79 | 1.6 | 16.2 | 1.4 |
| Example 80 | 5.1 | 47.4 | 4.2 |
| Example 81 | 1.6 | 6.5 | 1.2 |
| Example 83 | 0.9 | 6.0 | 0.5 |
| Example 85 | 1.7 | 5.6 | 0.6 |
| Example 86 | 1.8 | 15.0 | 0.8 |
| Example 87 | 4.8 | 40.6 | 1.5 |
| Example 88 | 0.3 | 1.4 | 0.2 |
| Example 89 | 0.6 | 4.8 | 0.4 |
| Example 90 | 1.7 | 9.4 | 0.6 |
| Example 91 | 0.5 | 3.2 | 0.6 |
| Example 92 | 1.4 | 6.0 | 1.0 |
| Example 93 | 1.2 | 3.5 | 1.2 |
| Example 94 | 0.4 | 2.4 | 0.4 |
| Example 95 | 0.5 | 3.4 | 0.4 |
| Example 96 | 0.4 | 1.2 | 0.4 |
| Example 97 | 0.4 | 1.4 | 0.3 |
| Example 98 | 0.9 | 4.6 | 0.5 |
| Example 99 | 0.5 | 1.9 | 0.4 |
| Example 100 | 1.0 | 4.1 | 0.7 |
| Example 101 | 0.9 | 2.6 | 0.2 |
| Example 102 | 1.1 | 2.0 | 0.7 |
| Example 103 | 0.7 | 2.4 | 0.7 |
| Example 104 | 1.0 | 1.6 | 0.4 |
| Example 105 | 1.5 | 2.2 | 0.4 |
| Example 106 | 1.1 | 3.1 | 0.4 |
| Example 107 | 2.7 | 7.4 | 1.5 |
| Example 108 | 1.8 | 3.9 | 0.5 |
| Example 109 | 0.9 | 4.1 | 0.3 |
| Example 110 | 0.7 | 2.6 | 0.3 |
| Example 111 | 0.6 | 2.0 | 0.4 |
| Example 112 | 0.7 | 3.4 | 0.5 |
| Example 113 | 0.6 | 2.2 | 0.4 |
| Example 114 | 1.2 | 7.5 | 1.0 |
| Example 115 | 0.8 | 2.6 | 0.2 |
| Example 116 | 0.8 | 4.6 | 0.7 |
| Example 117 | 0.7 | 4.1 | 0.3 |
| Example 118 | 0.7 | 3.5 | 0.3 |
| Example 119 | 1.7 | 6.9 | 1.2 |
| Example 120 | 1.1 | 2.9 | 0.9 |
| Example 121 | 0.9 | 3.4 | 0.3 |
| Example 122 | 0.6 | 3.5 | 0.2 |
| Example 123 | 0.8 | 7.1 | 0.6 |
| Example 124 | 1.4 | 15.7 | 0.7 |
| Example 125 | 303 | 481 | 84 |
| Example 126 | 5 | 50 | 3 |
| Example 127 | 30 | 697 | 30 |

Example 138 hERG Potassium Channel Assays for Non-Clinical Cardiac Safety Evaluation

The purpose of the test was to screen compounds for the activity on hERG channels as a non-clinical cardiac safety evaluation.

Advanced hERG experiments were performed at near-physiological temperature (34° C.) by HEKA EPC10 manual patch system (heka elektronik, EPC10 amplifier). The CHO cells (B'SYS GmbH) stably transfected hERG channel were initially held at −80 mV, depolarized to voltages between −40 mV (100 ms) to 20 mV (500 ms) to activate the hERG outward currents, and then repolarized to −40 mV (500 ms) to record the hERG tail currents, with an interpulse interval of 15 s. The recording environment included: Extracellular solution (in mM): 150 NaCl, 4 KCl, 1.2 CaCl$_2$), 1 MgCl$_2$ and 10 HEPES; pH adjusted to 7.2-7.4 with 5 M NaOH; Intracellular solution (in mM): 125 KCl, 10 NaCl, 5 EGTA, 10 HEPES, 0.1 Na$_2$GTP and 5 MgATP; pH adjusted to 7.2 with 1 M KOH. Current inhibitions in the presence of more than 4 concentrations in quadruplicate were used to fit hERG IC$_{50}$ by Graphpad prism V8.0.

Results from advanced hERG assay show that Example 24 exhibited a reduced inhibitory effect on hERG potassium channel compared to A122 and A252. The inhibitory concentration (IC$_{20}$) for Example 24 was 13.8 μM, which is 3-fold higher compared to A122 (IC$_{20}$ 4.6 M) or 4-fold higher compared to A252 (IC$_{20}$ 3.0 μM). This higher IC$_{20}$ suggests that Example 24 could have less concern regarding cardiovascular toxicity associated with hERG channel blockade.

TABLE 10

| | hERG test results | |
|---|---|---|
| | $IC_{50}$ (μM) | $IC_{20}$ (μM) |
| A252 | 11.0 | 3.0 |
| A122 | 16.9 | 4.6 |
| Example 24 | 63.7 | 13.8 |

Example 139

CYPA Binding Analysis by Surface Plasmon Resonance (SPR) Assay

The compounds of this invention created a tri-complex involving the active RAS protein and CYPA, necessitating the initial formation of a binary complex through the compound's interaction with CYPA. The stability of the drug-target complex, as indicated by its equilibrium dissociation constant ($K_D$), is thought to influence the length of target engagement, which in turn could lead to a prolonged effect in the washout experiments. Therefore, the objective of this study is to evaluate the binding kinetics of the compounds with CYPA to determine the stability of the CYPA-compound binary complex and to evaluate whether this stability correlates with the sustained inhibition of the target.

All SPR experiments were conducted on a Biacore 8K+ instrument (Cytiva). Recombinant biotinylated CYPA protein with a C-terminal AVI tag was purified and immobilized on flow cell 2 of SA chip (Cytiva, BR100531), with the flow cell 1 as the blank reference. The running buffer was HBS-P+ Buffer (Cytiva, BR100827, 0.01 M HEPES pH 7.4, 0.15 M NaCl, 0.05% v/v Surfactant P20), and the flow rate was 10 μL/min. The immobilization level was achieved to about 1800 response units (RU). Compounds were 3-fold serially diluted to 1.5-3333 nM using HBS-P+ Buffer with a final DMSO concentration of 1.5%, and then loaded to flow through the chip surface at a rate of 30 μL/min with HBS-P+ Buffer containing 1.5% DMSO as the running buffer. Experiments were performed at 25° C. The contact time and dissociation time were set to 60 s and 200 s, respectively. After binding and dissociation of each sample, the chip was regenerated using 1 M NaCl with a short contact time of 19 s at a rate of 60 μL/min. The sensorgrams were analyzed using Biacore Insight Evaluation software with 1:1 kinetics binding model to determine the association rate constant ($k_{on}$), dissociation rate constant ($k_{off}$) and equilibrium dissociation constant ($K_D$).

TABLE 11

| CYPA binding kinetics data in SPR assay | | | |
|---|---|---|---|
| Compound | $K_D$ (nM) | $k_{on}$ ($M^{-1}s^{-1}$) | $K_{off}$ ($s^{-1}$) |
| A122 | 30 | $1.9 \times 10^6$ | 0.056 |
| Example 24 | 13 | $1.4 \times 10^6$ | 0.019 |

The CYPA binding kinetics data in SPR assay showed that, compared to A122, Example 24 exhibited an obviously much higher binding affinity to CYPA (2.3-fold lower $K_D$) and an obviously much lower dissociation rate (2.9-fold lower $k_{off}$) that revealed a stronger stability of formed CYPA-compound binary complex. This result is consistent with the less potency shift of Example 24 observed in washout assay in Example 140.

Example 140

Washout Viability Assay:

The study aimed to investigate the relationship between the dynamics of target inhibition and its impact on cell proliferation by conducting in vitro washout experiments, with the understanding that thorough and persistent inhibition of the RAS-MAPK signaling pathway can be advantageous for achieving substantial efficacy.

Cancer cell lines NCI-H358, NCI-H2122, and SW480 (purchased from ATCC) were cultured in RPMI1640 (Thermo Fisher Scientific) medium plus 10% Fetal Bovine Serum (FBS, Thermo Fisher Scientific, 2.5 μg/mL puromycin and 1% Antibiotic-Antimycotic (Thermo Fisher Scientific) and plated at a density of 2,000 cells per well in 96-well assay plates (Corning-3699) and incubated overnight. On the assay day, compounds diluted to a final DMSO concentration of 0.5% were added to the wells. Following a 4-hour incubation period, the culture medium was removed, and the cells were washed three times with RPMI1640 medium only before being cultured in the abovementioned culture medium (RPMI1640+10% FBS+1% antibiotic-antimycotic). After 72 hours, a tenth of the volume of Cell Counting Kit-8 (Dojindo-CK04) was added to each well. The absorbance was measured (OD450 minus OD650) using an EnVision plate reader after a further 2-hour incubation. The $IC_{50}$ values were calculated by applying a four-parameter sigmoidal concentration-response curve fit to the data.

Table 12 summarizes the $IC_{50}$ values of Example 24 and A122 without or with washout. Without washout, Example 24 showed comparable or slightly higher potencies in individual cell lines in the anti-proliferation assay. Applying washout conditions, more precisely 4-hour compound treatment followed by three washing steps and after 72-hour viability assessment, mean $IC_{50}$ values increased for both compounds but differed in their extent. The $IC_{50}$ values of Example 24 shifted 5.6-, 1.3-, 6.7-fold, in NCI-H358, NCI-H2122, SW480 respectively, while the $IC_{50}$ values for A122 shifted by factors of 16.2-, 3.6-, 19.7-fold respectively.

Based on above comparison, Example 24 exhibited less potency shift after washout, in comparison to that of reference compound A122, with a more persistent cell growth inhibition which would be advantageous for achieving durable efficacy in clinic.

TABLE 12

| | IC50 shift in washout assay | | | | | |
|---|---|---|---|---|---|---|
| | NCI-H358 (KRAS G12C) | | NCI-H2122 (KRAS G12C) | | SW480 (KRAS G12V) | |
| | A122 | Example 24 | A122 | Example 24 | A122 | Example 24 |
| No-washout IC$_{50}$ (nM) | 2.0 | 1.0 | 8.0 | 6.7 | 2.4 | 1.3 |
| Washout IC$_{50}$ (nM) | 32.1 | 5.9 | 29.0 | 9.0 | 47.3 | 8.4 |
| IC$_{50}$ shift fold | 16.2 | 5.6 | 3.6 | 1.3 | 19.7 | 6.7 |

What is claimed is:

1. A compound of formula (Ib),

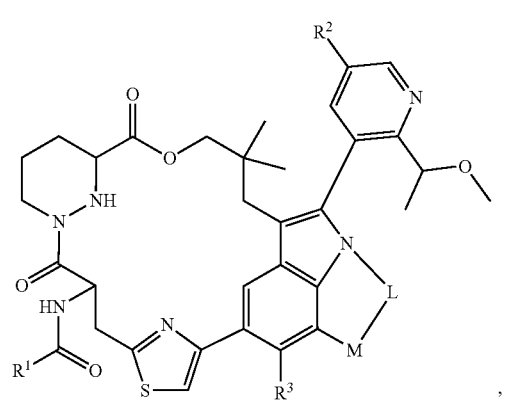

(Ib)

or a pharmaceutically acceptable salt thereof, wherein:
  $R^1$ is 2-oxabicyclo[2.1.1]hexanyl,
    3-oxabicyclo[3.1.0]hexanyl,
    6-bicyclo[3.1.0]hexanyl substituted twice by halogen,
    6-tricyclo[3.1.1.0$^{3,6}$]heptanyl,
    $C_{3-7}$cycloalkyl substituted by one, two, or three substituents independently selected from $C_{1-6}$alkyl, $C_{1-6}$alkylpyridinyl, $C_{1-6}$alkylpyrimidinyl, $C_{1-6}$alkyltetrazolyl, $C_{3-7}$cycloalkyl, haloC$_{1-6}$alkyl, halogen, halophenyl, hydroxy, phenyl, pyrazinyl, pyridazinyl, pyridinyl, pyrimidinyl, and thiazolyl, or tetrahydropyranyl;
  $R^2$ is 1,3,4,6,7,8,9,9a-octahydropyrido[1,2-a]pyrazinyl, 3,4,6,7,9,9a-hexahydro-1H-pyrazino[2,1-c][1,4]oxazinyl,
    morpholinyl, or
    piperazinyl unsubstituted or substituted by one or more substituents independently selected from $C_{1-6}$alkoxyC$_{1-6}$alkyl, $C_{1-6}$alkyl, $C_{3-7}$cycloalkyl, haloC$_{1-6}$alkyl, hydroxyC$_{1-6}$alkyl, morpholinylC$_{1-6}$alkyl, oxetanyl, oxopyrrolidinylC$_{1-6}$alkyl, and tetrahydrofuranyloxyC$_{1-6}$alkyl;
  $R^3$ is H or halogen;
  M is $C_{1-6}$alkylene or O; and
  L is $C_{1-6}$alkylene, hydroxyC$_{1-6}$alkylene, or haloC$_{1-6}$alkylene.

2. The compound of claim 1, or a pharmaceutically acceptable salt thereof, wherein:
  $R^1$ is $C_{3-7}$cycloalkyl substituted by one, two, or three substituents independently selected from $C_{1-6}$alkyl, $C_{1-6}$alkylpyridinyl, $C_{1-6}$alkylpyrimidinyl, $C_{1-6}$alkyltetrazolyl, $C_{3-7}$ cycloalkyl, haloC$_{1-6}$alkyl, halogen, halophenyl, hydroxy, phenyl, pyrazinyl, pyridazinyl, pyridinyl, pyrimidinyl, and thiazolyl; and
  $R^2$ is morpholinyl or
    piperazinyl unsubstituted or substituted by one substituent independently selected from $C_{1-6}$alkoxyC$_{1-6}$alkyl, $C_{1-6}$alkyl, $C_{3-7}$cycloalkyl, haloC$_{1-6}$alkyl, hydroxyC$_{1-6}$ alkyl, morpholinylC$_{1-6}$alkyl, oxetanyl, oxopyrrolidinylC$_{1-6}$alkyl, and tetrahydrofuranyloxyC$_{1-6}$alkyl.

3. The compound of claim 1, wherein the compound of formula (Ib) is a compound of formula (Ic):

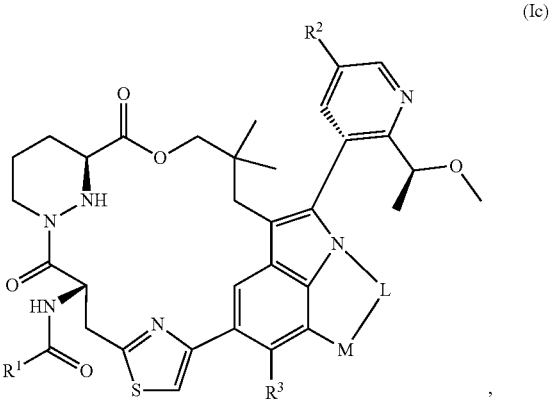

(Ic)

or a pharmaceutically acceptable salt thereof, wherein:
  $R^1$ is 2-oxabicyclo[2.1.1]hexanyl,
    3-oxabicyclo[3.1.0]hexanyl,
    6-bicyclo[3.1.0]hexanyl substituted twice by halogen,
    6-tricyclo[3.1.1.0$^{3,6}$]heptanyl,
    $C_{3-7}$cycloalkyl substituted by one, two, or three substituents independently selected from $C_{1-6}$alkyl, $C_{1-6}$alkylpyridinyl, $C_{1-6}$alkylpyrimidinyl, $C_{1-6}$alkyltetrazolyl, $C_{3-7}$ cycloalkyl, haloC$_{1-6}$alkyl, halogen, halophenyl, hydroxy, phenyl, pyrazinyl, pyridazinyl, pyridinyl, pyrimidinyl, and thiazolyl, or tetrahydropyranyl;
  $R^2$ is 1,3,4,6,7,8,9,9a-octahydropyrido[1,2-a]pyrazinyl, 3,4,6,7,9,9a-hexahydro-1H-pyrazino[2,1-c][1,4]oxazinyl,
    morpholinyl, or
    piperazinyl unsubstituted or substituted by one or more substituents independently selected from $C_{1-6}$alkoxyC$_{1-6}$alkyl, $C_{1-6}$alkyl, $C_{3-7}$cycloalkyl, haloC$_{1-6}$alkyl, hydroxyC$_{1-6}$alkyl, morpholinylC$_{1-6}$ alkyl, oxetanyl, oxopyrrolidinylC$_{1-6}$alkyl, and tetrahydrofuranyloxyC$_{1-6}$alkyl;
  $R^3$ is H or halogen;
  M is $C_{1-6}$alkylene or O; and
  L is $C_{1-6}$alkylene, hydroxyC$_{1-6}$alkylene, or haloC$_{1-6}$alkylene.

4. The compound of claim 3, or a pharmaceutically acceptable salt thereof, wherein $R^1$ is $C_{3-7}$ cycloalkyl substituted once or twice by substituents independently selected from $C_{1-6}$alkyl and pyridinyl.

5. The compound of claim 3, or a pharmaceutically acceptable salt thereof, wherein $R^1$ is 2,3-dimethyl-cyclopropyl or 2-(3-pyridinyl)cyclopropyl.

6. The compound of claim 3, or a pharmaceutically acceptable salt thereof, wherein $R^2$ is morpholinyl or $C_{1-6}$alkylpiperazinyl.

7. The compound of claim 3, or a pharmaceutically acceptable salt thereof, wherein $R^2$ is morpholinyl or 4-methylpiperazin-1-yl.

8. The compound of claim 3, or a pharmaceutically acceptable salt thereof, wherein M is $C_{1-6}$ alkylene.

9. The compound of claim 3, or a pharmaceutically acceptable salt thereof, wherein L is ethylene or difluoroethylene.

10. The compound of claim 3, or a pharmaceutically acceptable salt thereof, wherein:
    $R^1$ is $C_{3-7}$cycloalkyl substituted once or twice by substituents independently selected from $C_{1-6}$alkyl and pyridinyl;
    $R^2$ is morpholinyl or $C_{1-6}$alkylpiperazinyl;
    $R^3$ is H;
    M is $C_{1-6}$alkylene; and
    L is $C_{1-6}$alkylene or halo$C_{1-6}$alkylene.

11. A compound selected from:
    (1S,2S)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-methyl-cyclopropanecarboxamide;
    (1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-methyl-cyclopropanecarboxamide;
    (1S,2S)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-methyl-cyclopropanecarboxamide;
    (1S,2S)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15,24-dioxa-4-thia-9,21,30,31-tetrazahexacyclo[23.3.1.1$^{2,5}$.0$^{9,13}$.0$^{19,27}$.0$^{21,26}$]hentriaconta-1(28),2,5(31),19,25(29),26-hexaen-7-yl]-2-methyl-cyclopropanecarboxamide;
    (1S,2S)-2-(difluoromethyl)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]cyclopropanecarboxamide;
    (1S,5R,6r)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-3-oxabicyclo[3.1.0]hexane-6-carboxamide;
    (1S,2S)-N-[(7S,13S)-(20M)-20-[2-[(1S)-1-methoxyethyl]-5-morpholino-3-pyridyl]-17,17-dimethyl-8,14-dioxo-15,24-dioxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-methyl-cyclopropanecarboxamide;
    (1S,2S)-2-(difluoromethyl)-N-[(7S,13S)-(20M)-20-[2-[(1S)-1-methoxyethyl]-5-morpholino-3-pyridyl]-17,17-dimethyl-8,14-dioxo-15,24-dioxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]cyclopropanecarboxamide;
    (1S,5R,6r)-N-[(7S,13S)-(20M)-20-[2-[(1S)-1-methoxyethyl]-5-morpholino-3-pyridyl]-17,17-dimethyl-8,14-dioxo-15,24-dioxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-3-oxabicyclo[3.1.0]hexane-6-carboxamide;
    (1S,2S)-2-(difluoromethyl)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15,24-dioxa-4-thia-9,21,30,31-tetrazahexacyclo[23.3.1.1$^{2,5}$.0$^{9,13}$.0$^{19,27}$.0$^{21,26}$]hentriaconta-1(28),2,5(31),19,25(29),26-hexaen-7-yl]cyclopropanecarboxamide;
    (1S,5R,6r)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15,24-dioxa-4-thia-9,21,30,31-tetrazahexacyclo[23.3.1.1$^{2,5}$.0$^{9,13}$.0$^{19,27}$.0$^{21,26}$]hentriaconta-1(28),2,5(31),19,25(29),26-hexaen-7-yl]-3-oxabicyclo[3.1.0]hexane-6-carboxamide;
    (1S,5R,6r)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-3-oxabicyclo[3.1.0]hexane-6-carboxamide;
    (1S,2S)-2-(difluoromethyl)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]cyclopropanecarboxamide;
    (1S,5R,6r)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-3-oxabicyclo[3.1.0]hexane-6-carboxamide;
    (1R,2S)-2-cyclopropyl-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]cyclopropanecarboxamide;
    (1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-methyl-cyclopropanecarboxamide;
    (1S,2S)-N-[(7S,13S)-23,23-difluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-methyl-cyclopropanecarboxamide;

2,2-difluoro-N-[(7S,13S)-(20M)-20-[2-[(1S)-1-methoxy-ethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$0.1$^{9,11}$0.0$^{19,27}$0.0$^{21,26}$]hentriaconta-1(28),2,5(31),19,25(29),26-hexaen-7-yl]-1-methyl-cyclopropanecarboxamide;

(1S,2S)-2-(difluoromethyl)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15-oxa-4-thia-9,21,30,31-tetrazahexacyclo[23.3.1.1$^{2,5}$0.1$^{9,11}$0.0$^{19,27}$0.0$^{21,26}$]hentriaconta-1(28),2,5(31),19,25(29),26-hexaen-7-yl]cyclopropanecarboxamide;

(1S,2S)-N-[(7S,13S)-(20M)-20-[2-[(1S)-1-methoxy-ethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$0.1$^{9,11}$0.0$^{19,27}$0.0$^{21,26}$]hentriaconta-1(28),2,5(31),19,25(29),26-hexaen-7-yl]-2-phenyl-cyclopropanecarboxamide;

(1r,2R,3S)-N-[(7S,13S)-(20M)-20-[2-[(1S)-1-methoxy-ethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$0.1$^{9,11}$0.0$^{19,27}$0.0$^{21,26}$]hentriaconta-1(28),2,5(31),19,25(29),26-hexaen-7-yl]-2,3-dimethyl-cyclopropanecarboxamide;

(1S,2S)-N-[(7S,13S)-(20M)-20-[5-[(9αS)-3,4,6,7,9,9α-hexahydro-1H-pyrazino[2,1-c][1,4]oxazin-8-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-methyl-cyclopropanecarboxamide;

(1R,2R)-2-(2-fluorophenyl)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$0.1$^{9,11}$0.0$^{19,27}$0.0$^{21,26}$]hentriaconta-1(28),2,5(31),19,25(29),26-hexaen-7-yl]cyclopropanecarboxamide;

(1S,2S)-2-(2-fluorophenyl)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$0.1$^{9,11}$0.0$^{19,27}$0.0$^{21,26}$]hentriaconta-1(28),2,5(31),19,25(29),26-hexaen-7-yl]cyclopropanecarboxamide;

(1S,2S)-N-[(7S,13S)-(20M)-20-[2-[(1S)-1-methoxy-ethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$0.1$^{9,11}$0.0$^{19,27}$0.0$^{21,26}$]hentriaconta-1(28),2,5(31),19,25(29),26-hexaen-7-yl]-2-(2-pyridyl)cyclopropanecarboxamide;

(1S,2S)-N-[(7S,13S)-23,23-difluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$0.1$^{9,11}$0.0$^{19,27}$0.0$^{21,26}$]hentriaconta-1(29),2,5(31),19,25,27-hexaen-7-yl]-2-(difluoromethyl)cyclopropanecarboxamide;

(1S,2R)-N-[(7S,13S)-(20M)-20-[2-[(1S)-1-methoxy-ethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$0.1$^{9,11}$0.0$^{19,27}$0.0$^{21,26}$]hentriaconta-1(28),2,5(31),19,25(29),26-hexaen-7-yl]-2-methyl-cyclopropanecarboxamide;

(1S,2S)-2-(difluoromethyl)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$0.1$^{9,11}$0.0$^{19,27}$0.0$^{21,26}$]hentriaconta-1(28),2,5(31),19,25(29),26-hexaen-7-yl]cyclopropanecarboxamide;

(1S,5R,6r)-N-[(7S,13S)-(20M)-20-[2-[(1S)-1-methoxy-ethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$0.1$^{9,11}$0.0$^{19,27}$0.0$^{21,26}$]hentriaconta-1(28),2,5(31),19,25(29),26-hexaen-7-yl]-3-oxabicyclo[3.1.0]hexane-6-carboxamide;

(1R,2S)-2-cyclopropyl-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$0.1$^{9,11}$0.0$^{19,27}$0.0$^{21,26}$]hentriaconta-1(29),2,5(31),19,25,27-hexaen-7-yl]cyclopropanecarboxamide;

(1S,2S)-N-[(7S,13S)-(20M)-20-[2-[(1S)-1-methoxy-ethyl]-5-morpholino-3-pyridyl]-17,17,23,23-tetramethyl-8,14-dioxo-15,24-dioxa-4-thia-9,21,30,31-tetrazahexacyclo[23.3.1.1$^{2,5}$0.1$^{9,11}$0.0$^{19,27}$0.0$^{21,26}$]hentriaconta-1(28),2,5(31),19,25(29),26-hexaen-7-yl]-2-methyl-cyclopropanecarboxamide;

(1S,5R,6r)-N-[(7S,13S)-(20M)-20-[5-[(9αS)-3,4,6,7,9,9α-hexahydro-1H-pyrazino[2,1-c][1,4]oxazin-8-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-3-oxabicyclo[3.1.0]hexane-6-carboxamide;

(1S,2S)-N-[(7S,13S)-(20M)-20-[5-[(9αS)-3,4,6,7,9,9α-hexahydro-1H-pyrazino[2,1-c][1,4]oxazin-8-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(28),2,5(31),19,25(29),26-hexaen-7-yl]-2-(difluoromethyl)cyclopropanecarboxamide;

(1R,5S,6s)-N-[(7S,13S)-(20M)-20-[2-[(1S)-1-methoxy-ethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$0.1$^{9,11}$0.0$^{19,27}$0.0$^{21,26}$]hentriaconta-1(28),2,5(31),19,25(29),26-hexaen-7-yl]-3-oxabicyclo[3.1.0]hexane-6-carboxamide;

(1S,2S)-N-[(7S,13S)-(20M)-20-[2-[(1S)-1-methoxy-ethyl]-5-morpholino-3-pyridyl]-17,17-dimethyl-8,14-dioxo-15,24-dioxa-4-thia-9,21,30,31-tetrazahexacyclo[23.3.1.1$^{2,5}$0.1$^{9,11}$0.0$^{19,27}$0.0$^{21,26}$]hentriaconta-1(29),2,5(31),19,25,27-hexaen-7-yl]-2-phenyl-cyclopropanecarboxamide;

(1S,2S)-N-[(7S,13S)-(20M)-20-[2-[(1S)-1-methoxy-ethyl]-5-[4-(2,2,2-trifluoroethyl)piperazin-1-yl]-3-pyridyl]-17,17-dimethyl-8,14-dioxo-15,24-dioxa-4-thia-9,21,30,31-tetrazahexacyclo[23.3.1.1$^{2,5}$.0$^{9,13}$.0$^{19,27}$.0$^{21,26}$]hentriaconta-1(29),2,5(31),19,25,27-hexaen-7-yl]-2-phenyl-cyclopropanecarboxamide;

(1r,2S,3R)-N-[(7S,13S)-(20M)-20-[2-[(1S)-1-methoxy-ethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$0.1$^{9,13}$0.0$^{19,27}$0.0$^{21,26}$]hentriaconta-1(28),2,5(31),19,25(29),26-hexaen-7-yl]-2,3-dimethyl-cyclopropanecarboxamide;

(1S,2S)-N-[(7S,13S)-(20M)-20-[2-[(1S)-1-methoxy-ethyl]-5-morpholino-3-pyridyl]-17,17-dimethyl-8,14-dioxo-15-oxa-4-thia-9,21,30,31-tetrazahexacyclo[23.3.1.1$^{2,5}$0.1$^{9,13}$0.0$^{19,27}$0.0$^{21,26}$]hentriaconta-1(29),2,5(31),19,25,27-hexaen-7-yl]-2-phenyl-cyclopropanecarboxamide;

(1S,2S)-N-[(7S,13S)-(20M)-20-[2-[(1S)-1-methoxy-ethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$0.1$^{9,13}$0.0$^{19,27}$0.0$^{21,26}$]

hentriaconta-1(28),2,5(31),19,25(29),26-hexaen-7-yl]-2-pyrimidin-5-yl-cyclopropanecarboxamide;

(1S,5R)-3,3-difluoro-N-[(7S,13S)-(20M)-20-[2-[(1 S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]bicyclo[3.1.0]hexane-6-carboxamide;

(1S,2S)-N-[(7S,13S)-(20M)-20-[5-[(9αR)-1,3,4,6,7,8,9,9α-octahydropyrido[1,2-a]pyrazin-2-yl]-2-[(1S)-1-methoxyethyl]-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-methyl-cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-pyrimidin-4-yl-cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$ 0.1$^{9,11}$0.0$^{19,27}$0.0$^{21,26}$]hentriaconta-1(29),2,5(31),19,25,27-hexaen-7-yl]-2-phenyl-cyclopropanecarboxamide;

(1R,5S,6s)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-3-oxabicyclo[3.1.0]hexane-6-carboxamide;

(1S,2S)-N-[(7S,13S,22S)-(20M)-20-[2-[(1S)-1-methoxyethyl]-5-morpholino-3-pyridyl]-17,17,22-trimethyl-8,14-dioxo-15,24-dioxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-methyl-cyclopropanecarboxamide;

2,2-difluoro-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$ 0.1$^{9,11}$0.0$^{19,27}$0.0$^{21,26}$]hentriaconta-1(29),2,5(31),19,25,27-hexaen-7-yl]-1-methylcyclopropanecarboxamide;

N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$ 0.1$^{9,11}$0.0$^{19,27}$0.0$^{21,26}$]hentriaconta-1(29),2,5(31),19,25,27-hexaen-7-yl]-1,2-dimethylcyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-(3-pyridyl)cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-(4-pyridyl)cyclopropanecarboxamide;

(1R,2R)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-(4-pyridyl)cyclopropanecarboxamide;

2-(4-fluorophenyl)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$ 0.1$^{9,11}$0.0$^{19,27}$0.0$^{21,26}$]hentriaconta-1(29),2,5(31),19,25,27-hexaen-7-yl]cyclopropanecarboxamide;

(1S,5R,6r)-N-[(7S,13S)-23,23-difluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-3-oxabicyclo[3.1.0]hexane-6-carboxamide;

(1r,2R,3S)-N-[(7S,13S)-(20M)-20-[2-[(1S)-1-methoxyethyl]-5-morpholino-3-pyridyl]-17,17,23,23-tetramethyl-8,14-dioxo-15,24-dioxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2,3-dimethyl-cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-pyridazin-3-yl-cyclopropanecarboxamide;

(1R,2S)-2-cyclopropyl-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$ 0.1$^{9,11}$0.0$^{19,27}$0.0$^{21,26}$]hentriaconta-1(29),2,5(31),19,25,27-hexaen-7-yl]cyclopropanecarboxamide;

3,3-difluoro-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]cyclopentanecarboxamide;

N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-oxabicyclo[2.1.1]hexane-1-carboxamide;

(1S,2S)-N-[(7S,13S)-23,23-difluoro-(20M)-20-[2-[(1S)-1-methoxyethyl]-5-[4-(2,2,2-trifluoroethyl)piperazin-1-yl]-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-methyl-cyclopropanecarboxamide;

(1r,2R,3S)-N-[(7S,13S)-(20M)-20-[2-[(1S)-1-methoxyethyl]-5-morpholino-3-pyridyl]-17,17-dimethyl-8,14-dioxo-15,24-dioxa-4-thia-9,21,30,31-tetrazahexacyclo[23.3.1.1$^{2,5}$ 0.1$^{9,11}$0.0$^{19,27}$0.0$^{21,26}$]hentriaconta-1(29),2,5(31),19,25,27-hexaen-7-yl]-2,3-dimethyl-cyclopropanecarboxamide;

(1 r,2S,3R)-N-[(7S,13 S)-(20M)-20-[2-[(1 S)-1-methoxyethyl]-5-(4-methylpiperazin-1-yl)-3-pyridyl]-17,17,23,23-tetramethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2,3-dimethyl-cyclopropanecarboxamide;

trans-N-[(7S,13 S)-(20M)-20-[2-[(1 S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo

[23.3.1.1$^{2,5}$ 0.1$^{9,11}$0.0$^{19,27}$0.0$^{21,26}$]hentriaconta-1(29),2,5(31),19,25,27-hexaen-7-yl]-4-(1-methyltetrazol-5-yl)cyclohexanecarboxamide;

trans-4-hydroxy-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-4-methyl-cyclohexanecarboxamide;

N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]tricyclo[3.1.1.0$^{3,6}$]heptane-6-carboxamide;

(1r,2S,3R)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$ 0.1$^{9,13}$0.0$^{19,27}$0.0$^{21,26}$]hentriaconta-1(28),2,5(31),19,25(29),26-hexaen-7-yl]-2,3-dimethyl-cyclopropanecarboxamide;

(1S,2S)-N-[(7S,13S)-23,23-difluoro-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$ 0.1$^{9,13}$0.0$^{19,27}$0.0$^{21,26}$]hentriaconta-1(28),2,5(31),19,25(29),26-hexaen-7-yl]-2-methyl-cyclopropanecarboxamide;

(1r,2S,3R)-N-[(7S,13S)-23,23-difluoro-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$ 0.1$^{9,13}$0.0$^{19,27}$0.0$^{21,26}$]hentriaconta-1(28),2,5(31),19,25(29),26-hexaen-7-yl]-2,3-dimethyl-cyclopropanecarboxamide;

N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,13}$0.0$^{19,27}$0.0$^{21,26}$]hentriaconta-1(28),2,5(31),19,25(29),26-hexaen-7-yl]tetrahydropyran-4-carboxamide;

(1S,2S)-N-[(7S,13S)-23,23-difluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-phenyl-cyclopropanecarboxamide;

(1S,2S)-N-[(7S,13S)-23,23-difluoro-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-phenyl-cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-pyrimidin-2-yl-cyclopropanecarboxamide;

(1R,2R)-N-[(7S,13S)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-pyrimidin-2-yl-cyclopropanecarboxamide;

(1r,2S,3R)-N-[(7S,13S)-23,23-difluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(29),2,5(31),19,25,27-hexaen-7-yl]-2,3-dimethyl-cyclopropanecarboxamide;

(1r,2S,3R)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15,24-dioxa-4-thia-9,21,30,31-tetrazahexacyclo[23.3.1.1$^{2,5}$.0$^{9,13}$.0$^{19,27}$.0$^{21,26}$]hentriaconta-1(28),2,5(31),19,25(29),26-hexaen-7-yl]-2,3-dimethyl-cyclopropanecarboxamide;

(1r,2R,3S)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15-oxa-4-thia-9,21,30,31-tetrazahexacyclo[23.3.1.1$^{2,5}$ 0.1$^{9,13}$0.0$^{19,27}$0.0$^{21,26}$]hentriaconta-1(28),2,5(31),19,25(29),26-hexaen-7-yl]-2,3-dimethyl-cyclopropanecarboxamide;

(1r,2S,3R)-N-[(7S,13S)-23,23-difluoro-(20M)-20-[2-[(1S)-1-methoxyethyl]-5-[4-(2,2,2-trifluoroethyl)piperazin-1-yl]-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2,3-dimethyl-cyclopropanecarboxamide;

(1S,2S)-N-[(7S,13S)-(20M)-20-[2-[(1S)-1-methoxyethyl]-5-morpholino-3-pyridyl]-17,17-dimethyl-8,14-dioxo-15,24-dioxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-pyrimidin-5-yl-cyclopropanecarboxamide;

(1S,2S)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-(3-pyridyl)cyclopropanecarboxamide;

(1S,2S)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-(3-pyridyl)cyclopropanecarboxamide;

(1S,2S)-N-[(7S,13S)-23,23-difluoro-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-(3-pyridyl)cyclopropanecarboxamide;

(1S,2S)-N-[(7S,13S)-23,23-difluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-(3-pyridyl)cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-pyrimidin-5-yl-cyclopropanecarboxamide;

(1S,2S)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-pyrimidin-5-yl-cyclopropanecarboxamide;

(1S,2S)-N-[(7S,13S)-23,23-difluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$ 0.0²¹,²⁶]hentriaconta-1(28),2,5(31),19,25(29),26-hexaen-7-yl]-2-pyrimidin-5-yl-cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1²,⁵.1⁹,¹³.0¹⁹,²⁷.0²¹,²⁶]hentriaconta-1(28),2,5(31),19,25(29),26-hexaen-7-yl]-2-(3-pyridyl)cyclopropanecarboxamide;

(1S,2S)-N-[(7S,13S)-(20M)-20-[2-[(1S)-1-methoxyethyl]-5-morpholino-3-pyridyl]-17,17-dimethyl-8,14-dioxo-15,24-dioxa-4-thia-9,21,30,31-tetrazahexacyclo[23.3.1.1²,⁵.1⁹,¹³.0¹⁹,²⁷.0²¹,²⁶]hentriaconta-1(28),2,5(31),19,25(29),26-hexaen-7-yl]-2-(3-pyridyl)cyclopropanecarboxamide;

(1S,2S)-N-[(7S,13S)-(20M)-20-[2-[(1S)-1-methoxyethyl]-5-[4-(2,2,2-trifluoroethyl)piperazin-1-yl]-3-pyridyl]-17,17-dimethyl-8,14-dioxo-15,24-dioxa-4-thia-9,21,30,31-tetrazahexacyclo[23.3.1.1²,⁵.1⁹,¹³.0¹⁹,²⁷.0²¹,²⁶]hentriaconta-1(28),2,5(31),19,25(29),26-hexaen-7-yl]-2-(3-pyridyl)cyclopropanecarboxamide;

(1S,2S)-N-[(7S,13S)-(20M)-20-[2-[(1S)-1-methoxyethyl]-5-(4-methylpiperazin-1-yl)-3-pyridyl]-17,17-dimethyl-8,14-dioxo-15,24-dioxa-4-thia-9,21,30,31-tetrazahexacyclo[23.3.1.1²,⁵ 0.1⁹,¹³0.0¹⁹,²⁷0.0²¹,²⁶]hentriaconta-1(28),2,5(31),19,25(29),26-hexaen-7-yl]-2-pyrazin-2-yl-cyclopropanecarboxamide;

(1r,2R,3S)-N-[(7S,13S)-(20M)-20-[2-[(1S)-1-methoxyethyl]-5-(4-methylpiperazin-1-yl)-3-pyridyl]-17,17-dimethyl-8,14-dioxo-15,25-dioxa-4-thia-9,21,31,32-tetrazahexacyclo[24.3.1.1²,⁵.1⁹,¹³.0¹⁹,²⁸.0²¹,²⁷]dotriaconta-1(29),2,5(32),19,26(30),27-hexaen-7-yl]-2,3-dimethyl-cyclopropanecarboxamide;

(1r,2S,3R)-N-[(7S,13S)-(20M)-20-[5-[(9αR)-1,3,4,6,7,8,9,9a-octahydropyrido[1,2-a]pyrazin-2-yl]-2-[(1S)-1-methoxyethyl]-3-pyridyl]-17,17-dimethyl-8,14-dioxo-15-oxa-4-thia-9,21,30,31-tetrazahexacyclo[23.3.1.1²,⁵.0⁹,¹³.0¹⁹,²⁷.0²¹,²⁶]hentriaconta-1(28),2,5(31),19,25(29),26-hexaen-7-yl]-2,3-dimethyl-cyclopropanecarboxamide;

(1S,2S)-N-[(7S,13S)-(20M)-20-[5-[(9αR)-1,3,4,6,7,8,9,9α-octahydropyrido[1,2-a]pyrazin-2-yl]-2-[(1S)-1-methoxyethyl]-3-pyridyl]-17,17-dimethyl-8,14-dioxo-15-oxa-4-thia-9,21,30,31-tetrazahexacyclo[23.3.1.1²,⁵ 0.1⁹,¹³0.0¹⁹,²⁷0.0²¹,²⁶]hentriaconta-1(28),2,5(31),19,25(29),26-hexaen-7-yl]-2-(3-pyridyl)cyclopropanecarboxamide;

(1S,2S)-N-[(7S,13S)-(20M)-20-[5-[(9αR)-1,3,4,6,7,8,9,9α-octahydropyrido[1,2-a]pyrazin-2-yl]-2-[(1S)-1-methoxyethyl]-3-pyridyl]-17,17-dimethyl-8,14-dioxo-15-oxa-4-thia-9,21,30,31-tetrazahexacyclo[23.3.1.1²,⁵ 0.1⁹,¹³0.0¹⁹,²⁷0.0²¹,²⁶]hentriaconta-1(28),2,5(31),19,25(29),26-hexaen-7-yl]-2-pyrimidin-5-yl-cyclopropanecarboxamide;

(1S,2S)-N-[(7S,13S)-(20M)-20-[5-[(9αS)-3,4,6,7,9,9α-hexahydro-1H-pyrazino[2,1-c][1,4]oxazin-8-yl]-2-[(1S)-1-methoxyethyl]-3-pyridyl]-17,17-dimethyl-8,14-dioxo-15-oxa-4-thia-9,21,30,31-tetrazahexacyclo[23.3.1.1²,⁵.1⁹,¹³.0¹⁹,²⁷.0²¹,²⁶]hentriaconta-1(28),2,5(31),19,25(29),26-hexaen-7-yl]-2-(3-pyridyl)cyclopropanecarboxamide;

(1S,2S)-N-[(7S,13S)-(20M)-20-[5-[(9αS)-3,4,6,7,9,9α-hexahydro-1H-pyrazino[2,1-c][1,4]oxazin-8-yl]-2-[(1S)-1-methoxyethyl]-3-pyridyl]-17,17-dimethyl-8,14-dioxo-15-oxa-4-thia-9,21,30,31-tetrazahexacyclo[23.3.1.1²,⁵.1⁹,¹³.0¹⁹,²⁷.0²¹,²⁶]hentriaconta-1(28),2,5(31),19,25(29),26-hexaen-7-yl]-2-pyrimidin-5-yl-cyclopropanecarboxamide;

(1r,2R,3S)-N-[(7S,13S)-(20M)-20-[5-(4-cyclopropylpiperazin-1-yl)-2-[(1S)-1-methoxyethyl]-3-pyridyl]-17,17-dimethyl-8,14-dioxo-15,24-dioxa-4-thia-9,21,30,31-tetrazahexacyclo[23.3.1.1²,⁵ 0.1⁹,¹³0.0¹⁹,²⁷0.0²¹,²⁶]hentriaconta-1(28),2,5(31),19,25(29),26-hexaen-7-yl]-2,3-dimethyl-cyclopropanecarboxamide;

(1r,2R,3S)-N-[(7S,13S,23S)-23-hydroxy-(20M)-20-[2-[(1S)-1-methoxyethyl]-5-morpholino-3-pyridyl]-17,17-dimethyl-8,14-dioxo-15-oxa-4-thia-9,21,30,31-tetrazahexacyclo[23.3.1.1²,⁵ 0.1⁹,¹³0.0¹⁹,²⁷0.0²¹,²⁶]hentriaconta-1(28),2,5(31),19,25(29),26-hexaen-7-yl]-2,3-dimethyl-cyclopropanecarboxamide;

(1r,2R,3S)-N-[(7S,13S)-(20M)-20-[2-[(1S)-1-methoxyethyl]-5-piperazin-1-yl-3-pyridyl]-17,17-dimethyl-8,14-dioxo-15-oxa-4-thia-9,21,30,31-tetrazahexacyclo[23.3.1.1²,⁵ 0.1⁹,¹¹0.0¹⁹,²⁷0.0²¹,²⁶]hentriaconta-1(28),2,5(31),19,25(29),26-hexaen-7-yl]-2,3-dimethyl-cyclopropanecarboxamide;

(1r,2R,3S)-N-[(7S,13S)-20-[5-[4-(2,2-difluoroethyl)piperazin-1-yl]-2-[(1S)-1-methoxyethyl]-3-pyridyl]-17,17-dimethyl-8,14-dioxo-15-oxa-4-thia-9,21,30,31-tetrazahexacyclo[23.3.1.1²,⁵ 0.1⁹,¹¹0.0¹⁹,²⁷0.0²¹,²⁶]hentriaconta-1(28),2,5(31),19,25(29),26-hexaen-7-yl]-2,3-dimethyl-cyclopropanecarboxamide;

(1r,2R,3S)-N-[(7S,13S)-(20M)-20-[5-[4-(2-fluoroethyl)piperazin-1-yl]-2-[(1S)-1-methoxyethyl]-3-pyridyl]-17,17-dimethyl-8,14-dioxo-15-oxa-4-thia-9,21,30,31-tetrazahexacyclo[23.3.1.1²,⁵ 0.1⁹,¹¹0.0¹⁹,²⁷0.0²¹,²⁶]hentriaconta-1(28),2,5(31),19,25(29),26-hexaen-7-yl]-2,3-dimethyl-cyclopropanecarboxamide;

(1r,2R,3S)-N-[(7S,13S)-(20M)-20-[5-[4-(3-hydroxypropyl)piperazin-1-yl]-2-[(1S)-1-methoxyethyl]-3-pyridyl]-17,17-dimethyl-8,14-dioxo-15-oxa-4-thia-9,21,30,31-tetrazahexacyclo[23.3.1.1²,⁵ 0.1⁹,¹¹0.0¹⁹,²⁷0.0²¹,²⁶]hentriaconta-1(28),2,5(31),19,25(29),26-hexaen-7-yl]-2,3-dimethyl-cyclopropanecarboxamide;

(1R,2R)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1²,⁵ 0.1⁹,¹¹0.0¹⁹,²⁷0.0²¹,²⁶]hentriaconta-1(28),2,5(31),19,25(29),26-hexaen-7-yl]-2-(4-methylpyrimidin-5-yl)cyclopropanecarboxamide;

(1r,2R,3S)-N-[(7S,13S)-(20M)-20-[5-(4-ethylpiperazin-1-yl)-2-[(1S)-1-methoxyethyl]-3-pyridyl]-17,17-dimethyl-8,14-dioxo-15-oxa-4-thia-9,21,30,31-tetrazahexacyclo[23.3.1.1²,⁵ 0.1⁹,¹¹0.0¹⁹,²⁷0.0²¹,²⁶]hentriaconta-1(28),2,5(31),19,25(29),26-hexaen-7-yl]-2,3-dimethyl-cyclopropanecarboxamide;

(1R,2R)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1²,⁵ 0.1⁹,¹¹0.0¹⁹,²⁷0.0²¹,²⁶]hentriaconta-1(28),2,5(31),19,25(29),26-hexaen-7-yl]-2-thiazol-4-yl-cyclopropanecarboxamide;

(1r,2S,3R)-N-[(7S,13S)-(20M)-20-[2-[(1S)-1-methoxyethyl]-5-[4-(2-methoxyethyl)piperazin-1-yl]-3-pyridyl]-17,17-dimethyl-8,14-dioxo-15-oxa-4-thia-9,21,30,31-tetrazahexacyclo[23.3.1.1²,⁵ 0.1⁹,¹¹0.0¹⁹,²⁷0.0²¹,²⁶]hentriaconta-1(28),2,5(31),19,25(29),26-hexaen-7-yl]-2,3-dimethyl-cyclopropanecarboxamide;

(1R,2R)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1²,⁵ 0.1⁹,¹¹0.0¹⁹,²⁷0.0²¹,²⁶]

hentriaconta-1(28),2,5(31),19,25(29),26-hexaen-7-yl]-2-(2-methyl-3-pyridyl)cyclopropanecarboxamide;

(1r,2R,3S)-N-[(7S,13S)-(20M)-20-[2-[(1S)-1-methoxyethyl]-5-(4-tetrahydropyran-4-ylpiperazin-1-yl)-3-pyridyl]-17,17-dimethyl-8,14-dioxo-15-oxa-4-thia-9,21,30,31-tetrazahexacyclo[23.3.1.1$^{2,5}$.0.1$^{9,11}$0.0$^{19,27}$0.0$^{21,26}$]hentriaconta-1(28),2,5(31),19,25(29),26-hexaen-7-yl]-2,3-dimethyl-cyclopropanecarboxamide;

(1r,2R,3S)-N-[(7S,13S)-(20M)-20-[2-[(1S)-1-methoxyethyl]-5-[4-(oxetan-3-yl)piperazin-1-yl]-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2,3-dimethyl-cyclopropanecarboxamide;

(1r,2S,3R)-N-[(7S,13S)-(20M)-20-[2-[(1S)-1-methoxyethyl]-5-[4-[[(2S)-morpholin-2-yl]methyl]piperazin-1-yl]-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2,3-dimethyl-cyclopropanecarboxamide;

(1R,2R)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2-(5-methyl-3-pyridyl)cyclopropanecarboxamide;

(1r,2R,3S)-N-[(7S,13S)-(20M)-20-[2-[(1S)-1-methoxyethyl]-5-[4-[2-(2-oxopyrrolidin-1-yl)ethyl]piperazin-1-yl]-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2,3-dimethyl-cyclopropanecarboxamide;

(1r,2R,3S)-N-[(7S,13S)-(20M)-20-[2-[(1S)-1-methoxyethyl]-5-[4-(2-tetrahydrofuran-3-yloxyethyl)piperazin-1-yl]-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2,3-dimethyl-cyclopropanecarboxamide;

(1r,2R,3S)-N-[(7S,13S)-(20M)-20-[2-[(1S)-1-methoxyethyl]-5-[4-(3-methoxy-3-methyl-butyl)piperazin-1-yl]-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2,3-dimethyl-cyclopropanecarboxamide;

(1r,2S,3R)-N-[(7S,13S)-29-fluoro-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,30,31-tetrazahexacyclo[23.3.1.1$^{2,5}$ 0.1$^{9,11}$0.0$^{19,27}$0.0$^{21,26}$]hentriaconta-1(28),2,5(31),19,25(29),26-hexaen-7-yl]-2,3-dimethyl-cyclopropanecarboxamide;

(1S,2S)-N-[(7S,13S)-(20M)-20-[2-[(1S)-1-methoxyethyl]-5-morpholino-3-pyridyl]-17,17,22,22-tetramethyl-8,14-dioxo-15-oxa-4-thia-9,21,30,31-tetrazahexacyclo[23.3.1.1$^{2,5}$.1$^{9,13}$.0$^{19,27}$.0$^{21,26}$]hentriaconta-1(29),2,5(31),19,25,27-hexaen-7-yl]-2-methyl-cyclopropanecarboxamide;

(1r,2R,3S)-N-[(7S,13S)-(20M)-20-[2-[(1S)-1-methoxyethyl]-5-morpholino-3-pyridyl]-17,17-dimethyl-8,14-dioxo-15-oxa-4-thia-9,21,31,32-tetrazahexacyclo[24.3.1.1$^{2,5}$.1$^{9,13}$.0$^{9,28}$.0$^{21,27}$]dotriaconta-1(29),2,5(32), 19,26(30),27-hexaen-7-yl]-2,3-dimethyl-cyclopropanecarboxamide; or (1r,2R,3S)-N-[(7S,13S)-(20M)-20-[2-[(1S)-1-methoxyethyl]-5-(4-methylpiperazin-1-yl)-3-pyridyl]-17,17-dimethyl-8,14-dioxo-15-oxa-4-thia-9,21,32,33-tetrazahexacyclo[25.3.1.1$^{2,5}$.1$^{9,13}$.0$^{19,29}$.0$^{21,28}$]tritriaconta-1(30),2,5(33),19,27(31),28-hexaen-7-yl]-2,3-dimethyl-cyclopropanecarboxamide;

or a pharmaceutically acceptable salt thereof.

12. A compound of formula (Ia):

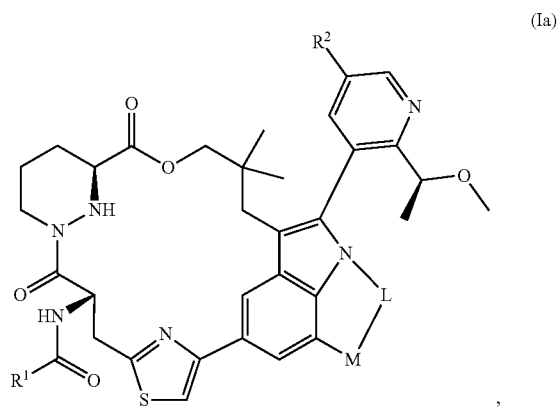

(Ia)

or a pharmaceutically acceptable salt thereof, wherein:

$R^1$ is 2-oxabicyclo[2.1.1]hexanyl,
3-oxabicyclo[3.1.0]hexanyl,
6-bicyclo[3.1.0]hexanyl substituted twice by halogen,
6-tricyclo[3.1.1.0$^{3,6}$]heptanyl,
$C_{3-7}$cycloalkyl substituted once, twice, or three times by substituents independently selected from $C_{1-6}$alkyl, $C_{1-6}$alkyltetrazolyl, $C_{3-7}$cycloalkyl, halo$C_{1-6}$alkyl, halogen, halophenyl, hydroxy, phenyl, pyridazinyl, pyridinyl, and pyrimidinyl, or
tetrahydropyranyl;

$R^2$ is 1,3,4,6,7,8,9,9a-octahydropyrido[1,2-a]pyrazinyl, 3,4,6,7,9,9a-hexahydro-1H-pyrazino[2,1-c][1,4]oxazinyl, morpholinyl, (halo$C_{1-6}$alkyl) piperazinyl, or $C_{1-6}$ alkylpiperazinyl;

M is $C_{1-6}$alkylene or O; and

L is $C_{1-6}$alkylene or halo$C_{1-6}$alkylene.

13. The compound of claim 12, or a pharmaceutically acceptable salt thereof, wherein $R^1$ is 2,3-dimethyl-cyclopropyl or 2-(3-pyridinyl)cyclopropyl;

$R^2$ is morpholinyl or 4-methylpiperazin-1-yl;

M is $CH_2$; and

L is

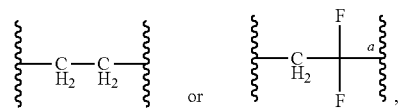

wherein bond "a" connects to M.

14. The compound of claim 12, wherein the compound is:

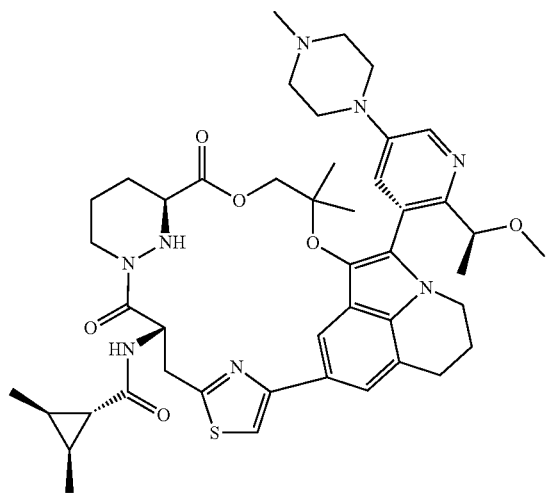

or a pharmaceutically acceptable salt thereof.

15. The compound of claim 12, wherein the compound is:

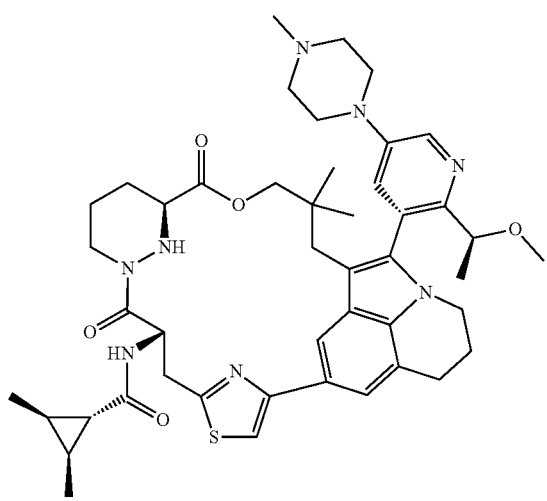

,

16. The compound of claim 12, wherein the compound is:

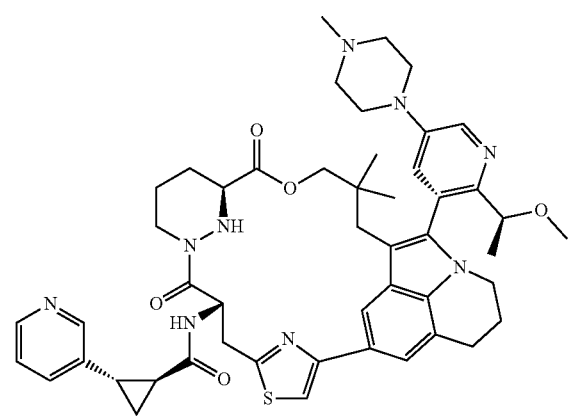

, or a pharmaceutically acceptable salt thereof.

17. The compound of claim 12, wherein the compound is:

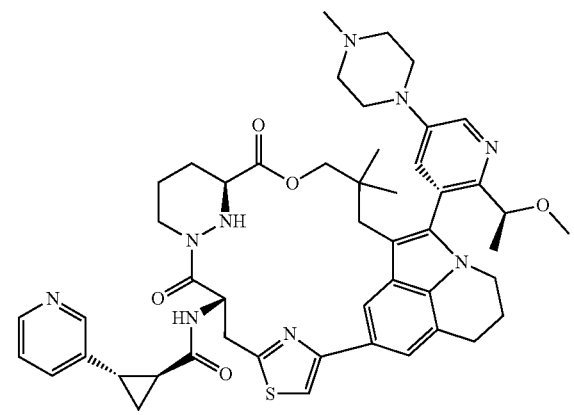

18. The compound of claim 12, wherein the compound is:

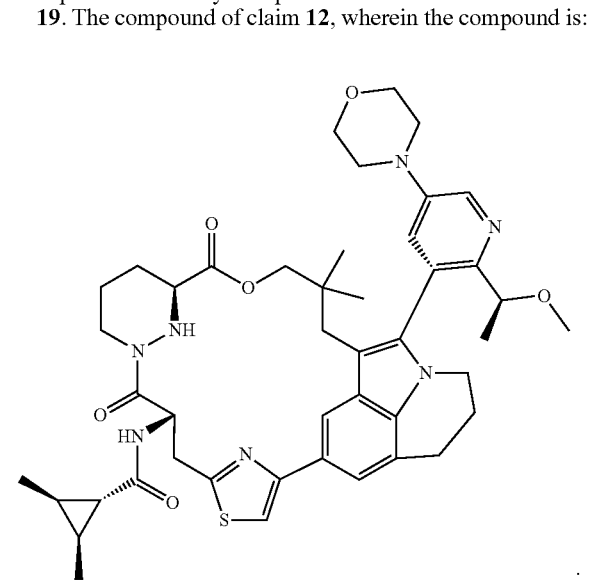

, or a pharmaceutically acceptable salt thereof.

19. The compound of claim 12, wherein the compound is:

20. The compound of claim 12, wherein the compound is:

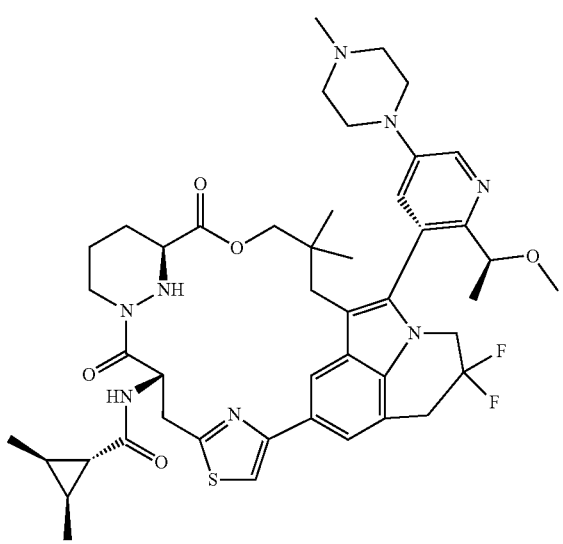

or a pharmaceutically acceptable salt thereof.

21. The compound of claim 12, wherein the compound is:

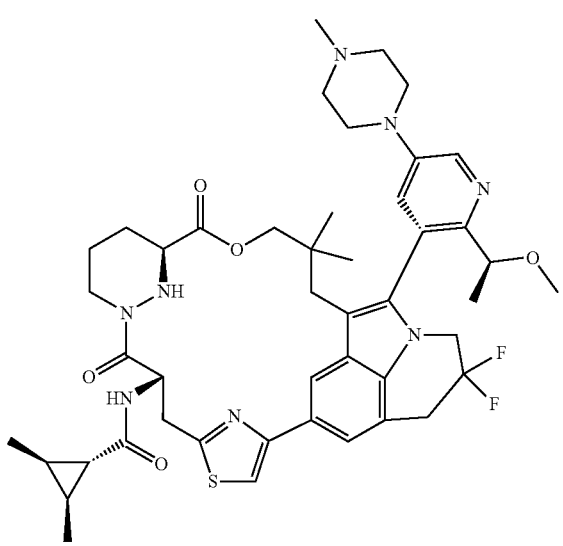

22. The compound of claim 12, wherein the compound is:

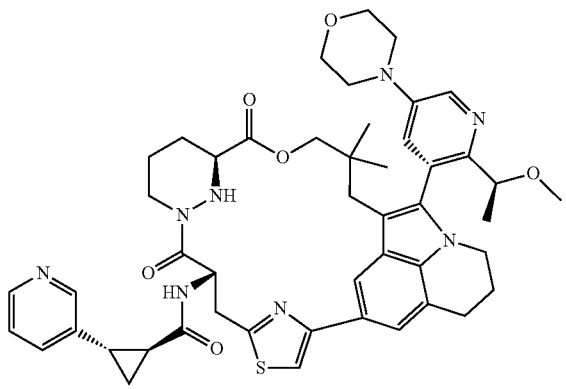

or a pharmaceutically acceptable salt thereof.

23. The compound of claim 12, wherein the compound is:

24. A pharmaceutical composition comprising a compound of claim 1, or a pharmaceutically acceptable salt thereof, and a pharmaceutically acceptable excipient.

25. A pharmaceutical composition comprising a compound of claim 11, or a pharmaceutically acceptable salt thereof, and a pharmaceutically acceptable excipient.

26. A pharmaceutical composition comprising a compound of claim 12, or a pharmaceutically acceptable salt thereof, and a pharmaceutically acceptable excipient.

27. A method for the treatment of cancer in a human subject in need thereof, comprising administering a therapeutically effective amount of a compound of claim 1, wherein the cancer is selected from the group consisting of pancreatic cancer, colorectal cancer, lung cancer, esophageal cancer, gallbladder cancer, melanoma ovarian cancer, endometrial cancer, and primary central nervous system (CNS) tumors.

* * * * *